(12) United States Patent
Sakamuri et al.

(10) Patent No.: US 11,981,703 B2
(45) Date of Patent: May 14, 2024

(54) POLYNUCLEOTIDE CONSTRUCTS

(71) Applicant: Sirius Therapeutics, Inc., Boston, MA (US)

(72) Inventors: Sukumar Sakamuri, San Diego, CA (US); Curt W. Bradshaw, San Diego, CA (US); Laxman Eltepu, San Diego, CA (US); Bryan R. Meade, San Diego, CA (US); Son Lam, San Diego, CA (US)

(73) Assignee: SIRIUS THERAPEUTICS, INC., Cambridge, MA (US)

( * ) Notice: Subject to any disclaimer, the term of this patent is extended or adjusted under 35 U.S.C. 154(b) by 773 days.

(21) Appl. No.: 16/326,542

(22) PCT Filed: Aug. 17, 2017

(86) PCT No.: PCT/US2017/047447
§ 371 (c)(1),
(2) Date: Feb. 19, 2019

(87) PCT Pub. No.: WO2018/035380
PCT Pub. Date: Feb. 22, 2018

(65) Prior Publication Data
US 2019/0202855 A1    Jul. 4, 2019

Related U.S. Application Data

(60) Provisional application No. 62/376,182, filed on Aug. 17, 2016.

(51) Int. Cl.
| | | |
|---|---|---|
| C07H 21/00 | (2006.01) | |
| C07F 9/24 | (2006.01) | |
| C07F 9/6558 | (2006.01) | |
| C07F 9/6561 | (2006.01) | |
| C07H 21/02 | (2006.01) | |
| C07H 21/04 | (2006.01) | |
| C12N 15/113 | (2010.01) | |
| C12N 15/85 | (2006.01) | |

(52) U.S. Cl.
CPC .......... *C07H 21/00* (2013.01); *C07F 9/2408* (2013.01); *C07F 9/65586* (2013.01); *C07F 9/65616* (2013.01); *C07H 21/02* (2013.01); *C07H 21/04* (2013.01); *C12N 15/113* (2013.01); *C12N 15/85* (2013.01); *C12N 2310/14* (2013.01)

(58) Field of Classification Search
CPC ...... C07H 21/00; C07F 9/2408; C12N 15/113
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,500,707 A | 2/1985 | Caruthers et al. |
| 4,517,338 A | 5/1985 | Urdea et al. |
| 4,659,774 A | 4/1987 | Webb et al. |
| 4,668,777 A | 5/1987 | Caruthers et al. |
| 4,672,110 A | 6/1987 | Letsinger |
| 4,711,955 A | 12/1987 | Ward et al. |
| 4,725,677 A | 2/1988 | Koster et al. |
| 4,751,180 A | 6/1988 | Cousens et al. |
| 4,806,463 A | 2/1989 | Goodchild et al. |
| 4,845,205 A | 7/1989 | Huynh Dinh et al. |
| 4,877,805 A | 10/1989 | Kligman |
| 4,935,233 A | 6/1990 | Bell et al. |
| 4,973,679 A | 11/1990 | Caruthers et al. |
| 4,975,282 A | 12/1990 | Cullis et al. |
| 4,980,378 A | 12/1990 | Wong et al. |
| 4,994,213 A | 2/1991 | Aitcheson et al. |
| 5,000,307 A | 3/1991 | Bruke |
| 5,000,958 A | 3/1991 | Fountain et al. |
| 5,023,087 A | 6/1991 | Yau-Young |
| 5,032,582 A | 7/1991 | Abra |
| 5,049,388 A | 9/1991 | Knight et al. |
| 5,082,866 A | 1/1992 | Wong et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,153,319 A | 10/1992 | Caruthers et al. |
| 5,169,637 A | 12/1992 | Lenk et al. |
| 5,175,273 A | 12/1992 | Bischofberger et al. |
| 5,194,266 A | 3/1993 | Abra et al. |
| 5,218,103 A | 6/1993 | Caruthers et al. |
| 5,268,464 A | 12/1993 | Brill |
| 5,278,302 A | 1/1994 | Caruthers et al. |

(Continued)

FOREIGN PATENT DOCUMENTS

| | | |
|---|---|---|
| CA | 2252144 A1 | 4/2000 |
| CA | 2929651 A1 | 5/2015 |

(Continued)

OTHER PUBLICATIONS

Iwamoto et al (PSJ Congress: The Pharmaceutical Society of Japan, (Mar. 25-28, 2015) (Year: 2015).*

(Continued)

*Primary Examiner* — Richard A Schnizer
(74) *Attorney, Agent, or Firm* — WILSON SONSINI GOODRICH & ROSATI

(57) ABSTRACT

Disclosed are polynucleotide constructs having a strand linked to a moiety carrying one or more auxiliary moieties. Also disclosed are polynucleotide constructs interrupted with a sugar analogue, and polynucleotide constructs with stereochemical^ enriched phosphorothioates. The polynucleotide constructs may be provided as hybridized polynucleotide constructs. Also featured are methods of delivery a polynucleotide construct to a cell and methods of reducing the expression of a protein in a cell by contacting the cell with the disclosed polynucleotide construct or hybridized polynucleotide construct.

13 Claims, 20 Drawing Sheets

Specification includes a Sequence Listing.

(56) References Cited

U.S. PATENT DOCUMENTS

| | | | |
|---|---|---|---|
| 5,319,079 A | 6/1994 | Reddy et al. |
| 5,356,633 A | 10/1994 | Woodle et al. |
| 5,367,066 A | 11/1994 | Urdea et al. |
| 5,409,704 A | 4/1995 | Bally et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,155 A | 9/1996 | Bailey et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,670,617 A | 9/1997 | Frankel et al. |
| 5,677,441 A | 10/1997 | Waldman et al. |
| 5,681,941 A | 10/1997 | Cook et al. |
| 5,688,525 A | 11/1997 | Adler-Moore et al. |
| 5,696,251 A * | 12/1997 | Arnold, Jr. ............ C07F 9/2408 536/25.32 |
| 5,733,523 A | 3/1998 | Kuijpers et al. |
| 5,760,209 A | 6/1998 | Cheruvallath et al. |
| 5,770,713 A | 6/1998 | Imbach et al. |
| 5,770,725 A | 6/1998 | Gosselin et al. |
| 5,789,562 A | 8/1998 | Seela et al. |
| 5,849,905 A | 12/1998 | Gosselin et al. |
| 5,874,104 A | 2/1999 | Adler-Moore et al. |
| 5,874,552 A | 2/1999 | Jones et al. |
| 5,902,879 A | 5/1999 | Polouchine |
| 5,936,077 A | 8/1999 | Pfleiderer et al. |
| 5,955,591 A | 9/1999 | Imbach et al. |
| 5,959,099 A | 9/1999 | Cheruvallath et al. |
| 5,968,506 A | 10/1999 | Weinrich et al. |
| 6,022,735 A | 2/2000 | Curiel et al. |
| 6,030,955 A | 2/2000 | Stein et al. |
| 6,077,663 A | 6/2000 | Curiel et al. |
| 6,118,020 A | 9/2000 | Buyuktimkin et al. |
| 6,124,445 A | 9/2000 | Imbach et al. |
| 6,221,355 B1 | 4/2001 | Dowdy |
| 6,316,003 B1 | 11/2001 | Frankel et al. |
| 6,326,358 B1 | 12/2001 | Manoharan |
| 6,326,478 B1 | 12/2001 | Cheruvallath et al. |
| 6,376,248 B1 | 4/2002 | Hawley-Nelson et al. |
| 6,399,756 B1 | 6/2002 | Cheruvallath et al. |
| 6,420,546 B1 | 7/2002 | Seliger et al. |
| 6,468,986 B1 | 10/2002 | Zuckermann et al. |
| 6,521,775 B2 | 2/2003 | Cheruvallath et al. |
| 6,531,590 B1 | 3/2003 | Manoharan et al. |
| 6,559,279 B1 | 5/2003 | Manoharan et al. |
| 6,610,837 B1 | 8/2003 | Guzaev et al. |
| 6,610,841 B1 | 8/2003 | Warren |
| 6,613,956 B1 | 9/2003 | Klippel et al. |
| 6,645,501 B2 | 11/2003 | Dowdy |
| 6,677,471 B2 | 1/2004 | Cheruvallath et al. |
| 6,747,142 B1 | 6/2004 | Polouchine |
| 6,841,535 B2 | 1/2005 | Divita et al. |
| 6,900,301 B2 | 5/2005 | Cook et al. |
| 6,900,540 B1 | 5/2005 | Teig et al. |
| 6,903,077 B1 | 6/2005 | Heintz |
| 6,906,182 B2 | 6/2005 | Ts'o et al. |
| 6,919,437 B1 | 7/2005 | Manoharan et al. |
| 7,045,309 B2 | 5/2006 | Johnson et al. |
| 7,084,248 B2 | 8/2006 | Summerton |
| 7,166,692 B2 | 1/2007 | Karas |
| 7,262,177 B2 | 8/2007 | Ts'O et al. |
| 7,420,031 B2 | 9/2008 | Karas |
| 7,491,805 B2 | 2/2009 | Vargeese et al. |
| 7,514,530 B2 | 4/2009 | Divita et al. |
| 7,713,944 B2 | 5/2010 | Kinberger et al. |
| 7,754,944 B2 | 7/2010 | Fu et al. |
| 7,785,610 B2 | 8/2010 | Fearon et al. |
| 7,879,813 B2 | 2/2011 | Chatterton |
| 8,114,973 B2 | 2/2012 | Siddiqi et al. |
| 8,153,361 B1 | 4/2012 | Benner |
| 8,158,770 B2 | 4/2012 | Wedekind et al. |
| 8,450,467 B2 | 5/2013 | Manoharan et al. |
| 8,476,083 B1 | 7/2013 | Algar et al. |
| 8,501,930 B2 | 8/2013 | Rozema et al. |
| 8,507,455 B2 | 8/2013 | Manoharan et al. |
| 8,541,569 B2 | 9/2013 | Srivastava et al. |
| 8,691,971 B2 | 4/2014 | Petersen |
| 8,853,132 B2 | 10/2014 | Heindl et al. |
| 8,859,755 B2 | 10/2014 | Wada et al. |
| 9,714,421 B2 | 7/2017 | Prakash et al. |
| 9,950,001 B2 | 4/2018 | Dowdy et al. |
| 11,505,569 B2 | 11/2022 | Albaek et al. |
| 11,597,744 B2 | 3/2023 | Sakamuri et al. |
| 2002/0013287 A1 | 1/2002 | Sampath et al. |
| 2003/0105026 A1 | 6/2003 | Kozhemyakin et al. |
| 2003/0143732 A1 | 7/2003 | Fosnaugh et al. |
| 2003/0225016 A1 | 12/2003 | Fearon et al. |
| 2004/0018140 A1 | 1/2004 | Karl et al. |
| 2004/0082774 A1 | 4/2004 | Guzaev et al. |
| 2004/0110205 A1 | 6/2004 | Wang |
| 2004/0116680 A1 | 6/2004 | Beier |
| 2004/0204377 A1 | 10/2004 | Rana |
| 2004/0229839 A1 | 11/2004 | Babu et al. |
| 2005/0042603 A1 | 2/2005 | Wang |
| 2005/0147993 A1 | 7/2005 | Khan |
| 2005/0191687 A1 | 9/2005 | Wang et al. |
| 2005/0239687 A1 | 10/2005 | Divita et al. |
| 2005/0260756 A1 | 11/2005 | Troy et al. |
| 2006/0030003 A1 | 2/2006 | Simon |
| 2006/0035815 A1 | 2/2006 | Chen et al. |
| 2006/0040882 A1 | 2/2006 | Chen et al. |
| 2006/0142232 A1 | 6/2006 | Kinberger et al. |
| 2006/0178297 A1 | 8/2006 | Troy et al. |
| 2006/0182736 A1 | 8/2006 | Kim et al. |
| 2006/0205665 A1 | 9/2006 | Bonny |
| 2006/0222657 A1 | 10/2006 | Dowdy et al. |
| 2006/0228725 A1 | 10/2006 | Salafsky |
| 2006/0275371 A1 | 12/2006 | Dai et al. |
| 2007/0015722 A1 * | 1/2007 | Kraynack ............ C12N 15/113 514/81 |
| 2007/0054279 A1 * | 3/2007 | Manoharan ........ A61K 31/7115 435/6.16 |
| 2007/0123450 A1 | 5/2007 | Kozhemyakin et al. |
| 2007/0207973 A1 | 9/2007 | Daifuku et al. |
| 2008/0027025 A1 | 1/2008 | Dowdy et al. |
| 2008/0153737 A1 | 6/2008 | Lieberman et al. |
| 2008/0227104 A1 | 9/2008 | Hayashizaki et al. |
| 2009/0012030 A1 | 1/2009 | Chatterton et al. |
| 2009/0093026 A1 | 4/2009 | Dowdy et al. |
| 2009/0093425 A1 | 4/2009 | Dowdy et al. |
| 2009/0098049 A1 | 4/2009 | Dowdy et al. |
| 2009/0124571 A1 * | 5/2009 | Morvan ................ C07H 21/00 536/25.3 |
| 2009/0203132 A1 * | 8/2009 | Swayze ................ C07D 207/12 435/375 |
| 2010/0047164 A1 | 2/2010 | Bigner et al. |
| 2010/0120164 A1 | 5/2010 | Salafsky |
| 2010/0255558 A1 | 10/2010 | Niemeyer et al. |
| 2011/0059180 A1 | 3/2011 | Barthelemy et al. |
| 2011/0137010 A1 | 6/2011 | Srivastava et al. |
| 2011/0312507 A1 | 12/2011 | Liu et al. |
| 2012/0035115 A1 | 2/2012 | Manoharan et al. |
| 2012/0040459 A1 | 2/2012 | Khvorova et al. |
| 2012/0070505 A1 | 3/2012 | Barthelemy et al. |
| 2012/0122235 A1 | 5/2012 | Chase et al. |
| 2012/0122779 A1 | 5/2012 | Kirshenbaum et al. |
| 2012/0142763 A1 | 6/2012 | Dowdy et al. |
| 2012/0156138 A1 * | 6/2012 | Smith .................... A61P 19/02 977/773 |
| 2012/0316224 A1 | 12/2012 | Verdine et al. |
| 2013/0040823 A1 | 2/2013 | Freskgard et al. |
| 2013/0052731 A1 | 2/2013 | Ma et al. |
| 2013/0066063 A1 | 3/2013 | Berry et al. |
| 2013/0123334 A1 | 5/2013 | Feinstein et al. |
| 2013/0149787 A1 | 6/2013 | Chase et al. |
| 2013/0171242 A1 | 7/2013 | Lim et al. |
| 2013/0184450 A1 | 7/2013 | Wada et al. |
| 2014/0045719 A1 | 2/2014 | Heindl et al. |

(56) References Cited

U.S. PATENT DOCUMENTS

| | | | |
|---|---|---|---|
| 2014/0081012 A1 | 3/2014 | DeSimone et al. |
| 2015/0197540 A1 | 7/2015 | Shimizu et al. |
| 2015/0238516 A1 | 8/2015 | Dowdy et al. |
| 2016/0257961 A1 | 9/2016 | Bradshaw et al. |
| 2017/0114341 A1 | 4/2017 | Bradshaw et al. |
| 2017/0355727 A1 | 12/2017 | Seth et al. |
| 2018/0303864 A1 | 10/2018 | Dowdy et al. |
| 2019/0194655 A1 | 6/2019 | Bradshaw et al. |
| 2020/0140476 A1 | 5/2020 | Sakamuri et al. |
| 2020/0392498 A1 | 12/2020 | Bradshaw et al. |
| 2022/0218829 A1 | 7/2022 | Bhat et al. |

FOREIGN PATENT DOCUMENTS

| | | |
|---|---|---|
| CN | 1079473 A | 12/1993 |
| CN | 101506368 A | 8/2009 |
| CN | 102459302 A | 5/2012 |
| CN | 104781271 A | 7/2015 |
| CN | 106061981 A | 10/2016 |
| DE | 2847064 A1 | 5/1980 |
| DE | 102005039726 B3 | 1/2007 |
| EP | 0586106 A1 | 3/1994 |
| EP | 1447412 A1 | 8/2004 |
| FR | 2834465 A1 | 7/2003 |
| JP | H05-505941 A | 9/1993 |
| JP | H10-509740 A | 9/1998 |
| JP | 2000-507928 A | 6/2000 |
| JP | 2004-536027 A | 12/2004 |
| JP | 2004-537535 A | 12/2004 |
| JP | 2005-507928 A | 3/2005 |
| JP | 2010-521657 A | 6/2010 |
| WO | WO-9014226 A1 | 11/1990 |
| WO | WO-91/14696 A1 | 10/1991 |
| WO | WO-93/12131 A1 | 6/1993 |
| WO | WO-93/12132 A1 | 6/1993 |
| WO | WO-93/14108 A1 | 7/1993 |
| WO | WO-93/16094 A2 | 8/1993 |
| WO | WO-93/24510 A1 | 12/1993 |
| WO | WO-94/26761 A1 | 11/1994 |
| WO | WO-94/26764 A1 | 11/1994 |
| WO | WO-95/32980 A1 | 12/1995 |
| WO | WO-96/06105 A1 | 2/1996 |
| WO | WO-96/11010 A1 | 4/1996 |
| WO | WO-96/40061 A1 | 12/1996 |
| WO | WO-97/06183 A1 | 2/1997 |
| WO | WO-97/14708 A1 | 4/1997 |
| WO | WO-97/47637 A1 | 12/1997 |
| WO | WO-98/11121 A1 | 3/1998 |
| WO | WO-98/39290 A1 | 9/1998 |
| WO | WO-98/39349 A1 | 9/1998 |
| WO | WO-98/42722 A1 | 10/1998 |
| WO | WO-99/55717 A1 | 11/1999 |
| WO | WO-00/00499 A1 | 1/2000 |
| WO | WO-00/02896 A1 | 1/2000 |
| WO | WO-00/03720 A1 | 1/2000 |
| WO | WO-00/11952 A1 | 3/2000 |
| WO | WO-00/23454 A1 | 4/2000 |
| WO | WO-00/40723 A2 | 7/2000 |
| WO | WO-00/47593 A1 | 8/2000 |
| WO | WO-00/50642 A1 | 8/2000 |
| WO | WO-00/55179 A1 | 9/2000 |
| WO | WO-01/16149 A2 | 3/2001 |
| WO | WO-01/49701 A1 | 7/2001 |
| WO | WO-01/60316 A2 | 8/2001 |
| WO | WO-01/72123 A1 | 10/2001 |
| WO | WO-01/72764 A1 | 10/2001 |
| WO | WO-02/04475 A1 | 1/2002 |
| WO | WO-02/18951 A2 | 3/2002 |
| WO | WO-02/20543 A2 | 3/2002 |
| WO | WO-02/20544 A1 | 3/2002 |
| WO | WO-02/043771 A2 | 6/2002 |
| WO | WO-02/079216 A1 | 10/2002 |
| WO | WO-02/081739 A2 | 10/2002 |
| WO | WO-03/000922 A2 | 1/2003 |
| WO | WO-03/004512 A1 | 1/2003 |
| WO | WO-03/019145 A2 | 3/2003 |
| WO | WO-03/039523 A2 | 5/2003 |
| WO | WO-03/042658 A2 | 5/2003 |
| WO | WO-03037276 A1 | 5/2003 |
| WO | WO-03/059394 A1 | 7/2003 |
| WO | WO-2004/007721 A1 | 1/2004 |
| WO | WO-2004/014312 A2 | 2/2004 |
| WO | WO-2004/028454 A2 | 4/2004 |
| WO | WO-2004/041194 A2 | 5/2004 |
| WO | WO-2004/044232 A1 | 5/2004 |
| WO | WO-2004/048545 A2 | 6/2004 |
| WO | WO-2004/091499 A2 | 10/2004 |
| WO | WO-2005/001143 A2 | 1/2005 |
| WO | WO-2005/019236 A1 | 3/2005 |
| WO | WO-2005/019237 A1 | 3/2005 |
| WO | WO-2005/034732 A2 | 4/2005 |
| WO | WO-2005/047468 A2 | 5/2005 |
| WO | WO-2005/062947 A2 | 7/2005 |
| WO | WO-2005/065150 A2 | 7/2005 |
| WO | WO-2005/084158 A2 | 9/2005 |
| WO | WO-2005/107463 A1 | 11/2005 |
| WO | WO-2005/115410 A2 | 12/2005 |
| WO | WO-2005/115479 A2 | 12/2005 |
| WO | WO-2005/115749 A1 | 12/2005 |
| WO | WO-2005/117991 A2 | 12/2005 |
| WO | WO-2006/000922 A2 | 1/2006 |
| WO | WO-2006/007721 A1 | 1/2006 |
| WO | WO-2006/028601 A2 | 3/2006 |
| WO | WO-2006/073458 A2 | 7/2006 |
| WO | WO-2007/002567 A1 | 1/2007 |
| WO | WO-2007/011946 A2 | 1/2007 |
| WO | WO-2007/070947 A1 | 6/2007 |
| WO | WO-2007/091269 A2 | 8/2007 |
| WO | WO-2007/125429 A2 | 11/2007 |
| WO | WO-2007125429 A2 | 11/2007 |
| WO | WO-2008/016906 A2 | 2/2008 |
| WO | WO-2008106730 A1 | 9/2008 |
| WO | WO-2008/120016 A1 | 10/2008 |
| WO | WO-2008/124150 A1 | 10/2008 |
| WO | WO-2008120016 A1 | 10/2008 |
| WO | WO-2009/017861 A2 | 2/2009 |
| WO | WO-2009/018332 A1 | 2/2009 |
| WO | WO-2009/089425 A1 | 7/2009 |
| WO | WO-2009/129120 A2 | 10/2009 |
| WO | WO-2009/144481 A2 | 12/2009 |
| WO | WO-2010/027512 A2 | 3/2010 |
| WO | WO-2010/039543 A2 | 4/2010 |
| WO | WO-2010/039548 A2 | 4/2010 |
| WO | WO-2010/048549 A2 | 4/2010 |
| WO | WO-2010/081114 A2 | 7/2010 |
| WO | WO-2010/090723 A2 | 8/2010 |
| WO | WO-2010/129853 A2 | 11/2010 |
| WO | WO-2010/135520 A1 | 11/2010 |
| WO | WO-2010/147831 A1 | 12/2010 |
| WO | WO-2011/002200 A2 | 1/2011 |
| WO | WO-2011/003018 A2 | 1/2011 |
| WO | WO-2011/005761 A1 | 1/2011 |
| WO | WO-2011/005860 A2 | 1/2011 |
| WO | WO-2011/015521 A1 | 2/2011 |
| WO | WO-2011/037731 A1 | 3/2011 |
| WO | WO-2011/038031 A1 | 3/2011 |
| WO | WO-2011/038158 A2 | 3/2011 |
| WO | WO-2011/076923 A1 | 6/2011 |
| WO | WO-2011/090793 A2 | 7/2011 |
| WO | WO-2011/103468 A2 | 8/2011 |
| WO | WO-2011/128374 A1 | 10/2011 |
| WO | WO-2011/133871 A1 | 10/2011 |
| WO | WO-2011/139695 A2 | 11/2011 |
| WO | WO-2011/139699 A2 | 11/2011 |
| WO | WO-2011/139911 A2 | 11/2011 |
| WO | WO-2012/030626 A2 | 3/2012 |
| WO | WO-2012030626 A2 | 3/2012 |
| WO | WO-2012/045075 A1 | 4/2012 |
| WO | WO-2012/051492 A2 | 4/2012 |
| WO | WO-2012/061719 A2 | 5/2012 |
| WO | WO-2012/068340 A2 | 5/2012 |
| WO | WO-2012/091091 A1 | 7/2012 |
| WO | WO-2012/094343 A1 | 7/2012 |
| WO | WO-2012/177949 A2 | 12/2012 |

(56) References Cited

FOREIGN PATENT DOCUMENTS

| WO | WO-2013/012758 A1 | 1/2013 | |
|---|---|---|---|
| WO | WO-2013/013068 A2 | 1/2013 | |
| WO | WO-2013/022967 A1 | 2/2013 | |
| WO | WO-2013/040429 A1 | 3/2013 | |
| WO | WO-2013/045939 A1 | 4/2013 | |
| WO | WO-2013/110902 A1 | 8/2013 | |
| WO | WO-2013/126034 A1 | 8/2013 | |
| WO | WO-2014012081 A2 | 1/2014 | |
| WO | WO-2014/031575 A1 | 2/2014 | |
| WO | WO-2014179629 A2 * | 11/2014 | ......... A61K 31/7088 |
| WO | WO-2015/069932 A1 | 5/2015 | |
| WO | WO-2015/168589 A2 | 11/2015 | |
| WO | WO-2015168589 A2 | 11/2015 | |
| WO | WO-2015/188197 A2 | 12/2015 | |
| WO | WO-2016/094677 A2 | 6/2016 | |
| WO | WO-2017/100461 A1 | 6/2017 | |
| WO | WO-2018035380 A1 | 2/2018 | |
| WO | WO-2018237194 A1 | 12/2018 | |
| WO | WO-2019/006455 A1 | 1/2019 | |

OTHER PUBLICATIONS

Pourceau et al (J. Org. Chem. 2008, 73, 6014-6017) (Year: 2008).*
Abramova et al., "Synthesis and properties of photolabile (caged) phosphotriester derivatives of dinucleoside phosphates," Russian J Bioorg Chem. 26(3):174-82 (2000).
Abu-Amer et al., "TAT fusion proteins containing tyrosine 42-deleted IkappaBalpha arrest osteoclastogenesis," J Biol Chem. 276(32):30499-503 (2001).
Alvarez et al., "Photocleavable protecting groups as nucleobase protections allowed the solid-phase synthesis of base-sensitive SATE-prooligonucleotides," J Org Chem. 64(17):6319-28 (1999).
Astriab-Fisher et al., "Conjugates of antisense oligonucleotides with the Tat and antennapedia cell-penetrating peptides: effects on cellular uptake, binding to target sequences, and biologic actions," Pharm Res. 19(6):744-54 (2002).
Barquinero et al., "Retroviral vectors: new applications for an old tool," Gene Ther. 11(Suppl 1):S3-9 (2004).
Beaucage et al., "Advances in the synthesis of oligonucleotides by the phosphoramidite approach," Tetrahedron. 48(12): 2223-311 (1992).
Beaucage et al., "Deoxynucleoside phosphoramidites—a new class of key intermediates for deoxypolynucleotide synthesis," Tetrahedron Lett. 22(20):1859-62 (1981).
Beaucage et al., "The synthesis of modified oligonucleotides by the phosphoramidite approach and their applications," Tetrahedron. 49(28):6123-94 (1993).
Behlke, "Progress towards in vivo use of siRNAs," Mol Ther. 13(4):644-70 (2006).
Bernstein et al., "The rest is silence," RNA. 7(11):1509-21 (2001).
Bologna et al., "The prooligonucleotide approach: synthesis of mixed phosphodiester and SATE phosphotriester prooligonucleotides using H-phosphonate and phosphoramidite chemistries," Eur J Org Chem. 2353-8 (1999).
Breslow et al., "Recognition and catalysis in nucleic acid chemistry," Proc Natl Acad Sci USA. 90(4):1201-7 (1993).
Brugidou et al., "The retro-inverso form of a homeobox-derived short peptide is rapidly internalised by cultured neurones: a new basis for an efficient intracellular delivery system," Biochem Biophys Res Commun. 214(2):685-93 (1995).
Chauhan et al., "PTD-fusion peptide as a delivery vehicle for siRNA to target HIV reservoirs," Mol Ther. 13(1):S277 (2006).
Chorev et al., "Recent developments in retro peptides and proteins—an ongoing topochemical exploration," Trends Biotechnol. 13(10):438-45 (1995).
Dias et al., "DNA-lipid systems. A physical chemistry study," Braz J Med Biol Res. 35(5):509-22 (2002).
Dominska et al., "Breaking down the barriers: siRNA delivery and endosome escape," J Cell Sci. 123(Pt 8):1183-9 (2010).

Eguchi et al., "Protein transduction domain of HIV-1 Tat protein promotes efficient delivery of DNA into mammalian cells," J Biol Chem. 276(28):26204-10 (2001).
El-Sagheer et al., "Synthesis of alkyne- and azide-modified oligonucleotides and their cyclization by the CuAAC (click) reaction," Curr Protoc Nucleic Acid Chem. Chapter 4:Unit 4.33, 35(1):4.33.1-4.33.21 (2008) (21 pages).
Elliott et al., "Intercellular trafficking and protein delivery by a herpesvirus structural protein," Cell. 88(2):223-33 (1997).
Explore the Power of Polyacrylamide [online]. Hydrosorb, Inc. 2002 [retrieved on Mar. 10, 2015] from URL <http://aquaben.com/wp-content/uploads/2013/06/powerofpolyacrylamide.pdf>.
Ferreira et al., "Lewis acid deprotection of silyl-protected oligonucleotides and base-sensitive oligonucleotide analogues," Tetrahedron Lett. 45(33):6287-90 (2004).
Frankel et al., "Cellular Uptake of the Tat Protein from Human Immunodeficiency Virus," Cell. 55(6):1189-93 (1988).
Gillet et al., "Site-specific incorporation of N-(deoxyguanosin-8-yl)-2-acetylaminofluorene (dG-AAF) into oligonucleotides using modified 'ultra-mild' DNA synthesis," Nucleic Acids Res. 33(6):1961-9 (2005).
Green et al., "Autonomous Functional Domains of Chemically Synthesized Human Immunodeficiency Virus Tat Trans-activator Protein," Cell. 55(6):1179-88 (1988).
Guerlavais-Dagland et al., "Fluoride-labile protecting groups for the synthesis of base-sensitive methyl-SATE oligonucleotide prodrugs," Eur J Org Chem. 2327-35 (2003).
Guzaev et al., "Synthesis of chimeric oligonucleotides containing internucleosidic phosphodiester and s-pivaloylthioethyl phosphotriester residues," Nucleosides Nucleotides Nucleic Acids. 20(4-7):1015-8 (2001).
Guzaev et al., "Synthesis of chimerical oligonucleotides containing internucleosidic phosphodiester and s-pivaloyl mercaptoethyl phosphotriester linkages," Nucleosides & Nucleotides. 18(6-7):1391-2 (1999).
Hamilton et al., "A species of small antisense RNA in post-transcriptional gene silencing in plants," Science. 286(5441):950-2 (1999).
Hannon et al., "Unlocking the potential of the human genome with RNA interference," Nature. 431(7006):371-8 (2004).
Hayakawa, "Toward an ideal synthesis of oligonucleotides: development of a novel phosphoramidite method with high capability," Bull Chem Soc Jpn. 74(9):1547-65 (2001).
Hecker et al., "Prodrugs of phosphates and phosphonates," J Med Chem. 51(8):2328-45 (2008).
Huston et al., "Protein engineering of antibody binding sites: recovery of specific activity in an anti-digoxin single-chain Fv analogue produced in *Escherichia coli*," Proc Natl Acad Sci U.S.A. 85(16):5879-83 (1988).
International Search Report and Written Opinion for International Application No. PCT/US2017/047447, dated Jan. 4, 2018 (17 pages).
Iyer et al., "3H-1,2-benzodithiole-3-one 1,1-dioxide as an improved sulfurizing reagent in the solid-phase synthesis of oligodeoxyribonucleoside phosphorothioates," J Am Chem Soc. 112:1253-4 (1990).
Joliot et al., "alpha-2,8-Polysialic acid is the neuronal surface receptor of antennapedia homeobox peptide," New Biol. 3(11):1121-34 (1991).
Joliot et al., "Antennapedia homeobox peptide regulates neural morphogenesis," Proc Natl Acad Sci U.S.A. 88(5):1864-8 (1991).
Joliot et al., "Transduction peptides: from technology to physiology," Nat Cell Biol. 6(3):189-96 (2004).
Josephson et al., "High-efficiency intracellular magnetic labeling with novel superparamagnetic-Tat peptide conjugates," Bioconjug Chem. 10(2):186-91 (1999).
Koppelhus et al., "Cell-dependent differential cellular uptake of PNA, peptides, and PNA-peptide conjugates," Antisense Nucleic Acid Drug Dev. 12(2):51-63 (2002) (19 pages).
Kosonen et al., "Hydrolysis and intramolecular transesterification of ribonucleoside 3'-phosphotriesters: the effect of alkyl groups on the

(56) References Cited

OTHER PUBLICATIONS general and specific acid-base-catalyzed reactions of 5'-O-pivaloyluridin-3'-yl dialkyl phosphates," J Chem Soc Perkin Trans 2. pp. 663-670 (1998).
Le Roux et al., "Neurotrophic activity of the Antennapedia homeodomain depends on its specific DNA-binding properties," Proc Natl Acad Sci U.S.A. 90(19):9120-4 (1993).
Letsinger et al., "Cationic oligonucleotides," J Am Chem Soc. 110(13):4470-1 (1988).
Leuschner et al., "Cleavage of the siRNA passenger strand during RISC assembly in human cells," EMBO Rep. 7(3):314-20 (2006).
Lewin et al., "Tat peptide-derivatized magnetic nanoparticles allow in vivo tracking and recovery of progenitor cells," Nat Biotechnol. 18(4):410-4 (2000).
Li et al., "Isolation and culture of adult mouse hepatocytes," Methods Mol Biol. 633:185-96 (2010).
Magzoub et al., "Modeling the endosomal escape of cell-penetrating peptides: transmembrane pH gradient driven translocation across phospholipid bilayers," Biochemistry 44(45):14890-7 (2005).
McGuigan et al., "Intracellular delivery of bioactive AZT nucleotides by aryl phosphate derivatives of Azt," J Med Chem. 36(8):1048-52 (1993).
Meade et al., "Efficient delivery of RNAi prodrugs containing reversible charge-neutralizing phosphotriester backbone modifications," Nat Biotechnol. 32(12):1256-61 (2014) (8 pages).
Meade, Bryan, Thesis: "Synthesis of Bioreversible, Phosphotriester-Modified siRNA Oligonucleotides," Doctor of Philosophy, Department of Cellular and Molecular Medicine, University of California San Diego, 2010.
Meister et al., "Mechanisms of gene silencing by double-stranded RNA," Nature 431(7006):343-9 (2004).
Micklefield, "Backbone modification of nucleic acids: synthesis, structure and therapeutic applications," Curr Med Chem. 8(10):1157-79 (2001).
Nagahara et al., "Transduction of full-length TAT fusion proteins into mammalian cells: TAT-p27Kip1 induces cell migration," Nat Med. 4(12):1449-52 (1998).
Newton et al., "Angiogenin single-chain immunofusions: influence of peptide linkers and spacers between fusion protein domains," Biochemistry. 35(2):545-53 (1996).
Ng et al., "An anti-transferrin receptor-avidin fusion protein exhibits both strong proapoptotic activity and the ability to deliver various molecules into cancer cells," Proc Natl Acad Sci U.S.A. 99(16):10706-11 (2002).
Novina et al., "The RNAi revolution," Nature. 430(6996):161-4 (2004).
Paolella et al., "Electrostatic mechanism for DNA bending by bZIP Proteins," Biochemistry. 36(33):10033-8 (1997).
Parrish et al., "Functional anatomy of a dsRNA trigger: differential requirement for the two trigger strands in RNA interference," Mol Cell. 6(5):1077-87 (2000).
Polyakov et al., "Novel Tat-peptide chelates for direct transduction of technetium-99m and rhenium into human cells for imaging and radiotherapy," Bioconjug Chem. 11(6):762-71 (2000).
Rattan et al., "Protein synthesis, posttranslational modifications, and aging," Ann N Y Acad Sci. 663:48-62 (1992).
Schlienger et al., "S-Acyl-2-thioethyl aryl phosphotriester derivatives as mononucleotide prodrugs," J Med Chem. 43(23):4570-4 (2000).
Schmidt et al., "RNA cleavage by hybridase. IV. Oligonucleotide probes with 2'-deoxy-2'-fluoronucleosides and arabinofuranosylcytosine," Bioorganicheskaya Khimiya. 17(6):823-30 (1991).
Schwarze et al., "In vivo protein transduction: delivery of a biologically active protein into the mouse," Science. 285(5433):1569-72 (1999).
Seifter et al., "Analysis for protein modifications and nonprotein cofactors," Methods Enzymol. 182:626-46 (1990).

Shafiee et al., "New bis(SATE) prodrug of AZT 5'-monophosphate: In vitro anti-HIV activity, stability, and potential oral absorption," J Pharm Sci. 90(4):448-63 (2001).
Snyder et al., "Recent advances in the use of protein transduction domains for the delivery of peptides, proteins and nucleic acids in vivo," Expert Opin Drug Deliv. 2(1):43-51 (2005).
Sontheimer, "Assembly and function of RNA silencing complexes," Nat Rev Mol Cell Biol. 6(2):127-38 (2005).
Spinelli et al., "Use of allylic protecting groups for the synthesis of base-sensitive prooligonucleotides," Eur J Org Chem. 49-56 (2002).
Tanabe et al., "Chemical ligation of oligodeoxynucleotides by X-irradiation and its application to regulation of G-quadruplex formation," Bioorg Med Chem Lett. 23(7):2098-2100 (2013).
Tosquellas et al., "The pro-oligonucleotide approach: solid phase synthesis and preliminary evaluation of model pro-dodecathymidylates," Nucleic Acids Res. 26(9):2069-74 (1998).
Turner et al., "RNA targeting with peptide conjugates of oligonucleotides, siRNA and PNA," Blood Cells Mol Dis. 38:1-7 (2007).
Villard et al., "Phenyl phosphotriester derivatives of AZT: Variations upon the SATE moiety," Bioorg Med Chem. 16(15):7321-9 (2008).
Wagner et al., "Pronucleotides: Toward the in vivo delivery of antiviral and anticancer nucleotides," Med Res Rev. 20(6):417-51 (2000).
Whitlow et al., "An improved linker for single-chain Fv with reduced aggregation and enhanced proteolytic stability," Protein Eng. 6(8):989-95 (1993).
Wunderbaldinger et al., "Tat peptide directs enhanced clearance and hepatic permeability of magnetic nanoparticles," Bioconjug Chem. 13(2):264-8 (2002).
Xie et al., "Harnessing in vivo siRNA delivery for drug discovery and therapeutic development," Drug Discov Today. 11(1-2):67-73 (2006).
Zuckermann et al., "Efficient methods for attachment of thiol specific probes to the 3'-ends of synthetic oligodeoxyribonucleotides," Nucleic Acids Res. 15(13):5305-21 (1987).
Chen et al., "Lipophilic siRNAs mediate efficient gene silencing in oligodendrocytes with direct CNS delivery," J Control Release. 144(2): 227-32 (2010).
Aaronson et al. Rapid HATU-mediated solution phase siRNA conjugation. Bioconjugate Chem. 22:1723-1728 (2011).
Caruthers. Oligonucleotides: Antisense Inhibitors of Gene Expression, pp. 7-24, J. S. Cohen, ed. (CRC Press, Inc. Boca Raton, Fla., 1989.
Dodd, et al. Normal T-cell response and in vivo magnetic resonance imaging of T cells loaded with HIV transactivator-peptide-derived superparamagnetic nanoparticles. J Immunol Methods. Oct. 1, 2001;256(1-2):89-105.
Eguchi et al.: Protein transduction domain of HIV-1 Tat protein promotes efficient delivery of DNA into mammalian cells. Journal of Biological Chemistry, 276(28): 26204-26210 (2001).
El-Sagheer et al. Synthesis of alkyne- and azide-modified oligonucleotides and their cyclization by the CuAAC (click) reaction. Curr Protoc Nucleic Acid Chem Chapter 4:Unit 4.33 (2008).
Englisch et al. Chemically Modified Oligonucleotides as Probes and Inhibitors. Angew. Chem. Int. Ed. Eng. 30:613-629 (1991).
Frankel et al. Cellular uptake of the tat protein from human immunodeficiency virus. Cell 55:1189-1193 (1988).
Lamoyi et al. Preparation of F(ab')2 fragments from mouse IgG of various subclasses. J. Immunol Methods 56:235-243 (1983).
Lennartz et al. Isolation and characterization of a mannose-specific endocytosis receptor from human placenta. J. Biol. Chem. 262:9942-9944 (1987).
Oka et al. Stereocontrolled synthesis of oligonucleotide analogs containing chiral internucleotidic phosphorus atoms. Chem. Soc. Rev. 40:5829-5843 (2011).
Oka et al. Stereocontrolled synthesis of oligoribonucleoside phosphorothioates by an oxazaphospholidine approach. Org. Lett. 11:967-970 (2009).
Parham. On the fragmentation of monoclonal IgG1, IgG2a, and IgG2b from BALB/c mice. J. Immunol 131:2895-902 (1983).

(56) References Cited

OTHER PUBLICATIONS

Sanghvi. Chapter 15: Heterocyclic Base Modifications In Nucleic Acids And Their Applications In Antisense Oligonucleotides. Antisense Research and Applications, Crookeand Lebleu Eds., CRC Press (pp. 273-288) (1993).

Taylor et al. Primary structure of the mannose receptor contains multiple motifs resembling carbohydrate-recognition domains. J. Biol. Chem. 265:12156-62 (1990).

The Concise Encyclopedia of Polymer Science and Engineering, Kroschwitz, J.I., Ed., John Wiley & Sons pp. 858-859 (1990).

Wu et al. 2'-OMe-phosphorodithioate-modified siRNAs show increased loading into the RISC complex and enhanced anti-tumour activity. Nat. Commun. 5:3459 (2013).

Yang et al. Gene silencing activity of siRNA molecules containing phosphorodithioate substitutions. ACS Chem. Biol. 7:1214-1220 (2012).

Gurevich et al. Phosphorus-containing derivatives of indole and pyrrole (review). Chemistry of Heterocyclic Compounds 36(12):1361-401 (2000).

Haussecker. The RNAi Therapeutics Blog, https://rnaitherapeutics.blogspot.com/search?q=solstice, retrieved Mar. 23, 2020 (2013) (11 pages).

Li et al. Chiral Amino alcohol Derived Bis-phosphoramidite Pincer Palladium Complexes and Their Applications in Asymmetric allylation of aldimines. Organometallics. 29:1379-1387 (2010).

PCT/US2018/040592 International Search Report and Written Opinion dated Aug. 31, 2018.

U.S. Appl. No. 16/627,091 Office Action dated Jun. 25, 2021.

U.S. Appl. No. 16/627,091 Office Action dated Jun. 3, 2022.

Zuckermann, et al. Efficient methods for attachment of thiol specific probes to the 3'-ends of synthetic oligodeoxyribonucleotides. Nucleic Acids Res. Jul. 10, 1987;15(13):5305-21.

\* cited by examiner pX3X3 in Z40        mX5X5 in Z52 eX5X5 in Z53        m1X5X5 in Z54

(GalNAc)

FIGS. 19-20
FIG. 19
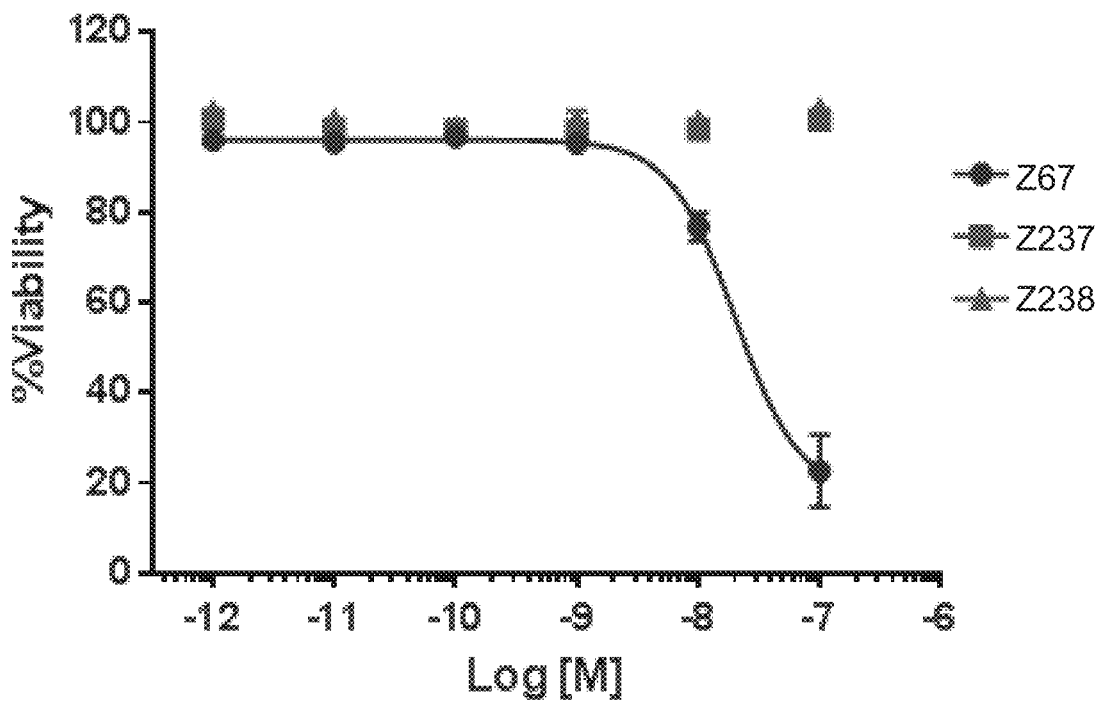
FIG. 20
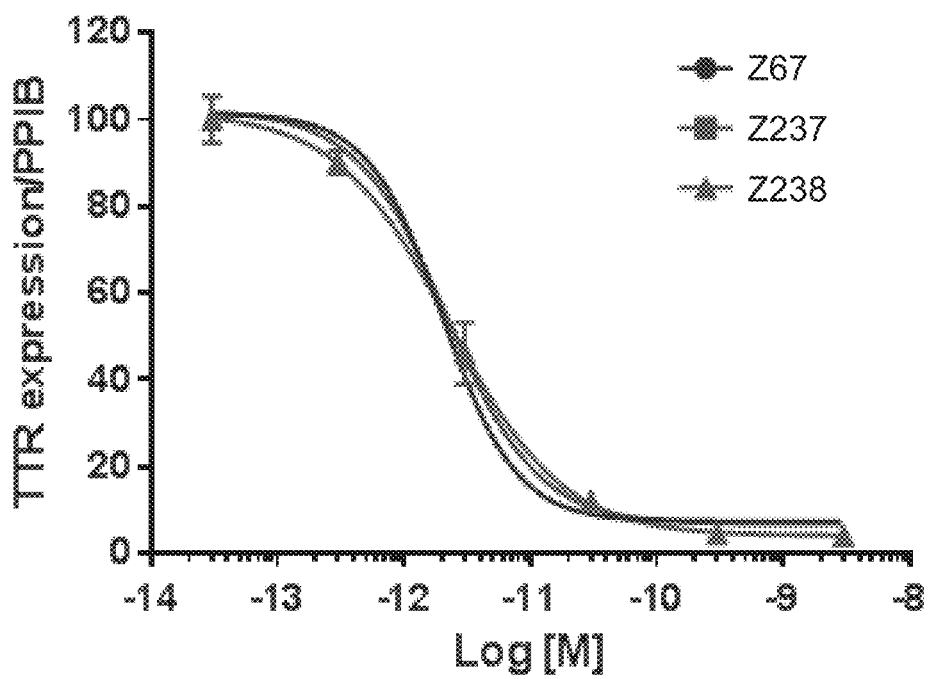

POLYNUCLEOTIDE CONSTRUCTS

CROSS-REFERENCE TO RELATED APPLICATIONS

This application is a U.S. National Stage Entry of International Application No. PCT/US17/47447, filed internationally on Aug. 17, 2017, which claims the benefit of U.S. Provisional Patent Application No. 62/376,182, filed Aug. 17, 2016, all of which are incorporated herein by reference in their entireties.

FIELD OF THE INVENTION

This invention relates to compositions and methods for transfecting cells.

SEQUENCE LISTING

The instant application contains a Sequence Listing which has been submitted electronically in ASCII format and is hereby incorporated by reference in its entirety. Said ASCII copy, created on Jun. 9, 2022, is named 61382-804_831_Sequence-Listing.txt and is 21,024 bytes in size.

BACKGROUND

Nucleic acid delivery to cells both in vitro and in vivo has been performed using various recombinant viral vectors, lipid delivery systems, and electroporation. Such techniques have sought to treat various diseases and disorders by knocking-out gene expression and providing genetic constructs for gene therapy or to study various biological systems.

The discovery of RNA interference (RNAi) as a cellular mechanism that selectively degrades mRNAs allows for both the targeted manipulation of cellular phenotypes in cell culture and the potential for development of directed therapeutics (Behlke, Mol. Ther. 13, 644-670, 2006; Xie et al., Drug Discov. Today 11, 67-73, 2006). However, because of their size and negative (anionic) charged nature, siRNAs are macromolecules with no ability to enter cells. Indeed, siRNAs are 25× in excess of Lipinski's "Rule of 5s" for cellular delivery of membrane diffusible molecules that generally limits size to less than 500 Da. Consequently, in the absence of a delivery vehicle or transfection agent, naked siRNAs do not enter cells, even at millimolar concentrations (Barquinero et al., Gene Ther. 11 Suppl 1, S3-9, 2004). Significant attention has been focused on the use of cationic lipids that both condense the siRNA and punch holes in the cellular membrane to solve the siRNA delivery problem. Although widely used, transfection reagents fail to achieve efficient delivery into many cell types, especially primary cells and hematopoietic cell lineages (T and B cells, macrophage). Moreover, lipofection reagents often result in varying degrees of cytotoxicity ranging from mild in tumor cells to high in primary cells.

Accordingly, there is a need for polynucleotide constructs with increased ability to transfect cells. Particularly desirable are polynucleotide constructs capable of targeting a predetermined cell population.

SUMMARY OF THE INVENTION

In general, the invention provides polynucleotide constructs. Certain constructs have a polynucleotide linked to a branched moiety carrying one or more auxiliary moieties (e.g., targeting moieties). The polynucleotide constructs may be provided as hybridized polynucleotide constructs. Other constructs are described herein.

In one aspect, the invention provides a polynucleotide construct.

The polynucleotide construct of the invention may contain a polynucleotide bonded to at least one group of formula (I):

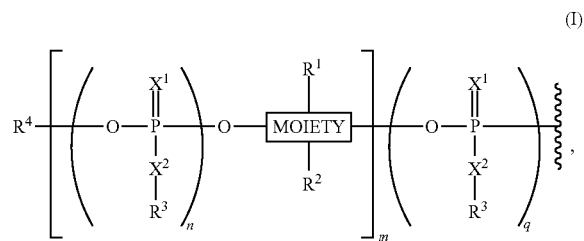

or a salt thereof, or a stereoisomer thereof,
where
each $X^1$ is independently O or S;
each $X^2$ is independently O, S, NH, or a bond;
MOIETY is optionally substituted $C_{2-10}$ alkane-tetrayl or a group $-M^1-M^2-M^3-$, where each $M^1$ and each $M^3$ is independently absent or optionally substituted $C_{1-6}$ alkylene, and $M^2$ is optionally substituted $C_{3-9}$ heterocycle-tetrayl, optionally substituted $C_{6-10}$ arene-tetrayl, or optionally substituted $C_{3-8}$ cycloalkane-tetrayl;
each $R^1$ and each $R^2$ is independently H, optionally substituted $C_{1-16}$ alkyl, optionally substituted $C_{2-16}$ heteroalkyl, a conjugation moiety, or -LinkA(-T)$_p$, provided that at least one $R^1$ or at least one $R^2$ is a conjugation moiety or -LinkA(-T)$_p$;
each $R^3$ is independently H, optionally substituted $C_{1-16}$ alkyl, optionally substituted $C_{2-16}$ heteroalkyl, optionally substituted $C_{2-16}$ alkenyl, optionally substituted $C_{2-16}$ alkynyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl, a conjugation moiety, or -LinkA(-T)$_p$;
$R^4$ is H, optionally substituted $C_{1-6}$ alkyl, -LinkA(-T)$_p$, or -Sol;
each LinkA is independently a multivalent linker (e.g., including —C(O)—N(H)— (e.g., at least one multivalent linker including —C(O)—N(H)— bonded to T));
each T is independently an auxiliary moiety;
Sol is a solid support;
m is an integer from 1 to 6;
each n is independently 0 or 1;
each p is independently an integer from 1 to 6; and
q is an integer from 0 to 3.

The polynucleotide construct of the invention may contain a strand interrupted by at least one internucleoside, abasic spacer of formula (III):

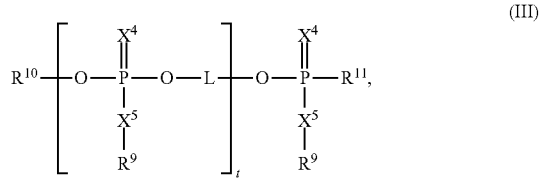

wherein
L is a sugar analogue;
each $X^4$ is independently O or S;
each $X^5$ is independently O, S, NH, or a bond;
each $R^9$ is independently H, optionally substituted $C_{1-6}$ alkyl, optionally substituted $C_{2-6}$ alkenyl, optionally substituted $C_{2-6}$ alkynyl, optionally substituted $(C_{1-9}$ heterocyclyl)-$C_{1-6}$-alkyl, optionally substituted $(C_{6-10}$ aryl)-$C_{1-6}$-alkyl, optionally substituted $(C_{3-8}$ cycloalkyl)-$C_{1-6}$-alkyl, -LinkA(-T)$_p$, or a conjugation moiety;
each LinkA is independently a multivalent linker (e.g., including —C(O)—N(H)—); each T is independently an auxiliary moiety;
$R^{10}$ is a bond to a 3'-carbon atom of a nucleoside (x) in the strand;
$R^{11}$ is a bond to a 5'-oxygen atom of a nucleoside (x+t+1) in the strand;
p is an integer from 1 to 6; and
t is an integer from 1 to 6.

In some embodiments, t is 1. In further embodiments, $R^9$ is H. In yet further embodiments, $X^4$ is O or S. In still further embodiments, $X^5$ is O. In particular embodiments, (x) is 2, 3, 4, or 5. In certain embodiments, (x) is 13, 14, 15, or 16. In other embodiments, the construct contains only 1 or only 2 internucleoside, abasic spacers. In certain embodiments, the sugar analogue is optionally substituted $C_{2-6}$ alkylene, optionally substituted $C_{2-6}$ alkenylene, optionally substituted $C_5$ cycloalkane-1,3-diyl, optionally substituted $C_5$ cycloalkene-1,3-diyl, optionally substituted heterocycle-1,3-diyl (e.g., optionally substituted pyrrolidine-2,5-diyl, optionally substituted tetrahydrofuran-2,5-diyl, or optionally substituted tetrahydrothiophene-2,5-diyl), or optionally substituted $(C_{1-4}$ alkyl)-$(C_{3-8}$ cycloalkylene) (e.g., optionally substituted $(C_1$ alkyl)-$(C_3$ cycloalkylene)). In certain embodiments, the sugar analogue is selected from the group consisting of:

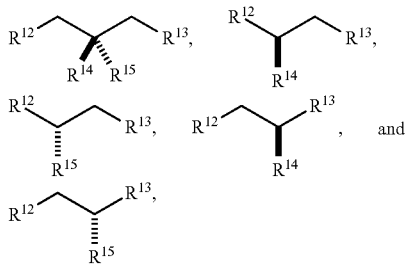

where
$R^{12}$ is a bond to an oxygen atom bonded to —P($X^4$)(—$X^5R^9$)— in formula (III);
$R^{13}$ is a bond to an oxygen atom bonded to another —P($X^4$)(—$X^5R^9$)— in formula (III); each of $R^{14}$ and $R^{15}$ is independently H, optionally substituted $C_{1-6}$ alkyl, or —(CH$_2$)$_{t1}$—OR$^Z$, where n is an integer from 1 to 6, and R$^Z$ is optionally substituted $C_{1-6}$ alkyl, optionally substituted $C_{2-6}$ alkenyl, optionally substituted $C_{2-6}$ alkynyl, optionally substituted $C_{6-14}$ aryl, optionally substituted $C_{3-8}$ cycloalkyl, optionally substituted $(C_{1-9}$ heterocyclyl)-$C_{1-6}$-alkyl, optionally substituted $(C_{6-10}$ aryl)-$C_{1-6}$-alkyl, or optionally substituted $(C_{3-8}$ cycloalkyl)-$C_{1-6}$-alkyl.

In some embodiments, at least on of $R^{14}$ and $R^{15}$ is not H. The polynucleotide construct of the invention may contain a strand containing at least one 2'-modified nucleoside.

In other embodiments, all nucleosides in the strand are independently 2'-modified nucleosides. In certain embodiments, at least 80% of nucleosides in the strand are 2'-modified nucleosides. In further embodiments, each 2'-modified nucleoside is independently a 2'-alkoxy nucleoside (e.g., 2'-methoxy nucleoside). In yet further embodiments, at least one of the second, twelfth, fourteenth, and sixteenth nucleosides in the strand is a 2'-fluoro nucleoside. In still further embodiments, the second, twelfth, fourteenth, and sixteenth nucleosides or the twelfth, fourteenth, and sixteenth nucleosides in the strand are all independently 2'-fluoro nucleosides. In further embodiments, the seventh, ninth, and/or eleventh nucleoside in the strand is a 2'-fluoro nucleoside. In some embodiments, the remaining nucleosides are 2'-alkoxy nucleosides (e.g., 2'-methoxy nucleosides).

The polynucleotide construct of the invention may contain a strand including a seed region including a hypoxanthine nucleobase-containing nucleoside (e.g., inosine). In certain embodiments, the hypoxanthine nucleobase-containing nucleoside is the second nucleoside in the strand. In further embodiments, the hypoxanthine nucleobase-containing nucleoside is the third nucleoside in the strand. In yet further embodiments, the hypoxanthine nucleobase-containing nucleoside is the fourth nucleoside in the strand. In still further embodiments, the hypoxanthine nucleobase-containing nucleoside is the fifth nucleoside in the strand. In particular embodiments, the hypoxanthine nucleobase-containing nucleoside is the sixth nucleoside in the strand.

The polynucleotide construct of the invention may contain a strand including at least one stereochemically enriched phosphorothioate. In some embodiments, the strand includes only 1, 2, 3, or 4 stereochemically enriched phosphorothioate. In further embodiments, at least one (e.g., one or two) stereochemically enriched phosphorothioate is disposed between two consecutive nucleosides that are two of six 5'-terminal nucleosides of the strand. In yet further embodiments, at least one (e.g., one or two) stereochemically enriched phosphorothioate is disposed between two consecutive nucleosides that are two of six 3'-terminal nucleosides of the strand. In still further embodiments, one stereochemically enriched phosphorothioate is covalently bonded between the first nucleoside and the second nucleoside within the strand. In still further embodiments, one stereochemically enriched phosphorothioate is covalently bonded between the second nucleoside and the third nucleoside within the strand. In some embodiments, one stereochemically enriched phosphorothioate is covalently bonded between the twenty-first nucleoside and the twenty-second nucleoside within the strand. In certain embodiments, one stereochemically enriched phosphorothioate is covalently bonded between the twenty-second nucleoside and the twenty-third nucleoside within the strand. In particular embodiments, the stereochemically enriched phosphorothioate has $R_P$ stereochemical identity. In certain embodiments, the stereochemically enriched phosphorothioate has $S_P$ stereochemical identity.

In further embodiments, the strand contains 19 or more nucleosides. In yet further embodiments, the strand comprises fewer than 100 nucleosides (e.g., fewer than 50 or fewer than 32 nucleosides).

The invention also provides a hybridized polynucleotide containing a passenger strand and a guide strand loadable into a RISC complex.

In the hybridized polynucleotide, at least one of the strands may be bonded to at least one group of formula (I). In some embodiments, the passenger strand is the polynucleotide construct of the invention, or a salt thereof, or a stereoisomer thereof; where the at least one group of formula (I) is bonded to a 5'-terminus, 3'-terminus, internucleoside phosphate, internucleoside phosphorothioate, or internucleoside phosphorodithioate of the passenger strand. In other embodiments, at least one of the strands is bonded to at least one group of formula (I):

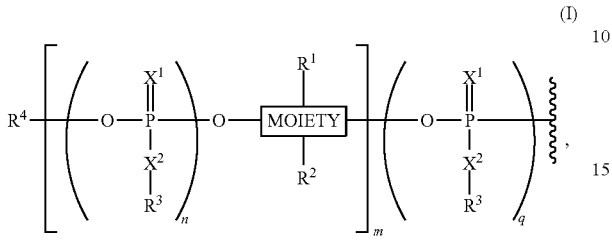

or a salt thereof, or a stereoisomer thereof,
where
each $X^1$ is independently O or S;
each $X^2$ is independently O, S, NH, or a bond;
MOIETY is optionally substituted $C_{2-10}$ alkane-tetrayl or a group $-M^1-M^2-M^3-$, where each $M^1$ and each $M^3$ is independently absent or optionally substituted $C_{1-6}$ alkylene, and $M^2$ is optionally substituted $C_{3-9}$ heterocycle-tetrayl, optionally substituted $C_{6-10}$ arene-tetrayl, or optionally substituted $C_{3-8}$ cycloalkane-tetrayl;
each $R^1$ and each $R^2$ is independently H, optionally substituted $C_{1-16}$ alkyl, optionally substituted $C_{2-16}$ heteroalkyl, a conjugation moiety, or -LinkA(-T)$_p$, provided that at least one $R^1$ or at least one $R^2$ is a conjugation moiety or -LinkA(-T)$_p$;
each $R^3$ is independently H, optionally substituted $C_{1-16}$ alkyl, optionally substituted $C_{2-16}$ heteroalkyl, optionally substituted $C_{2-16}$ alkenyl, optionally substituted $C_{2-16}$ alkynyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl, a conjugation moiety, or -LinkA(-T)$_p$;
$R^4$ is H, optionally substituted $C_{1-6}$ alkyl, -LinkA(-T)$_p$, or -Sol;
each LinkA is independently a multivalent linker;
each T is independently an auxiliary moiety;
Sol is solid support;
m is an integer from 1 to 6;
each n is independently 0 or 1;
each p is independently an integer from 1 to 6; and
q is an integer from 0 to 3.

A group of formula (I) may be bonded to a 5'-terminus, 3'-terminus, internucleoside phosphate, internucleoside phosphorothioate, and/or internucleoside phosphorodithioate of the strand in the polynucleotide construct of the invention or the hybridized polynucleotide construct of the invention (e.g., a passenger strand). In some embodiments, a group of formula (I) is bonded to a 3'-terminus of the passenger strand. When a group of formula (I) is bonded to an internucleoside phosphate, internucleoside phosphorothioate, or internucleoside phosphorodithioate, q may be 0.

The polynucleotide construct contains no more than one Sol. Similarly, the hybridized polynucleotide construct contains no more than one Sol.

In certain embodiments, $R^1$ and $R^2$ are attached to the same atom in MOIETY. In further embodiments, MOIETY, $R^1$, and $R^2$ combine to form:

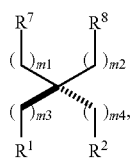

where
$R^7$ is a bond to an oxygen atom that is proximal to $R^4$,
$R^8$ is a bond to an oxygen atom that is proximal to the strand, and
each of m1, m2, m3, and m4 is independently an integer from 0 to 6, provided that the quaternary carbon in formula (Ia) is bonded to 0 or 1 atoms other than carbon and hydrogen, and provided that the sum of m1, m2, m3 and m4 is less than 10.

In some embodiments, each $X^2$ is independently O, S, or NH (e.g., each $X^2$ is independently O or S).

In particular embodiments, when the at least one group of formula (I) is bonded to an internucleoside phosphate, internucleoside phosphorothioate, or internucleoside phosphorodithioate, q is 0.

In certain embodiments, the strand contains at least one nucleoside substituted at position 2 with optionally substituted $C_{1-6}$ alkoxy, optionally substituted $C_{2-12}$ alkoxyalkyl, halogen, or cyano.

The hybridized polynucleotide of the invention may contain a strand interrupted by at least one internucleoside, abasic spacer of formula (III):

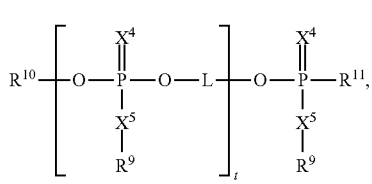

wherein
L is a sugar analogue;
each $X^4$ is independently O or S;
each $X^5$ is independently O, S, NH, or a bond;
each $R^9$ is independently H, optionally substituted $C_{1-6}$ alkyl, optionally substituted $C_{2-6}$ alkenyl, optionally substituted $C_{2-6}$ alkynyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl, -LinkA(-T)$_p$, or a conjugation moiety;
each LinkA is independently a multivalent linker (e.g., including —C(O)—N(H)—);
each T is independently an auxiliary moiety;
$R^{10}$ is a bond to a 3'-carbon atom of a nucleoside (x) in the strand;
$R^{11}$ is a bond to a 5'-oxygen atom of a nucleoside (x+t+1) in the strand;
p is an integer from 1 to 6; and
t is an integer from 1 to 6.

In some embodiments, t is 1. In further embodiments, $R^9$ is H. In yet further embodiments, $X^4$ is O or S. In still further embodiments, $X^5$ is O. In particular embodiments, (x) is 2, 3, 4, or 5. In certain embodiments, (x) is 13, 14, 15, or 16. In other embodiments, the construct contains only 1 or only 2 internucleoside, abasic spacers. In certain embodiments, the sugar analogue is optionally substituted $C_{2-6}$ alkylene, optionally substituted $C_{2-6}$ alkenylene, optionally substituted $C_5$ cycloalkane-1,3-diyl, optionally substituted $C_5$ cycloalkene-1,3-diyl, optionally substituted heterocycle-1,3-diyl (e.g., optionally substituted pyrrolidine-2,5-diyl, optionally substituted tetrahydrofuran-2,5-diyl, or optionally substituted tetrahydrothiophene-2,5-diyl), or optionally substituted ($C_{1-4}$ alkyl)-($C_{3-8}$ cycloalkylene) (e.g., optionally substituted ($C_1$ alkyl)-($C_3$ cycloalkylene)). In certain embodiments, the sugar analogue is selected from the group consisting of:

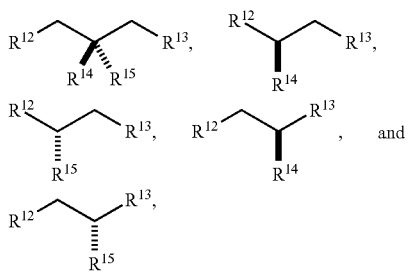

where
$R^{12}$ is a bond to an oxygen atom bonded to —P($X^4$)(—$X^5R^9$)— in formula (III);
$R^{13}$ is a bond to an oxygen atom bonded to another —P($X^4$)(—$X^5R^9$)— in formula (III); each of $R^{14}$ and $R^{15}$ is independently H, optionally substituted $C_{1-6}$ alkyl, or —(CH$_2$)$_n$—OR$^Z$, where n is an integer from 1 to 6, and $R^Z$ is optionally substituted $C_{1-6}$ alkyl, optionally substituted $C_{2-6}$ alkenyl, optionally substituted $C_{2-6}$ alkynyl, optionally substituted $C_{6-14}$ aryl, optionally substituted $C_{3-8}$ cycloalkyl, optionally substituted ($C_{1-9}$ heterocyclyl)-$C_{1-6}$-alkyl, optionally substituted ($C_{6-10}$ aryl)-$C_{1-6}$-alkyl, or optionally substituted ($C_{3-8}$ cycloalkyl)-$C_{1-6}$-alkyl.

In some embodiments, at least on of $R^{14}$ and $R^{15}$ is not H.

The hybridized polynucleotide of the invention may contain a strand containing at least one 2'-modified nucleoside. In other embodiments, all nucleosides in the strand are independently 2'-modified nucleosides. In certain embodiments, at least 80% of nucleosides in the strand are 2'-modified nucleosides. In further embodiments, each 2'-modified nucleoside is independently a 2'-alkoxy nucleoside (e.g., 2'-methoxy nucleoside). In yet further embodiments, at least one of the second, twelfth, fourteenth, and sixteenth nucleosides in the strand is a 2'-fluoro nucleoside. In still further embodiments, the second, twelfth, fourteenth, and sixteenth nucleosides or the twelfth, fourteenth, and sixteenth nucleosides in the strand are all independently 2'-fluoro nucleosides. In further embodiments, the seventh, ninth, and/or eleventh nucleoside in the strand is a 2'-fluoro nucleoside. In one embodiment, in one strand, the second, twelfth, fourteenth, and/or sixteenth nucleoside in the strand is a 2'-fluoro nucleoside, and, in the other strand, the seventh, ninth, and/or eleventh nucleoside in the strand is a 2'-fluoro nucleoside. In some embodiments, the remaining nucleosides are 2'-alkoxy nucleosides (e.g., 2'-methoxy nucleosides).

The hybridized polynucleotide of the invention may contain a strand including a seed region including a hypoxanthine nucleobase-containing nucleoside (e.g., inosine). In certain embodiments, the hypoxanthine nucleobase-containing nucleoside is the second nucleoside in the strand. In further embodiments, the hypoxanthine nucleobase-containing nucleoside is the third nucleoside in the strand. In yet further embodiments, the hypoxanthine nucleobase-containing nucleoside is the fourth nucleoside in the strand. In still further embodiments, the hypoxanthine nucleobase-containing nucleoside is the fifth nucleoside in the strand. In particular embodiments, the hypoxanthine nucleobase-containing nucleoside is the sixth nucleoside in the strand.

The hybridized polynucleotide of the invention may contain a strand including at least one stereochemically enriched phosphorothioate. In some embodiments, the strand includes only 1, 2, 3, or 4 stereochemically enriched phosphorothioates. In further embodiments, at least one (e.g., one or two) stereochemically enriched phosphorothioate is disposed between two consecutive nucleosides that are two of six 5'-terminal nucleosides of the strand. In yet further embodiments, at least one (e.g., one or two) stereochemically enriched phosphorothioate is disposed between two consecutive nucleosides that are two of six 3-terminal nucleosides of the strand. In still further embodiments, one stereochemically enriched phosphorothioate is covalently bonded between the first nucleoside and the second nucleoside within the strand. In still further embodiments, one stereochemically enriched phosphorothioate is covalently bonded between the second nucleoside and the third nucleoside within the strand. In some embodiments, one stereochemically enriched phosphorothioate is covalently bonded between the twenty-first nucleoside and the twenty-second nucleoside within the strand. In certain embodiments, one stereochemically enriched phosphorothioate is covalently bonded between the twenty-second nucleoside and the twenty-third nucleoside within the strand. In particular embodiments, the stereochemically enriched phosphorothioate has $R_P$ stereochemical identity. In certain embodiments, the stereochemically enriched phosphorothioate has $S_P$ stereochemical identity.

In further embodiments, the strand contains 19 or more nucleosides. In yet further embodiments, the strand comprises fewer than 100 nucleosides (e.g., fewer than 50 or fewer than 32 nucleosides).

In some embodiments, the strand contains from 1 to 5 of the non-bioreversible, internucleoside phosphotriesters. In certain embodiments, one of the non-bioreversible, internucleoside phosphotriesters connects the second nucleoside and the third nucleoside of the strand. In particular embodiments, one of the non-bioreversible, internucleoside phosphotriesters connects the fifth nucleoside and the sixth nucleoside of the strand. In further embodiments, one of the non-bioreversible, internucleoside phosphotriesters connects the seventeenth nucleoside and the eighteenth nucleoside of the strand. In yet further embodiments, one of the non-bioreversible, internucleoside phosphotriesters connects the nineteenth nucleoside and the twentieth nucleoside of the strand. In still further embodiments, one of the non-bioreversible, internucleoside phosphotriesters connects the twentieth nucleoside and the twenty-first nucleoside of the strand. In other embodiments, the at least one non-bioreversible, internucleoside phosphotriester connects two consecutive nucleosides that are two of six 5'- or six 3'-terminal nucleosides of the strand. In yet other embodiments, the strand contains one or more internucleoside phosphonates. In still other embodiments, the one or more internucleoside phosphonates connects two consecutive nucleosides that are two of six 5'- or six 3'-terminal nucleosides of the strand.

In particular embodiments, the strand contains 10 or more nucleosides (e.g., 15 or more nucleosides or 19 or more nucleosides). In certain embodiments, the strand contains fewer than 100 nucleosides (e.g., 50 or fewer nucleosides, 40 or fewer nucleosides, or 32 or fewer nucleosides). In further embodiments, the strand contains from 15 to 50 nucleosides (e.g., from 15 to 40 nucleosides, from 19 to 40 nucleosides, from 15 to 32 nucleosides, or from 19 to 32 nucleosides).

In some embodiments, the strand is interrupted by at least one internucleoside, abasic spacer.

In certain embodiments, the strand contains at least one 2'-modified nucleoside (e.g., all nucleosides in the strand are independently 2'-modified nucleosides).

In some embodiments, when the at least one group of formula (I) is bonded to an internucleoside phosphate, internucleoside phosphorothioate, or internucleoside phosphorodithioate, q is 0.

In particular embodiments, at least one of the strands contains at least one phosphorodithioate or at least one stereochemically enriched internucleoside phosphorothioate. In certain embodiments, at least one of the strands contains at least one nucleoside is a 2'-modified nucleoside.

In further embodiments, at least one -LinkA(-T)$_p$ is of formula (II) (e.g., each -LinkA(-T)$_p$ is independently of formula (II)):

-Q$^1$-Q$^2$([-Q$^3$-Q$^4$-Q$^5$]$_s$-Q$^6$-T)$_p$, (II)

where
each s is independently an integer from 0 to 20, where the repeating units are same or different;
Q$^1$ is a conjugation linker;
Q$^2$ is a linear group, if p is 1, or a branched group, if p is an integer from 2 to 6; each Q$^3$ and each Q$^6$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—;
each Q$^4$ is independently absent, optionally substituted C$_{1-12}$ alkylene, optionally substituted C$_{2-12}$ alkenylene, optionally substituted C$_{2-12}$ alkynylene, optionally substituted C$_{2-12}$ heteroalkylene, optionally substituted C$_{6-10}$ arylene, optionally substituted C$_{1-9}$ heteroarylene, or optionally substituted C$_{1-9}$ heterocyclylene;
each Q$^5$ is independently absent, —CO—, —NH—, —O—, —S—, —SO$_2$—, —CH$_2$—, —C(O)O—, —OC(O)—, —C(O)NH—, —NH—C(O)—, —NH—CH(R$^a$)—C(O)—, or —C(O)—CH(R$^a$)—NH—; and
each R$^a$ is independently H or an amino acid side chain.

In certain embodiments, each Q$^4$ is independently absent, optionally substituted C$_{1-12}$ alkylene, optionally substituted C$_{2-12}$ alkenylene, optionally substituted C$_{2-12}$ alkynylene, optionally substituted C$_{2-12}$ heteroalkylene, or optionally substituted C$_{1-9}$ heterocyclylene. In particular embodiments, at least one of Q$^3$, Q$^4$, and Q$^5$ is present in formula (II). In other embodiments, Q$^1$ is —O-Q$^L$QC where Q$^L$ is optionally substituted C$_{2-12}$ heteroalkylene, optionally substituted C$_{1-12}$ alkylene, or -(optionally substituted C$_{1-6}$ alkylene)-(optionally substituted C$_{6-10}$ arylene)- (e.g., optionally substituted C$_{2-12}$ heteroalkylene or optionally substituted C$_{1-12}$ alkylene); and Q$^C$ is (i) optionally substituted C$_{2-12}$ heteroalkylene containing —C(O)—N(H)—, —N(H)—C(O)—, —S(O)$_2$—N(H)—, or —N(H)—S(O)$_2$—; (ii) optionally substituted C$_{1-12}$ heterocyclylene; (iii) optionally substituted C$_{1-12}$ thioheterocyclylene; (iv) cyclobut-3-ene-1,2-dione-3,4-diyl; or (v) pyrid-2-yl hydrazone. In still other embodiments, Q$^L$ is optionally substituted C$_{2-12}$ heteroalkylene, optionally substituted C$_{1-12}$ alkylene. In yet other embodiments, Q$^1$ contains:

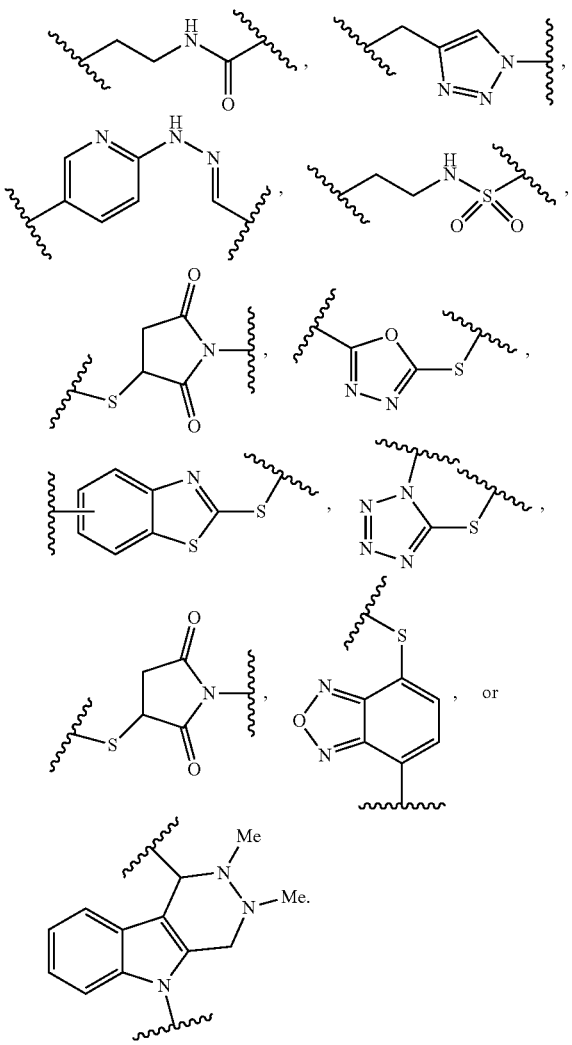

In still other embodiments, p is 1, and Q$^2$ is a linear group of formula -[Q$^3$-Q$^4$-Q$^5$]$_s$-.

In some embodiments, p is an integer from 2 to 6, and Q$^2$ is a branched group of formula -[Q$^3$-Q$^4$-Q$^5$]$_s$-Q$^7$(-[Q$^3$-Q$^4$-Q$^5$]$_s$-(Q$^7$)$_{p1}$)$_{p2}$, where Q$^7$ is optionally substituted C$_{1-6}$ alkane-triyl, optionally substituted C$_{1-6}$ alkane-tetrayl, optionally substituted C$_{2-6}$ heteroalkane-triyl, or optionally substituted C$_{2-6}$ heteroalkane-tetrayl;
where
p1 is 0 or 1;
p2 is 0, 1, 2, or 3;
where,
when p1 is 0, LinkA is a trivalent or tetravalent linker, and,
when p1 is 1, LinkA is a tetravalent, pentavalent, or hexavalent linker.

In certain embodiments, at least one T is a targeting moiety. In particular embodiments, at least one T is an asialoglycoprotein receptor ligand, mannose, folate, prostate specific membrane antigen (PSMA), or an antibody or an antigen-binding fragment thereof. In further embodiments, at least one T is the asialoglycoprotein receptor ligand (e.g., at least one T is N-acetyl galactosamine). In yet further embodiments, N-acetyl galactosamine contains an anomeric carbon bonded to LinkA, where the anomeric carbon is part of a hemiaminal group. In still further embodiments, the anomeric carbon of N-acetyl galactosamine is bonded to an amide nitrogen atom. In some embodiments, at least one T is a cell penetrating peptide. In certain embodiments, at least one T is an endosomal escape moiety.

In particular embodiments, the at least one group of formula (I) is linked to a nucleoside that is one of five 5'- or five 3'-terminal nucleosides. In other embodiments, the strand is bonded to 1, 2, 3, or 4 groups of formula (I), where the groups of formula (I) are same or different.

In further embodiments, the strand contains at least one non-bioreversible, internucleoside phosphotriester.

In some embodiments, the at least one non-bioreversible, internucleoside phosphotriester is a phosphate, phosphorothioate, or phosphorodithioate that is substituted with a substituent selected independently from the group consisting of optionally substituted $C_{2-16}$ alkyl; optionally substituted $C_{3-16}$ alkenyl; optionally substituted $C_{3-16}$ alkynyl; optionally substituted $C_{3-8}$ cycloalkyl; optionally substituted $C_{3-8}$ cycloalkenyl; optionally substituted ($C_{3-8}$ cycloalkyl)-$C_{1-4}$-alkyl; optionally substituted ($C_{3-8}$ cycloalkenyl)-$C_{1-4}$-alkyl; optionally substituted $C_{6-14}$ aryl; optionally substituted ($C_{6-14}$ aryl)-$C_{1-4}$-alkyl; optionally substituted $C_{1-9}$ heteroaryl having 1 to 4 heteroatoms selected from N, O, and S; optionally substituted ($C_{1-9}$ heteroaryl)-$C_{1-4}$-alkyl having 1 to 4 heteroatoms selected from N, O, and S; optionally substituted $C_{2-9}$ heterocyclyl having 1 to 4 heteroatoms selected from N, O, and S, where the heterocyclyl does not contain an S—S bond; optionally substituted ($C_{2-9}$ heterocyclyl)-$C_{1-4}$-alkyl having 1 to 4 heteroatoms selected from N, O, and S, where the heterocyclyl does not contain an S—S bond; and a group of the following structure:

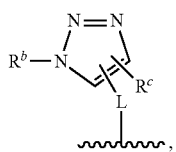

where
L is $C_{2-6}$ alkylene;
$R^b$ is optionally substituted $C_{2-6}$ alkyl; optionally substituted $C_{6-14}$ aryl; optionally substituted ($C_{6-14}$ aryl)-$C_{1-4}$-alkyl; optionally substituted $C_{3-8}$ cycloalkyl; optionally substituted ($C_{3-8}$ cycloalkyl)-$C_{1-4}$-alkyl; optionally substituted $C_{1-9}$ heteroaryl having 1 to 4 heteroatoms selected from the group consisting of N, O, and S; optionally substituted ($C_{1-9}$ heteroaryl)-$C_{1-4}$-alkyl having 1 to 4 heteroatoms selected from the group consisting of N, O, and S; optionally substituted $C_{2-9}$ heterocyclyl having 1 to 4 heteroatoms selected from the group consisting of N, O, and S, where the heterocyclyl does not contain an S—S bond; optionally substituted ($C_{2-9}$ heterocyclyl)-$C_{1-4}$-alkyl having 1 to 4 heteroatoms selected from N, O, and S, where the heterocyclyl does not contain an S—S bond; and a poly(ethylene glycol) terminated with —OH, $C_{1-6}$ alkoxy, or —COOH; and
$R^c$ is H or $C_{1-6}$ alkyl.

In other embodiments, the at least one non-bioreversible, internucleoside phosphotriester is a phosphate, phosphorothioate, or phosphorodithioate substituted with a substituent that is $C_{2-16}$ alkyl,

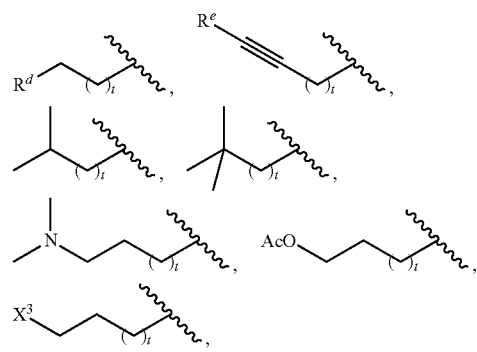

or a group formed by cycloaddition reaction of

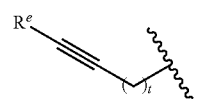

with an azido-containing substrate,
where
t is an integer from 1 to 6;
$R^d$ is optionally substituted $C_6$ aryl; optionally substituted $C_{4-5}$ heteroaryl that is a six member ring containing 1 or 2 nitrogen atoms; or optionally substituted $C_{4-5}$ heterocyclyl that is a six member ring containing 1 or 2 nitrogen atoms;
$R^6$ is H or $C_{1-6}$ alkyl;
$X^3$ is a halogen, —COOR$^5$, or —CONR$^6_2$, where each of $R^5$ and $R^6$ is independently H, optionally substituted $C_{1-6}$ alkyl, optionally substituted $C_{6-14}$ aryl, optionally substituted $C_{1-9}$ heteroaryl, or optionally substituted $C_{2-9}$ heterocyclyl; and
the azido-containing substrate is

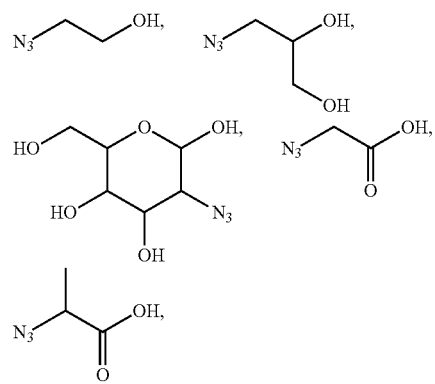

$N_3$-PEG-OH, $N_3$-PEG-COOH.

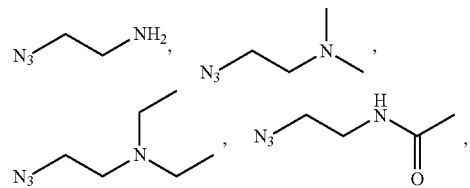

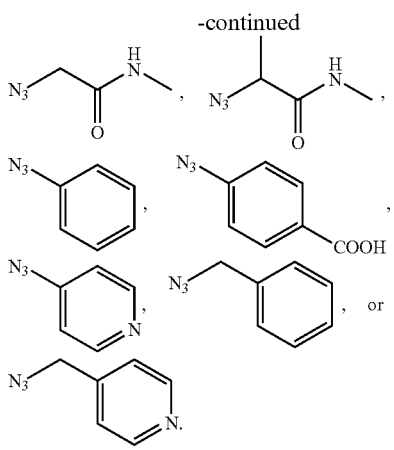

In some embodiments, the hybridized polynucleotide construct contains from 1 to 6 groups of formula (I), where the groups of formula (I) are same or different. In certain embodiments, the passenger strand contains at least one non-bioreversible, internucleoside phosphotriester. In particular embodiments, the guide strand contains at least one non-bioreversible, internucleoside phosphotriester. In further embodiments, the guide strand contains from 1 to 5 of the non-bioreversible, internucleoside phosphotriesters. In yet further embodiments, the at least one non-bioreversible, internucleoside phosphotriester connects two consecutive nucleosides that are two of six 5'- or six 3'-terminal nucleosides of the guide strand. In still further embodiments, one of the non-bioreversible, internucleoside phosphotriesters connects the second nucleoside and the third nucleoside of the guide strand. In other embodiments, one of the non-bioreversible, internucleoside phosphotriesters connects the fifth nucleoside and the sixth nucleoside of the guide strand. In yet other embodiments, one of the non-bioreversible, internucleoside phosphotriesters connects the seventeenth nucleoside and the eighteenth nucleoside of the guide strand. In still other embodiments, one of the non-bioreversible, internucleoside phosphotriesters connects the nineteenth nucleoside and the twentieth nucleoside of the guide strand. In certain embodiments, one of the non-bioreversible, internucleoside phosphotriesters connects the twentieth nucleoside and the twenty-first nucleoside of the guide strand. In particular embodiments, the passenger strand contains from 1 to 5 of the non-bioreversible phosphotriesters. In some embodiments, the at least one non-bioreversible, internucleoside phosphotriester connects two consecutive nucleosides that are two of six 5'- or six 3'-terminal nucleosides of the passenger strand.

In further embodiments, the passenger strand or the guide strand is interrupted by at least one internucleoside, abasic spacer. In yet further embodiments, the guide strand is interrupted by one internucleoside, abasic spacer. In still further embodiments, the passenger strand is interrupted by one internucleoside, abasic spacer.

In some embodiments, the guide strand or the passenger strand contains one or more phosphonates.

In particular embodiments, the guide strand contains 10 or more nucleosides (e.g., 15 or more nucleosides or 19 or more nucleosides). In certain embodiments, the guide strand contains fewer than 100 nucleosides (e.g., 50 or fewer nucleosides, 40 or fewer nucleosides, or 32 or fewer nucleosides). In further embodiments, the guide strand contains from 15 to 50 nucleosides (e.g., from 15 to 40 nucleosides, from 19 to 40 nucleosides, from 15 to 32 nucleosides, or from 19 to 32 nucleosides).

In further embodiments, the passenger strand contains 10 or more nucleosides (e.g., 15 or more nucleosides or 19 or more nucleosides). In yet further embodiments, the passenger strand contains fewer than 100 nucleosides (e.g., 50 or fewer nucleosides, 40 or fewer nucleosides, or 32 or fewer nucleosides). In still further embodiments, the passenger strand contains from 15 to 50 nucleosides (e.g., from 15 to 40 nucleosides, from 19 to 40 nucleosides, from 15 to 32 nucleosides, or from 19 to 32 nucleosides).

In certain embodiments, the 3'-end of the passenger strand is hybridized to the 5'-end of the guide strand to form a blunt.

The invention further provides a method of delivering a polynucleotide construct to a cell by contacting the cell with the polynucleotide construct of the invention, or a salt thereof, or a stereoisomer thereof, or with the hybridized polynucleotide construct of the invention, or a salt thereof, or a stereoisomer thereof, where, after the contacting, the polynucleotide construct resides inside the cell.

The invention also provides a method of reducing the expression of a protein in a cell by contacting the cell with the polynucleotide construct of the invention, or a salt thereof, or a stereoisomer thereof, or with the hybridized polynucleotide construct of the invention, or a stereoisomer thereof, where, after the contacting, expression of the protein in the cell is reduced.

The invention provides a compound of formula (IV):

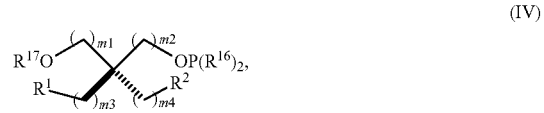

where each of $R^1$ and $R^2$ is independently H, optionally substituted $C_{1-16}$ alkyl, optionally substituted $C_{2-16}$ heteroalkyl, or a conjugation moiety;

each $R^{16}$ is independently dialkylamino, 2-cyanoethyl, or a conjugation moiety, provided that at least one $R^{16}$ is dialkylamino;

$R^{17}$ is a hydroxyl protecting group; and each of m1, m2, m3, and m4 is independently an integer from 0 to 6, provided that the sum of m1 and m2 is not 0;

where, when both $R^1$ and $R^2$ are a conjugation moiety containing optionally substituted $C_{2-16}$ alkynyl, $R^{16}$ is dialkylamino or a conjugation moiety.

In certain embodiments, at least one of $R^1$ and $R^2$ is a conjugation moiety.

In some embodiments, m1 is 0 or 1. In further embodiments, m2 is 0 or 1.

In particular embodiments, $R^1$ is H or the conjugation moiety, where the conjugation moiety is $[-Q^3-Q^4-Q^5]_s-Q^{C1}$, where $Q^{C1}$ is optionally substituted $C_{1-6}$ alkyl containing —COOR$^{21}$ or —CHO, optionally substituted $C_{2-12}$ alkynyl, optionally substituted N-protected amino, azido, N-maleimido, S-protected thiol,

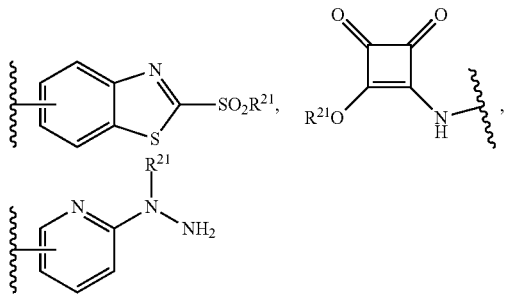

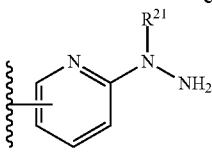

or N-protected version thereof,

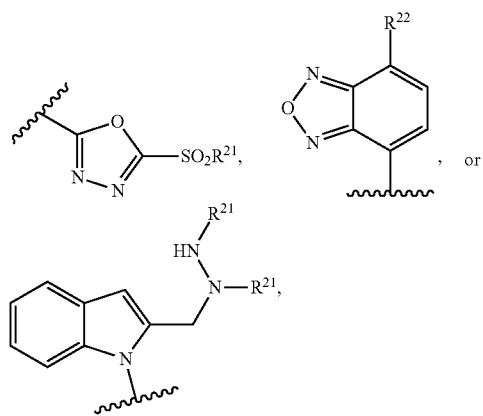

or N-protected version thereof,

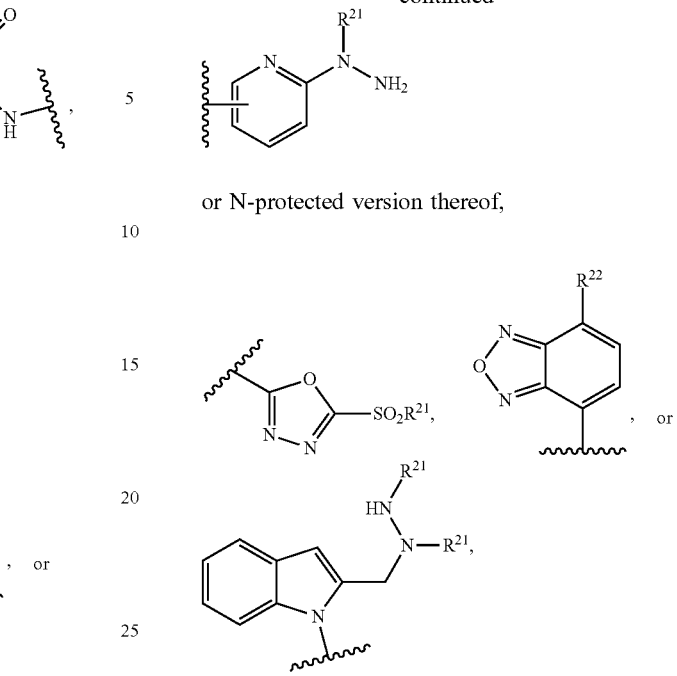

where each $R^{21}$ is independently H or optionally substituted $C_{1-6}$ alkyl, and $R^{22}$ is halogen;

each $Q^3$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—;

each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene;

each $Q^5$ is independently absent, —CO—, —NH—, —O—, —S—, —SO$_2$—, —CH$_2$—, —C(O)O—, —OC(O)—, —C(O)NH—, —NH—C(O)—, —NH—CH($R^a$)—C(O)—, or —C(O)—CH($R^a$)—NH—; and each s is independently an integer from 0 to 20.

In certain embodiments, $Q^3$ in $R^1$ is —O—. In further embodiments, $Q^4$ in $R^1$ is absent or optionally substituted $C_{2-12}$ heteroalkylene, and $Q^5$ in $R^1$ is absent.

In yet further embodiments, $R^2$ is H or the conjugation moiety, where the conjugation moiety is $[-Q^3-Q^4-Q^5]_s-Q^{C1}$, where $Q^{C1}$ is optionally substituted $C_{1-6}$ alkyl containing —COOR$^{21}$ or —CHO, optionally substituted $C_{2-12}$ alkynyl, optionally substituted N-protected amino, azido, N-maleimido, S-protected thiol,

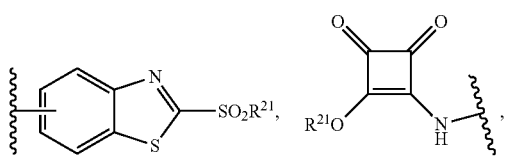

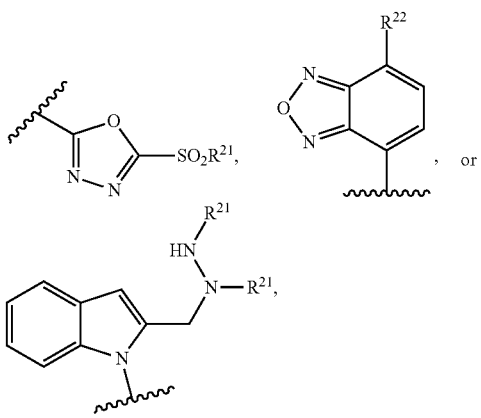

or N-protected version thereof, where each $R^{21}$ is independently H or optionally substituted $C_{1-6}$ alkyl, and $R^{22}$ is halogen;

each $Q^3$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—;

each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene;

each $Q^5$ is independently absent, —CO—, —NH—, —O—, —S—, —SO$_2$—, —CH$_2$—, —C(O)O—, —OC(O)—, —C(O)NH—, —NH—C(O)—, —NH—CH($R^a$)—C(O)—, or —C(O)—CH($R^a$)—NH—; and each s is independently an integer from 0 to 20.

In still further embodiments, $Q^3$ in $R^2$ is —O—. In particular embodiments, $Q^4$ in $R^2$ is absent or optionally substituted $C_{2-12}$ heteroalkylene, and $Q^5$ in $R^2$ is absent.

Definitions

The term "about," as used herein, represents a value that is ±10% of the recited value.

The term "activated carbonyl," as used herein, represents a functional group having the formula of —C(O)R$^A$ where R$^A$ is a halogen, optionally substituted $C_{1-6}$ alkoxy, optionally substituted $C_{6-10}$ aryloxy, optionally substituted $C_{2-9}$ heteroaryloxy (e.g., 1H-benzotriazol-1-yloxy), optionally substituted $C_2$-$C_9$ heterocyclyloxy (e.g., —OSu), optionally substituted pyridinium (e.g., 4-dimethylaminopyridinium), or —N(OMe)Me.

The term "activated phosphorus center," as used herein, represents a trivalent phosphorus (III) or a pentavalent phosphorus (V) center, in which at least one of the substituents is a halogen, optionally substituted $C_{1-6}$ alkoxy, optionally substituted $C_{6-10}$ aryloxy, phosphate, diphosphate, triphosphate, tetraphosphate, optionally substituted pyridinium (e.g., 4-dimethylaminopyridinium), or optionally substituted ammonium.

The term "activated silicon center," as used herein, represents a tetrasubstituted silicon center, in which at least one of the substituents is a halogen, optionally substituted $C_{1-6}$ alkoxy, or amino.

The term "activated sulfur center," as used herein, represents a tetravalent sulfur where at least one of the substituents is a halogen, optionally substituted $C_{1-6}$ alkoxy, optionally substituted $C_{6-10}$ aryloxy, phosphate, diphosphate, triphosphate, tetraphosphate, optionally substituted pyridinium (e.g., 4-dimethylaminopyridinium), or optionally substituted ammonium.

The term "alkane-tetrayl," as used herein, represents a tetravalent, acyclic, straight or branched chain, saturated hydrocarbon group having from 1 to 16 carbons, unless otherwise specified. Alkane-tetrayl may be optionally substituted as described for alkyl.

The term "alkane-triyl," as used herein, represents a trivalent, acyclic, straight or branched chain, saturated hydrocarbon group having from 1 to 16 carbons, unless otherwise specified. Alkane-triyl may be optionally substituted as described for alkyl.

The term "alkanoyl," as used herein, represents a hydrogen or an alkyl group (e.g., a haloalkyl group) that is attached to the parent molecular group through a carbonyl group and is exemplified by formyl (i.e., a carboxaldehyde group), acetyl, propionyl, butyryl, isobutyryl, and the like. Exemplary unsubstituted alkanoyl groups include from 1 to 7 carbons. In some embodiments, the alkyl group is further substituted with 1, 2, 3, or 4 substituents as described herein.

The term "($C_{x1-y1}$ aryl)-$C_{x2-y2}$-alkyl," as used herein, represents an aryl group of x1 to y1 carbon atoms attached to the parent molecular group through an alkylene group of x2 to y2 carbon atoms. Exemplary unsubstituted ($C_{x1-y1}$ aryl)-$C_{x2-y2}$-alkyl groups are from 7 to 16 carbons. In some embodiments, the alkylene and the aryl each can be further substituted with 1, 2, 3, or 4 substituent groups as defined herein for the respective groups. Other groups followed by "alkyl" are defined in the same manner, where "alkyl" refers to a $C_{1-6}$ alkylene, unless otherwise noted, and the attached chemical structure is as defined herein.

The term "alkenyl," as used herein, represents acyclic monovalent straight or branched chain hydrocarbon groups of containing one, two, or three carbon-carbon double bonds. Non-limiting examples of the alkenyl groups include ethenyl, prop-1-enyl, prop-2-enyl, 1-methylethenyl, but-1-enyl, but-2-enyl, but-3-enyl, 1-methylprop-1-enyl, 2-methylprop-1-enyl, and 1-methylprop-2-enyl. Alkenyl groups may be optionally substituted with 1, 2, 3, or 4 substituent groups selected, independently, from the group consisting of aryl, cycloalkyl, heterocyclyl (e.g., heteroaryl), as defined herein, and the substituent groups described for alkyl.

The term "alkenylene," as used herein, refers to a straight or branched chain alkenyl group with one hydrogen removed, thereby rendering this group divalent. The valency of alkenylene defined herein does not include the optional substituents. Non-limiting examples of the alkenylene groups include ethen-1,1-diyl; ethen-1,2-diyl; prop-1-en-1,1-diyl, prop-2-en-1,1-diyl; prop-1-en-1,2-diyl; prop-1-en-1,3-diyl; prop-2-en-1,1-diyl; prop-2-en-1,2-diyl; but-1-en-1,1-diyl; but-1-en-1,2-diyl; but-1-en-1,3-diyl; but-1-en-1,4-diyl; but-2-en-1,1-diyl; but-2-en-1,2-diyl; but-2-en-1,3-diyl; but-2-en-1,4-diyl; but-2-en-2,3-diyl; but-3-en-1,1-diyl; but-3-en-1,2-diyl; but-3-en-1,3-diyl; but-3-en-2,3-diyl; buta-1,2-dien-1,1-diyl; buta-1,2-dien-1,3-diyl; buta-1,2-dien-1,4-diyl; buta-1,3-dien-1,1-diyl; buta-1,3-dien-1,2-diyl; buta-1,3-dien-1,3-diyl; buta-1,3-dien-1,4-diyl; buta-1,3-dien-2,3-diyl; buta-2,3-dien-1,1-diyl; and buta-2,3-dien-1,2-diyl. The alkenylene group may be unsubstituted or substituted (e.g., optionally substituted alkenylene) as described for alkenyl groups.

The term "alkoxy," as used herein, represents a chemical substituent of formula —OR, where R is a $C_{1-6}$ alkyl group, unless otherwise specified. In some embodiments, the alkyl group can be further substituted in the manner described for alkyl groups.

The term "alkyl," as used herein, refers to an acyclic straight or branched chain saturated hydrocarbon group having from 1 to 16 carbons, unless otherwise specified. Alkyl groups are exemplified by methyl; ethyl; n- and iso-propyl; n-, sec-, iso- and tert-butyl; neopentyl, and the like, and may be optionally substituted with one, two, three, or, in the case of alkyl groups of two carbons or more, four substituents independently selected from the group consisting of: (1) alkoxy; (2) alkylsulfinyl; (3) amino; (4) arylalkoxy; (5) (arylalkyl)aza; (6) azido; (7) halo; (8) (heterocyclyl)oxy; (9) (heterocyclyl)aza; (10) hydroxy; (11) nitro; (12) oxo; (13) aryloxy; (14) sulfide; (15) thioalkoxy; (16) thiol; (17) alkanoyl; (18) —$CO_2R^A$, where $R^A$ is selected from the group consisting of (a) alkyl, (b) aryl, (c) hydrogen, and (d) arylalkyl; (19) —$C(O)NR^BR^C$, where each of $R^B$ and $R^C$ is, independently, selected from the group consisting of (a) hydrogen, (b) alkyl, (c) aryl, and (d) aryl-alkylene; (20) —$SO_2R^D$, where $R^D$ is selected from the group consisting of (a) alkyl, (b) aryl, and (c) aryl-alkylene; (21) —$SO_2NR^ER^F$, where each of $R^E$ and $R^F$ is, independently, selected from the group consisting of (a) hydrogen, (b) alkyl, (c) aryl and (d) arylalkyl; (22) silyl; (23) cyano; and (24) —$S(O)R^H$ where $R^H$ is selected from the group consisting of (a) hydrogen, (b) alkyl, (c) aryl, and (d) arylalkyl. In some embodiments, each of these groups can be further substituted (e.g., with unsubstituted substituents) as described herein.

The term "alkylamino," as used herein, refers to a group —$N(R^{N1})_2$, in which each $R^{N1}$ is independently H or alkyl, provided that at least one $R^{N1}$ is alkyl. Alkylamino may be optionally substituted; each alkyl in optionally substituted alkylamino is independently and optionally substituted as described for alkyl.

The term "alkylene," as used herein, refers to a saturated divalent hydrocarbon group derived from a straight or branched chain saturated hydrocarbon by the removal of two hydrogen atoms. The valency of alkylene defined herein does not include the optional substituents. Non-limiting examples of the alkylene group include methylene, ethane-1,2-diyl, ethane-1,1-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, and butane-2,2-diyl, butane-2,3-diyl. The term "$C_{x-y}$ alkylene" represents alkylene groups having between x and y carbons. Exemplary values for x are 1, 2, 3, 4, 5, and 6, and exemplary values for y are 2, 3, 4, 5, 6, 7, 8, 9, 10, 11, and 12. In some embodiments, the alkylene can be further substituted with 1, 2, 3, or 4 substituent groups as defined herein for an alkyl group. Similarly, the suffix "ene" designates a divalent radical of the corresponding monovalent radical as defined herein. For example, alkenylene, alkynylene, arylene, aryl alkylene, cycloalkylene, cycloalkyl alkylene, cycloalkenylene, heteroarylene, heteroaryl alkylene, heterocyclylene, and heterocyclyl alkylene are divalent forms of alkenyl, alkynyl, aryl, aryl alkyl, cycloalkyl, cycloalkyl alkyl cycloalkenyl, heteroaryl, heteroaryl alkyl, heterocyclyl, and heterocyclyl alkyl. For aryl alkylene, cycloalkyl alkylene, heteroaryl alkylene, and heterocyclyl alkylene, the two valences in the group may be located in the acyclic portion only or one in the cyclic portion and one in the acyclic portion. For example, the alkylene group of an aryl-$C_1$-alkylene or a heterocyclyl-$C_1$-alkylene can be further substituted with an oxo group to afford the respective aryloyl and (heterocyclyl)oyl substituent group.

The term "alkyleneoxy," as used herein, refers to a divalent group —R—O—, in which R is alkylene. Alkylene in alkyleneoxy may be unsubstituted or substituted (e.g., optionally substituted alkyleneoxy) as described for alkyl.

The term "alkynyl," as used herein, represents monovalent straight or branched chain hydrocarbon groups of from two to sixteen carbon atoms containing at least one carbon-carbon triple bond and is exemplified by ethynyl, 1-propynyl, and the like. Alkynyl groups may be optionally substituted with 1, 2, 3, or 4 substituent groups that are selected, independently, from aryl, alkenyl, cycloalkyl, and heterocyclyl (e.g., heteroaryl), as described herein, and the substituent groups described for alkyl.

The term "alkynylene," as used herein, refers to a straight-chain or branched-chain divalent substituent including one or two carbon-carbon triple bonds and containing only C and H when unsubstituted. An unsubstituted alkynylene contains from two to sixteen carbon atoms, unless otherwise specified. The valency of alkynylene defined herein does not include the optional substituents. Non-limiting examples of the alkenylene groups include ethyn-1,2-diyl; prop-1-yn-1,3-diyl; prop-2-yn-1,1-diyl; but-1-yn-1,3-diyl; but-1-yn-1,4-diyl; but-2-yn-1,1-diyl; but-2-yn-1,4-diyl; but-3-yn-1,1-diyl; but-3-yn-1,2-diyl; but-3-yn-2,2-diyl; and buta-1,3-diyn-1,4-diyl. The alkynylene group may be unsubstituted or substituted (e.g., optionally substituted alkynylene) as described for alkynyl groups.

The term "amino," as used herein, represents —N($R^{N1}$)$_2$, where, if amino is unsubstituted, both $R^{N1}$ are H; or, if amino is substituted, each $R^{N1}$ is independently H, —OH, —NO$_2$, —N($R^{N2}$)$_2$, —SO$_2$O$R^{N2}$, —SO$_2$$R^{N2}$, —SO$R^{N2}$, —CO-O$R^{N2}$, an N-protecting group, alkyl, alkenyl, alkynyl, alkoxy, aryl, arylalkyl, aryloxy, cycloalkyl, cycloalkenyl, heteroalkyl, or heterocyclyl, provided that at least one $R^{N1}$ is not H, and where each $R^{N2}$ is independently H, alkyl, or aryl. Each of the substituents may itself be unsubstituted or substituted with unsubstituted substituent(s) defined herein for each respective group. In some embodiments, amino is unsubstituted amino (i.e., —NH$_2$) or substituted amino (e.g., —NH$R^{N1}$), where $R^{N1}$ is independently —OH, —SO$_2$O$R^{N2}$, —SO$_2$$R^{N2}$, —SO$R^{N2}$, —COO$R^{N2}$, optionally substituted alkyl, or optionally substituted aryl, and each $R^{N2}$ can be optionally substituted alkyl or optionally substituted aryl. In some embodiments, substituted amino may be alkylamino, in which the alkyl groups are optionally substituted as described herein for alkyl. In certain embodiments, an amino group is —NH$R^{N1}$, in which $R^{N1}$ is optionally substituted alkyl. Non-limiting examples of —NH$R^{N1}$, in which $R^{N1}$ is optionally substituted alkyl, include: optionally substituted alkylamino, a proteinogenic amino acid, a non-proteinogenic amino acid, a $C_{1-6}$ alkyl ester of a proteinogenic amino acid, and a $C_{1-6}$ alkyl ester of a non-proteinogenic amino acid.

The term "aminoalkyl," as used herein, represents a chemical substituent of formula —R'—R", where R' is alkylene, and R" is amino. Aminoalkyl may be optionally substituted as defined for each of the two portions.

The term "arene-tetrayl," as used herein, represents a tetravalent group formed by replacing three hydrogen atoms in an aryl group with valencies. Arene-tetrayl can be optionally substituted as described for aryl.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents independently selected from the group consisting of: (1) alkanoyl (e.g., formyl, acetyl, and the like); (2) alkyl (e.g., alkoxyalkyl, alkylsulfinylalkyl, aminoalkyl, azidoalkyl, acylalkyl, haloalkyl (e.g., perfluoroalkyl), hydroxyalkyl, nitroalkyl, or thioalkoxyalkyl); (3) alkenyl; (4) alkynyl; (5) alkoxy (e.g., perfluoroalkoxy); (6) alkylsulfinyl; (7) aryl; (8) amino; (9) arylalkyl; (10) azido; (11) cycloalkyl; (12) cycloalkylalkyl; (13) cycloalkenyl; (14) cycloalkenylalkyl; (15) halo; (16) heterocyclyl (e.g., heteroaryl); (17) (heterocyclyl)oxy; (18) (heterocyclyl)aza; (19) hydroxy; (20) nitro; (21) thioalkoxy; (22) —(CH$_2$)$_q$CO$_2$$R^A$, where q is an integer from zero to four, and $R^A$ is selected from the group consisting of (a) alkyl, (b) aryl, (c) hydrogen, and (d) arylalkyl; (23) —(CH$_2$)$_q$CONR$^B$R$^C$, where q is an integer from zero to four and where $R^B$ and $R^C$ are independently selected from the group consisting of (a) hydrogen, (b) alkyl, (c) aryl, and (d) arylalkyl; (24) —(CH$_2$)$_q$SO$_2$$R^D$, where q is an integer from zero to four and where $R^D$ is selected from the group consisting of (a) alkyl, (b) aryl, and (c) arylalkyl; (25) —(CH$_2$)$_q$SO$_2$NR$^E$R$^F$, where q is an integer from zero to four and where each of $R^E$ and $R^F$ is, independently, selected from the group consisting of (a) hydrogen, (b) alkyl, (c) aryl, and (d) arylalkyl; (26) thiol; (27) aryloxy; (28) cycloalkoxy; (29) arylalkoxy; (30) heterocyclylalkyl (e.g., heteroarylalkyl); (31) silyl; (32) cyano; and (33) —S(O)$R^H$ where $R^H$ is selected from the group consisting of (a) hydrogen, (b) alkyl, (c) aryl, and (d) arylalkyl. In some embodiments, each of these groups can be further substituted (e.g., with unsubstituted substituents) as described herein.

The term "aryl alkyl," as used herein, represents an alkyl group substituted with an aryl group. Each of the aryl and alkyl portions may be independently unsubstituted or substituted (e.g., optionally substituted aryl alkyl) as described for the individual groups.

The term "auxiliary moiety," as used herein, refers to a moiety that is a targeting moiety (e.g., a cell-surface receptor ligand), a peptide, a carbohydrate, a neutral organic polymer, a positively charged polymer, or an endosomal escape moiety, which can be conjugated to a polynucleotide construct disclosed herein. Although the name for a particular auxiliary moiety may imply a free molecule, it will be understood that the name of the particular auxiliary moiety includes a monovalent group. One skilled in the art will readily understand appropriate points of attachment of a particular auxiliary moiety to a polynucleotide construct.

The term "aza," as used herein, represents a divalent —N($R^{N1}$)— group or a trivalent —N=group. The aza group may be unsubstituted, where $R^{N1}$ is H or absent, or substituted, where $R^{N1}$ is as defined for "amino." Aza may also be referred to as "N," e.g., "optionally substituted N." Two aza groups may be connected to form "diaza."

The term "azido," as used herein, represents an $N_3$ group.

The term "carbocyclic," as used herein, represents an optionally substituted $C_{3-12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

The term "carbohydrate," as used herein, represents a monosaccharide having from one to seven carbon atoms (which may be linear, branched or cyclic) with an oxygen, nitrogen, halogen, or sulfur atom bonded to each carbon atom. Non-limiting examples of carbohydrates include mannose, galactose, galactosamine, and N-acetylgalactosamine (GalNAc).

The term "carbonyl," as used herein, represents a C(O) group. Examples of functional groups which contain a "carbonyl" include esters, ketones, aldehydes, anhydrides, acyl chlorides, amides, carboxylic acids, and carboxylates.

The term "complementary" in reference to a polynucleotide, as used herein, means Watson-Crick complementary.

The term "cycloaddition reaction" as used herein, represents reaction of two components in which [4n+2] π electrons are involved in bond formation when there is either no activation, activation by a chemical catalyst, or activation using thermal energy, and n is 1, 2, or 3. A cycloaddition reaction is also a reaction of two components in which [4n] π electrons are involved, there is photochemical activation, and n is 1, 2, or 3. Desirably, [4n+2] π electrons are involved in bond formation, and n=1. Representative cycloaddition reactions include the reaction of an alkene with a 1,3-diene (Diels-Alder reaction), the reaction of an alkene with an α,β-unsaturated carbonyl (hetero Diels-Alder reaction), and the reaction of an alkyne with an azido compound (e.g., Huisgen cycloaddition).

The term "cycloalkane-tetrayl," as used herein, represents a tetravalent group formed by replacing three hydrogen atoms in a cycloalkyl group with valencies. Cycloalkane-tetrayl can be optionally substituted as described for cycloalkyl.

The term "cycloalkenyl," as used herein, refers to a non-aromatic carbocyclic group having from three to ten carbons (e.g., a $C_3$-$C_{10}$ cycloalkylene), unless otherwise specified. Non-limiting examples of cycloalkenyl include cycloprop-1-enyl, cycloprop-2-enyl, cyclobut-1-enyl, cyclobut-1-enyl, cyclobut-2-enyl, cyclopent-1-enyl, cyclopent-2-enyl, cyclopent-3-enyl, norbornen-1-yl, norbornen-2-yl, norbornen-5-yl, and norbornen-7-yl. The cycloalkenyl group may be unsubstituted or substituted (e.g., optionally substituted cycloalkenyl) as described for cycloalkyl.

The term "cycloalkenylene," as used herein, refers to a divalent carbocyclic non-aromatic group having from three to ten carbons (e.g., $C_3$-$C_{10}$ cycloalkenylene), unless otherwise specified. Non-limiting examples of the cycloalkenylene include cycloprop-1-en-1,2-diyl; cycloprop-2-en-1,1-diyl; cycloprop-2-en-1,2-diyl; cyclobut-1-en-1,2-diyl; cyclobut-1-en-1,3-diyl; cyclobut-1-en-1,4-diyl; cyclobut-2-en-1,1-diyl; cyclobut-2-en-1,4-diyl; cyclopent-1-en-1,2-diyl; cyclopent-1-en-1,3-diyl; cyclopent-1-en-1,4-diyl; cyclopent-1-en-1,5-diyl; cyclopent-2-en-1,1-diyl; cyclopent-2-en-1,4-diyl; cyclopent-2-en-1,5-diyl; cyclopent-3-en-1,1-diyl; cyclopent-1,3-dien-1,2-diyl; cyclopent-1,3-dien-1,3-diyl; cyclopent-1,3-dien-1,4-diyl; cyclopent-1,3-dien-1,5-diyl; cyclopent-1,3-dien-5,5-diyl; norbornadien-1,2-diyl; norbornadien-1,3-diyl; norbornadien-1,4-diyl; norbornadien-1,7-diyl; norbornadien-2,3-diyl; norbornadien-2,5-diyl; norbornadien-2,6-diyl; norbornadien-2,7-diyl; and norbornadien-7,7-diyl. The cycloalkenylene may be unsubstituted or substituted (e.g., optionally substituted cycloalkenylene) as described for cycloalkyl.

The term "cycloalkyl," as used herein, refers to a cyclic alkyl group having from three to ten carbons (e.g., a $C_3$-$C_{10}$ cycloalkyl), unless otherwise specified. Cycloalkyl groups may be monocyclic or bicyclic. Bicyclic cycloalkyl groups may be of bicyclo[p.q.0]alkyl type, in which each of p and q is, independently, 1, 2, 3, 4, 5, 6, or 7, provided that the sum of p and q is 2, 3, 4, 5, 6, 7, or 8. Alternatively, bicyclic cycloalkyl groups may include bridged cycloalkyl structures, e.g., bicyclo[p.q.r]alkyl, in which r is 1, 2, or 3, each of p and q is, independently, 1, 2, 3, 4, 5, or 6, provided that the sum of p, q, and r is 3, 4, 5, 6, 7, or 8. The cycloalkyl group may be a spirocyclic group, e.g., spiro[p.q]alkyl, in which each of p and q is, independently, 2, 3, 4, 5, 6, or 7, provided that the sum of p and q is 4, 5, 6, 7, 8, or 9. Non-limiting examples of cycloalkyl include cyclopropyl, cyclobutyl, cyclopentyl, cyclohexyl, cycloheptyl, 1-bicyclo[2.2.1.]heptyl, 2-bicyclo[2.2.1.]heptyl, 5-bicyclo[2.2.1.]heptyl, 7-bicyclo[2.2.1.]heptyl, and decalinyl. The cycloalkyl group may be unsubstituted or substituted as defined herein (e.g., optionally substituted cycloalkyl). The cycloalkyl groups of this disclosure can be optionally substituted with: (1) alkanoyl (e.g., formyl, acetyl, and the like); (2) alkyl (e.g., alkoxyalkyl, alkylsulfinylalkyl, aminoalkyl, azidoalkyl, acylalkyl, haloalkyl (e.g., perfluoroalkyl), hydroxyalkyl, nitroalkyl, or thioalkoxyalkyl); (3) alkenyl; (4) alkynyl; (5) alkoxy (e.g., perfluoroalkoxy); (6) alkylsulfinyl; (7) aryl; (8) amino; (9) arylalkyl; (10) azido; (11) cycloalkyl; (12) cycloalkylalkyl; (13) cycloalkenyl; (14) cycloalkenylalkyl; (15) halo; (16) heterocyclyl (e.g., heteroaryl); (17) (heterocyclyl)oxy; (18) (heterocyclyl)aza; (19) hydroxy; (20) nitro; (21) thioalkoxy; (22) —$(CH_2)_qCO_2R^A$, where q is an integer from zero to four, and $R^A$ is selected from the group consisting of (a) alkyl, (b) aryl, (c) hydrogen, and (d) arylalkyl; (23) —$(CH_2)_qCONR^BR^C$, where q is an integer from zero to four and where $R^B$ and $R^C$ are independently selected from the group consisting of (a) hydrogen, (b) alkyl, (c) aryl, and (d) arylalkyl; (24) —$(CH_2)_qSO_2R^D$, where q is an integer from zero to four and where $R^D$ is selected from the group consisting of (a) alkyl, (b) aryl, and (c) arylalkyl; (25) —$(CH_2)_qSO_2NR^ER^F$, where q is an integer from zero to four and where each of $R^E$ and $R^F$ is, independently, selected from the group consisting of (a) hydrogen, (b) alkyl, (c) aryl, and (d) arylalkyl; (26) thiol; (27) aryloxy; (28) cycloalkoxy; (29) arylalkoxy; (30) heterocyclylalkyl (e.g., heteroarylalkyl); (31) silyl; (32) cyano; and (33) —$S(O)R^H$ where $R^H$ is selected from the group consisting of (a) hydrogen, (b) alkyl, (c) aryl, and (d) arylalkyl. In some embodiments, each of these groups can be further substituted (e.g., with unsubstituted substituents) as described herein.

The term "cycloalkylene," as used herein, refers to a divalent group that is cycloalkyl, as defined herein, in which one hydrogen atom is replaced with a valency. Cycloalkylene may be unsubstituted or substituted (e.g., optionally substituted cycloalkylene) as described for cycloalkyl.

The term "cycloalkyl alkyl," as used herein, represents an alkyl group substituted with a cycloalkyl group. Each of the cycloalkyl and alkyl portions may be independently unsubstituted or substituted (e.g., optionally substituted cycloalkyl alkyl) as described for the individual groups.

The term "dialkylamino," as used herein, represents a group —$N(R^{N1})_2$, in which each $R^{N1}$ is independently alkyl. Dialkylamino may be optionally substituted; each alkyl in optionally substituted dialkylamino is independently and optionally substituted as described for alkyl.

The term "electrophile" or "electrophilic group," as used herein, represents a functional group that is attracted to electron rich centers and is capable of accepting pairs of electrons from one or more nucleophiles so as to form one or more covalent bonds. Electrophiles include, but are not limited to, cations; polarized neutral molecules; azides; activated silicon centers; activated carbonyls; alkyl halides; alkyl pseudohalides; epoxides; electron-deficient aryls; activated phosphorus centers; and activated sulfur centers. Typically encountered electrophiles include polarized neutral molecules, such as alkyl halides, acyl halides, carbonyl containing compounds, such as aldehydes, and atoms which are connected to good leaving groups, such as mesylates, triflates, and tosylates.

The term "endosomal escape moiety," as used herein, represents a moiety which enhances the release of endosomal contents or facilitates for the escape of a molecule from an internal cellular compartment (e.g., an endosome), as compared to a reference molecule that differs only in that it lacks an endosomal escape moiety.

The term "halo," as used herein, represents a halogen selected from bromine, chlorine, iodine, and fluorine.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens, or, when the halogen group is F, haloalkyl group can be perfluoroalkyl. In some embodiments, the haloalkyl group can be further optionally substituted with 1, 2, 3, or 4 substituent groups as described herein for alkyl groups.

The term "heteroalkane-tetrayl," as used herein refers to an alkane-tetrayl group interrupted once by one heteroatom; twice, each time, independently, by one heteroatom; three times, each time, independently, by one heteroatom; or four times, each time, independently, by one heteroatom. Each heteroatom is, independently, O, N, or S. In some embodiments, the heteroatom is O or N. An unsubstituted $C_{X-Y}$ heteroalkane-tetrayl contains from X to Y carbon atoms as well as the heteroatoms as defined herein. The heteroalkane-tetrayl group may be unsubstituted or substituted (e.g., optionally substituted heteroalkane-tetrayl), as described for heteroalkyl.

The term "heteroalkane-triyl," as used herein refers to an alkane-triyl group interrupted once by one heteroatom; twice, each time, independently, by one heteroatom; three times, each time, independently, by one heteroatom; or four times, each time, independently, by one heteroatom. Each heteroatom is, independently, O, N, or S. In some embodiments, the heteroatom is O or N. An unsubstituted $C_{X-Y}$ heteroalkane-triyl contains from X to Y carbon atoms as well as the heteroatoms as defined herein. The heteroalkane-triyl group may be unsubstituted or substituted (e.g., optionally substituted heteroalkane-triyl), as described for heteroalkyl.

The term "heteroalkyl," as used herein refers to an alkyl, alkenyl, or alkynyl group interrupted once by one heteroatom; twice, each time, independently, by one heteroatom; three times, each time, independently, by one heteroatom; or four times, each time, independently, by one heteroatom. Each heteroatom is, independently, O, N, or S. In some embodiments, the heteroatom is O or N. An unsubstituted $C_{X-Y}$ heteroalkyl contains from X to Y carbon atoms as well as the heteroatoms as defined herein. The heteroalkyl group may be unsubstituted or substituted (e.g., optionally substituted heteroalkyl). When heteroalkyl is substituted and the substituent is bonded to the heteroatom, the substituent is selected according to the nature and valency of the heteroatom. Thus, the substituent, if present, bonded to the heteroatom, valency permitting, is selected from the group consisting of =O, —N($R^{N2}$)$_2$, —SO$_2$O$R^{N3}$, —SO$_2$$R^{N2}$, —SO$R^{N3}$, —COO$R^{N3}$, an N-protecting group, alkyl, alkenyl, alkynyl, aryl, cycloalkyl, cycloalkenyl, cycloalkynyl, heterocyclyl, or cyano, where each $R^{N2}$ is independently H, alkyl, cycloalkyl, cycloalkenyl, cycloalkynyl, aryl, or heterocyclyl, and each $R^{N3}$ is independently alkyl, cycloalkyl, cycloalkenyl, cycloalkynyl, aryl, or heterocyclyl. Each of these substituents may itself be unsubstituted or substituted with unsubstituted substituent(s) defined herein for each respective group. When heteroalkyl is substituted and the substituent is bonded to carbon, the substituent is selected from those described for alkyl, provided that the substituent on the carbon atom bonded to the heteroatom is not Cl, Br, or I. It is understood that carbon atoms are found at the termini of a heteroalkyl group.

The term "heteroaryl," as used herein, represents that subset of heterocyclyls, as defined herein, which include an aromatic ring system that contains at least one heteroatom. Thus, heteroaryls contain 4n+2 pi electrons within the mono- or multicyclic ring system. Heteroaryl can be unsubstituted or substituted (e.g., optionally substituted heteroaryl) with 1, 2, 3, or 4 substituents groups as defined for heterocyclyl.

The term "heteroaryl alkyl," as used herein, represents an alkyl group substituted with a heteroaryl group. Thus, heteroaryl alkyl is a heterocyclyl alkyl group, in which the heterocyclyl includes at least one aromatic ring system including a heteroatom. Each of the heteroaryl and alkyl portions may be independently unsubstituted or substituted (e.g., optionally substituted heteroaryl alkyl) as described for the individual groups.

The term "heterocycle-tetrayl," as used herein, represents a tetravalent group formed by replacing three hydrogen atoms in a heterocyclyl group with valencies. Heterocycle-tetrayl can be optionally substituted as described for heterocyclyl.

The term "heterocyclyl," as used herein, represents a 5-, 6-, or 7-membered ring or a fused ring system of two, three, or four rings, each of which is independently a 5-, 6-, or 7-membered ring, unless otherwise specified, provided that at least one of the rings contains one, two, three, or four heteroatoms independently selected from the group consisting of nitrogen, oxygen, and sulfur. The 5-membered ring has zero to two double bonds, and the 6- and 7-membered rings have zero to three double bonds. An unsubstituted heterocyclyl contains from one to twelve carbon atoms, unless specified otherwise. In some embodiments, an unsubstituted heterocyclyl contains at least two carbon atoms. In certain embodiments, an unsubstituted heterocyclyl contains up to nice carbon atoms. The fused "heterocyclyl" be a bridged multicyclic structure in which one or more carbons and/or heteroatoms bridges two non-adjacent members of a monocyclic ring, e.g., as found in a quinuclidinyl group. In some embodiments, the fused "heterocyclyl" includes bicyclic, tricyclic, and tetracyclic groups, in which at least one of the rings includes one or more heteroatoms as defined herein, and the remaining rings are carbocyclic rings, e.g., an aryl ring, a cyclohexane ring, a cyclohexene ring, a cyclopentane ring, a cyclopentene ring. Non-limiting examples of such fused heterocyclyls include indolyl, quinolyl, isoquinolyl, tetrahydroquinolyl, benzofuryl, benzothienyl, tropanes, and 1,2,3,5,8,8a-hexahydroindolizine. Non-limiting examples of heterocyclyls include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, purinyl, thiadiazolyl (e.g., 1,3,4-thiadiazole), tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Still other exemplary heterocyclyls are: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Heterocyclic groups also include groups of the formula

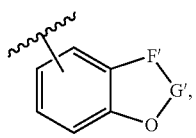

where
F' is selected from the group consisting of —CH$_2$—, —CH$_2$O—, and —O—, and G' is selected from the group consisting of —C(O)— and —(C(R')(R''))$_v$—, where each of R' and R'' is, independently, selected from the group consisting of hydrogen or alkyl of one to four carbon atoms, and v is one to three and includes groups, such as 1,3-benzodioxolyl, 1,4-benzodioxanyl, and the like. Any of the heterocyclyl groups mentioned herein may be optionally substituted with one, two, three, four, or five substituents independently selected from the group consisting of: (1) alkanoyl (e.g., formyl, acetyl, and the like); (2) alkyl (e.g., alkoxyalkylene, alkylsulfinylalkylene, aminoalkylene, azidoalkylene, acylalkylene, haloalkylene (e.g., perfluoroalkyl), hydroxyalkylene, nitroalkylene, or thioalkoxyalkylene); (3) alkenyl; (4) alkynyl; (5) alkoxy (e.g., perfluoroalkoxy); (6) alkylsulfinyl; (7) aryl; (8) amino; (9) aryl-alkylene; (10) azido; (11) cycloalkyl; (12) cycloalkyl-alkylene; (13) cycloalkenyl; (14) cycloalkenyl-alkylene; (15) halo; (16) heterocyclyl (e.g., heteroaryl); (17) (heterocyclyl)oxy; (18) (heterocyclyl)aza; (19) hydroxy; (20) oxo; (21) nitro; (22) sulfide; (23) thioalkoxy; (24) —(CH$_2$)$_q$CO$_2$R$^A$, where q is an integer from zero to four, and R$^A$ is selected from the group consisting of (a) alkyl, (b) aryl, (c) hydrogen, and (d) aryl-alkylene; (25) —(CH$_2$)$_q$CONR$^B$R$^C$, where q is an integer from zero to four and where R$^B$ and R$^C$ are independently selected from the group consisting of (a) hydrogen, (b) alkyl, (c) aryl, and (d) aryl-alkylene; (26) —(CH$_2$)$_q$SO$_2$R$^D$, where q is an integer from zero to four and where R$^D$ is selected from the group consisting of (a) alkyl, (b) aryl, and (c) aryl-alkylene; (27) —(CH$_2$)$_q$SO$_2$NR$^E$R$^F$, where q is an integer from zero to four and where each of R$^E$ and R$^F$ is, independently, selected from the group consisting of (a) hydrogen, (b) alkyl, (c) aryl, and (d) aryl-alkylene; (28) thiol; (29) aryloxy; (30) cycloalkoxy; (31) arylalkoxy; (31) heterocyclyl-alkylene (e.g., heteroaryl-alkylene); (32) silyl; (33) cyano; and (34) —S(O)R$^H$ where R$^H$ is selected from the group consisting of (a) hydrogen, (b) alkyl, (c) aryl, and (d) aryl-alkylene. In some embodiments, each of these groups can be independently unsubstituted or substituted with unsubstituted substituent(s) as described herein for each of the recited groups. For example, the alkylene group of an aryl-C$_1$-alkylene or a heterocyclyl-C$_1$-alkylene can be further substituted with an oxo group to afford the respective aryloyl and (heterocyclyl)oyl substituent group.

The term "heterocyclyl alkyl," as used herein, represents an alkyl group substituted with a heterocyclyl group. Each of the heterocyclyl and alkyl portions may be independently unsubstituted or substituted (e.g., optionally substituted heterocyclyl alkyl) as described for the individual groups.

The terms "hydroxyl" and "hydroxy," as used interchangeably herein, represent an —OH group.

The term "internucleoside, abasic spacer," as used herein, represents a divalent group lacking nucleobases and thus lacking capability to engage in base-pairing interactions.

The term "interrupted," as used herein, refers to a structural modification to a strand, where one or more nucleosides are replaced with an internucleoside, abasic spacer, provided that the replaced nucleosides are neither a first nor a last nucleoside in the strand, and provided that the number of the sugar analogues in the internucleoside, abasic spacer is same as the number of the replaced nucleosides. The term "LNA," as used herein, refers to a locked nucleic acid, which is known in the art. See, e.g., WO 1999/014226.

The term "loadable into a RISC complex," as used herein, refers to the capability of a guide strand to be loaded into a RISC complex and the RISC-mediated degradation of a passenger strand hybridized to the guide strand. For example, this polynucleotide includes unsubstituted or bioreversibly substituted phosphate groups between the three contiguous nucleotides including a natural RISC-mediated cleavage site. Certain guide strands loadable into a RISC complex include a 5'-terminal nucleoside that is bonded to 5'-terminal or internucleoside phosphates or phosphorothioates that are either unsubstituted or substituted bioreversibly. The preferred natural RISC-mediated cleavage site is located on the passenger strand between two nucleosides that are complementary to the tenth and eleventh nucleotides of the guide strand.

The term "multivalent linker," as used herein, represents a linking group including two or more valencies (e.g., from two to seven or from two to four valencies).

The term "nitro," as used herein, represents an —NO₂ group.

The term "non-bioreversible linker," as used herein, refers to a multivalent moiety that is not bioreversible and thus does not include a disulfide or thioester. A first group non-bioreversibly linked to a second group, thus, is linked through the non-bioreversible linker.

A "non-proteinogenic amino acid" is an amino acid not naturally produced or found in a mammal. Non-proteinogenic amino acids are known in the art. Non-proteinogenic amino acids are commercially available, e.g., from Merck KGaA, Darmstadt, Germany.

The term "nucleobase," as used herein, represents a nitrogen-containing heterocyclic ring found at the 1' position of the sugar moiety of a nucleotide or nucleoside. Nucleobases can be unmodified or modified. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; those disclosed in *The Concise Encyclopedia Of Polymer Science And Engineering*, pages 858-859, Kroschwitz, J. I., ed. John Wiley & Sons, 1990; those disclosed by Englisch et al., *Angewandte Chemie, International Edition,* 1991, 30, 613; and those disclosed by Sanghvi, Y. S., Chapter 15, Antisense Research and Applications, pages 289 302, (Crooke et al., ed., CRC Press, 1993). Certain nucleobases are particularly useful for increasing the binding affinity of the polymeric compounds of the invention, including 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications 1993, CRC Press, Boca Raton, pages 276-278). These may be combined, in particular embodiments, with 2'-O-methoxyethyl sugar modifications. United States patents that teach the preparation of certain of these modified nucleobases as well as other modified nucleobases include, but are not limited to, the above noted U.S. Pat. Nos. 3,687,808; 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,594,121; 5,596,091; 5,614,617; and 5,681,941. For the purposes of this disclosure, "modified nucleobases," as used herein, further represents nucleobases, natural or non-natural, which include one or more protecting groups as described herein.

The terms "nucleophile," as used herein, represent an optionally substituted functional group that engages in the formation of a covalent bond by donating electrons from electron pairs or -r bonds. Nucleophiles may be selected from alkenes, alkynes, aryl, heteroaryl, diaza groups, hydroxy groups, alkoxy groups, aryloxy groups, amino groups, alkylamino groups, anilido groups, thio groups, and thiophenoxy groups.

The term "nucleoside," as used herein, represents a sugar-nucleobase combination. The sugar is a modified sugar containing a nucleobase at the anomeric carbon or an optionally modified 3,5-dideoxypentafuranose containing a nucleobase at the anomeric carbon and a bond to another group at each of the positions 3 and 5. The pentafuranose may be 3,5-dideoxyribose or 2,3,5-trideoxyribose or a 2 modified version thereof, in which position 2 is substituted with OR, R, halo (e.g., F), SH, SR, NH₂, NHR, NR₂, or CN, where R is an optionally substituted $C_{1-6}$ alkyl (e.g., ($C_{1-6}$ alkoxy)-$C_{1-6}$-alkyl) or optionally substituted ($C_{6-14}$ aryl)-$C_{1-4}$-alkyl. The modified sugars are non-ribose sugars, such as mannose, arabinose, glucopyranose, galactopyranose, 4-thioribose, and other sugars, heterocycles, or carbocycles. In some embodiments, the term "nucleoside" refers to a divalent group having the following structure:

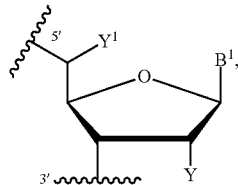

in which B¹ is a nucleobase; Y is H, halogen (e.g., F), hydroxyl, optionally substituted $C_{1-6}$ alkoxy (e.g., methoxy or methoxyethoxy), or a protected hydroxyl group; Y¹ is H or $C_{1-6}$ alkyl (e.g., methyl) and each of 3' and 5' indicate the position of a bond to another group. Nucleosides also include locked nucleic acids (LNA), glycerol nucleic acids, morpholino nucleic acids, and threose nucleic acids.

The term "nucleotide," as used herein, refers to a nucleoside that further includes a phosphate; phosphorothioate; phosphorodithioate; phosphonate; phosphoramidate; or an internucleoside, non-bioreversible group. In certain nucleotides (e.g., those based on optionally modified 3,5-dideoxypentafuranose), the phosphate; phosphorothioate; phosphorodithioate; phosphonate; phosphoramidate; or an internucleoside, non-bioreversible group is bonded to the 3 or 5 position of the nucleoside.

The terms "oxa" and "oxy," as used interchangeably herein, represents a divalent oxygen atom that is connected to two groups (e.g., the structure of oxy may be shown as —O—).

The term "oxo," as used herein, represents a divalent oxygen atom that is connected to one group (e.g., the structure of oxo may be shown as =O).

The term "phosphonate," as used herein, refers to a monovalent or divalent group having the structure —O—P(=O)(-A)-O—B, where A is alkyl or aryl, and B is a valency, if phosphonate is divalent, or H, if phosphonate is monovalent, or a salt thereof.

The term "phosphoramidate," as used herein, refers to a monovalent or divalent group having the structure —O—P(=X)(-A)-O—B, where A is amino, X is O or S, and B is a valency, if phosphoramidate is divalent, or H, if phosphoramidate is monovalent, or a salt thereof.

The term "phosphotriester," as used herein, refers to a phosphate, phosphorothioate, or phosphorodithioate, in which all three valences are substituted.

The term "peptide," as used herein, represents two or more amino acid residues linked by peptide bonds. Moreover, for purposes of this disclosure, the term "peptide" and the term "protein" are used interchangeably herein in all contexts. A variety of peptides may be used within the scope of the methods and compositions provided herein. Peptides made synthetically may include substitutions of amino acids known in the art as not naturally encoded by DNA (e.g., a non-naturally occurring amino acid).

The terms "photolytic activation" or "photolysis," as used herein, represent the promotion or initiation of a chemical reaction by irradiation of the reaction with light. The wavelengths of light suitable for photolytic activation range between 200-500 nm and include wavelengths that range from 200-260 nm and 300-460 nm. Other useful ranges include 200-230 nm, 200-250 nm, 200-275 nm, 200-300 nm, 200-330 nm, 200-350 nm, 200-375 nm, 200-400 nm, 200-430 nm, 200-450 nm, 200-475 nm, 300-330 nm, 300-350 nm, 300-375 nm, 300-400 nm, 300-430 nm, 300-450 nm, 300-475 nm, and 300-500 nm.

The term "protecting group," as used herein, represents a group intended to protect a functional group (e.g., a hydroxyl, an amino, or a carbonyl) from participating in one or more undesirable reactions during chemical synthesis (e.g., polynucleotide synthesis). The term "O-protecting group," as used herein, represents a group intended to protect an oxygen containing (e.g., phenol, hydroxyl or carbonyl) group from participating in one or more undesirable reactions during chemical synthesis. The term "N-protecting group," as used herein, represents a group intended to protect a nitrogen containing (e.g., an amino or hydrazine) group from participating in one or more undesirable reactions during chemical synthesis. Commonly used O- and N-protecting groups are disclosed in Greene, "Protective Groups in Organic Synthesis," 3$^{rd}$ Edition (John Wiley & Sons, New York, 1999), which is incorporated herein by reference. Exemplary O- and N-protecting groups include alkanoyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl. N-protecting groups useful for protection of amines in nucleobases include phenoxyacetyl and (4-isopropyl)phenoxyacetyl.

The term "pyrid-2-yl hydrazone," as used herein, represents a group of the structure:

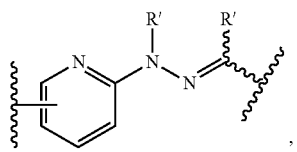

where each R' is independently H or optionally substituted $C_{1-6}$ alkyl. Pyrid-2-yl hydrazone may be unsubstituted (i.e., each R' is H).

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and aryl-alkylene ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkylene groups such as benzyl, triphenylmethyl, benzyloxymethyl, and the like and silyl groups such as trimethylsilyl, and the like. Useful N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "stereochemically enriched," as used herein, refers to a local stereochemical preference for one enantiomer of the recited group over the opposite enantiomer of the same group. Thus, a strand containing a stereochemically enriched phosphorothioate is a strand, in which a phosphorothioate of predetermined stereochemistry is present in preference to a phosphorothioate of stereochemistry that is opposite of the predetermined stereochemistry. This preference can be expressed numerically using a diastereomeric ratio for the phosphorothioate of the predetermined stereochemistry. The diastereomeric ratio for the phosphorothioate of the predetermined stereochemistry is the molar ratio of the diastereomers having the identified phosphorothioate with the predetermined stereochemistry relative to the diastereomers having the identified phosphorothioate with the stereochemistry that is opposite of the predetermined stereochemistry. The diastereomeric ratio for the phosphorothioate of the predetermined stereochemistry may be greater than or equal to 1.1 (e.g., greater than or equal to 4, greater than or equal to 9, greater than or equal to 19, or greater than or equal to 39).

The term "strand," as used herein, represents a structure containing 11 or more contiguous nucleosides covalently bound together by phosphates; phosphorothioates; phosorodithioates; phosphonates; phosphoramidates; internucleoside, abasic spacers; and/or internucleoside, non-bioreversible groups; and their combinations; provided that two contiguous nucleosides are linked by one and only one group selected from the group consisting of a phosphate; phosphorothioate; phoshorodithioate; phosphonate; phosphoramidate; internucleoside, abasic spacer; and internucleoside, non-bioreversible group. A strand includes a 5'-terminus and a 3'-terminus. Nucleosides within the strands disclosed herein are numbered starting at the 5'-terminus of the strand. When a nucleoside is replaced with a sugar analogue as part of an internucleoside, abasic spacer, the numbered nucleoside refers to the sugar analogue replacing such numbered nucleoside. A strand may be optionally capped at the 5'-terminus and/or at the 3'-terminus with a phosphate, diphosphate, triphosphate, phosphorothioate, diphosphorothioate, triphosphorothioate, phosphorodithioate, disphorodithioate, triphosphorodithioate, phosphonate, phosphoramidate, or a group of formula (I). A strand contains from zero to four internucleoside, abasic spacers. Typically, a strand may contain one or more of internucleoside groups selected from the group consisting of phosphorothioate; phoshorodithioate; phosphonate; phosphoramidate; and internucleoside, non-bioreversible group within the sequence of six terminal nucleosides. A strand can include from 11 to 100 (e.g., from 19 to 50 or from 19 to 32) nucleosides.

The term "subject," as used herein, represents a human or non-human animal (e.g., a mammal).

The term "sugar analogue," as used herein, represents a divalent or trivalent group that is a $C_{3-6}$ monosaccharide or $C_{3-6}$ alditol (e.g., glycerol), which is modified to replace two hydroxyl groups with bonds to the oxygen atoms that are bonded to groups —P($X^4$)(—$X^5R^9$)— in formula (III). A sugar analogue does not contain a nucleobase capable of engaging in hydrogen bonding with a nucleobase in a complementary strand. A sugar analogue is cyclic or acyclic. Further optional modifications included in a sugar analogue are: a replacement of one, two, or three of the remaining hydroxyl groups or carbon-bonded hydrogen atoms with H; optionally substituted $C_{1-6}$ alkyl; -LinkA(-T)$_p$; a conjugation moiety; —(CH$_2$)$_{t1}$—OR$^Z$, where t1 is an integer from 1 to 6, and $R^Z$ is optionally substituted $C_{1-6}$ alkyl, optionally substituted $C_{2-6}$ alkenyl, optionally substituted $C_{2-6}$ alkynyl, optionally substituted $C_{6-14}$ aryl, optionally substituted $C_{3-8}$ cycloalkyl, optionally substituted ($C_{1-9}$ heterocyclyl)-$C_{1-6}$-alkyl, optionally substituted ($C_{6-10}$ aryl)-$C_{1-6}$-alkyl, or optionally substituted ($C_{3-8}$ cycloalkyl)-$C_{1-6}$-alkyl; introduction of one or two unsaturation(s) (e.g., one or two double bonds); and replacement of one, two, or three hydrogens or hydroxyl groups with substituents as defined for alkyl, alkenyl, cycloalkyl, cycloalkenyl, or heterocyclyl. Non-limiting examples of sugar analogues are optionally substituted $C_{2-6}$ alkylene, optionally substituted $C_{2-6}$ alkenylene, optionally substituted $C_5$ cycloalkane-1,3-diyl, optionally substituted $C_5$ cycloalkene-1,3-diyl, optionally substituted heterocycle-1,3-diyl (e.g., optionally substituted pyrrolidine-2,5-diyl, optionally substituted tetrahydrofuran-2,5-diyl, or optionally substituted tetrahydrothiophene-2,5-diyl), or optionally substituted ($C_{1-4}$ alkyl)-($C_{3-8}$ cycloalkylene) (e.g., optionally substituted ($C_1$ alkyl)-($C_3$ cycloalkylene)).

The term "sulfide" as used herein, represents a divalent —S— or =S group.

The term "targeting moiety," as used herein, represents a moiety (e.g., a small molecule, e.g., a carbohydrate) that specifically binds or reactively associates or complexes with a receptor or other receptive moiety associated with a given target cell population. A polynucleotide construct or a hybridized polynucleotide construct of the invention contains one or more ligands (e.g., from 1 to 6 ligands, from 1 to 3 ligands, or 1 ligand). The ligand can be an antibody or an antigen-binding fragment or an engineered derivative thereof (e.g., Fcab or a fusion protein (e.g., scFv)). Alternatively, the ligand is a small molecule (e.g., N-acetylgalactosamine, mannose, or folate). A hybridized polynucleotide construct of the invention that includes one or more ligands may exhibit $K_d$ of less than 100 nM for the target, to which the ligands bind. $K_d$ is measured using methods known in the art, e.g., using surface plasmon resonance (SPR), e.g., using Biacore™ system (GE Healthcare, Little Chalfont, the United Kingdom).

The term "terminal nucleoside," as used herein, refers to a nucleoside that is located within six contiguous nucleosides including one nucleoside that contains one and only one bond linking it to another nucleoside through a phosphate; phosphorothioate; phoshorodithioate; phosphonate; phosphoramidate; internucleoside, abasic spacer; or internucleoside, non-bioreversible group.

The term "therapeutically effective dose," as used herein, represents the quantity of an siRNA, or polynucleotide according to the invention necessary to ameliorate, treat, or at least partially arrest the symptoms of a disease or disorder (e.g., to inhibit cellular proliferation). Amounts effective for this use will, of course, depend on the severity of the disease and the weight and general state of the subject. Typically, dosages used in vitro may provide useful guidance in the amounts useful for in vivo administration of the pharmaceutical composition, and animal models may be used to determine effective dosages for treatment of particular disorders.

The term "thiocarbonyl," as used herein, represents a C(=S) group. Non-limiting example of functional groups containing a "thiocarbonyl" includes thioesters, thioketones, thioaldehydes, thioanhydrides, thioacyl chlorides, thioamides, thiocarboxylic acids, and thiocarboxylates.

The term "thioheterocyclylene," as used herein, represents a divalent group —S—R'—, where R' is a heterocyclylene as defined herein.

The term "thiol," as used herein, represents an —SH group.

The term "disorder," as used herein, is intended to be generally synonymous, and is used interchangeably with, the terms "disease," "syndrome," and "condition" (as in a medical condition), in that all reflect an abnormal condition presented by a subject, or one of its parts, that impairs normal functioning, and is typically manifested by distinguishing signs and symptoms.

The term "treating" as used in reference to a disorder in a subject, is intended to refer to reducing at least one symptom of the disorder by administrating a therapeutic (e.g., a nucleotide construct of the invention) to the subject.

BRIEF DESCRIPTION OF THE DRAWINGS

FIG. 19 is a chart showing Heb3b hepatocytes viability after incubation with Z67, Z237, or Z238.

FIG. 20 is a chart showing TTR expression in primary mouse hepatocytes after incubation with Z67, Z237, or Z238. IC50 for Z67=$2.020 \times 10^{-12}$ M. IC50 for Z237=$2.196 \times 10^{-12}$ M. IC50 for Z238=$2.286 \times 10^{-12}$ M. The TTR expression levels were normalized to PPIB expression levels.

DETAILED DESCRIPTION

Figure 1:
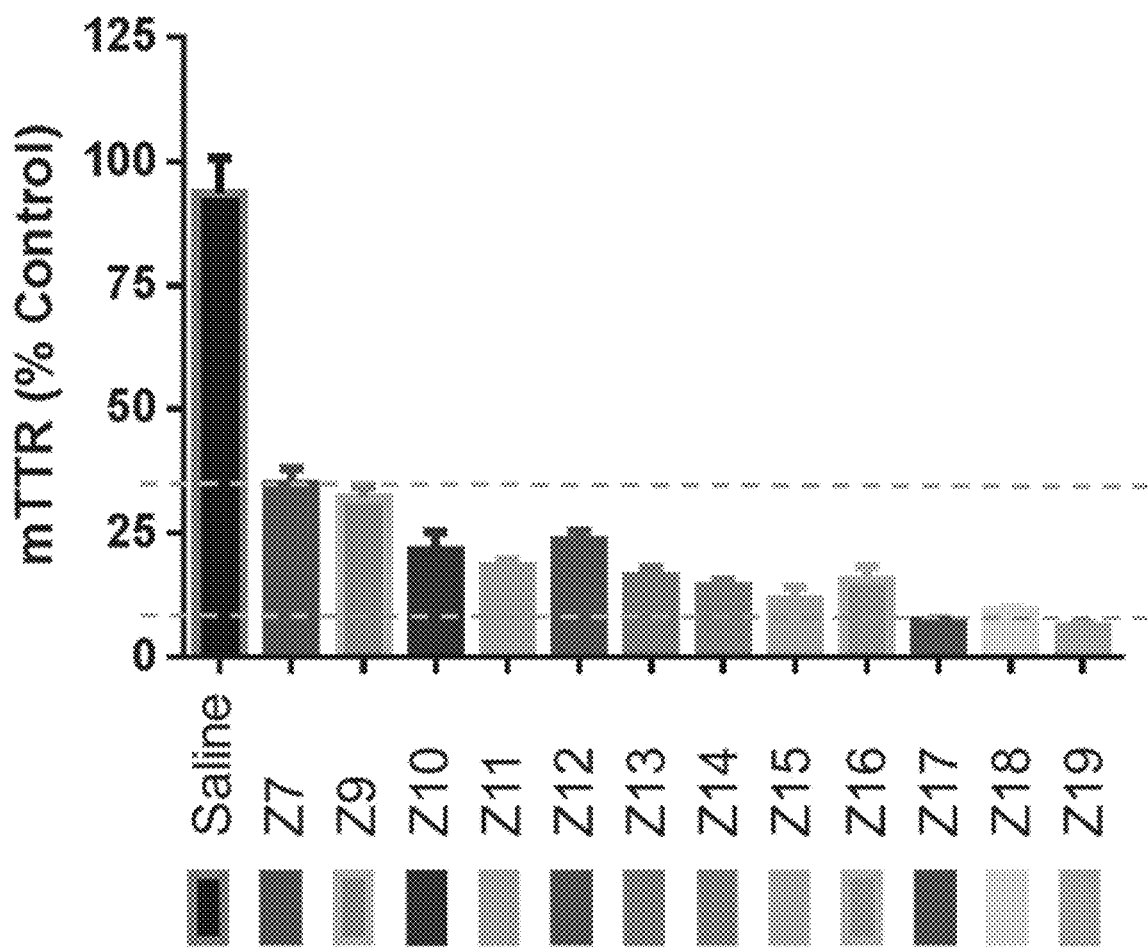
FIG. 1 is a chart showing the mTTR serum levels in mice measured 6 days after a single 0.7 mg/kg subcutaneous dosing of the mice with the tested compositions. The data are normalized to the mTTR serum levels observed after subcutaneous administration of saline.
Figure 2:
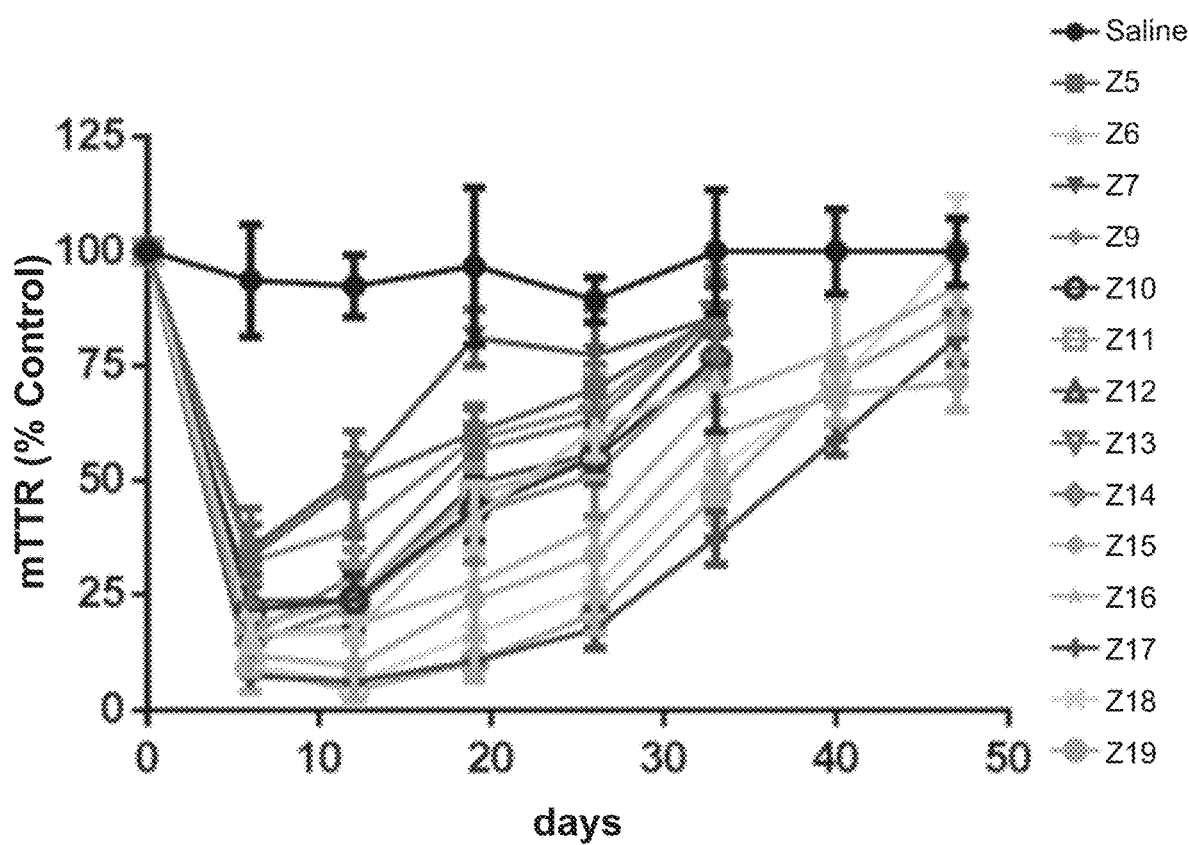
FIG. 2 is a chart showing the mTTR serum levels in mice measured at predetermined time periods after a single 0.7 mg/kg subcutaneous dosing of the mice with the tested compositions. The data are normalized to the mTTR serum levels observed after subcutaneous administration of saline.
Figure 3:
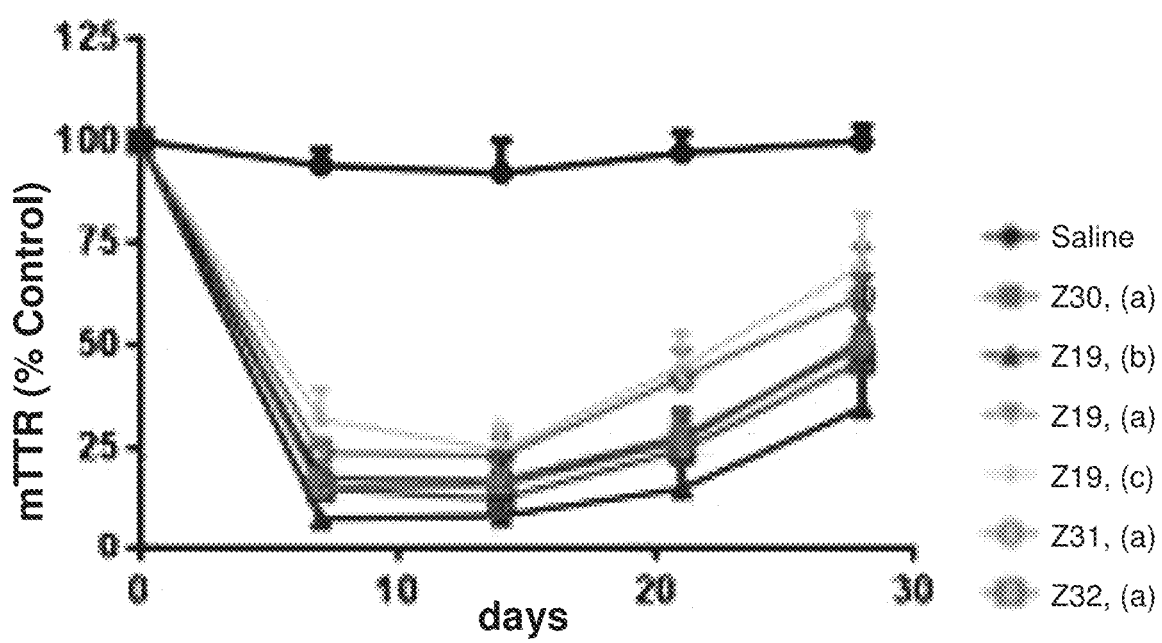
FIG. 3 is a chart showing the mTTR serum levels in mice measured at predetermined time periods after subcutaneous administration of a predetermined amount of the tested compositions to the mice. The data are normalized to the mTTR serum levels observed after subcutaneous administration of saline. In this chart, the dosages are identified as (a), (b), and (c), where (a) represents 0.5 mg/kg dosing, (b) represents 1.0 mg/kg dosing, and (c) represents 0.25 mg/kg dosing.
Figure 4:
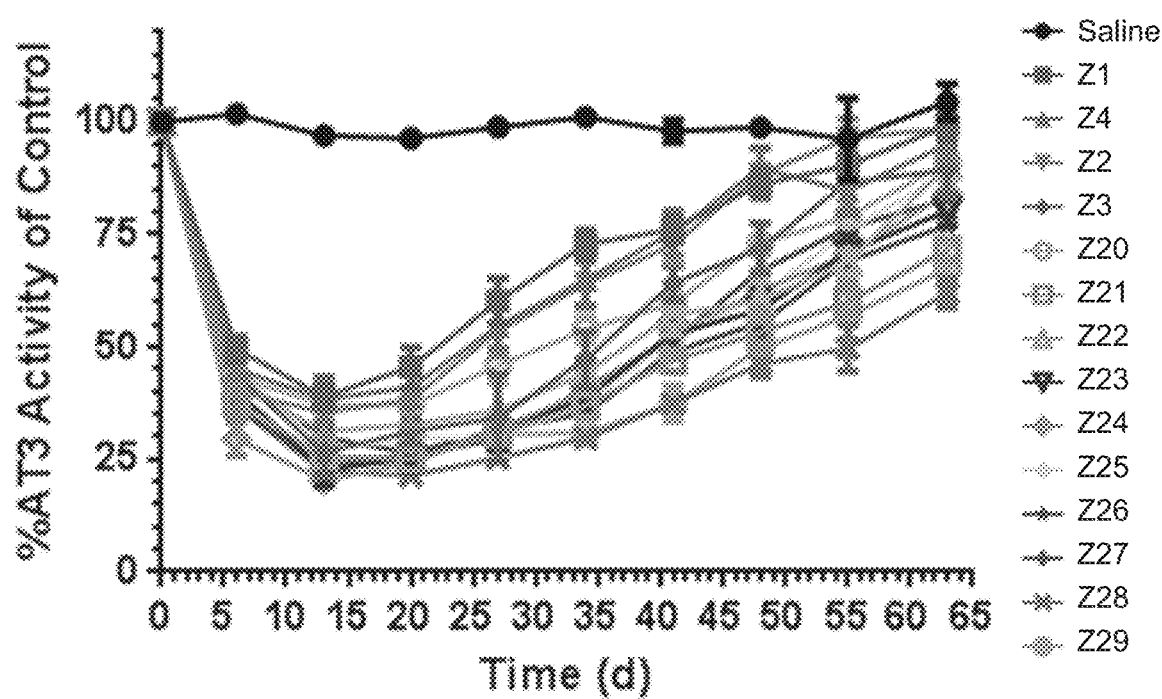
FIG. 4 is a chart showing AT3 activity in mice measured at predetermined time periods after a single 0.4 mg/kg subcutaneous dosing of the mice with the tested compositions. The data are normalized to the AT3 activity observed in mice after subcutaneous administration of saline.
Figure 5:
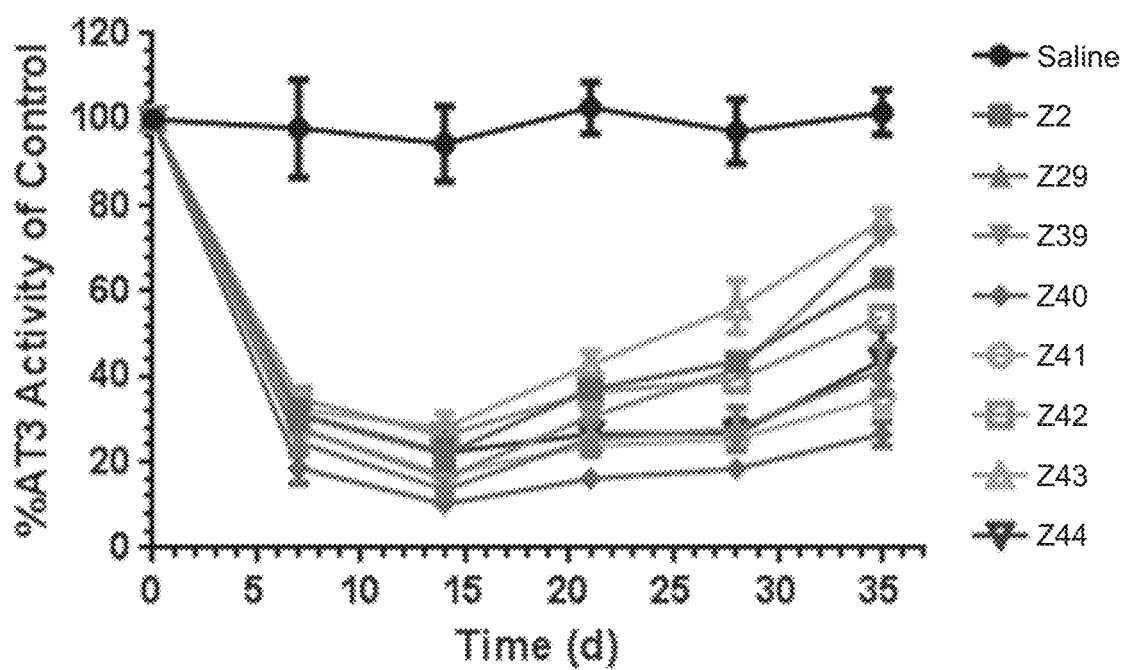
FIG. 5 is a chart showing AT3 activity in mice measured at predetermined time periods after a single 0.5 mg/kg subcutaneous dosing of the mice with the tested compositions. The data are normalized to the AT3 activity observed in mice after subcutaneous administration of saline.
Figure 6:
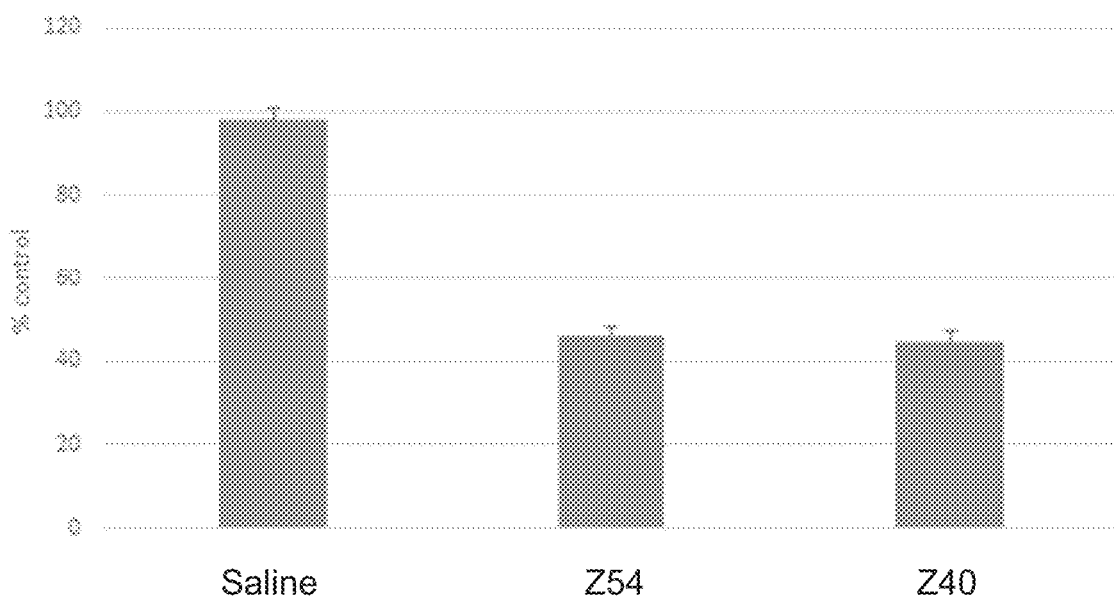
FIG. 6 is a chart showing AT3 activity in mice measured 7 days after a single 0.25 mg/kg subcutaneous dosing of the mice with the tested compositions.
Figure 7:
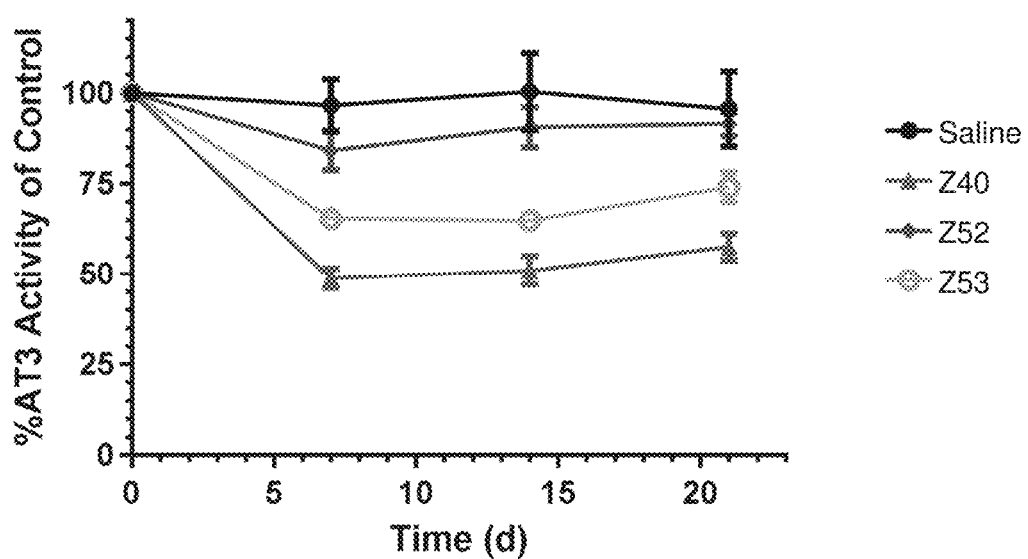
FIG. 7 is a chart showing AT3 activity in mice measured at predetermined time periods after a single 0.125 mg/kg subcutaneous dosing of the mice with the tested compositions.

In general, the invention provides polynucleotide constructs, e.g., having a polynucleotide linked to a branched moiety carrying one or more auxiliary moieties. The polynucleotide constructs may be provided as hybridized polynucleotide constructs.

The polynucleotide constructs of the invention may exhibit a superior activity, an extended duration of action, and/or reduced off-target effects (e.g., reduced off-target cytotoxicity). In particular, inclusion of at least one group of formula (I); one or more internucleoside, abasic spacers; stereochemically enriched internucleoside phosphorothioates; and/or 2'-substitution pattern in the polynucleotide construct of the invention may provide one or more of these effects.

A polynucleotide construct of the invention may contain a strand bonded to at least one group of formula (I):

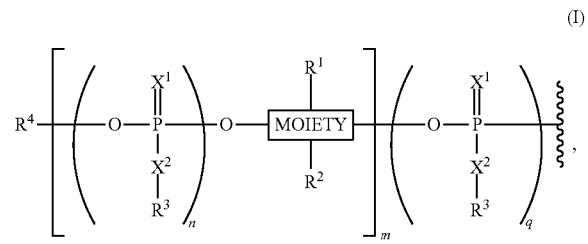

or a salt thereof, or a stereoisomer thereof,
where
each $X^1$ is independently O or S;
each $X^2$ is independently O, S, NH, or a bond;
MOIETY is optionally substituted $C_{2-10}$ alkane-tetrayl or a group -$M^1$-$M^2$-$M^3$-, wherein each $M^1$ and each $M^3$ is independently absent or optionally substituted $C_{1-6}$ alkylene, and $M^2$ is optionally substituted $C_{3-9}$ heterocycle-tetrayl, optionally substituted $C_{6-10}$ arene-tetrayl, or optionally substituted $C_{3-8}$ cycloalkane-tetrayl;
each $R^1$ and each $R^2$ is independently H, optionally substituted $C_{1-16}$ alkyl, optionally substituted $C_{2-16}$ heteroalkyl, a conjugation moiety, or -LinkA(-T)$_p$, provided that at least one $R^1$ or at least one $R^2$ is a conjugation moiety or -LinkA(-T)$_p$;
each $R^3$ is independently H, optionally substituted $C_{1-16}$ alkyl, optionally substituted $C_{2-16}$ heteroalkyl, optionally substituted $C_{2-16}$ alkenyl, optionally substituted $C_{2-16}$ alkynyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl, a conjugation moiety, or -LinkA$(-T)_p$;

$R^4$ is H, optionally substituted $C_{1-6}$ alkyl, -LinkA$(-T)_p$, or -Sol;

each LinkA is independently a multivalent linker (e.g., including —C(O)—N(H)— (e.g., at least one multivalent linker including —C(O)—N(H)— bonded to T));

each T is independently an auxiliary moiety;

Sol is solid support;

m is an integer from 1 to 6;

each n is independently 0 or 1;

each p is independently an integer from 1 to 6; and q is an integer from 0 to 3.

The at least one group of formula (I) may be bonded to a 5-terminus, 3-terminus, internucleoside phosphate, internucleoside phosphorothioate, or internucleoside phosphorodithioate of the polynucleotide. When the at least one group of formula (I) is bonded to an internucleoside phosphate, internucleoside phosphorothioate, or internucleoside phosphorodithioate, q is 0. The polynucleotide construct contains no more than one Sol.

A polynucleotide construct of the invention may contain an internucleoside, abasic spacer. The internucleoside, abasic spacer may be of formula (III):

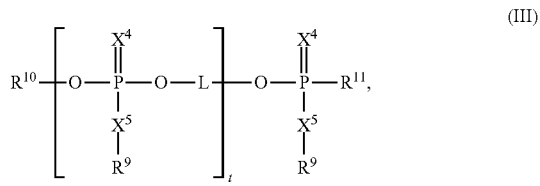

(III)

where

L is a sugar analogue;

each $X^4$ is independently O or S;

each $X^5$ is independently O, S, NH, or a bond;

each $R^9$ is independently H, optionally substituted $C_{1-6}$ alkyl, optionally substituted $C_{2-6}$ alkenyl, optionally substituted $C_{2-6}$ alkynyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl, -LinkA$(-T)_p$, or a conjugation moiety;

each LinkA is independently a multivalent linker (e.g., including —C(O)—N(H)—);

each T is independently an auxiliary moiety;

$R^{10}$ is a bond to a 3'-carbon atom of a nucleoside (x) in the strand;

$R^{11}$ is a bond to a 5'-oxygen atom of a nucleoside (x+t+1) in the strand;

p is an integer from 1 to 6; and t is an integer from 1 to 6.

A polynucleotide construct containing an internucleoside, abasic spacer may exhibit reduced off-target effects, when the polynucleotide construct is a guide strand in siRNA. In particular, an internucleoside, abasic spacer (e.g., an internucleotide, abasic spacer of formula (III) in which t is 1) may be included in a guide strand (e.g., within the seed region of the guide strand). In some embodiments, an internucleoside, abasic spacer (e.g., an internucleotide, abasic spacer of formula (III) in which t is 1) may be bonded to the 3' carbon atom of the second, third, fourth, or fifth nucleoside of a guide strade. In certain embodiments, an internucleoside, abasic spacer (e.g., an internucleotide, abasic spacer of formula (III) in which t is 1) may be bonded to the 3' carbon atom of the thirteenth, fourteenth, fifteenth, or sixteenth nucleoside of a guide strade.

A polynucleotide construct of the invention may include a high content of 2'-alkoxy nucleosides (e.g., at least 80% of nucleosides in the polynucleotide construct may be independently 2'-alkoxy nucleosides). Such polynucleotide constructs of the invention may include a 2'-substitution pattern, in which at least one of the second, twelfth, fourteenth, and sixteenth nucleosides is a 2'-fluoro nucleoside and the remaining nucleosides are independently 2'-alkoxy nucleosides. In some embodiments, the second, twelfth, fourteenth, and sixteenth nucleosides or the twelfth, fourteenth, and sixteenth nucleosides are independently 2'-fluoro nucleoside and the remaining nucleosides are independently 2'-alkoxy nucleosides. In other embodiments, the seventh, ninth, and/or eleventh nucleoside in the strand is a 2'-fluoro nucleoside. Polynucleotide constructs of the invention having a high content of 2'-alkoxy nucleosides (e.g., those having the 2'-substitution pattern described herein) may exhibit superior efficacy and/or extended duration of action, when the polynucleotide construct is a guide strand in siRNA.

In a composition, the polynucleotide constructs of the invention may contain one or more (e.g., from 1 to 20, from 1 to 10, or from 1 to 5) stereochemically enriched (e.g., internucleoside) phosphorothioates (e.g., having diastereomeric excess of at least 10%, at least 50%, at least 60%, at least 70%, at least 80%, or at least 90%, e.g., up to about 99%, for the P-stereogenic center). The polynucleotide constructs of the invention may contain one or more (e.g., from 1 to 20, from 1 to 10, or from 1 to 5; e.g., internucleoside) phosphorodithioates. The phosphorodithioates may be non-P-stereogenic in the polynucleotide constructs of the invention. Phosphorothioates and phosphorodithioates may enhance the stability of the polynucleotide construct to exonuclease activity of serum. Non-P-stereogenic phosphorodithioates may simplify the synthesis of the polynucleotide constructs of the invention by reducing the number of possible diastereomers. Typically, the phosphorothioate or phosphorodithioate may connect two contiguous nucleosides within the six 3'-terminal nucleosides and the six 5'-terminal nucleosides of a polynucleotide construct of the invention. In the polynucleotide construct, the strand may have 19 or more nucleosides. The strand may have fewer than 100 nucleosides (e.g., fewer than 50 nucleosides or fewer than 32 nucleosides). When the polynucleotide construct is a guide strand, the stereochemically enriched phosphorothioate (e.g., $R_P$-enriched phosphorothioate) may be covalently bonded to the first nucleoside (e.g., the 3'-carbon atom of the first nucleoside) and the second nucleoside (e.g., the 5'-carbon atom of the second nucleoside). Additionally or alternatively, when the polynucleotide construct is a guide strand, the stereochemically enriched phosphorothioate (e.g., $R_P$-enriched phosphorothioate) may be covalently bonded to the $2^{nd}$ nucleoside (e.g., the 3'-carbon atom of the $2^{nd}$ nucleoside) and the $3^{rd}$ nucleoside (e.g., the 5'-carbon atom of the $3^{rd}$ nucleoside). Additionally or alternatively, when the polynucleotide construct is a guide strand, the stereochemically enriched phosphorothioate (e.g., $S_P$-enriched phosphorothioate) may be covalently bonded to the $21^{st}$ nucleoside (e.g., the 3-carbon atom of the $21^{st}$ nucleoside) and the $22^{nd}$ nucleoside (e.g., the 5'-carbon atom of the $22^{nd}$ nucleoside). Further, additionally or alternatively, when the polynucleotide construct is a guide strand, the stereochemically enriched phosphorothioate (e.g., SP-enriched phosphorothioate) may be covalently bonded to the $22^{nd}$ nucleoside (e.g., the 3-carbon atom of the $22^{nd}$ nucleoside)

and the 23$^{rd}$ nucleoside (e.g., the 5'-carbon atom of the 23$^{rd}$ nucleoside). Combinations of a 5' R$_P$-enriched phosphorothioate (e.g., R$_P$-enriched phosphorothioate covalently bonded to the first nucleoside (e.g., the 3'-carbon atom of the first nucleoside) and the second nucleoside (e.g., the 5'-carbon atom of the second nucleoside) and a 3' SP-enriched phosphorothioate (e.g., SP-enriched phosphorothioate covalently bonded to the 21$^{st}$ nucleoside (e.g., the 3'-carbon atom of the 21$^{st}$ nucleoside) and the 22$^{nd}$ nucleoside (e.g., the 5'-carbon atom of the 22$^{nd}$ nucleoside)) in a guide strand can produce superior efficacy and/or duration of action, e.g., as measured by the reduction in the activity of the target relative to a reference guide strand that lacks the combination of a 5' R$_P$-enriched phosphorothioate and a 3' S$_P$-enriched phosphorothioate. The invention also provides a hybridized polynucleotide containing a passenger strand and a guide strand loadable into a RISC complex. At least one of the strands may be bonded to the group of formula (I). Such polynucleotide constructs may exhibit a more potent activity relative to polynucleotide constructs having the same number of auxiliary moieties. For example, as illustrated in FIG. 1, hybridized polynucleotide constructs Z18 and Z19 suppress gene expression more efficiently per administered unit relative to hybridized polynucleotide constructs Z7 and Z9. Such polynucleotide constructs may also exhibit a prolonged activity relative to polynucleotide constructs having the same number of auxiliary moieties. For example, as illustrated in FIG. 1, hybridized polynucleotide constructs Z18 and Z19 suppress gene expression for a longer period of time per administered unit relative to hybridized polynucleotide constructs Z7 and Z9.

The hybridized polynucleotide construct may include a guide strand having 19 or more nucleosides. The guide strand may have fewer than 100 nucleosides (e.g., fewer than 50 nucleosides or fewer than 32 nucleosides). The hybridized polynucleotide construct may include a passenger strand having 19 or more nucleosides. The passenger strand may have fewer than 100 nucleosides (e.g., fewer than 50 nucleosides or fewer than 32 nucleosides). In some embodiments, each of the passenger and guide strands will independently include from 19 to 50 nucleosides (e.g., from 19 to 32 nucleoside). The passenger and guide strands can be complimentary to each other over at least 8 contiguous nucleosides (e.g., over at least 12 contiguous nucleosides or over at least 15 contiguous nucleosides).

In addition to the moieties described above, the polynucleotide construct may contain one or more of non-bioreversible phosphotriesters, bioreversible phosphotriesters, phosphoramidates, phosphonates. Bioreversible phosphotriesters that may be used in the present polynucleotide constructs are described in, e.g., WO 2015/188197.

Moiety

The polynucleotide constructs of the invention may contain at least one (e.g., 1, 2, 3, or 4) group of formula (I), which includes MOIETY that is optionally substituted C$_{2-10}$ alkane-tetrayl or a group -M$^1$-M$^2$-M$^3$-, wherein each M$^1$ and each M$^3$ is independently absent or optionally substituted C$_{1-6}$ alkylene, and M$^2$ is optionally substituted C$_{3-9}$ heterocycle-tetrayl, optionally substituted C$_{6-10}$ arene-tetrayl, or optionally substituted C$_{3-8}$ cycloalkane-tetrayl. In formula (I), MOIETY, R$^1$, and R$^2$ may combine to form

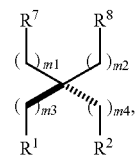
(Ia)

where
R$^7$ is a bond to an oxygen atom that is proximal to R$^4$,
R$^8$ is a bond to an oxygen atom that is proximal to the strand, and
each of m1, m2, m3, and m4 is independently an integer from 0 to 6,
provided that the quaternary carbon in formula (Ia) is bonded to O or 1 atoms other than carbon and hydrogen, and provided that the sum of m1, m2, m3 and m4 is less than 10.

In particular, MOIETY, R$^1$, and R$^2$ may combine to form

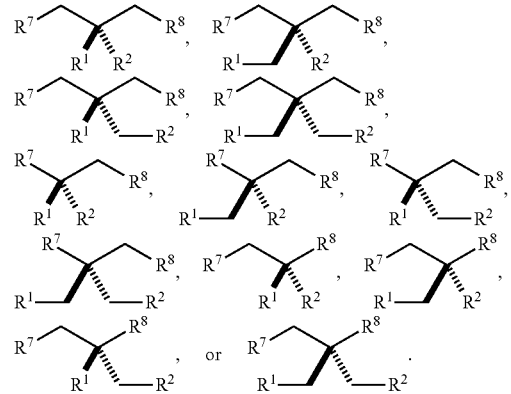

Non-limiting examples of groups formed by the combination of MOIETY, R$^1$, and R$^2$ are:

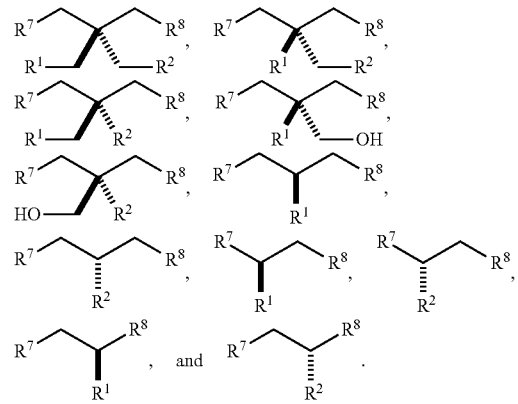

Auxiliary Moieties and LinkA

The polynucleotide constructs of the invention may include an auxiliary moiety (e.g., a targeting moiety) non-bioreversibly linked to MOIETY. The auxiliary moiety is T in group -LinkA(-T)$_p$. Group -LinkA(-T)$_p$ may be bonded to MOIETY or to —X$^2$P(X$^1$)(–)$_2$, where X$^1$ is O or S, and X$^2$ is O, S, NH, or a bond. In some embodiments, X$^1$ is O. In certain embodiments, X$^2$ is O or S (e.g., X$^2$ is O).

Group -LinkA- can include from 0 to 3 multivalent monomers (e.g., optionally substituted $C_{1-6}$ alkane-triyl, optionally substituted $C_{1-6}$ alkane-tetrayl, or trivalent nitrogen atom) and one or more divalent monomers (e.g., from 1 to 40), where each divalent monomer is independently optionally substituted $C_{1-6}$ alkylene; optionally substituted $C_{2-6}$ alkenylene; optionally substituted $C_{2-6}$ alkynylene; optionally substituted $C_{3-8}$ cycloalkylene; optionally substituted $C_{3-8}$ cycloalkenylene; optionally substituted $C_{6-14}$ arylene; optionally substituted $C_{1-9}$ heteroarylene having 1 to 4 heteroatoms selected from N, O, and S; optionally substituted $C_{1-9}$ heterocyclylene having 1 to 4 heteroatoms selected from N, O, and S; imino; optionally substituted N; O; or $S(O)_m$, wherein m is 0, 1, or 2. In some embodiments, each monomer is independently optionally substituted $C_{1-6}$ alkylene; optionally substituted $C_{3-8}$ cycloalkylene; optionally substituted $C_{3-8}$ cycloalkenylene; optionally substituted $C_{6-14}$ arylene; optionally substituted $C_{1-9}$ heteroarylene having 1 to 4 heteroatoms selected from N, O, and S; optionally substituted $C_{1-9}$ heterocyclylene having 1 to 4 heteroatoms selected from N, O, and S; imino; optionally substituted N; O; or $S(O)_m$, where m is 0, 1, or 2 (e.g., m is 2). In certain embodiments, each monomer is independently optionally substituted $C_{1-6}$ alkylene; optionally substituted $C_{3-8}$ cycloalkylene; optionally substituted $C_{3-8}$ cycloalkenylene; optionally substituted $C_{6-14}$ arylene; optionally substituted $C_{1-9}$ heteroarylene having 1 to 4 heteroatoms selected from N, O, and S; optionally substituted $C_{1-9}$ heterocyclylene having 1 to 4 heteroatoms selected from N, O, and S; optionally substituted N; O; or $S(O)_m$, where m is 0, 1, or 2 (e.g., m is 2). The non-bioreversible linker connecting the auxiliary moiety to the conjugating moiety or to the reaction product thereof can include from 2 to 500 (e.g., from 2 to 300 or from 2 to 200) of such monomers. Group -LinkA- may include a poly(alkylene oxide) (e.g., polyethylene oxide, polypropylene oxide, poly(trimethylene oxide), polybutylene oxide, poly(tetramethylene oxide), and diblock or triblock copolymers thereof). In some embodiments, the non-bioreversible linker includes polyethylene oxide (e.g., poly(ethylene oxide) having a molecular weight of less than 1 kDa).

Group -LinkA(-T)$_p$ in formula (I) may be prepared by a process described in the sections below. In some instances, -LinkA(-T)$_p$ is of formula (II):

$$-Q^1-Q^2([-Q^3-Q^4-Q^5]_s-Q^6-T)_p,\quad (II)$$

where
each s is independently an integer from 0 to 20 (e.g., from 0 to 10), where the repeating units are the same or different;
$Q^1$ is a conjugation linker (e.g., [-Q$^3$-Q$^4$-Q$^5$]$_s$-Q$^C$-, where $Q^C$ is optionally substituted $C_{2-12}$ heteroalkylene (e.g., a heteroalkylene containing —C(O)—N(H)—, —N(H)—C(O)—, —S(O)$_2$—N(H)—, or —N(H)—S(O)$_2$—), optionally substituted $C_{1-12}$ thioheterocyclylene (e.g.,

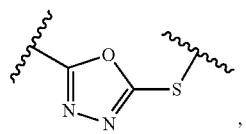

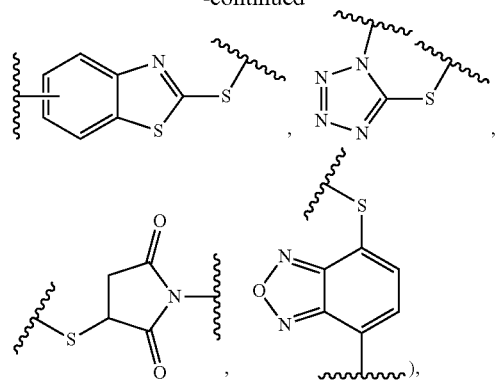

optionally substituted $C_{1-12}$ heterocyclylene (e.g., 1,2,3-triazole-1,4-diyl or

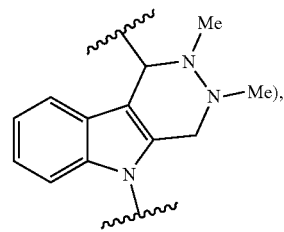

cyclobut-3-ene-1,2-dione-3,4-diyl, or pyrid-2-yl hydrazone);
$Q^2$ is a linear group (e.g., [-Q$^3$-Q$^4$-Q$^5$]$_s$-), if p is 1, or a branched group (e.g., [-Q$^3$-Q$^4$-Q$^5$]$_s$-Q$^7$([-Q$^3$-Q$^4$-Q$^5$]$_s$-(Q$^7$)$_{p1}$)$_{p2}$, where p1 is 0 or 1, p2 is 0, 1, 2, or 3), if p is an integer from 2 to 6;
each $Q^3$ and each $Q^6$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—;
each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, optionally substituted $C_{6-10}$ arylene, optionally substituted $C_{1-9}$ heteroarylene, or optionally substituted $C_{1-9}$ heterocyclylene;
each $Q^5$ is independently absent, —CO—, —NH—, —O—, —S—, —SO$_2$—, —CH$_2$—, —C(O)O—, —OC(O)—, —C(O)NH—, —NH—C(O)—, —NH—CH(R$^a$)—C(O)—, or —C(O)—CH(R$^a$)—NH—;
each $Q^7$ is independently optionally substituted $C_{1-6}$ alkane-triyl, optionally substituted $C_{1-6}$ alkane-tetrayl, optionally substituted $C_{2-6}$ heteroalkane-triyl, or optionally substituted $C_{2-6}$ heteroalkane-tetrayl; and
each R$^a$ is independently H or an amino acid side chain; provided that at least one of $Q^3$, $Q^4$, and $Q^5$ is present.

In some embodiments, each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene. In certain embodiments, s is 1, 2, 3, 4, 5, 6, 7, 8, 9, 10, 11, 12, 13, 14, 15, 16, 17, 18, 19, or 20.

Thus, in formula (II), LinkA may include a single branching point, if each p1 is 0, or multiple branching points, if at least one p1 is 1.

In formula (II), $Q^1$ may be $-O-Q^L-Q^C$ where $Q^L$ is optionally substituted $C_{2-12}$ heteroalkylene, optionally substituted $C_{1-12}$ alkylene, or -(optionally substituted $C_{1-6}$ alkylene)-(optionally substituted $C_{6-10}$ arylene)-. In some embodiments, $Q^L$ is optionally substituted $C_{2-12}$ heteroalkylene or optionally substituted $C_{1-12}$ alkylene. In formula (II), $Q^C$ may be:

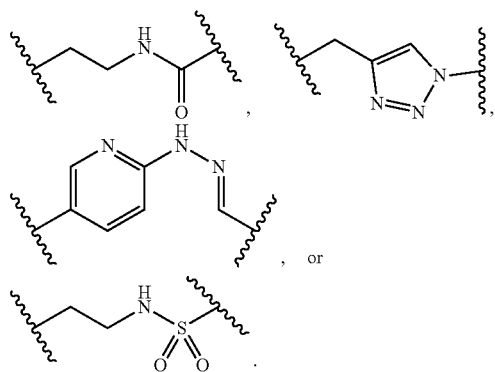

In formula (II), $Q^2$ may be a linear group of formula $[-Q^3-Q^4-Q^5]_s-$, where $Q^3$, $Q^4$, and $Q^5$ are as defined for formula (II). Alternatively, $Q^2$ may be a branched group $[-Q^3-Q^4-Q^5]_s-Q^7([-Q^3-Q^4-Q^5]_s-(Q^7)_{p1})_{p2}$, where each $Q^7$ is independently optionally substituted $C_{1-6}$ alkane-triyl, optionally substituted $C_{1-6}$ alkane-tetrayl, optionally substituted $C_{2-6}$ heteroalkane-triyl, or optionally substituted $C_{2-6}$ heteroalkane-tetrayl;

where
p1 is 0 or 1;
p2 is 0, 1, 2, or 3;
where,
when p1 is 0, LinkA is a trivalent or tetravalent linker, and,
when p1 is 1, LinkA is a tetravalent, pentavalent, or hexavalent linker.

In certain embodiments, p1 is 0.
In some embodiments, $Q^7$ is:

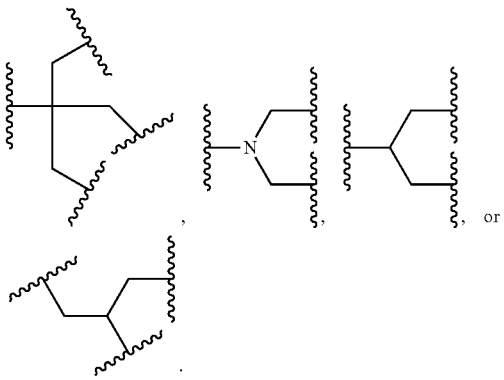

Compounds that may be used in the preparation of group -LinkA(-T)$_p$ in formula (I) are described herein as well as in WO 2015/188197. Non-limiting examples of -LinkA include:

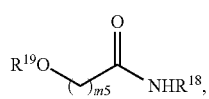

(i)

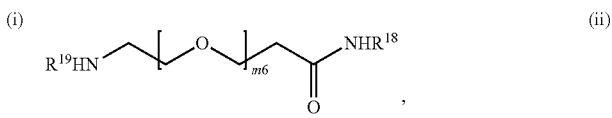

(ii)

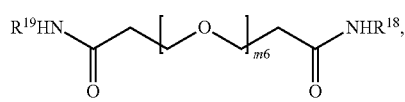

(iii)

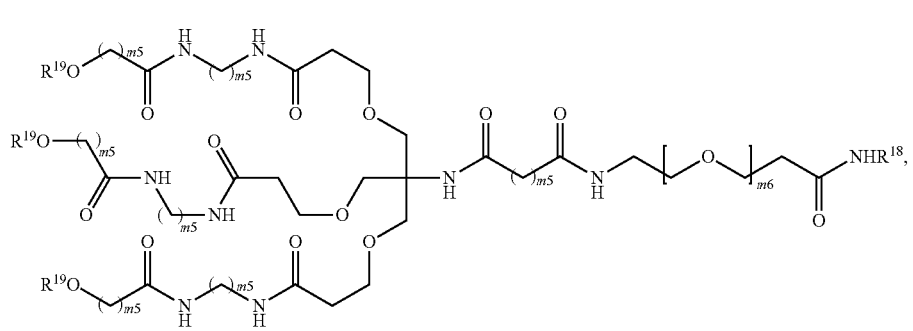

(iv)

-continued
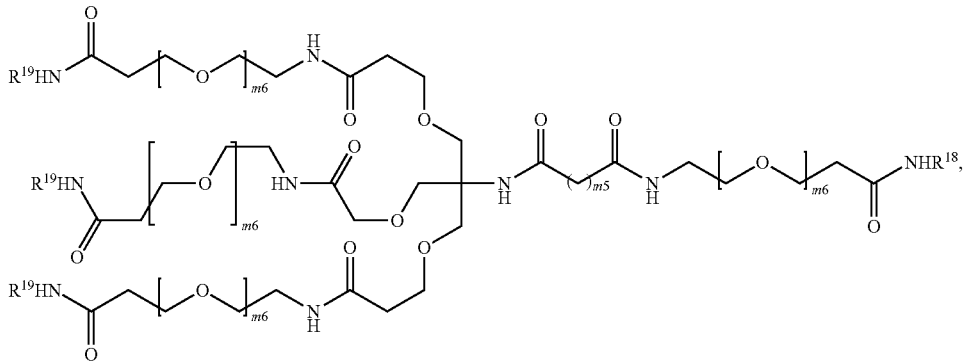
(v)
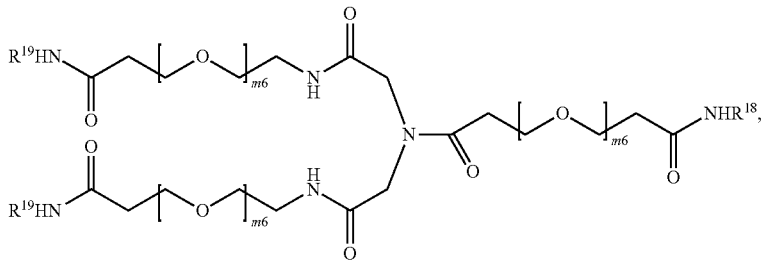
(vi)
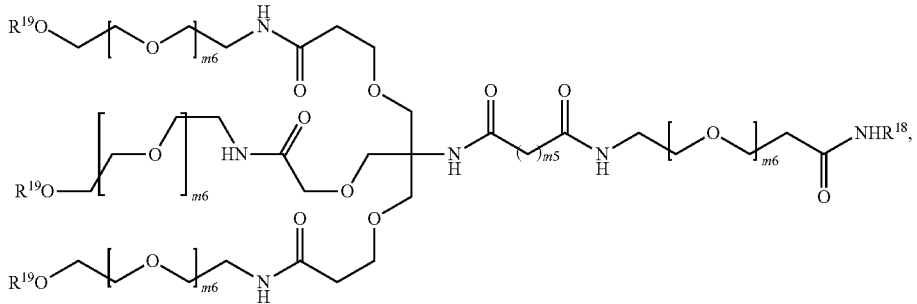
(vii)
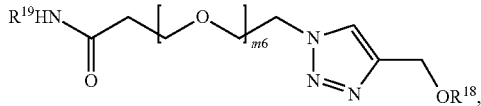
(viii)
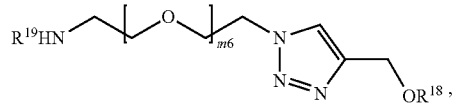
(ix)
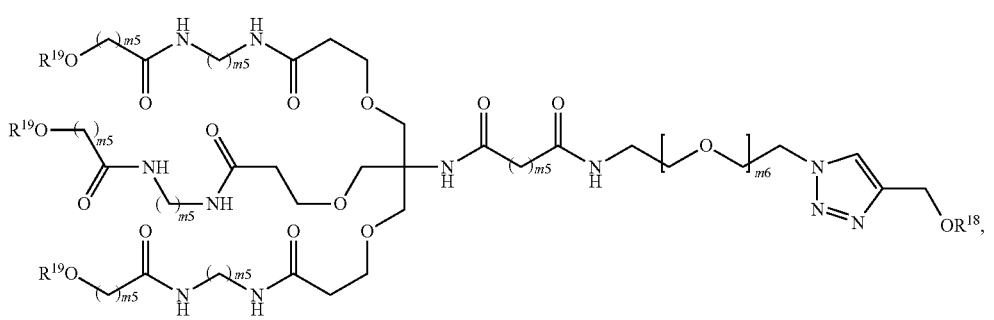
(x)

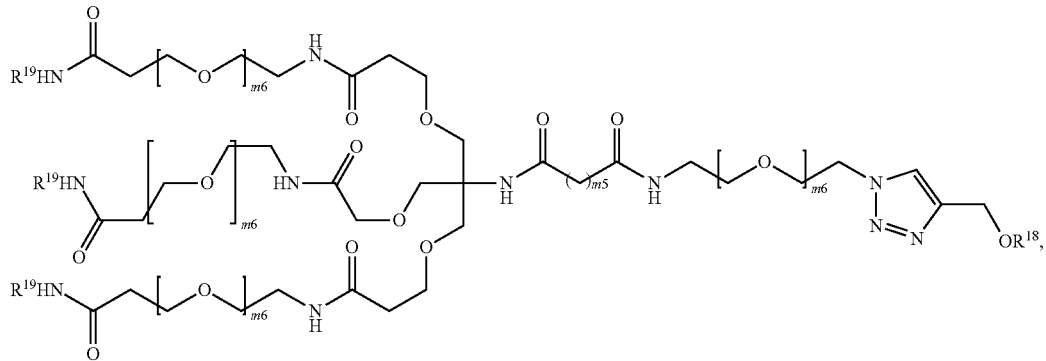
(xi)
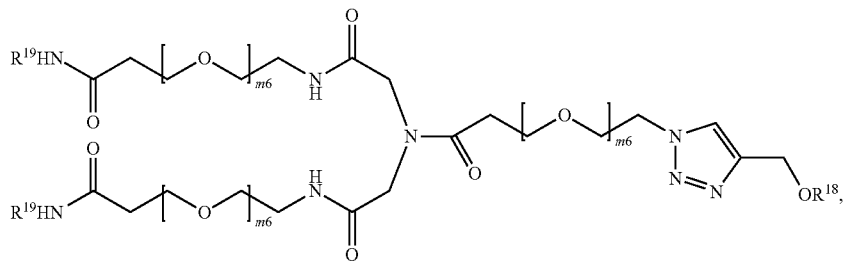
(xii)
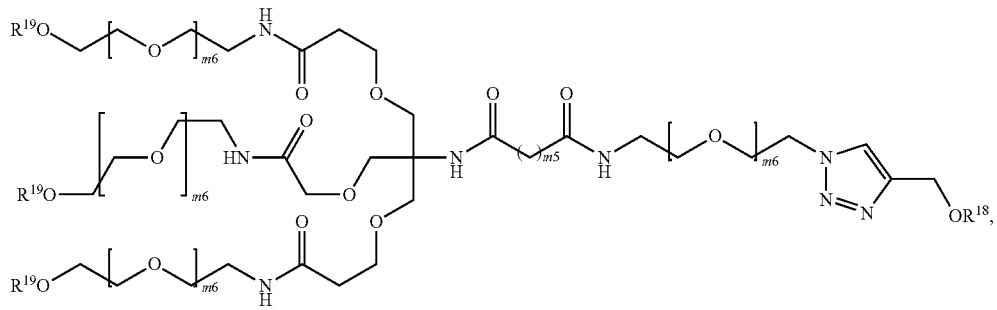
(xiii)
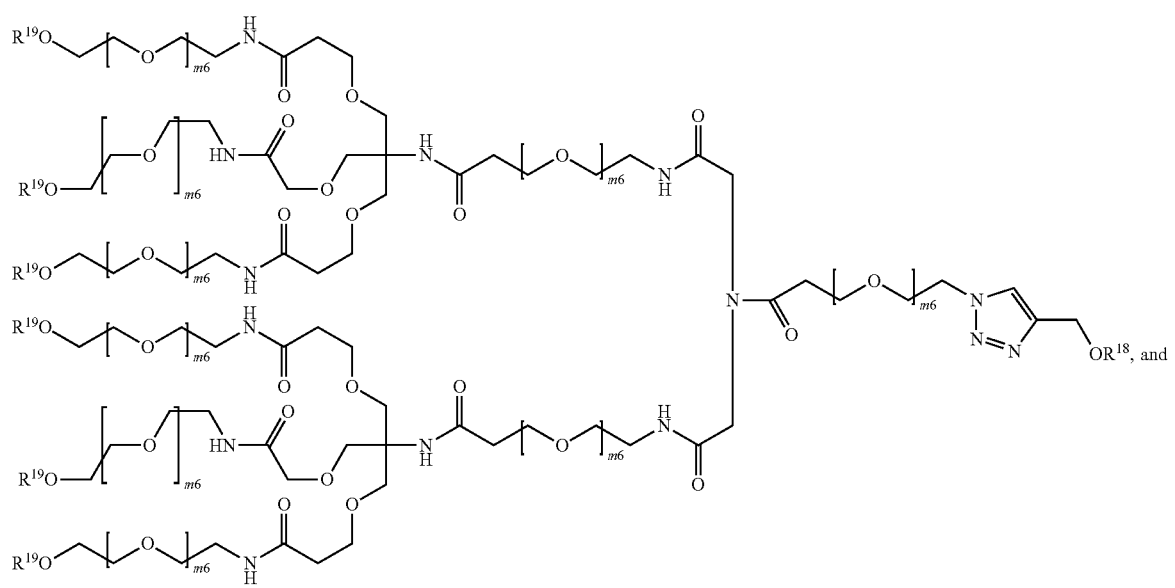
(xiv)

-continued
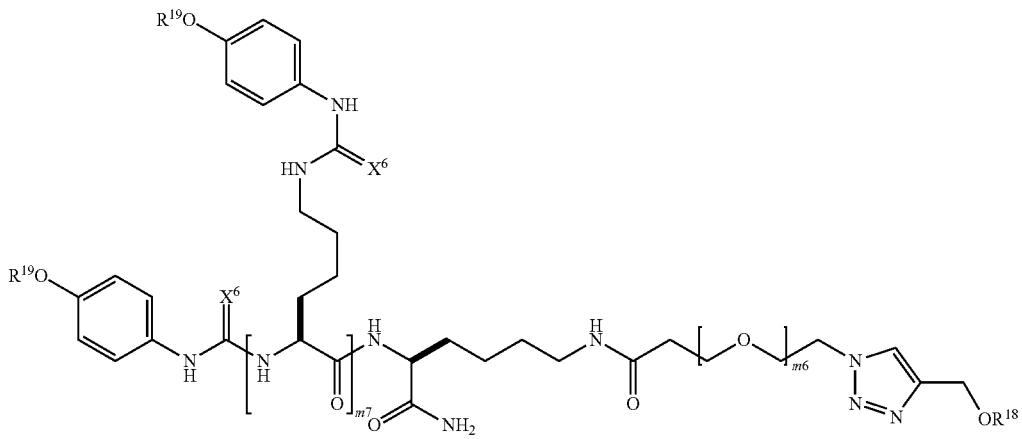
(xv)
where
R[18] is a bond to MOIETY,
each R[19] is independently a bond to auxiliary moiety,
each m5 is independently an integer from 1 to 20,
each m6 is independently an integer from 1 to 10,
m7 is an integer from 1 to 6, and
each X[6] is independently O or S.
In formula (II), when the conjugation linker is of formula $[-Q^3-Q^4-Q^5]_s-Q^C-$, $-Q^2([-Q^3-Q^4-Q^5]_s-Q^6-T)_p$ may be:
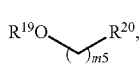
(xvi)
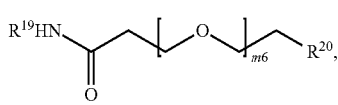
(xvii)
(xviii)
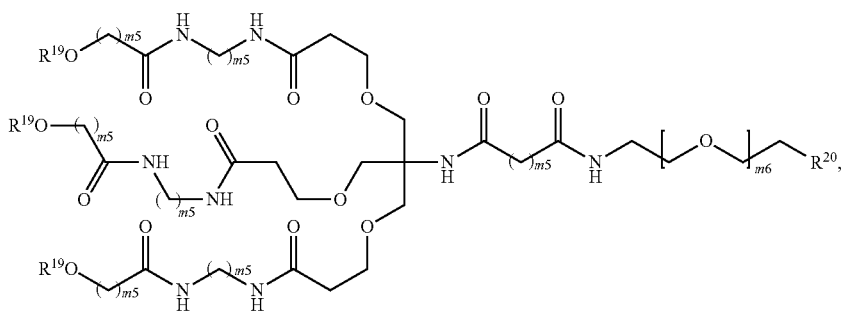
(xix)
(xx)
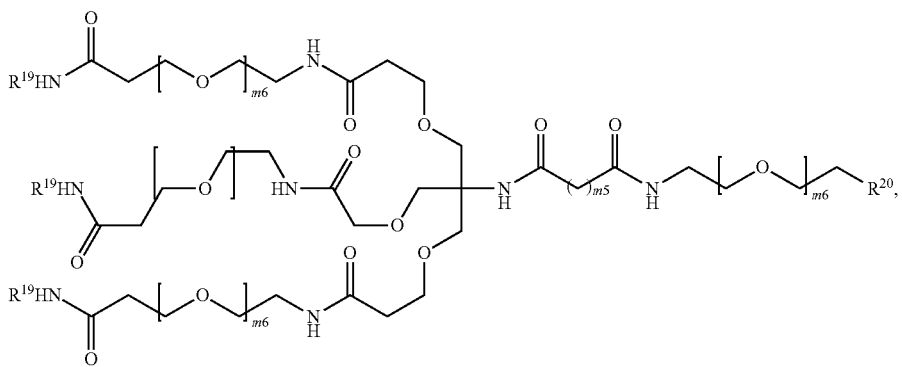

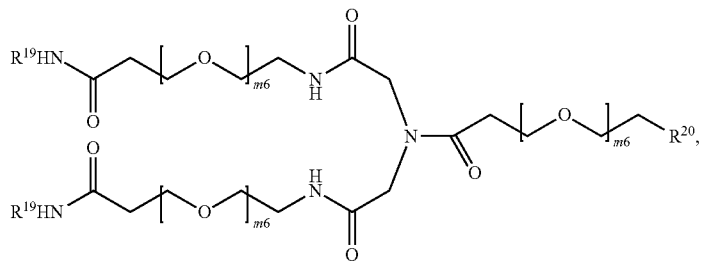
(xxi)
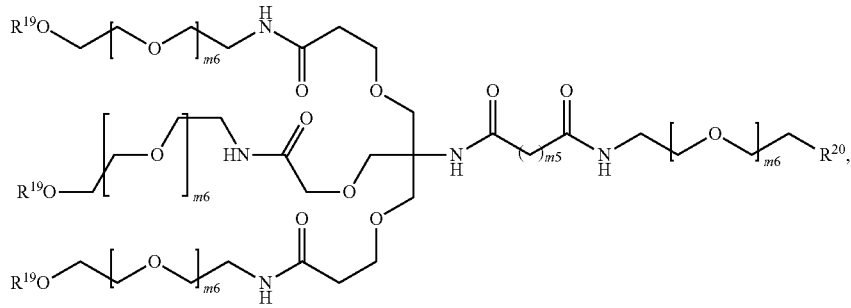
(xxii)
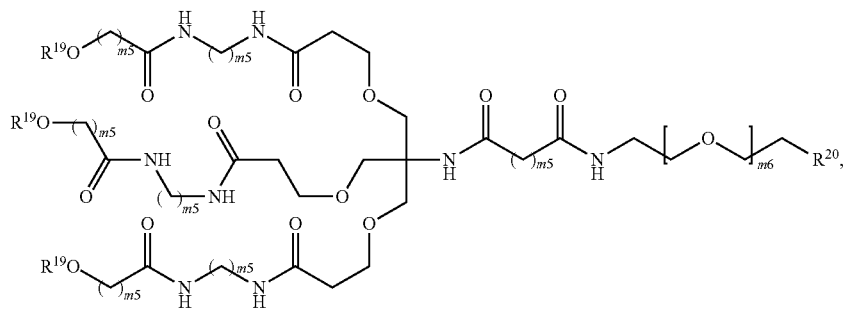
(xxiii)
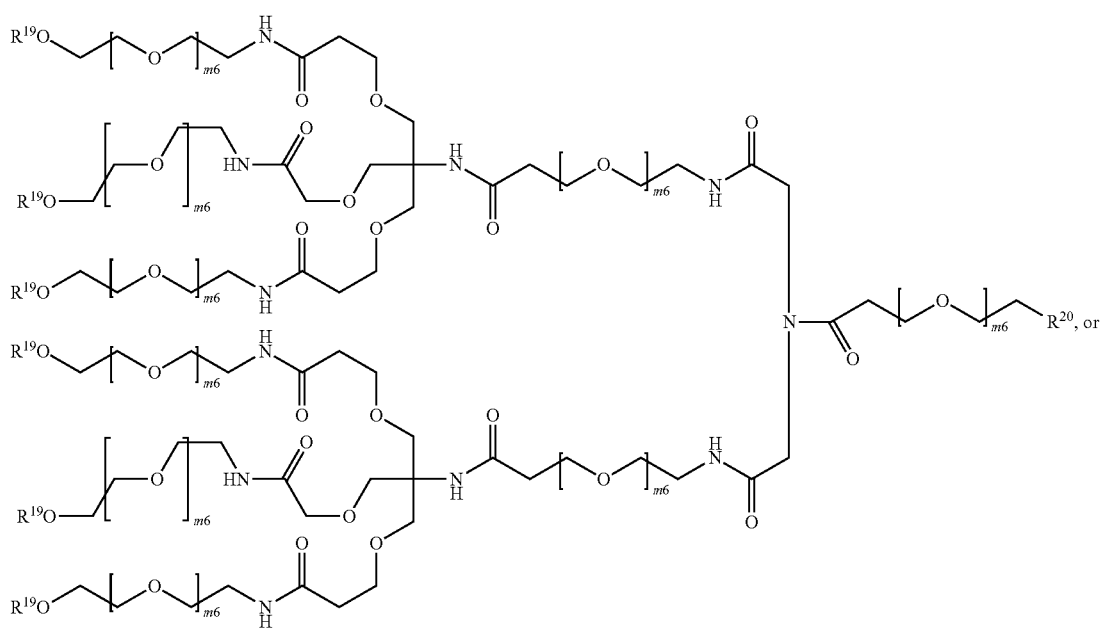
(xxiv)

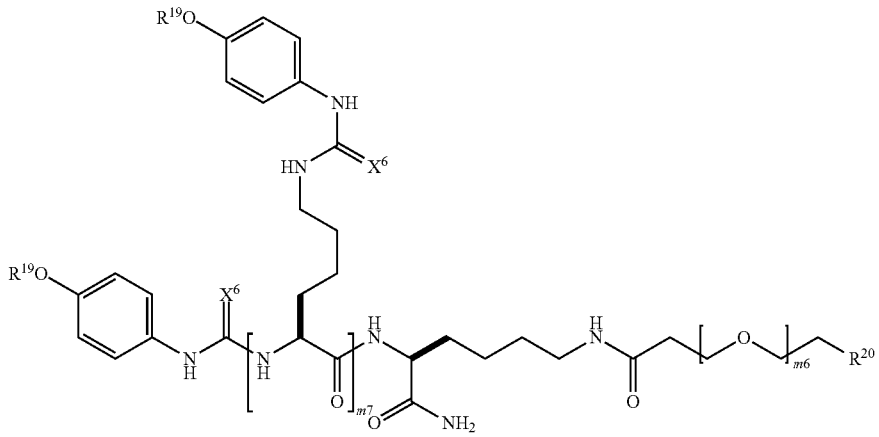

(xxv)

where
R$^{20}$ is a bond to Q$^C$ in Q$^1$,
each R$^{19}$ is independently a bond to an auxiliary moiety,
each m5 is independently an integer from 1 to 20,
each m6 is independently an integer from 1 to 10,
m7 is an integer from 1 to 6, and
each X$^6$ is independently O or S.

Various auxiliary moieties can be conjugated to the polynucleotide constructs of the invention, and the auxiliary moieties can provide desirable biological or chemical effects. Biological effects include, but are not limited to, inducing intracellularization, binding to a cell surface, targeting a specific cells type, allowing endosomal escape, altering the half-life of the polynucleotide in vivo, and providing a therapeutic effect. Chemical effects include, but are not limited to, changing the solubility, charge, size, and reactivity. The auxiliary moieties that may be used in the preparation of group -LinkA(-T)$_p$ in formula (I) are described herein as well as in WO 2015/188197.

Targeting Moieties

The polynucleotide constructs of the invention and the hybridized polynucleotide constructs of the invention may include one or more targeting moieties as auxiliary moieties. A targeting moiety is selected based on its ability to target constructs of the invention to a desired or selected cell population that expresses the corresponding binding partner (e.g., either the corresponding receptor or ligand) for the selected targeting moiety. For example, a construct of the invention could be targeted to hepatocytes expressing asialoglycoprotein (ASGP-R) by selecting a targeting moiety containing N-acetyl galactosamine (GalNAc) as the targeting moiety. A targeting moiety (i.e., an intracellular targeting moiety) that targets a desired site within the cell (e.g., endoplasmic reticulum, Golgi apparatus, nucleus, or mitochondria) may be included in the hybridized polynucleotide constructs disclosed herein. Non-limiting examples of the intracellular targeting moieties are provided in WO 2015/069932 and in WO 2015/188197; the disclosure of the intracellular targeting moieties in WO 2015/069932 and in WO 2015/188197 is incorporated herein by reference.

A construct of the invention, thus, may include one or more targeting moieties selected from the group consisting of intracellular targeting moieties, extracellular targeting moieties, and combinations thereof. Thus, the inclusion of one or more targeting moieties (e.g., extracellular targeting moieties including targeting moieties independently selected from the group consisting of folate, mannose, N-acetyl galactosamine, and prostate specific membrane antigen) and one or more intracellular targeting moiety (e.g., a moiety targeting endoplasmic reticulum, Golgi apparatus, nucleus, or mitochondria) in the polynucleotide construct of the invention can facilitate the delivery of the polynucleotides to a specific site within the specific cell population. In some embodiments, the targeting moiety contains one or more mannose carbohydrates. Mannose targets the mannose receptor, which is a 175 KDa membrane-associated receptor that is expressed on sinusoidal liver cells and antigen presenting cells (e.g., macrophages and dendritic cells). It is a highly effective endocytotic/recycling receptor that binds and internalizes mannosylated pathogens and proteins (Lennartz et. al. *J. Biol. Chem.* 262:9942-9944, 1987; Taylor et. al. *J. Biol. Chem.* 265:12156-62, 1990).

Some of the targeting moieties of the invention are described herein. In some embodiments, the targeting moiety contains or specifically binds to a protein selected from the group including insulin, insulin-like growth factor receptor 1 (IGF1R), IGF2R, insulin-like growth factor (IGF; e.g., IGF 1 or 2), mesenchymal epithelial transition factor receptor (c-met; also known as hepatocyte growth factor receptor (HGFR)), hepatocyte growth factor (HGF), epidermal growth factor receptor (EGFR), epidermal growth factor (EGF), heregulin, fibroblast growth factor receptor (FGFR), platelet-derived growth factor receptor (PDGFR), platelet-derived growth factor (PDGF), vascular endothelial growth factor receptor (VEGFR), vascular endothelial growth factor (VEGF), tumor necrosis factor receptor (TNFR), tumor necrosis factor alpha (TNF-α), TNF-β, folate receptor (FOLR), folate, transferrin, transferrin receptor (TfR), mesothelin, Fc receptor, c-kit receptor, c-kit, an integrin (e.g., an α4 integrin or a β-1 integrin), P-selectin, sphingosine-1-phosphate receptor-1 (S1PR), hyaluronate receptor, leukocyte function antigen-1 (LFA-1), CD4, CD11, CD18, CD20, CD25, CD27, CD52, CD70, CD80, CD85, CD95 (Fas receptor), CD106 (vascular cell adhesion molecule 1 (VCAM1), CD166 (activated leukocyte cell adhesion molecule (ALCAM)), CD178 (Fas ligand), CD253 (TNF-related apoptosis-inducing ligand (TRAIL)), ICOS ligand, CCR2, CXCR3, CCR5, CXCL12 (stromal cell-derived factor 1 (SDF-1)), interleukin 1 (IL-1), IL-1ra, IL-2, IL-3, IL-4, IL-6, IL-7, IL-8, CTLA-4, MART-1, gp100, MAGE-1, ephrin (Eph) receptor, mucosal addressin cell adhesion molecule 1 (MAdCAM-1), carcinoembryonic antigen (CEA), Lewisy, MUC-1, epithelial cell adhesion molecule (EpCAM), cancer antigen 125 (CA125), prostate specific membrane antigen (PSMA), TAG-72 antigen, and fragments thereof. In further embodiments, the targeting moiety contains erythroblastic leukemia viral oncogene homolog (ErbB) receptor (e.g., ErbB1 receptor; ErbB2 receptor; ErbB3 receptor; and ErbB4 receptor). In some embodiments, the targeting moiety contains one or more (e.g., from 1 to 6) N-acetyl galactosamines (GalNAc). In certain embodiments, the targeting moiety contains one or more (e.g., from 1 to 6) mannoses. In other embodiments, the targeting moiety contains a folate ligand. The folate ligand has the structure:

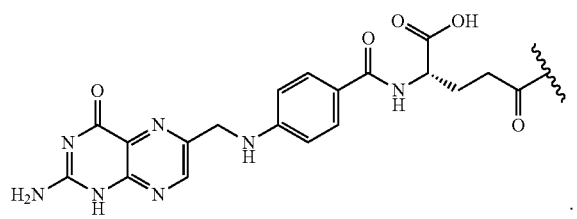 [SMILES: *C(=O)CC[C@H](NC(=O)c1ccc(NCc2cnc3[nH]c(N)nc(=O)c3n2)cc1)C(=O)O]

Certain targeting moieties may include bombesin, gastrin, gastrin-releasing peptide, tumor growth factors (TGF) (e.g., TGF-α or TGF-β), or vaccinia virus growth factor (VVGF). Non-peptidyl targeting moieties can also be used in the targeting moieties and may include, for example, steroids, carbohydrates, vitamins, and lectins. Some targeting moieties may include a polypeptide, such as somatostatin or somatostatin analog (e.g., octreotide or Ianreotide), bombesin, or an antibody or antigen-binding fragment thereof. Antibodies may be of any recognized class or subclass, e.g., IgG, IgA, IgM, IgD, or IgE. Typical are those antibodies which fall within the IgG class. The antibodies can be derived from any species according techniques known in the art. Typically, however, the antibody is of human, murine, or rabbit origin. In addition, the antibody may be polyclonal or monoclonal, but is typically monoclonal. Human or chimeric (e.g., humanized) antibodies may be used in targeting moieties. Targeting moieties may include an antigen-binding fragment of an antibody. Such antibody fragments may include, for example, the Fab', F(ab')$_2$, Fv, or Fab fragments, singledomain antibody, ScFv, or other antigen-binding fragments. Fc fragments may also be employed in targeting moieties. Such antibody fragments can be prepared, for example, by proteolytic enzyme digestion, for example, by pepsin or papain digestion, reductive alkylation, or recombinant techniques. The materials and methods for preparing antibody fragments are well-known to those skilled in the art. See, e.g., Parham, *J. Immunology*, 131:2895, 1983; Lamoyi et al., *J. Immunological Methods*, 56:235, 1983.

Other peptides for use as a targeting auxiliary moiety in nucleotide constructs of the invention can be selected from KiSS peptides and analogs, urotensin II peptides and analogs, GnRH I and II peptides and analogs, depreotide, vapreotide, vasoactive intestinal peptide (VIP), cholecystokinin (CCK), RGD-containing peptides, melanocyte-stimulating hormone (MSH) peptide, neurotensin, calcitonin, glutathione, YIGSR (leukocyte-avid peptides, e.g., P483H, which contains the heparin-binding region of platelet factor-4 (PF-4) and a lysine-rich sequence), atrial natriuretic peptide (ANP), β-amyloid peptides, delta-opioid antagonists (such as ITIPP(psi)), annexin-V, endothelin, leukotriene B4 (LTB4), chemotactic peptides (e.g., N-formyl-methionyl-leucyl-phenylalanine-lysine (fMLFK), GP IIb/IIIa receptor antagonists (e.g., DMP444), human neutrophil elastase inhibitor (EPI-HNE-2 and EPI-HNE-4), plasmin inhibitor, antimicrobial peptides, apticide (P280 and P274), thrombospondin receptor (including analogs such as TP-1300), bitistatin, pituitary adenylyl cyclase type I receptor (PAC1), fibrin α-chain, peptides derived from phage display libraries, and conservative substitutions thereof.

One or more (e.g., from 1 to 6) targeting moieties can be linked to MOIETY or to $X^2$ in formula (I) through -LinkA-.

In some embodiments, the targeting moiety includes one or more (e.g., from 1 to 6 or from 1 to 3) asialoglycoprotein receptor ligands (e.g., GalNAc). In some embodiments, an asialoglycoprotein receptor ligand (e.g., GalNAc) ligand is attached to -LinkA- through an anomeric carbon (e.g., where the anomeric carbon is the carbon atom in an acetal or a hemiaminal). An asialoglycoprotein receptor ligand (e.g., GalNAc) attached to a linker through a hemiaminal may produce a hybridized polynucleotide construct having superior efficacy in gene silencing as compared to hybridized polynucleotide constructs having the asialoglycoprotein receptor ligand (e.g., GalNAc) attached to a linker through an acetal.

Endosomal Escape Moieties

One or more endosomal escape moieties (e.g., from 1 to 6 or from 1 to 3) can be attached to a polynucleotide construct or a hybridized polynucleotide construct disclosed herein as an auxiliary moiety. Exemplary endosomal escape moieties include chemotherapeutics (e.g., quinolones such as chloroquine); fusogenic lipids (e.g., dioleoylphosphatidyl-ethanolamine (DOPE)); and polymers such as polyethylenimine (PEI); poly(beta-amino ester)s; polypeptides, such as polyarginines (e.g., octaarginine) and polylysines (e.g., octalysine); proton sponges, viral capsids, and peptide transduction domains as described herein. For example, fusogenic peptides can be derived from the M2 protein of influenza A viruses; peptide analogs of the influenza virus hemagglutinin; the HEF protein of the influenza C virus; the transmembrane glycoprotein of filoviruses; the transmembrane glycoprotein of the rabies virus; the transmembrane glycoprotein (G) of the vesicular stomatitis virus; the fusion protein of the Sendai virus; the transmembrane glycoprotein of the Semliki forest virus; the fusion protein of the human respiratory syncytial virus (RSV); the fusion protein of the measles virus; the fusion protein of the Newcastle disease virus; the fusion protein of the visna virus; the fusion protein of murine leukemia virus; the fusion protein of the HTL virus; and the fusion protein of the simian immunodeficiency virus (SIV). Other moieties that can be employed to facilitate endosomal escape are described in Dominska et al., *Journal of Cell Science*, 123(8):1183-1189, 2010. Specific examples of endosomal escape moieties including moieties suitable for conjugation to the hybridized polynucleotide constructs disclosed herein are provided, e.g., in WO 2015/188197; the disclosure of these endosomal escape moieties is incorporated by reference herein.

One or more endosomal escape moieties (e.g., from 1 to 6 or from 1 to 3) can be attached to a MOIETY or $X^2$ in formula (I) through -LinkA-, as described herein.

Cell Penetrating Peptides

One or more cell penetrating peptides (e.g., from 1 to 6 or from 1 to 3) can be attached to a polynucleotide construct or a hybridized polynucleotide construct disclosed herein as an auxiliary moiety.

The CPP can be linked to the hybridized polynucleotide bioreversibly through a disulfide linkage, as disclosed herein. Thus, upon delivery to a cell, the CPP can be cleaved intracellularly, e.g., by an intracellular enzyme (e.g., protein disulfide isomerase, thioredoxin, or a thioesterase) and thereby release the polynucleotide.

CPPs are known in the art (e.g., TAT or Arga) (Snyder and Dowdy, 2005, *Expert Opin. Drug Deliv.* 2, 43-51). Specific examples of CPPs including moieties suitable for conjugation to the hybridized polynucleotide constructs disclosed herein are provided, e.g., in WO 2015/188197; the disclosure of these CPPs is incorporated by reference herein.

CPPs are positively charged peptides that are capable of facilitating the delivery of biological cargo to a cell. It is believed that the cationic charge of the CPPs is essential for their function. Moreover, the transduction of these proteins does not appear to be affected by cell type, and these proteins can efficiently transduce nearly all cells in culture with no apparent toxicity (Nagahara et al., *Nat. Med.* 4:1449-52, 1998). In addition to full-length proteins, CPPs have also been used successfully to induce the intracellular uptake of DNA (Abu-Amer, supra), antisense polynucleotides (Astriab-Fisher et al., *Pharm. Res,* 19:744-54, 2002), small molecules (Polyakov et al., *Bioconjug. Chem.* 11:762-71, 2000) and even inorganic 40 nm iron particles (Dodd et al., *J. Immunol. Methods* 256:89-105, 2001; Wunderbaldinger et al., *Bioconjug. Chem.* 13:264-8, 2002; Lewin et al., *Nat. Biotechnol.* 18:410-4, 2000; Josephson et al., *Bioconjug. Chem.* 10:186-91, 1999) suggesting that there is considerable flexibility in particle size in this process.

In one embodiment, a CPP useful in the methods and compositions of the invention includes a peptide featuring substantial alpha-helicity. It has been discovered that transfection is optimized when the CPP exhibits significant alpha-helicity. In another embodiment, the CPP includes a sequence containing basic amino acid residues that are substantially aligned along at least one face of the peptide. A CPP useful in the invention may be a naturally occurring peptide or a synthetic peptide.

One or more cell penetrating peptides (e.g., from 1 to 6 or from 1 to 3) can be attached to a MOIETY or $X^2$ in formula (I) through -LinkA-, as described herein.

Polymers

The polynucleotide constructs and the hybridized polynucleotide constructs disclosed herein can also include covalently attached neutral polymer-based auxiliary moieties. Neutral polymers include poly($C_{1-6}$ alkylene oxide), e.g., poly(ethylene glycol) and poly(propylene glycol) and copolymers thereof, e.g., di- and triblock copolymers. Other examples of polymers include esterified poly(acrylic acid), esterified poly(glutamic acid), esterified poly(aspartic acid), poly(vinyl alcohol), poly(ethylene-co-vinyl alcohol), poly (N-vinyl pyrrolidone), poly(ethyloxazoline), poly(alkylacrylates), poly(acrylamide), poly(N-alkylacrylamides), poly(N-acryloylmorpholine), poly(lactic acid), poly(glycolic acid), poly(dioxanone), poly(caprolactone), styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyurethane, N-isopropylacrylamide polymers, and poly(N,N-dialkylacrylamides). Exemplary polymer auxiliary moieties may have molecular weights of less than 100, 300, 500, 1000, or 5000 Da (e.g., greater than 100 Da). Other polymers are known in the art.

One or more polymers (e.g., from 1 to 6 or from 1 to 3) can be attached to a MOIETY or $X^2$ in formula (I) through -LinkA-, as described herein.

Solid Support

The polynucleotide constructs or the hybridized polynucleotide constructs disclosed herein may include a group -Sol, where Sol is solid support. Cleavable solid supports that may be used with the polynucleotide construct are known in the art. Non-limiting examples of the solid support include, e.g., controlled pore glass or macroporous polystyrene bonded to a strand through a cleavable linker (e.g., succinate-based linker) known in the art (e.g., UnyLinker™)

Conjugation Moieties

The polynucleotide constructs or the hybridized polynucleotide constructs disclosed herein may include a conjugation moiety, which may be reacted with a -LinkA(-T)$_p$ precursor. A conjugation moiety includes at least one functional group that is capable of undergoing a conjugation reaction (e.g., a cycloaddition reaction (e.g., dipolar cycloaddition)), amidation reaction, nucleophilic aromatic substitution). For example, a conjugation moiety may include azido, optionally substituted $C_{2-12}$ alkynyl, —COOR$^{21}$, —CHO, N-maleimido, S-protected thiol,

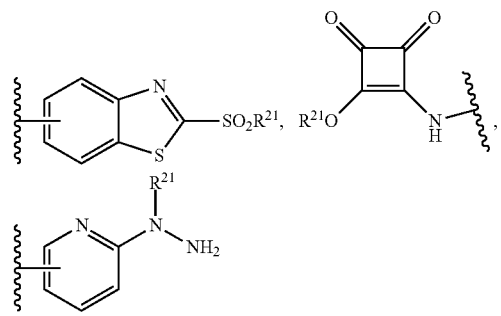

or N-protected version thereof,

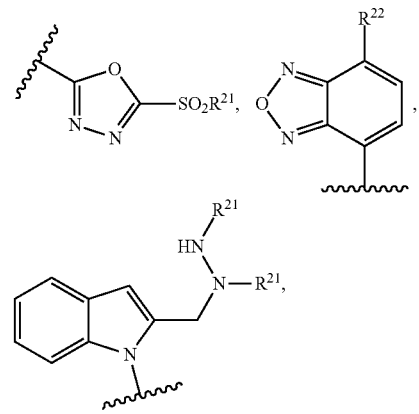

or —NHR$^{N1}$; where R$^{N1}$ is H, N-protecting group, or optionally substituted $C_{1-6}$ alkyl; each R$^{21}$ is independently H or optionally substituted $C_{1-6}$ alkyl; and R$^{22}$ is halogen (e.g., F). The conjugation moiety may be protected until auxiliary moiety is conjugated to the polynucleotide construct. For example, a conjugation moiety that is protected may include —COOR$^{PGO}$ or —NHR$^{PGN}$, where R$^{PGO}$ is an O-protecting group (e.g., a carboxyl protecting group), and R$^{PGN}$ is an N-protecting group. In some embodiments, a conjugation moiety is a group [-Q$^3$-Q$^4$-Q$^5$]$_s$-Q$^{C1}$, where Q$^{C1}$ is optionally substituted $C_{2-12}$ alkynyl, optionally substituted N-protected amino, azido, N-maleimido, S-protected thiol,

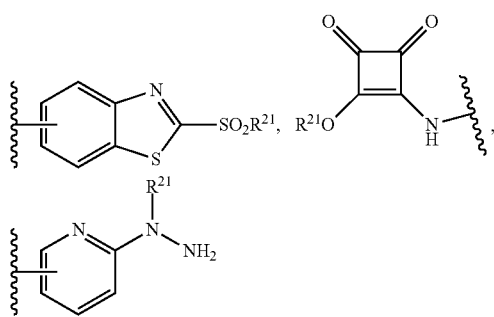

or N-protected version thereof,

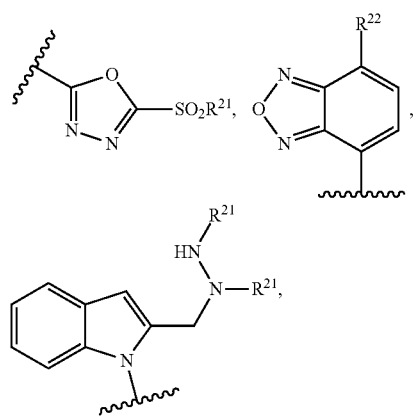

—NHR$^{N1}$, or optionally substituted C$_{1-16}$ alkyl containing —COOR$^{21}$ or —CHO;

each Q$^3$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—;

each Q$^4$ is independently absent, optionally substituted C$_{1-12}$ alkylene, optionally substituted C$_{2-12}$ alkenylene, optionally substituted C$_{2-12}$ alkynylene, optionally substituted C$_{2-12}$ heteroalkylene, or optionally substituted C$_{1-9}$ heterocyclylene;

each Q$^5$ is independently absent, —CO—, —NH—, —O—, —S—, —SO$_2$—, —CH$_2$—, —C(O)O—, —OC(O)—, —C(O)NH—, —NH—C(O)—, —NH—CH(R$^a$)—C(O)—, or —C(O)—CH(R$^a$)—NH—;

each s is independently an integer from 0 to 20;

R$^{N1}$ is H, N-protecting group, or optionally substituted C$_{1-6}$ alkyl;

each R$^{21}$ is independently H or optionally substituted C$_{1-6}$ alkyl; and

R$^{22}$ is halogen (e.g., F).

Internucleoside, Abasic Spacers

In those cases where a hybridized polynucleotide construct is contemplated for use as siRNA, a reduction of miRNA-like off-target effects is desirable. The inclusion of one or more (e.g., one or two) internucleoside, abasic spacers in the hybridized polynucleotide constructs may reduce or even eliminate miRNA-like off-target effects, as the internucleoside, abasic spacers lack nucleobases that are capable of engaging in base-pairing interactions and alleviate steric hindrance. Thus, the polynucleotide constructs and the hybridized polynucleotide constructs disclosed herein may include one or more (e.g., one or two) internucleoside, abasic spacers. When the polynucleotide construct includes two or more of the internucleoside, abasic spacers, their structures may be same or different. In certain embodiments, a passenger strand contains one internucleoside, abasic spacer (e.g., a guide strand may be free of internucleoside, abasic spacers). In other embodiments, a guide strand contains one internucleoside, abasic spacer (e.g., a passenger strand may be free of internucleoside, abasic spacers). In yet other embodiments, a guide strand contains one internucleoside, abasic spacer, and a passenger strand contains one internucleoside, abasic spacer. In further embodiments, a passenger strand includes an internucleoside, abasic spacer between a nucleoside number (x) and a nucleoside number (x+t+1), where x is an integer from 2 to 7. In yet further embodiments, a guide strand includes an internucleoside, abasic spacer between a nucleoside number (x) and a nucleoside number (x+t+1), where x is an integer from 2 to 7.

An internucleoside, abasic spacer may be of formula (III):

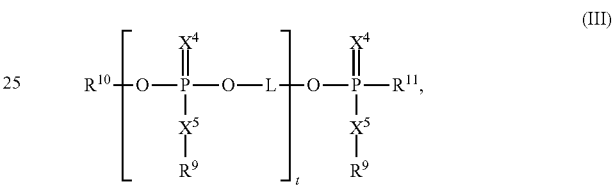

(III)

where

L is a sugar analogue;

each X$^4$ is independently O or S;

each X$^5$ is independently O, S, NH, or a bond;

each R$^9$ is independently H, optionally substituted C$_{1-6}$ alkyl, optionally substituted C$_{2-6}$ alkenyl, optionally substituted C$_{2-6}$ alkynyl, optionally substituted (C$_{1-9}$ heterocyclyl)-C$_{1-6}$-alkyl, optionally substituted (C$_{6-10}$ aryl)-C$_{1-6}$-alkyl, optionally substituted (C$_{3-8}$ cycloalkyl)-C$_{1-6}$-alkyl, -LinkA(-T)$_p$, or a conjugation moiety;

each LinkA is independently a multivalent linker (e.g., including —C(O)—N(H)—);

each T is independently an auxiliary moiety;

R$^{10}$ is a bond to a 3'-carbon atom of a nucleoside (x) in the strand;

R$^{11}$ is a bond to a 5'-oxygen atom of a nucleoside (x+t+1) in the strand;

p is an integer from 1 to 6; and t is an integer from 1 to 6.

In some embodiments, each X$^4$ is O. In particular embodiments, each X$^5$ is O. In certain embodiments, each R$^9$ is H. In other embodiments, the sugar analogue is substituted with one or two groups independently selected from the group consisting of -LinkA(-T)$_p$ and a conjugation moiety.

Sugar Analogue

A sugar analogue is a divalent or trivalent group that is a C$_{3-6}$ monosaccharide or C$_{3-6}$ alditol (e.g., glycerol), which is modified to replace two hydroxyl groups with bonds to the oxygen atoms that are bonded to groups —P(X$^4$)(—X$^5$R$^9$)— in formula (III). A sugar analogue is cyclic or acyclic. Further optional modifications included in a sugar analogue are: a replacement of one, two, or three of the remaining hydroxyl groups or carbon-bonded hydrogen atoms with H; optionally substituted C$_{1-6}$ alkyl; -LinkA(-T)$_p$, a conjugation moiety; —(CH$_2$)$_{t1}$—OR$^Z$, where t1 is an integer from 1 to 6, and R$^Z$ is optionally substituted C$_{1-6}$ alkyl, optionally substituted C$_{2-6}$ alkenyl, optionally substituted $C_{2-6}$ alkynyl, optionally substituted $C_{6-14}$ aryl, optionally substituted $C_{3-8}$ cycloalkyl, optionally substituted $(C_{1-9}$ heterocyclyl$)$-$C_{1-6}$-alkyl, optionally substituted $(C_{6-10}$ aryl$)$-$C_{1-6}$-alkyl, or optionally substituted $(C_{3-8}$ cycloalkyl$)$-$C_{1-6}$-alkyl; introduction of one or two unsaturation(s) (e.g., one or two double bonds); and replacement of one, two, or three hydrogens or hydroxyl groups with substituents as defined for alkyl, alkenyl, cycloalkyl, cycloalkenyl, or heterocyclyl. Non-limiting examples of sugar analogues are optionally substituted $C_{2-6}$ alkylene, optionally substituted $C_{2-6}$ alkenylene, optionally substituted $C_5$ cycloalkane-1,3-diyl, optionally substituted $C_5$ cycloalkene-1,3-diyl, optionally substituted heterocycle-1,3-diyl (e.g., optionally substituted pyrrolidine-2,5-diyl, optionally substituted tetrahydrofuran-2,5-diyl, or optionally substituted tetrahydrothiophene-2,5-diyl), or optionally substituted $(C_{1-4}$ alkyl$)$-$(C_{3-8}$ cycloalkylene$)$ (e.g., optionally substituted $(C_1$ alkyl$)$-$(C_3$ cycloalkylene$)$). Non-limiting examples of sugar analogues are:

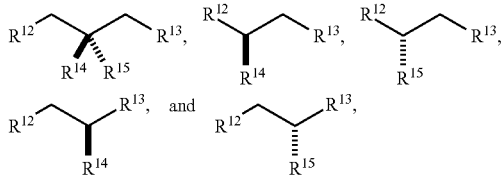

where
$R^{12}$ is a bond to an oxygen atom bonded to $-P(X^4)(-X^5R^9)-$ in formula (III);
$R^{13}$ is a bond to an oxygen atom bonded to another $-P(X^4)(-X^5R^9)-$ in formula (III); each of $R^{14}$ and $R^{15}$ is independently H, optionally substituted $C_{1-6}$ alkyl, or $-(CH_2)_{n1}-OR^Z$, where n is an integer from 1 to 6, and $R^Z$ is optionally substituted $C_{1-6}$ alkyl, optionally substituted $C_{2-6}$ alkenyl, optionally substituted $C_{2-6}$ alkynyl, optionally substituted $C_{6-14}$ aryl, optionally substituted $C_{3-8}$ cycloalkyl, optionally substituted $(C_{1-9}$ heterocyclyl$)$-$C_{1-6}$-alkyl, optionally substituted $(C_{6-10}$ aryl$)$-$C_{1-6}$-alkyl, or optionally substituted $(C_{3-8}$ cycloalkyl$)$-$C_{1-6}$-alkyl.

In some embodiments, at least on of $R^{14}$ and $R^{15}$ is not H.

Non-Bioreversible Phosphotriesters

The polynucleotide constructs of the invention may also include a non-bioreversible phosphotriester (e.g., a phosphate or a phosphorothioate that is substituted with a group that does not include a disulfide or a thioester). The non-bioreversible phosphotriester can be an internucleoside non-bioreversible phosphotriester (e.g., a non-bioreversible phosphotriester disposed outside the seed region of the hybridized polynucleotide construct). Preferred positions for internucleoside non-bioreversible phosphotriesters in the guide strand are those between the second and third nucleosides, the fifth and the sixth nucleosides, the seventeenth and the eighteenth nucleosides, the nineteenth and the twentieth nucleosides, or the twentieth and the twenty-first nucleosides (the count starts at the 5'-terminus of the guide strand). Preferred positions for the non-bioreversible phosphotriesters in the passenger strand are those that do not connect two contiguous nucleosides at the natural RISC-mediated cleavage site.

The non-bioreversible phosphotriester may be a phosphate, phosphorothioate, or phosphorodithioate substituted with a substituent selected independently from the group consisting of optionally substituted $C_{2-16}$ alkyl; optionally substituted $C_{3-16}$ alkenyl; optionally substituted $C_{3-16}$ alkynyl; optionally substituted $C_{3-8}$ cycloalkyl; optionally substituted $C_{3-8}$ cycloalkenyl; optionally substituted $(C_{3-8}$ cycloalkyl$)$-$C_{1-4}$-alkyl; optionally substituted $(C_{3-8}$ cycloalkenyl$)$-$C_{1-4}$-alkyl; optionally substituted $C_{6-14}$ aryl; optionally substituted $(C_{6-14}$ aryl$)$-$C_{1-4}$-alkyl; optionally substituted $C_{1-9}$ heteroaryl having 1 to 4 heteroatoms selected from N, O, and S; optionally substituted $(C_{1-9}$ heteroaryl$)$-$C_{1-4}$-alkyl having 1 to 4 heteroatoms selected from N, O, and S; optionally substituted $C_{2-9}$ heterocyclyl having 1 to 4 heteroatoms selected from N, O, and S, where the heterocyclyl does not contain an S—S bond; optionally substituted $(C_{2-9}$ heterocyclyl$)$-$C_{1-4}$-alkyl having 1 to 4 heteroatoms selected from N, O, and S, where the heterocyclyl does not contain an S—S bond; and a group of the following structure:

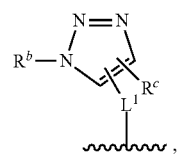

where
L is $C_{1-6}$ alkylene;
$R^b$ is optionally substituted $C_{2-6}$ alkyl; optionally substituted $C_{6-14}$ aryl; optionally substituted $(C_{6-14}$ aryl$)$-$C_{1-4}$-alkyl; optionally substituted $C_{3-8}$ cycloalkyl; optionally substituted $(C_{3-8}$ cycloalkyl$)$-$C_{1-4}$-alkyl; optionally substituted $C_{1-9}$ heteroaryl having 1 to 4 heteroatoms selected from the group consisting of N, O, and S; optionally substituted $(C_{1-9}$ heteroaryl$)$-$C_{1-4}$-alkyl having 1 to 4 heteroatoms selected from the group consisting of N, O, and S; optionally substituted $C_{2-9}$ heterocyclyl having 1 to 4 heteroatoms selected from the group consisting of N, O, and S, wherein the heterocyclyl does not contain an S—S bond; optionally substituted $(C_{2-9}$ heterocyclyl$)$-$C_{1-4}$-alkyl having 1 to 4 heteroatoms selected from N, O, and S, wherein the heterocyclyl does not contain an S—S bond; and a poly(ethylene glycol) terminated with —OH, $C_{1-6}$ alkoxy, or —COOH; and
$R^c$ is H or $C_{1-6}$ alkyl.

The non-bioreversible phosphotriester may be a phosphate, a phosphorothioate, or a phosphorodithioate substituted with a substituent that is $C_{2-16}$ alkyl,

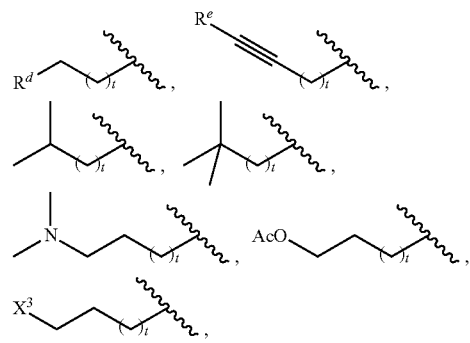

or a group formed by cycloaddition reaction of

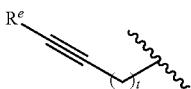

with an azido-containing substrate,
where
t is an integer from 1 to 6;
$R^d$ is optionally substituted $C_6$ aryl; optionally substituted $C_{4-5}$ heteroaryl that is a six member ring containing 1 or 2 nitrogen atoms; or optionally substituted $C_{4-5}$ heterocyclyl that is a six member ring containing 1 or 2 nitrogen atoms;
$R^e$ is H or $C_{1-6}$ alkyl;
$X^3$ is a halogen, —$COOR^5$, or —$CONR^6{}_2$, where $R^5$ and each $R^6$ are independently H, optionally substituted $C_{1-6}$ alkyl, optionally substituted $C_{6-14}$ aryl, optionally substituted $C_{1-9}$ heteroaryl, or optionally substituted $C_{2-9}$ heterocyclyl; and
the azido-containing substrate is

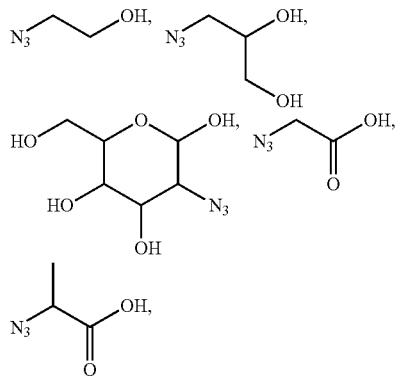

$N_3$-PEG-OH, $N_3$-PEG-COOH,

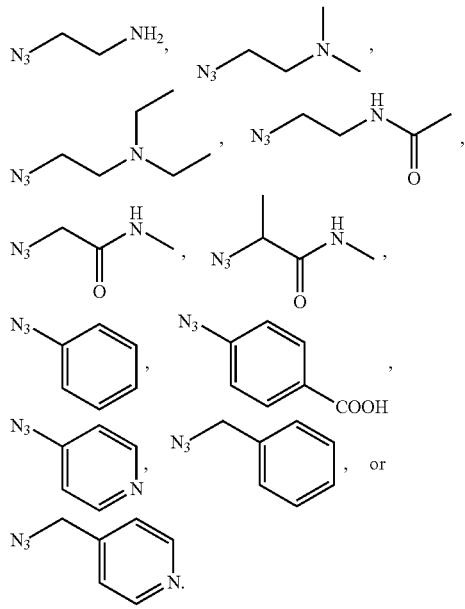

Preparation of the Polynucleotide Constructs

The invention further provides methods for manufacturing the polynucleotide constructs of the invention. Methods for the preparation of nucleotides and polynucleotides are known in the art. For example, the practice of phosphoramidite chemistry to prepare polynucleotides is known from the published work of Caruthers and Beaucage and others. See, e.g., U.S. Pat. Nos. 4,458,066; 4,500,707; 5,132,418; 4,415,732; 4,668,777; 4,973,679; 5,278,302, 5,153,319; 5,218,103; 5,268,464; 5,000,307; 5,319,079; 4,659,774; 4,672,110; 4,517,338; 4,725,677; and RE34,069, each of which is herein incorporated by reference, describe methods of polynucleotide synthesis. Additionally, the practice of phosphoramidite chemistry has been systematically reviewed by Beaucage et al., *Tetrahedron*, 48: 2223-2311, 1992; and Beaucage et al., *Tetrahedron*, 49:6123-6194, 1993, as well as references referred to therein, all of which are herein incorporated by reference. Synthesis principles useful in the synthesis of the polynucleotide constructs of the invention are disclosed in PCT/US2014/064401 and in PCT/US2015/034749; the disclosure of syntheses of polynucleotide constructs in PCT/US2014/064401 and in PCT/US2015/034749 is incorporated herein by reference.

Nucleic acid synthesizers are commercially available, and their use is generally understood by persons of ordinary skill in the art as being effective in generating nearly any polynucleotide of reasonable length which may be desired.

In practicing phosphoramidite chemistry, useful 5'OH sugar blocking groups are trityl, monomethoxytrityl, dimethoxytrityl and trimethoxytrityl, especially dimethoxytrityl (DMTr). In practicing phosphoramidite chemistry, useful phosphite activating groups are dialkyl substituted nitrogen groups and nitrogen heterocycles. One approach includes the use of the di-isopropylamino activating group.

Polynucleotides can be synthesized by a Mermade-6 solid phase automated polynucleotide synthesizer or any commonly available automated polynucleotide synthesizer. Triester, phosphoramidite, or hydrogen phosphonate coupling chemistries (described in, for example, M. Caruthers, *Oligonucleotides: Antisense Inhibitors of Gene Expression*, pp. 7-24, J. S. Cohen, ed. (CRC Press, Inc. Boca Raton, Fla., 1989); *Oligonucleotide synthesis, a practical approach*, Ed. M. J. Gait, IRL Press, 1984; and Oligonucleotides and Analogues, *A Practical Approach*, Ed. F. Eckstein, IRL Press, 1991) are employed by these synthesizers to provide the desired polynucleotides. The Beaucage reagent, as described in, for example, *Journal of American Chemical Society*, 112:1253-1255, 1990, or elemental sulfur, as described in Beaucage et al., Tetrahedron Letters 22:1859-1862, 1981, is used with phosphoramidite or hydrogen phosphonate chemistries to provide substituted phosphorothioate polynucleotides.

For example, the reagents containing the protecting groups recited herein can be used in numerous applications where protection is desired. Such applications include, but are not limited to, both solid phase and solution phase, polynucleotide synthesis and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. For use with phosphoramidite chemistry, various phosphoramidite reagents are commercially available, including 2'-deoxy phosphoramidites, 2'-O-methyl phosphoramidites and 2'-O-hydroxyl phosphoramidites. Any other means for such synthesis may also be employed. The actual synthesis of the polynucleotides is well within the talents of those skilled in the art. It is also well known to use similar techniques to prepare other polynucleotides such as the phosphorothioates, methyl phosphonates and alkylated derivatives. It is also well known to use similar techniques and commercially available modified phosphoramidites and controlled-pore glass (CPG) products such as biotin, Cy3, fluorescein, acridine or psoralen-modified phosphoramidites and/or CPG (available from Glen Research, Sterling Va.) to synthesize fluorescently labeled, biotinylated or other conjugated polynucleotides.

Phosphoramidites used in the synthesis of the polynucleotide constructs of the invention may be of formula (IV):

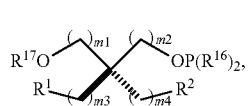

(IV)

where
each of $R^1$ and $R^2$ is independently H, optionally substituted $C_{1-16}$ alkyl, optionally substituted $C_{2-16}$ heteroalkyl, or a conjugation moiety (e.g., including an optionally substituted N-protected amino, optionally substituted $C_{1-16}$ alkyl containing —$COOR^{21}$ or —CHO, optionally substituted $C_{2-16}$ alkynyl, azido, N-maleimido, S-protected thiol,

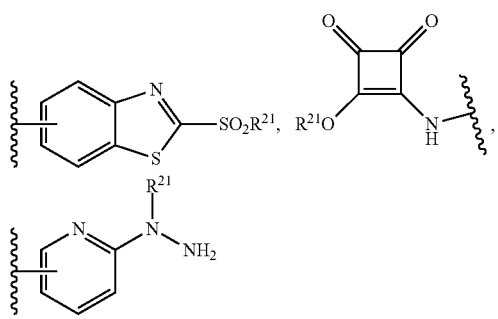

or N-protected version thereof,

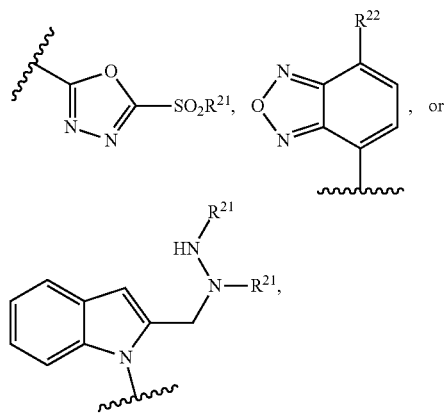

where each $R^{21}$ is independently H or optionally substituted $C_{1-6}$ alkyl, and $R^{22}$ is halogen (e.g., F));
each $R^{16}$ is independently dialkylamino, 2-cyanoethyl, or a conjugation moiety, provided that at least one $R^{16}$ is dialkylamino;

$R^{17}$ is a hydroxyl protecting group; and
each of m1, m2, m3, and m4 is independently an integer from 0 to 6, provided that the sum of m1 and m2 is not 0.

In some instances of formula (IV), when both $R^1$ and $R^2$ are a conjugation moiety including optionally substituted $C_{2-16}$ alkynyl, the remaining $R^{16}$ is dialkylamino or a conjugation moiety.

In certain instances of formula (IV), each of $R^1$ and $R^2$ is independently H, optionally substituted $C_{1-16}$ alkyl, optionally substituted $C_{2-16}$ heteroalkyl, or $[-Q^3-Q^4-Q^5]_s-Q^{C1}$
where
$Q^{C1}$ is optionally substituted $C_{2-12}$ alkynyl or optionally substituted N-protected amino;
each $Q^3$ is independently absent, —CO—, —NH—, —O—, —S—, —$SO_2$—, —OC(O)—, —COO—, —NHC(O)—, —C(O)NH—, —$CH_2$—, —$CH_2NH$—, —$NHCH_2$—, —$CH_2O$—, or —$OCH_2$—;
each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene;
each $Q^5$ is independently absent, —CO—, —NH—, —O—, —S—, —$SO_2$—, —$CH_2$—, —C(O)O—, —OC(O)—, —C(O)NH—, —NH—C(O)—, —NH—CH($R^a$)—C(O)—, or —C(O)—CH($R^a$)—NH—; and
each s is independently an integer from 0 to 20.

Conjugation

Preparation of polynucleotide constructs of the invention may involve conjugating an auxiliary moiety to a non-bioreversible attached to a phosphate or a phosphorothioate in the polynucleotide construct. The auxiliary moiety and the linker include complementary conjugating moieties. The location of attachment in a polynucleotide construct is determined by the positioning of the phosphates or phosphorothioates bearing the linker. Thus, a polynucleotide construct containing one more conjugating moieties will react, under appropriate conditions, with one or more complementary conjugating moieties on auxiliary moieties. The auxiliary moiety may intrinsically possess the conjugating moiety, e.g., terminal or lysine amine groups and thiol groups in peptides, or it may be modified to include a small linking group to introduce the conjugating moiety. Introduction of such linking groups is well known in the art. It will be understood that an auxiliary moiety attached to a nucleotide construct of the invention includes any necessary linking group.

Diverse bond-forming methods can be used to conjugate the auxiliary moiety to the nucleotide constructs described herein. Exemplary reactions include: cycloaddition between an azide and an alkyne to form a triazole; the Diels-Alder reaction between a dienophile and a diene/hetero-diene; bond formation via other pericyclic reactions such as the ene reaction; amide or thioamide bond formation; sulfonamide bond formation; alcohol or phenol alkylation (e.g., with diazo compounds), condensation reactions to form oxime, hydrazone, or semicarbazide group, conjugate addition reactions by nucleophiles (e.g., amines and thiols), disulfide bond formation, and nucleophilic substitution at a carboxylic functionality (e.g., by an amine, thiol, or hydroxyl nucleophile). Other exemplary methods of bond formation are described herein and known in the art.

Nucleophile/Electrophile Reactions

Nucleophiles and electrophiles can engage in bond forming reactions selected from, without limitation, net insertion by an electrophile into a C—H bond, net insertion by an electrophile into an O—H bond, net insertion by an electrophile into an N—H bond, addition of the electrophile across an alkene, addition of the electrophile across an alkyne, addition to electrophilic carbonyl centers, substitution at electrophilic carbonyl centers, addition to ketenes, nucleophilic addition to isocyanates, nucleophilic addition to isothiocyanates, nucleophilic substitution at activated silicon centers, nucleophilic displacement of an alkyl halide, nucleophilic displacement at an alkyl pseudohalide, nucleophilic addition/elimination at an activated carbonyl, 1,4-conjugate addition of a nucleophile to an α, β-unsaturated carbonyl, nucleophilic ring opening of an epoxide, nucleophilic aromatic substitution of an electron deficient aromatic compound, a nucleophilic addition to activated phosphorus centers, nucleophilic substitution at activated phosphorous centers, nucleophilic addition to activated sulfur centers, and nucleophilic substitution at activated sulfur centers.

A nucleophilic conjugating moiety may be selected from optionally substituted alkenes, optionally substituted alkynes, optionally substituted aryl, optionally substituted heterocyclyl, hydroxyl groups, amino groups, alkylamino groups, anilido groups, and thio groups.

An electrophilic conjugating moiety may be selected from azides, activated silicon centers, activated carbonyls, anhydrides, isocyanates, thioisocyanates, succinimidyl esters, sulfosuccinimidyl esters, maleimides, alkyl halides, alkyl pseudohalides, epoxides, episulfides, aziridines, electron-deficient aryls, activated phosphorus centers, and activated sulfur centers.

For example, conjugation can occur via a condensation reaction to form a linkage that is a hydrazone bond. In another non-limiting example, conjugation may be performed through Pictet-Spengler reaction. Alternatively, conjugation may be performed by substituting a leaving group in a squarate, 2-sulfonyl-1,3-benzothiazole, 5-sulfonyl-1,2,3,4-tetrazole, 2-sulfonyl-1,3,4-oxadiazole, or 4-halobenzofurazan.

Conjugation via the formation of an amide bond can be mediated by activation of a carboxyl-based conjugating moiety and subsequent reaction with a primary amine-based conjugating moiety. Activating agents can be various carbodiimides like: EDC (1-Ethyl-3-(3-dimethylaminopropyl) carbodiimide hydrochloride), EDAC (1-ethyl-3(3-dimethylaminopropyl)carbodiimide hydrochloride), DCC (dicyclohexyl carbodiimide), CMC (1-Cyclohexyl-3-(2-morpholinoethyl) carbodiimide), DIC (diisopropyl carbodiimide) or Woodward's reagent K (N-ethyl-3-phenylisoxazolium-3'-sulfonate). Reaction of an activated NHS-Ester-based conjugating moiety with a primary amine-based conjugating moiety also results in formation of an amide bond.

Ether formation can also be used to conjugate auxiliary moieties to the nucleotide constructs of the invention. Conjugation via ether linkages can be mediated by reaction of an epoxide-based conjugating moiety with a hydroxy-based conjugating moiety.

Conjugation via the formation of thioether linkages can be performed by reacting a sulfhydryl based conjugating moieties with maleimide-based conjugating moieties or by reacting with epoxide-based conjugating moieties. Maleimide-based conjugating moieties can be introduced by SMCC (succinimidyl-4-(N-maleimidomethyl)cyclohexane-1-carboxylate), sulfo-SMCC (sulfosuccinimidyl 4-(N-maleidomethyl)-cyclohexane-1-carboxylate), MBS (m-Maleimidobenzoyl-N-hydroxysuccinimide ester), sulfo-MBS (m-Maleimidobenzoyl-N-sulfohydroxy succinimide ester), SMPB (Succinimidyl-4-(p-maleidophenyl)butyrate), sulfo-SMPB (sulfosuccinimidyl 4-(p-maleimidophenyl)butyrate), GMBS (N-α-maleimidobuturyl-oxysuccinimide ester), or sulfo GMBS (N-α-maleimidobuturyl-oxysulfosuccinimide ester).

Conjugation via the formation of a carbamate linkage can be performed by reaction of a hydroxy-based conjugating moiety with CDI (N,N'-carbonyldiimidazole) or DSC (N,N'-disuccinimidyl carbonate) or N-hydroxysuccinimidylchloroformate and subsequent reaction with an amine-based conjugating moiety.

Photolytic and Thermolytic Conjugation

Alternatively, the conjugating moiety can employ photolytic or thermolytic activation in order to form the desired covalent bond. Conjugating moieties that include azido functionality are one example. Thus, conjugation can also be achieved by the introduction of a photoreactive conjugating moiety. Photoreactive conjugating moieties are aryl azides, halogenated aryl azides, benzophenones certain diazo compounds and diazirine derivatives. They react with amino-based conjugating moieties or with conjugating moieties that have activated hydrogen bonds.

The azido-based conjugating moieties are UV labile and, upon photolysis, can lead to the formation of nitrene electrophiles that can react with nucleophilic conjugating moieties such as aryl-based conjugating moieties or alkenyl-based conjugating moieties. Alternatively, the heating of these azido compounds can also result in nitrene formation.

Cycloaddition Reactions

Cycloaddition reactions can be used to form the desired covalent bond. Representative cycloaddition reactions include, but are not limited to, the reaction of an alkene-based conjugating moiety with a 1,3-diene-based conjugating moiety (Diels-Alder reaction), the reaction of an alkene-based conjugating moiety with an α,β-unsaturated carbonyl-based conjugating moiety (hetero Diels-Alder reaction), and the reaction of an alkyne-based conjugating moiety with an azido-based conjugating moiety (Hüisgen cycloaddition). Selected, non-limiting examples of conjugating moieties that include reactants for cycloaddition reactions are: alkenes, alkynes, 1,3-dienes, α,β-unsaturated carbonyls, and azides. For example, the Hüisgen cycloaddition (click reaction) between azides and alkynes has been used for the functionalization of diverse biological entities.

Pharmaceutical Compositions

Delivery of hybridized polynucleotide constructs of the invention can be achieved by contacting a cell with the construct using a variety of methods known to those of skill in the art. In particular embodiments, a nucleotide construct of the invention is formulated with various excipients, vehicles, and carriers, as described more fully elsewhere herein.

A pharmaceutical composition according to the invention can be prepared to include a hybridized polynucleotide construct disclosed herein, into a form suitable for administration to a subject using carriers, excipients, and vehicles. Frequently used excipients include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable vehicles include aqueous solutions, non-toxic excipients, including salts, preservatives, buffers and the like, as described, for instance, in *Remington: The Science and Practice of Pharmacy*, $21^{st}$ Ed., Gennaro, Ed., Lippencott Williams & Wilkins (2005), and The United States Pharmacopeia: The National Formulary (USP 36 NF31), published in 2013. The pH and exact concentration of the various components of the pharmaceutical composition are adjusted according to routine skills in the art. See Goodman and Gilman's, The Pharmacological Basis for Therapeutics.

The pharmaceutical compositions according to the invention may be administered locally or systemically. The therapeutically effective amounts will vary according to factors, such as the degree of infection in a subject, the age, sex, and weight of the individual. Dosage regimes can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (e.g., subcutaneous, intravenous, intraorbital, and the like), oral administration, ophthalmic application, inhalation, topical application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. The composition will typically be sterile and fluid to the extent that easy syringability exists. Typically the composition will be stable under the conditions of manufacture and storage and preserved against the contaminating action of microorganisms, such as bacteria and fungi. The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols, such as mannitol, sorbitol, or sodium chloride are used in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

It is especially advantageous to formulate parenteral compositions in dosage unit form for ease of administration and uniformity of dosage. Dosage unit form as used herein, refers to physically discrete units suited as unitary dosages for the subject to be treated; each unit containing a predetermined quantity of pharmaceutical composition is calculated to produce the desired therapeutic effect in association with the required pharmaceutical vehicle. The specification for the dosage unit forms of the invention are related to the characteristics of the pharmaceutical composition and the particular therapeutic effect to be achieve. The principal pharmaceutical composition is compounded for convenient and effective administration in effective amounts with a suitable pharmaceutically acceptable vehicle in an acceptable dosage unit. In the case of compositions containing supplementary active ingredients, the dosages are determined by reference to the usual dose and manner of administration of the ingredients.

For topical formulations, the base composition can be prepared with any solvent system, such as those Generally Regarded as Safe (GRAS) by the U.S. Food & Drug Administration (FDA). GRAS solvent systems include many short chain hydrocarbons, such as butane, propane, n-butane, or a mixture thereof, as the delivery vehicle, which are approved by the FDA for topical use. The topical compositions can be formulated using any dermatologically acceptable vehicle. Exemplary vehicles include a solid vehicle, such as alumina, clay, microcrystalline cellulose, silica, or talc; and/or a liquid vehicle, such as an alcohol, a glycol, or a water-alcohol/glycol blend. The compounds may also be administered in liposomal formulations that allow compounds to enter the skin. Such liposomal formulations are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; and PCT Publication No. WO 96/40061. Examples of other appropriate vehicles are described in U.S. Pat. Nos. 4,877,805, 4,980,378, 5,082,866, 6,118,020 and EP Publication No. 0586106A1. Suitable vehicles of the invention may also include mineral oil, petrolatum, polydecene, stearic acid, isopropyl myristate, polyoxyl 40 stearate, stearyl alcohol, or vegetable oil.

Topical compositions can be provided in any useful form. For example, the compositions of the invention may be formulated with a carrier, e.g., as solutions, emulsions (including microemulsions), suspensions, creams, foams, lotions, gels, powders, balm, or other typical solid, semi-solid, or liquid compositions used for application to the skin or other tissues where the compositions may be used. Such compositions may contain other excipients typically used in such products, such as colorants, fragrances, thickeners, antimicrobials, solvents, surfactants, detergents, gelling agents, antioxidants, fillers, dyestuffs, viscosity-controlling agents, preservatives, humectants, emollients (e.g., natural or synthetic oils, hydrocarbon oils, waxes, or silicones), hydration agents, chelating agents, demulcents, solubilizing excipients, adjuvants, dispersants, skin penetration enhancers, plasticizing agents, preservatives, stabilizers, demulsifiers, wetting agents, sunscreens, emulsifiers, moisturizers, astringents, deodorants, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

In some formulations, the composition is formulated for ocular application. For example, a pharmaceutical formulation for ocular application can include a polynucleotide construct as described herein in an amount that is, e.g., up to 99% by weight mixed with a physiologically acceptable ophthalmic vehicle medium such as water, buffer, saline, glycine, hyaluronic acid, mannitol, and the like. For ophthalmic delivery, a polynucleotide construct as described herein may be combined with ophthalmologically acceptable preservatives, co-solvents, surfactants, viscosity enhancers, penetration enhancers, buffers, sodium chloride, or water to form an aqueous, sterile ophthalmic suspension or solution. Ophthalmic solution formulations may be prepared by dissolving the polynucleotide construct in a physiologically acceptable isotonic aqueous buffer. Further, the ophthalmic solution may include an ophthalmologically acceptable surfactant to assist in dissolving the inhibitor. Viscosity building agents, such as hydroxymethyl cellulose, hydroxyethyl cellulose, methylcellulose, polyvinylpyrrolidone, or the like may be added to the compositions of the invention to improve the retention of the compound.

Topical compositions can be delivered to the surface of the eye, e.g., one to four times per day, or on an extended delivery schedule such as daily, weekly, bi-weekly, monthly, or longer, according to the routine discretion of a skilled clinician. The pH of the formulation can range from about 4 to about 9, or from about 4.5 to about 7.4.

The pharmaceutical composition can be orally administered, for example, in a carrier, e.g., in an enteric-coated unit dosage form. The pharmaceutical composition and other ingredients can also be enclosed in a hard or soft-shell gelatin capsule or compressed into tablets. For oral therapeutic administration, the pharmaceutical composition can be incorporated with excipients and used in the form of ingestible tablets, troches, capsules, pills, wafers, and the like. Such compositions and preparations should contain at least 1% by weight of active compound. The percentage of the compositions and preparations can, of course, be varied and can conveniently be between about 5% to about 80% of the weight of the unit. The tablets, troches, pills, capsules, and the like can also contain the following: a binder, such as gum tragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Any material used in preparing any dosage unit form should be of pharmaceutically acceptable purity and substantially non-toxic in the amounts employed. In addition, the pharmaceutical composition can be incorporated into sustained-release preparations and formulations.

For nucleotide constructs of the invention, suitable pharmaceutically acceptable salts include (i) salts formed with cations such as sodium, potassium, ammonium, magnesium, calcium, polyamines such as spermine and spermidine, etc.; (ii) acid addition salts formed with inorganic acids, for example hydrochloric acid, hydrobromic acid, sulfuric acid, phosphoric acid, and the like; and (iii) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like.

While the hybridized polynucleotide constructs described herein may not require the use of excipients for delivery to the target cell, the use of excipients may be advantageous in some embodiments. Thus, for delivery to the target cell, the hybridized polynucleotide constructs of the invention can non-covalently bind an excipient to form a complex. The excipient can be used to alter biodistribution after delivery, to enhance uptake, to increase half-life or stability of the strands in the hybridized polynucleotide constructs (e.g., improve nuclease resistance), and/or to increase targeting to a particular cell or tissue type.

Exemplary excipients include a condensing agent (e.g., an agent capable of attracting or binding a nucleic acid through ionic or electrostatic interactions); a fusogenic agent (e.g., an agent capable of fusing and/or being transported through a cell membrane); a protein to target a particular cell or tissue type (e.g., thyrotropin, melanotropin, lectin, glycoprotein, surfactant protein A, or any other protein); a lipid; a lipopolysaccharide; a lipid micelle or a liposome (e.g., formed from phospholipids, such as phosphotidylcholine, fatty acids, glycolipids, ceramides, glycerides, cholesterols, or any combination thereof); a nanoparticle (e.g., silica, lipid, carbohydrate, or other pharmaceutically-acceptable polymer nanoparticle); a polyplex formed from cationic polymers and an anionic agent (e.g., a CRO), where exemplary cationic polymers include polyamines (e.g., polylysine, polyarginine, polyamidoamine, and polyethylene imine); cholesterol; a dendrimer (e.g., a polyamidoamine (PAMAM) dendrimer); a serum protein (e.g., human serum albumin (HSA) or low-density lipoprotein (LDL)); a carbohydrate (e.g., dextran, pullulan, chitin, chitosan, inulin, cyclodextrin, or hyaluronic acid); a lipid; a synthetic polymer, (e.g., polylysine (PLL), polyethylenimine, poly-L-aspartic acid, poly-L-glutamic acid, styrene-maleic acid anhydride copolymer, poly(L-lactide-co-glycolic) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymer, pseudopeptide-polyamine, peptidomimetic polyamine, or polyamine); a cationic moiety (e.g., cationic lipid, cationic porphyrin, quaternary salt of a polyamine, or alpha helical peptide); a multivalent sugar (e.g., multivalent lactose, multivalent galactose, N-acetyl-galactosamine, N-acetyl-glucosamine, multivalent mannose, or multivalent fucose); a vitamin (e.g., vitamin A, vitamin E, vitamin K, vitamin B, folic acid, vitamin B12, riboflavin, biotin, or pyridoxal); a cofactor; or a drug to disrupt cellular cytoskeleton to increase uptake (e.g., taxol, vincristine, vinblastine, cytochalasin, nocodazole, japlakinolide, latrunculin A, phalloidin, swinholide A, indanocine, or myoservin).

Other therapeutic agents as described herein may be included in a pharmaceutical composition of the invention in combination with a nucleotide construct of the invention.

Intracellular Activity of the Hybridized Polynucleotide Constructs

The invention provides compositions and methods for delivering hybridized polynucleotide constructs disclosed herein. The invention therefore provides methods and compositions useful for delivery of non-coding nucleotide constructs that exert a regulating effect on gene or protein expression through RNA interference (RNAi). RNA interference (RNAi) is the process whereby messenger RNA (mRNA) is degraded by small interfering RNA (siRNA) derived from double-stranded RNA (dsRNA) containing an identical or very similar nucleotide sequence to that of a target gene to be silenced. This process prevents the production of a protein encoded by the targeted gene through post-transcriptional, pre-translational manipulation. Accordingly, silencing of dominant disease genes or other target genes can be accomplished.

In vivo RNAi proceeds by a process in which the dsRNA is cleaved into short interfering RNAs (siRNAs) by an enzyme called Dicer, a dsRNA endoribonuclease, (Bernstein et al., 2001; Hamilton & Baulcombe, 1999, Science 286: 950; Meister and Tuschl, 2004, Nature 431, 343-9), thus producing multiple molecules from the original single dsRNA. siRNAs are loaded into the multimeric RNAi Silencing Complex (RISC) resulting in both catalytic activation and mRNA target specificity (Hannon and Rossi, Nature 431, 371-378, 2004; Novina and Sharp, Nature 430, 161-164, 2004). During siRNA loading into RISC, the antisense or guide strand is separated from the siRNA and remains docked in Argonaute-2 (Ago2), the RISC catalytic subunit (Leuschner et al., EMBO Rep. 7, 314-320, 2006). Certain cellular compartments, such as endoplasmic reticulum (ER), Golgi apparatus, ER-Golgi intermediate compartment (ERGIC), P-bodies, and early endosomes are enriched in Ago2. mRNAs exported from the nucleus into the cytoplasm are thought to pass through activated RISCs prior to ribosomal arrival, thereby allowing for directed, post-transcriptional, pre-translational regulation of gene expression. In theory, each and every cellular mRNA can be regulated by induction of a selective RNAi response.

The ability of siRNAs to efficiently induce an RNAi response in mammalian cells in vitro is known (Sontheimer, Nat. Rev. Mol. Cell. Biol. 6, 127-138, 2005). Typically, the $IC_{50}$ for siRNAs is in the 10-100 pM range, significantly below the best drugs with $IC_{50}$ values in the 1-10 nM range. Consequently, due to its exquisite selectivity, RNAi has become a corner-stone for directed manipulation of cellular phenotypes, mapping genetic pathways, discovering and validating therapeutic targets, and has significant therapeutic potential.

Aspects of RNAi include (1) dsRNA is the interfering agent; (2) the process can be sequence-specific and is remarkably potent (only a few dsRNA molecules per cell are required for effective interference); (3) the interfering activity (and presumably the dsRNA) can cause interference in cells and tissues far removed from the site of introduction. However, effective delivery of dsRNA is difficult. For example, a 21 bp dsRNA with a molecular weight of 13,860 Daltons cannot traverse the cell membrane to enter the cytoplasm, due to (1) the size and (2) the accumulation of negative charges on the RNA molecule at physiologically relevant pH levels. The methods and compositions of the invention provide the delivery of nucleotide constructs, such as dsRNA, into a cell through charge neutralization and improved uptake.

dsRNA including siRNA sequences that are complementary to a nucleotide sequence of the target gene can be prepared in any number of methods, e.g., those described herein. Methods and techniques for identifying siRNA sequences are known in the art. The siRNA nucleotide sequence can be obtained from the siRNA Selection Program, Whitehead Institute for Biomedical Research, Massachusetts Institute of Technology, Cambridge, Mass. (currently available at http:[//]sirna.wi.mit.edu; note that brackets have been added to remove hyperlinks) after supplying the Accession Number or GI number from the National Center for Biotechnology Information website (available on the World Wide Web at ncbi.nlm.nih.gov). Alternatively, dsRNA containing appropriate siRNA sequences can be ascertained using the strategy of Miyagishi and Taira (2003). Commercially available RNAi designer algorithms also exist (http:[//]rnaidesigner.invitrogen.com/rnaiexpress/). Preparation of RNA to order is commercially available.

Nucleotide constructs of the invention may also act as miRNA to induce cleavage of mRNA. Alternatively, nucleotide constructs of the invention may act as antisense agents to bind to mRNA, either to induce cleavage by RNase or to sterically block translation.

Exemplary methods by which the nucleotide constructs of the invention can be transported into a cell are described herein.

The following examples are meant to illustrate the invention. They are not meant to limit the invention in any way.

EXAMPLES

Precursors

Precursors useful in the preparation of the polynucleotides of the invention are provided in WO 2015/188197 (e.g., phosphoramidites, targeting moieties, and bioreversible groups containing PEG chains).

Phosphoramidites and Other Monomers

Nucleoside-containing intermediates useful in the synthesis of polynucleotides of the invention are disclosed in WO 2015/188197 (e.g., compounds U1-U54, A1-A15, $C_{1-9}$, and G1-G12 in WO 2015/188197).

Commercially available phosphoramidites were purchased from Glen Research (Sterling, VA) or ChemGenes (Wilmington, MA). When required, other phosphoramidtes were prepared from appropriately protected nucleosides using standard reaction conditions described here or elsewhere.

Example 1. Synthesis of Intermediates

X1 and X2 Linker Synthesis—Scheme 1:

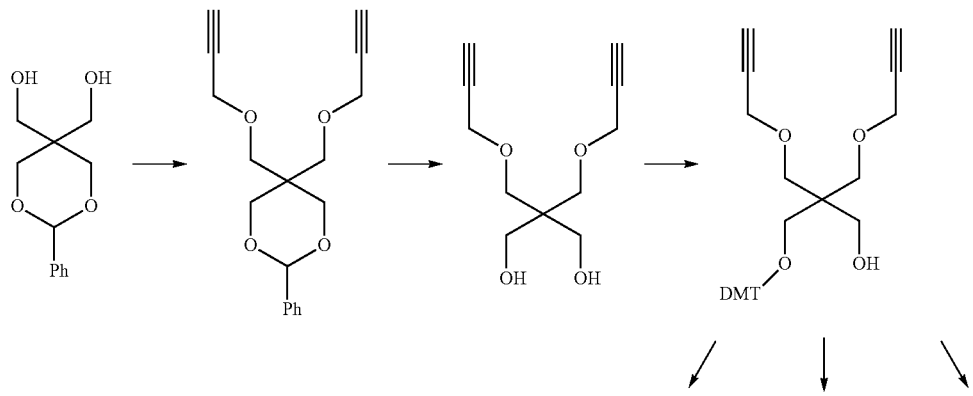

-continued

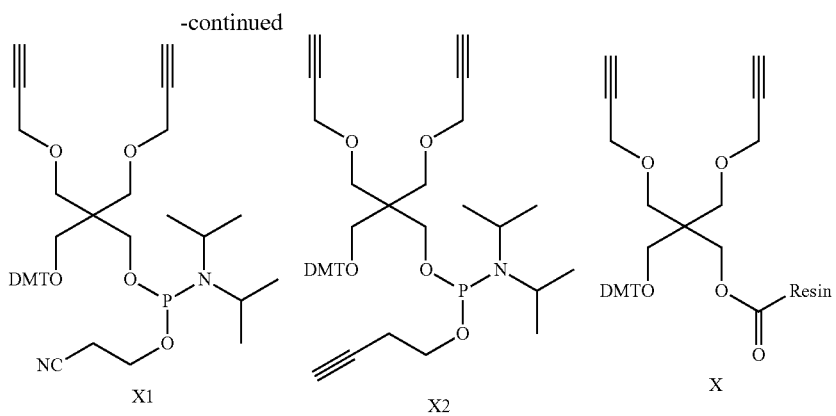

Compound S110

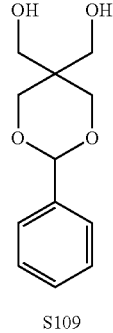

Compound S111

To a suspension of NaH (13.2 g, 60% in mineral oil, 230.0 mmol) in THF (40 mL) under argon at 0° C. was added a solution of diol (S109, 4.92 g, 22.0 mmol) in THF (20 mL) dropwise; the resulting mixture was warmed to room temperature and stirred for 1 h. The reaction mixture was cooled to 0° C., a solution of propargyl bromide (18.6 g, 158.4 mmol) in THF (25 mL) was added slowly, and the resulting mixture was warmed to room temperature and stirred overnight at 40° C. After the product was consumed, as observed by TLC, the reaction was quenched by dropwise addition of water at 0° C., and the resulting mixture was extracted with dichloromethane (50 mL×2). The combined organic layers were washed with brine and dried over anhydrous $Na_2SO_4$, filtered, and evaporated to give a residue, which was purified by flash silica gel column using ISCO companion (hexane/ethyl acetate, 0-30%) to give 5.92 g (89.5%) of compound S110 as an oil. $^1$H NMR (500 MHz, $CDCl_3$; ppm): δ7.49-7.47 (dd, J 8.0, 1.5 Hz, 2H), 7.38-7.34 (m, 3H), 5.43 (s, 1H), 4.21 (d, J 2.5 Hz, 2H), 4.12 (t, J 2.5 Hz, 4H), 4.10 (s, 1H), 3.91 (s, 1H), 3.89 (s, 1H), 3.37 (s, 2H); ESI MS for $C_{18}H_{20}O_4$ calculated 300.34, observed [M+H]$^+$ 301.3

Bis-propargyl compound S110 (5.9 g, 19.64 mmol) was dissolved in acetic acid/water mixture (60 mL, 75:25), and the reaction was continued at 50° C. for 2 h. After completion of the reaction, the solution was evaporated and co-evaporated with toluene (2×20 mL). The residue was purified directly without any workup by flash silica gel chromatography using ISCO companion (hexane/ethyl acetate, 20-80%) to give 3.02 g (72.5%) of the compound S111 as an oil. $^1$H NMR (500 MHz, $CDCl_3$; ppm): δ4.15 (d, J 2.5 Hz, 4H), 3.68 (s, 4H), 3.59 (s, 4H), 2.44 (t, J2.5 Hz, 2H), 2.30-2.40 (br, 2H); ESI MS for $C_{11}H_{16}O_4$ calculated 212.24, observed [M+H]$^+$ 213.2

Compound S112

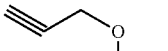

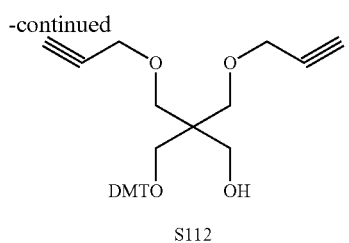

S112

To a solution of diol S111 (3.0 g, 14.2 mmol), N,N-diisopropylethylamine (3.15 mL, 17.0 mmol), and DMAP (0.36 g, 2.83 mmol) in dichloromethane (25 mL) at 0° C. was added dropwise a solution of dimethoxytrityl chloride (4.8 g, 14.2 mmol) in dichloromethane (40 mL), and the reaction continued at room temperature overnight. The mixture was diluted with dichloromethane and washed with water followed by brine, and the organic layers were dried over anhydrous $Na_2SO_4$, filtered, and evaporated. The resulting residue was purified by flash silica gel column using ISCO companion (hexane/ethyl acetate, 0-40%) to give 5.29 g (73%) of the mono DMT protected compound S112 as white solid. $^1$H NMR (500 MHz, $CDCl_3$; ppm): δ7.4-7.42 (m, 2H), 7.32-7.31 (m, 4H), 7.28-7.25 (m, 2H), 6.84-6.81 (m, 4H), 4.09 (d, J 2.5 Hz, 4H), 3.79 (s, 6H), 3.67 (d, J 6.0 Hz, 2H), 3.64-3.56 (m, 4H), 3.13 (s, 2H), 2.39 (t, J2.5 Hz, 2H); ESI MS for $C_{32}H_{34}O_6$ calculated 514.6, observed [M+Na]$^+$ 537.4

Compound S113

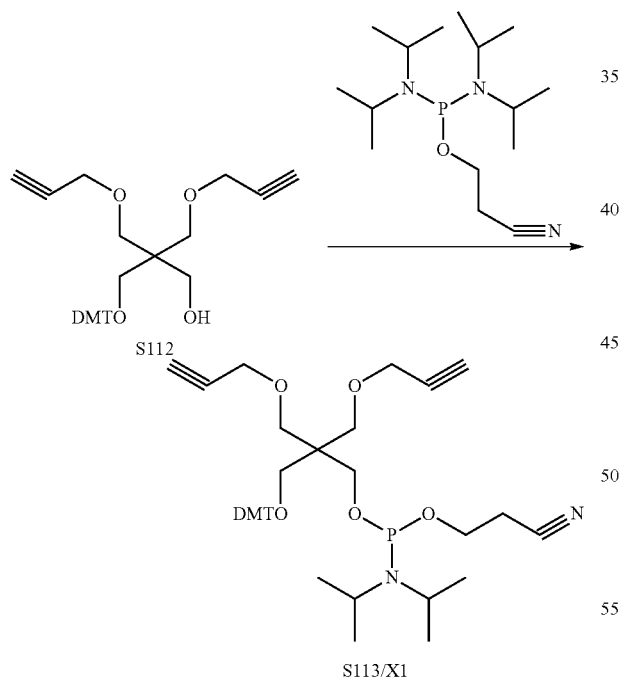

S113/X1

To a solution of DMT-protected compound S112 (0.5 g, 0.98 mmol) in dichloromethane (4 mL) was added dropwise a solution of 2'-cyanoethyl-N,N,N',N'-tetraisopropyl phosphoramidite (0.58 g, 1.95 mmol) in dichloromethane (3 mL) at room temperature followed by 5-benzylthio-1H-tetrazole (BTT; 0.25 M solution in acetonitrile, 0.78 mL, 0.18 mmol) under argon atmosphere. The reaction was continued until the starting material disappeared (2 h), and the crude mixture was diluted with 20 mL of dichloromethane, washed sequentially with saturated $NaHCO_3$ solution (10 mL) and brine (10 mL), and dried over anhydrous $Na_2SO_4$. The solvent was evaporated in vacuo, and the crude mixture was purified by silica gel column chromatography using ethyl acetate/hexane having 3% triethylamine as a co-solvent (0-30% gradient on Combi Flash Rf Instrument) to give 0.53 g of compound S113 (75%) as an oil. ESI MS for $C_{41}H_{51}N_2O_7P$ Calculated 714.82, Observed 715.6 [M+H]$^+$; $^{31}$P NMR (202 MHz, $CDCl_3$): δ147.89

Compound S114

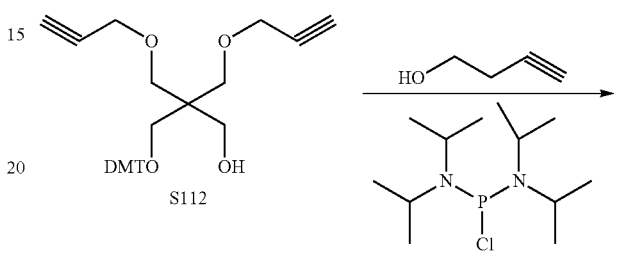

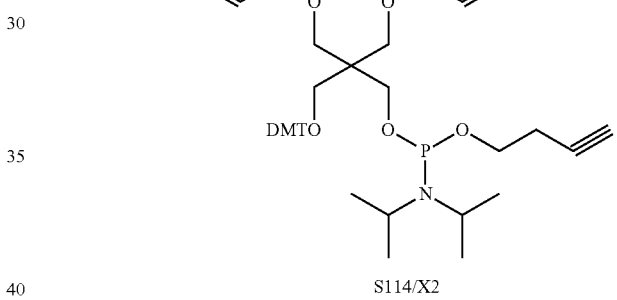

S114/X2

To a −78° C. solution of DMT-protected compound S112 (0.98 g, 1.9 mmol) and N,N-diisopropylethylamine (0.39 mL, 2.09 mmol) in 8.0 mL of dry dichloromethane under argon atmosphere was added dropwise a dichloromethane (4.0 mL) solution of bis-(N,N-diisopropylamino)-chlorophosphine (0.56 g, 2.09 mmol). The reaction mixture was allowed to warm to room temperature while stirring was maintained for 1 h. A solution of 3-butyne-1-ol (0.14 g, 1.9 mmol) in 2.0 mL of dry dichloromethane was added at room temperature; the resulting mixture was stirred for 10 minutes, at which time a 0.25M solution of ETT in acetonitrile (4.6 mL, 1.15 mmol) was added, and stirring continued for an additional 3 h. After completion of the reaction, as observed by the disappearance of the starting material by TLC, the crude mixture was diluted with 20 mL of dichloromethane and washed sequentially with saturated $NaHCO_3$ solution (10 mL) and brine (10 mL) and dried over anhydrous $Na_2SO_4$. The volatiles were evaporated in vacuo, and the crude mixture was purified by silica gel column chromatography using ethyl acetate/hexane with 3% triethylamine as solvent system (0-40% gradient on Combi Flash Rf Instrument) to give 0.33 g of compound S114 (25%) as an oil. ESI MS for $C_{42}H_{52}NO_7P$ Calculated 713.83, Observed 714.7 [M+H]$^+$; $^{31}$P NMR (202 MHz, $CDCl_3$): δ146.89

X3 and X4 Linker Synthesis—Scheme 2:

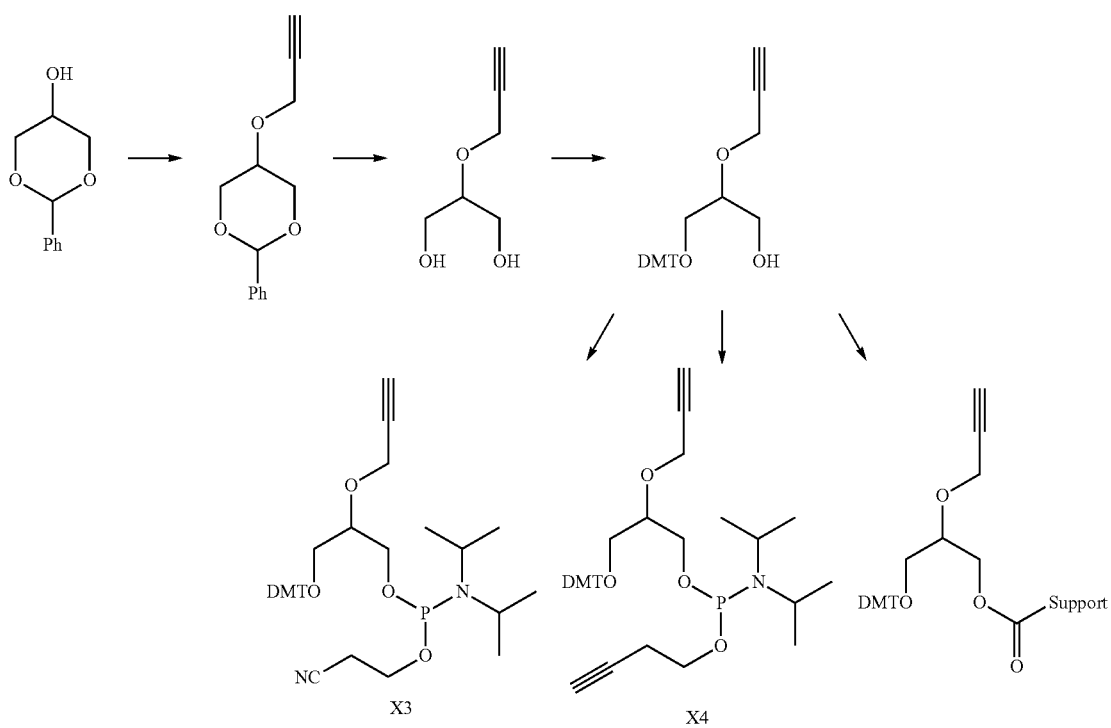

Compound S116

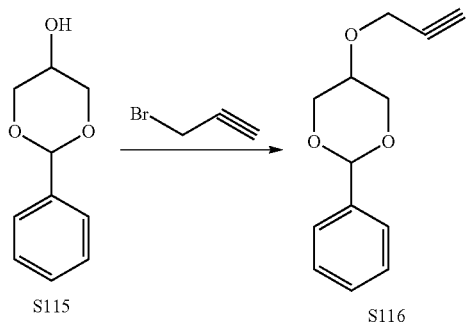

Compound S116 was prepared using the protocol described for compound S110 in 91% yield as oil. $^1$H NMR (500 MHz, CDCl$_3$; ppm): δ7.51 (d, J 7.5 Hz, 2H), 7.37-7.32 (m, 3H), 5.56 (s, 1H), 3.37-3.35 (m, 4H), 4.10-4.07 (dd, J 13.0 Hz, J2.5 Hz, 2H), 3.65-3.64 (m, 1H), 2.43-2.42 (t, J 6.5 Hz, 1H); ESI MS for C$_{13}$H$_{14}$O$_3$ calculated 218.24, observed [M+H]$^+$ 219.2

Compound S117

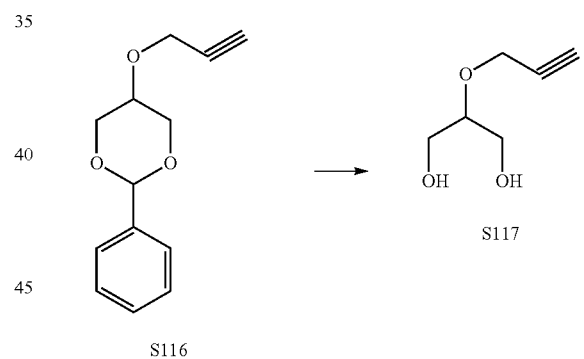

Compound S117 was prepared using the protocol described for compound S111 in 91% yield as oil. $^1$H NMR (500 MHz, CDCl$_3$; ppm): δ4.33 (s, 2H), 3.83-3.70 (m, 5H), 2.48 (s, 1H), 2.04 (br, 2H); ESI MS for C$_6$H$_{10}$O$_3$ calculated 130.14, observed [M+Na]$^+$ 153.0

Compound S118

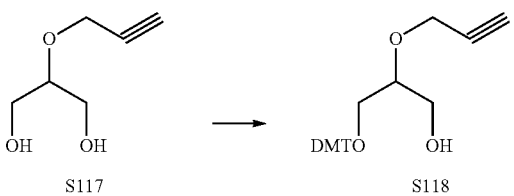

Compound S118 was prepared using the protocol described for compound S112 in 54% yield as a white solid. $^1$H NMR (500 MHz, CDCl$_3$; ppm): δ7.43 (d, J 7.5 Hz, 2H), 7.37-7.27 (m, 5H), 7.23-7.16 (m, 2H), 6.83 (d, J 9.0 Hz, 3H), 6.78-6.76 (dd J 8.5 Hz, 1H), 4.35-4.22 (m, 2H), 3.77 (s, 6H) 3.76-3.72 (m, 2H), 3.71-3.64 (m, 1H), 3.27-3.19 (m, 2H), 2.48 (t, J 4.5 Hz, 1H), 2.03-1.96 (m, 1H); ESI MS for $C_{27}H_{28}O_5$ calculated 432.50, observed [M+Na]$^+$ 455.4
Compound S119 for $C_{36}H_{45}N_2O_6P$ Calculated 632.7, Observed 633.5 [M+H]$^+$; $^{31}$P NMR (202 MHz, CDCl$_3$): δ149.05, 148.96.
Compound S120

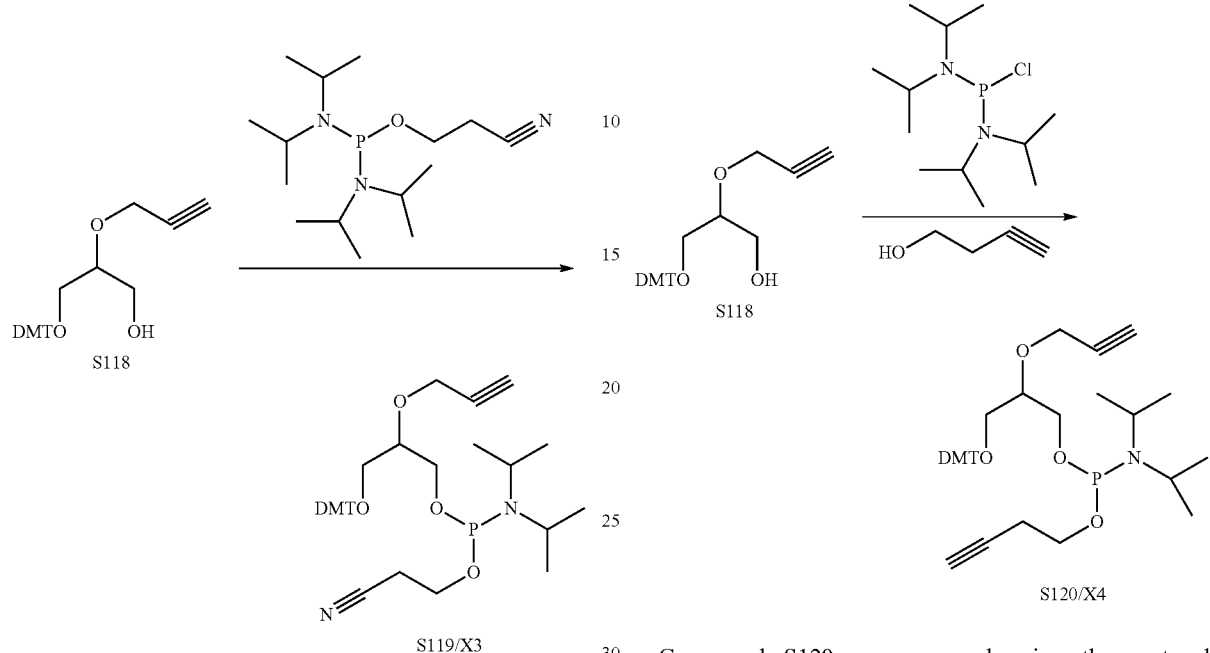

Compound S119 was prepared using the protocol described for compound S113 in 86% yield as oil. ESI MS Compound S120 was prepared using the protocol described for compound S114 in 47% yield as oil. ESI MS for $C_{37}H_{46}NO_6P$ Calculated 631.73, Observed 632.5 [M+H]$^+$; $^{31}$P NMR (202 MHz, CDCl$_3$): δ147.80, 147.71

Synthesis of Linkers X5 and X6

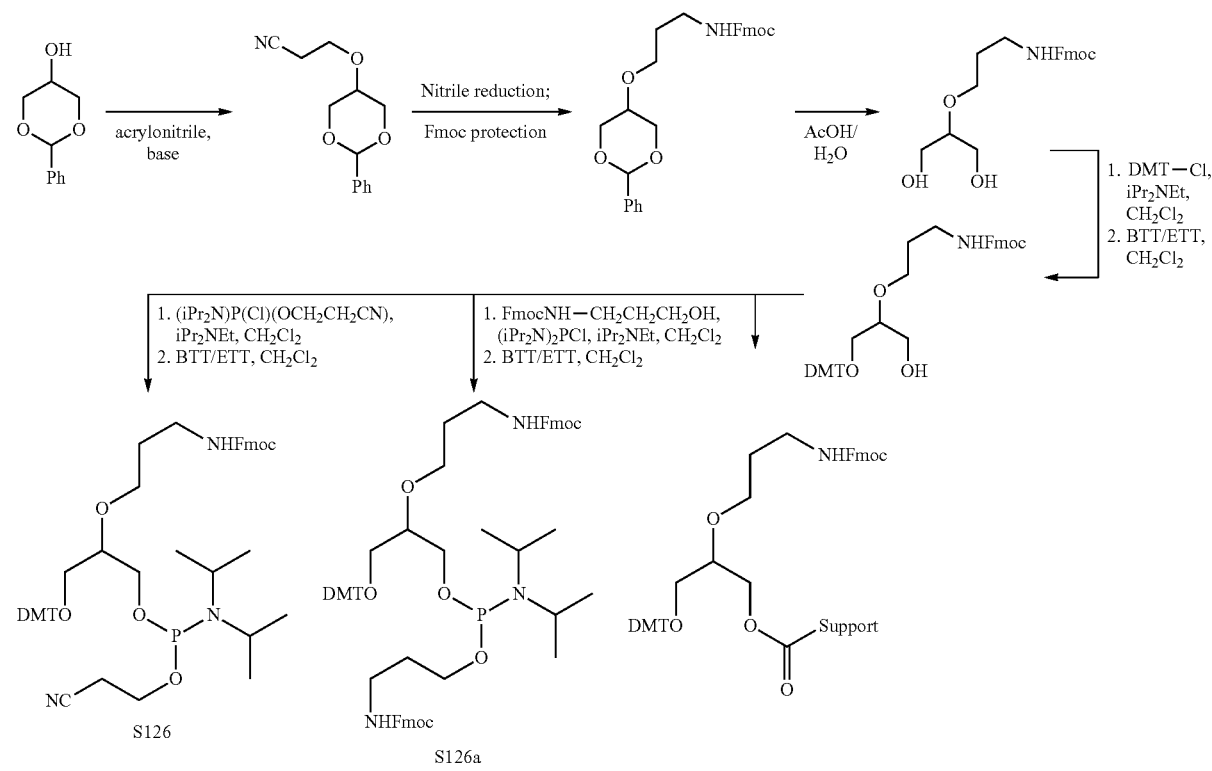

Compound S121

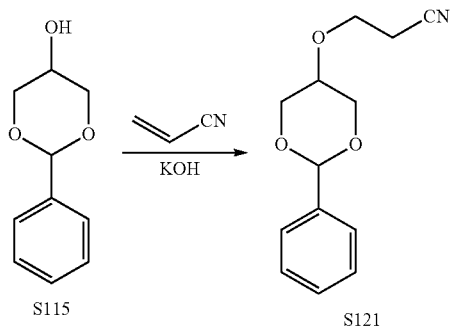

To a solution of S115 (4.0 g, 22.2 mmol) in dioxane (25 mL) was added a solution of KOH (0.12 g, 2.2 mmol) dissolved in minimum amount of water, and the resulting mixture was stirred for at least 30 minutes at room temperature. The mixture was cooled to 0° C., a solution of acrylonitrile (2.35 g, 44.4 mmol) in dioxane (15 mL) was added dropwise, and the resulting mixture was allowed to react at room temperature for overnight. Volatiles were evaporated in vacuo, the residue was diluted with water, and the pH was adjusted to near neutral. The crude product was extracted with ethyl acetate (2×50 mL), and the combined organic layers were washed with brine and dried over anhydrous $Na_2SO_4$, filtered, and evaporated to give a residue, which was purified by flash silica gel column using ISCO companion (dichloromethane/methanol, 0-5%) to give 3.1 g (60%) of the compound S121 as white solid. $^1$H NMR (500 MHz, $CDCl_3$; ppm): δ7.49 (d, J 7.0 Hz, 2H), 7.36-7.34 (m, 3H), 5.56 (s, 1H), 3.36 (d, J 13.0 Hz 2H), 4.10-4.07 (dd, J 13.0 Hz, J 2.0 Hz, 2H), 3.84 (t, J 6.5 Hz, 2H), 3.42 (m, 1H), 3.69 (t, J 6.5 Hz, 2H); ESI MS for $C_{13}H_{15}NO_3$ calculated 233.2, observed [M+Na]$^+$ 256.3

Compound S122

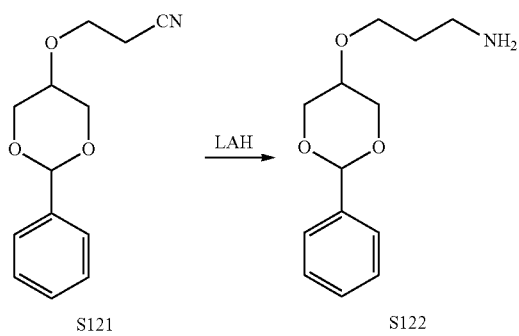 [SMILES: N#CCCOC1COC(c2ccccc2)OC1 ; "LAH" ; NCCCOC1COC(c2ccccc2)OC1 ; "S122" ; "S121"]

To a suspension of lithium aluminum hydride (0.83 g, 4.0 mmol) in THF (10 mL) at 0° C. was added dropwise a solution of compound S121 (1.28 g, 5.5 mmol) in THF (15 mL), the resulting mixture was warmed to room temperature, and stirring was continued for 3 h. After completion of the reaction, the reaction mixture was cooled to 0° C. and quenched by dropwise addition of ice cold water as required (ca. 2-3 mL). Additional ca. 8 mL of water were added, and the crude product was extracted into ethyl acetate (2×25 mL). The combined organic layers were washed with brine, dried over anhydrous $Na_2SO_4$, filtered, and evaporated to give compound S122, which was used in the subsequent step without further purification. $^1$H NMR (500 MHz, $CDCl_3$; ppm): δ7.49 (d, J 7.0 Hz, 2H), 7.40-7.32 (m, 3H), 5.55 (d, J 5.0 Hz, 1H), 4.34 (d, J 13.0 Hz, 1H), 4.20-4.11 (dd, J 12.0 Hz 4H), 4.05-4.03 (d, J 13.0 Hz, J 2.0 Hz, 1H), 3.66-3.62 (m, 2H), 3.27 (m, 1H), 2.86 (t, J 6.5 Hz, 1H), 2.16 (br, 2H); ESI MS for $C_{13}H_{19}NO_3$ calculated 237.2, observed [M+H]$^+$ 238.2

Compound S123

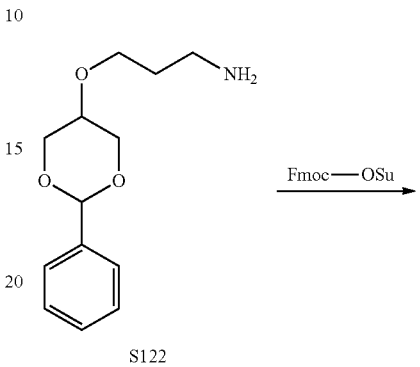

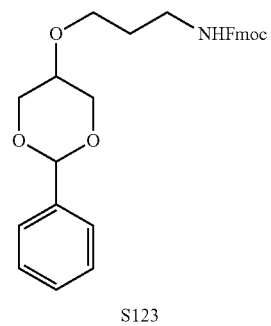

To compound S122 (1.0 g, 4.2 mmol) and N,N-diisopropylethylamine (2.3 mL, 12.6 mmol) in dichloromethane (8 mL) at 0° C. was added dropwise a solution of Fmoc-OSu (1.7 g, 5.0 mmol), and the resulting mixture was allowed to react at room temperature for 3 h. After completion, the reaction mixture diluted with dichloromethane (10 mL) and washed with water followed by brine. The organic layer separated, dried over anhydrous $Na_2SO_4$, filtered, and evaporated to give a residue. The residue was purified by flash silica gel column using ISCO companion (hexane/ethyl acetate, 0-50%) to give 0.65 g (35%) of the compound S123 as a white solid. $^1$H NMR (500 MHz, $CDCl_3$; ppm): δ7.75 (d, J 7.5 Hz, 2H), 7.58 (d, J 7.5 Hz, 2H), 7.51 (d, J 7.5 Hz, 2H), 7.37 (t, J 7.5 Hz, 2H), 7.31-7.26 (m, 5H), 5.57 (s, 1H), 5.48 (br, 1H), 4.46-4.32 (m, 4H), 4.15 (d, J 7.0 Hz, 1H), 4.06 (t, J 12.5 Hz 2H), 3.67 (m, 2H), 3.54 (m, 2H), 3.41 (s, 1H), 1.88 (t, J 6.0 Hz, 2H); ESI MS for $C_{28}H_{29}NO_5$ calculated 459.5, observed [M+Na]$^+$ 482.5

Compound S124

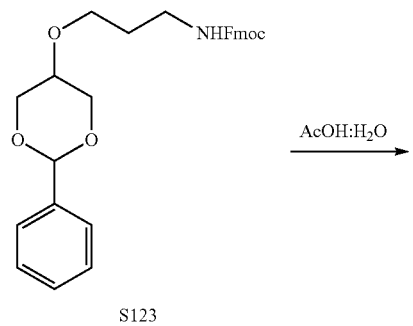

Compound S126a

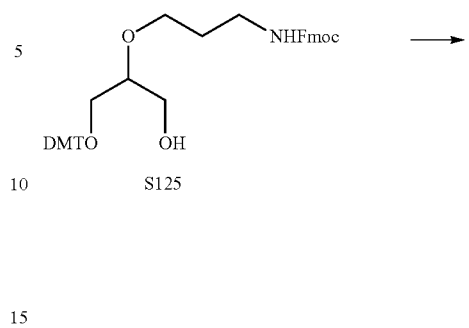

Compound S124 was prepared using the protocol described for compound S111 with quantitative yields as an oil. $^1$H NMR (500 MHz, CDCl$_3$; ppm): δ7.76 (d, J 7.5 Hz, 2H), 7.58 (d, J 7.5 Hz, 2H), 7.39 (t, J 7.5 Hz, 2H), 7.32 (t, J 7.5 Hz, 2H), 5.18 (br, 1H), 4.44 (d, J 6.5 Hz, 2H), 4.21 (t, J 6.5 Hz, 1H), 4.76-4.73 (dd, J 11.5, 3.5 Hz 2H), 3.67-60 (m, 4H), 3.42 (m, 1H), 3.37 (br, 2H), 2.07 (m, 2H), 1.75 (br, 2H); ESI MS for C$_{21}$H$_{25}$NO$_5$ calculated 371.4, observed [M+Na]$^+$ 394.3

Compound S125

Compound S126a was prepared using the protocol described for compound S131 in 40% yield as oil. ESI MS for $^{31}$P NMR (202 MHz, CDCl$_3$): δ147.19. ESI MS for C$_{66}$H$_{74}$N$_3$O$_{10}$P calculated 1100.2, observed [M+H]$^+$ 1101.4.

Compound S126

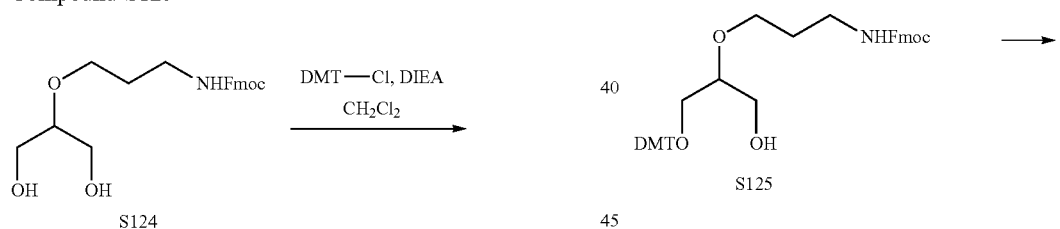

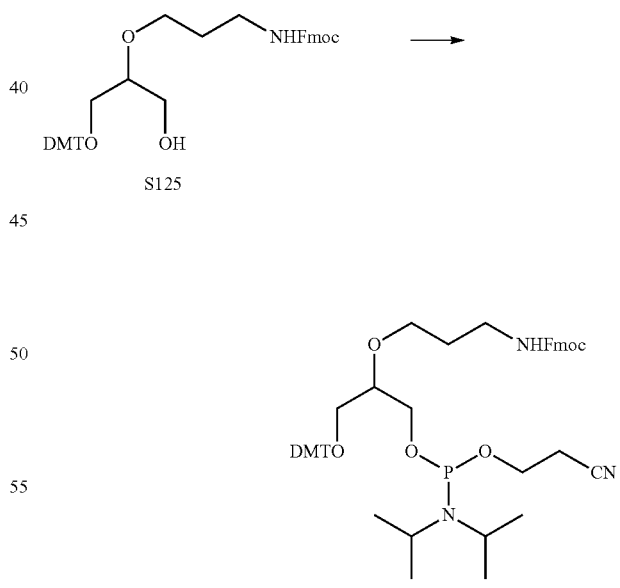

Compound S125 was prepared using the protocol described for compound S112 in 48% yield as a white solid. $^1$H NMR (500 MHz, CDCl$_3$; ppm): δ7.75 (t, J 7.5 Hz, 2H), 7.58 (t, J 7.5 Hz, 2H), 7.40-7.38 (m, 3H), 7.32-27 (m, 7H), 7.18-7.16 (m, 3H), 6.83 (t, J 7.0 Hz, 4H), 5.16 (br, 1H), 4.44 (d, J 6.5 Hz, 2H), 4.20 (m, 1H), 3.80 (s, 3H), 3.79 (m, 1H), 3.76 (s, 3H), 3.74 (m, 2H), 3.66-3.62 (m, 4H), 3.43-3.37 (m, 2H), 2.31 (br, 1H), 1.76 (br, 2H); ESI MS for C$_{42}$H$_{43}$NO$_7$ calculated 673.7, observed [M+Na]$^+$ 696.7

Compound S126 was prepared using the protocol described for compound S113 in 78% yield as an oil. ESI MS for C$_{51}$H$_{60}$N$_3$O$_8$P Calculated 874.0, Observed 896.9 [M+Na]$^+$, 913.0 [M+K]$^+$; $^{31}$P NMR (202 MHz, CDCl$_3$; ppm): δ148.90, 148.76

Synthesis of Linkers S131 and S131a—General Scheme:
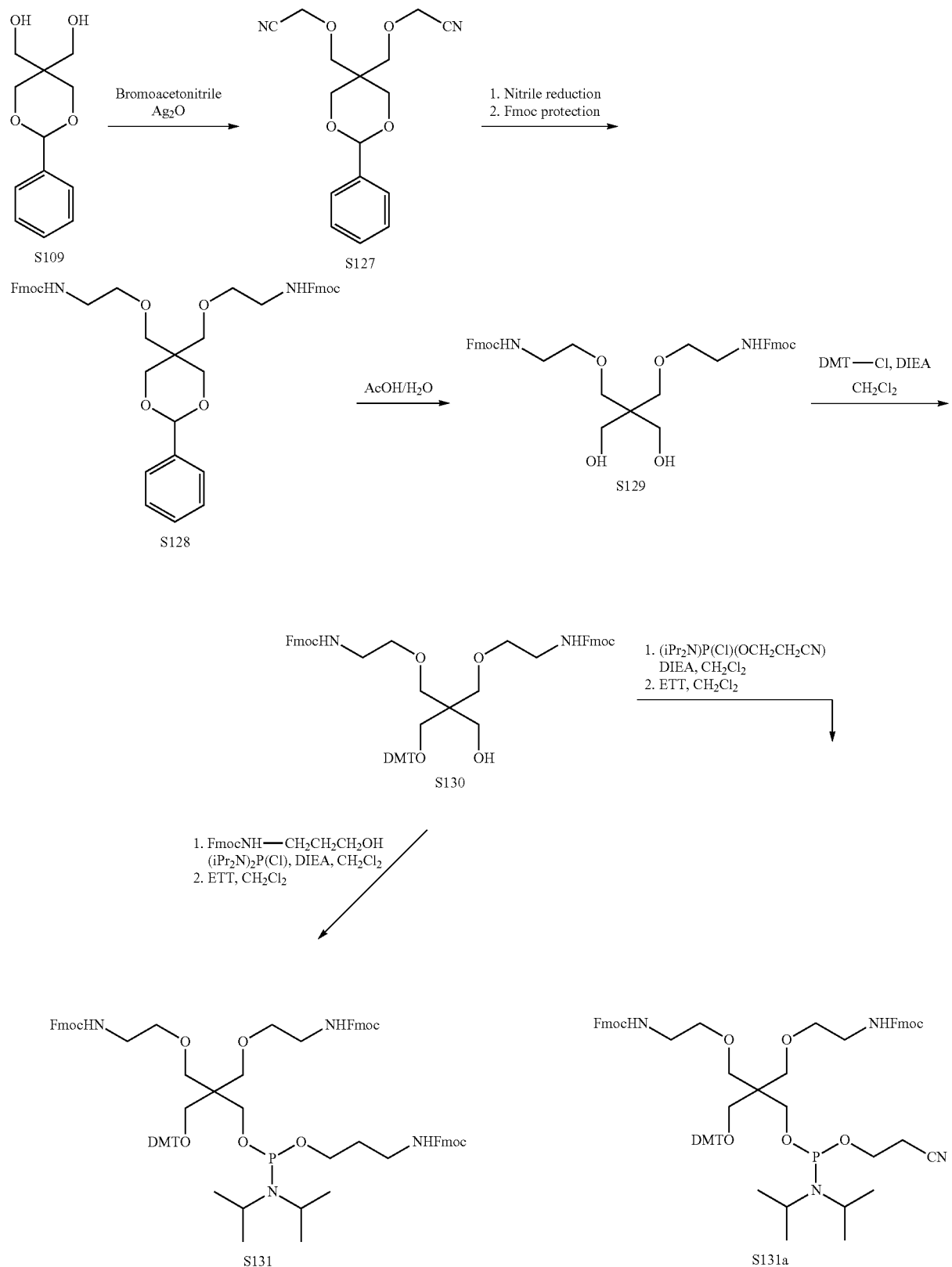

Compound S127

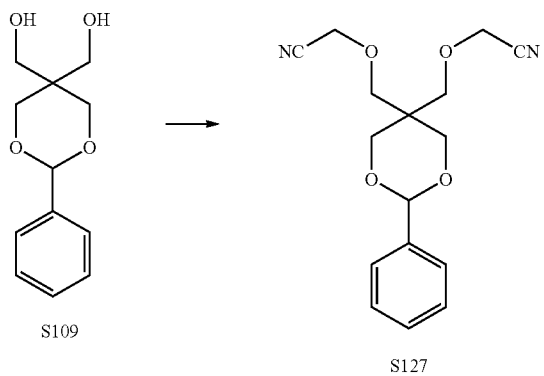 [SMILES: OCC1(CO)COC(c2ccccc2)OC1 ; N#CCOCC1(COCC#N)COC(c2ccccc2)OC1 ; "S109" ; "S127"]

To a solution of S109 (10.0 g, 44.6 mmol) in dichloromethane (180 mL) under argon were added bromoacetonitrile (13.0 g, 108.4 mmol), Silver(I) oxide (20.7 g, 89.2 mmol), and tetrabutylammonium iodide (3.3 g, 8.92 mmol), and the resulting mixture was stirred overnight. The mixture was filtered over Celite®, and the filtrate was evaporated to give a black residue, which was subjected to flash silica gel column purification on ISCO companion (hexane/ethyl acetate, 15-90%) to give 5.55 g (41%) of the desired compound S127 as a viscous oil. ESI MS for $C_{16}H_{18}N_2O_4$ calculated 302.3, observed [M+H]$^+$ 303.3.

Compound S128

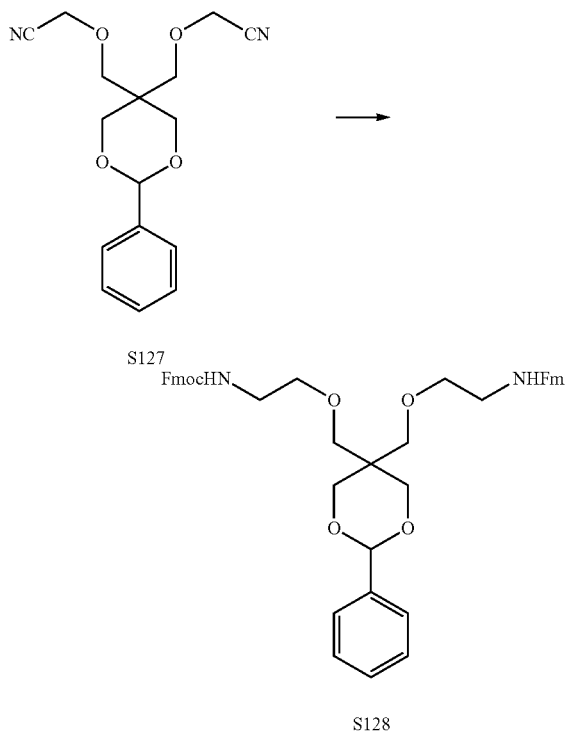

To a solution of compound S127 (5.55 g, 18.4 mmol) in THF (80 mL) was added a solution of LiAlH$_4$ in THF (2M, 37.0 mL, 74.0 mmol) under argon, and the mixture was heated to 55° C. for 5 h. After completion of the reaction, the mixture was cooled to 0° C. and quenched carefully with an aqueous solution of Sodium potassium tartrate (1M, 20 mL). To this mixture was added dichloromethane (30 mL) followed by addition of Fmoc-OSu (18.6 g, 55.2 mmol) and DIEA (9.6 mL, 55.0 mmol). The mixture was stirred vigorously for 1 h, and then extracted with dichloromethane (3×30 mL). The combined organic layers were washed with brine, and dried over anhydrous sodium sulfate. The mixture was filtered and then evaporated to give a residue, which was subjected to flash silica gel column purification on ISCO companion (hexane/ethyl acetate, 20-90%) to give 5.04 g (36%) of S128 as a white foam. $^1$H NMR (500 MHz, CDCl$_3$; ppm): δ7.75 (4H, dd, J 7.5, 4.5 Hz), 7.58 (4H, t, J 7.0 Hz), 7.48 (2H, d, J 7.0 Hz), 7.41-7.34 (7H, m), 7.32-7.26 (4H, m), 5.44 (1H, s), 5.15-5.05 (2H, m), 4.44 (2H, d, J 5.5 Hz), 4.38 (2H, d, J 6.0 Hz), 4.25-4.15 (2H, m), 4.10 (2H, d, J 11.5 Hz), 3.82 (2H, d, J 11.5 Hz), 3.78 (2H, s), 3.53 (2H, s), 3.42 (2H, s), 3.36-3.27 (4H, m), 3.25 (2H, s); ESI MS for $C_{46}H_{46}N_2O_8$ calculated 754.9, observed [M+H]$^+$ 755.3.

Compound S129

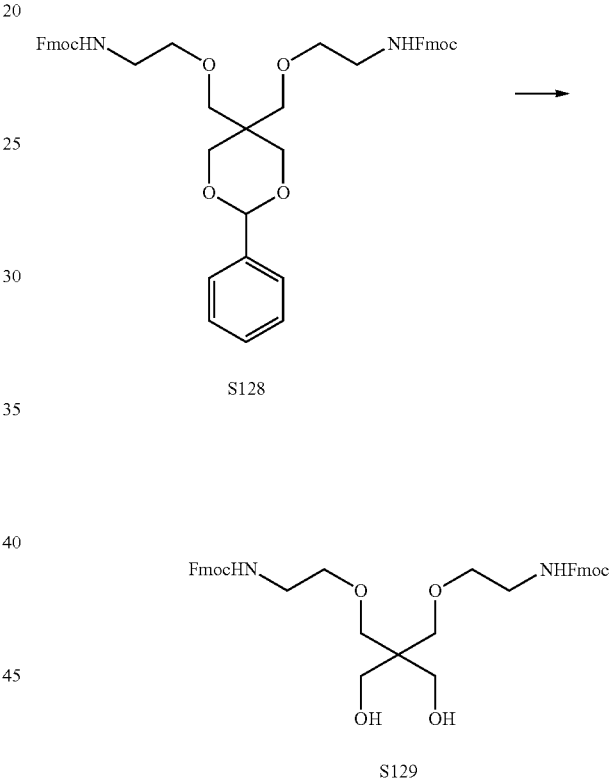

Compound S128 (1.1 g, 1.51 mmol) was dissolved in AcOH/H$_2$O mixture (10 mL, 3:1), and the reaction was continued at 55° C. for 5 h. After completion of the reaction, the volatiles were evaporated and co-evaporated with toluene (2×20 mL), and the residue was subjected to flash silica gel column purification on ISCO companion (hexane/ethyl acetate, 30-100%) to give 0.54 g (54%) of S129 as white foam. $^1$H NMR (500 MHz, CDCl$_3$; ppm): δ7.75 (4H, d, J 7.5 Hz), 7.58 (4H, d, J 7.5 Hz), 7.39 (4H, t, J 7.5 Hz), 7.30 (4H, t, J 7.5 Hz), 5.20-5.05 (2H, m), 4.41 (4H, d, J 6.5 Hz), 4.21 (4H, t, J 6.5 Hz), 3.64 (4H, s), 3.48 (8H, s), 3.36 (4H, s); ESI MS for $C_{39}H_{42}N_2O_8$ calculated 666.7, observed [M+H]$^+$ 667.3.

Compound S130

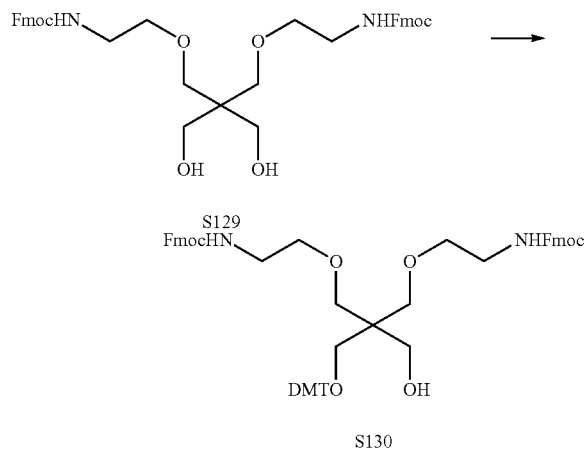

To a solution of diol S129 (0.73 g, 1.1 mmol), DIPEA (0.19 mL, 1.1 mmol) and DMAP (0.013 g, 0.11 mmol) in dichloromethane (6 mL) at 0° C. was added a solution of DMTrCl (0.34 g, 0.99 mmol) in dichloromethane (1.0 mL) dropwise. The resulting mixture was warmed to room temperature and stirred overnight. the mixture was evaporated to give a residue, which was subjected to flash silica gel column purification on a ISCO (hexane/ethyl acetate, 20-100%) to give 0.47 g (44%) of the mono dimethoxytrityl protected compound S130 as a white foam. $^1$H NMR (500 MHz, CDCl$_3$; ppm): δ7.75 (4H, d, J 7.5 Hz), 7.58 (4H, d, J7.5 Hz), 7.39 (4H, t, J7.5 Hz), 7.32-7.25 (8H, m), 7.17 (4H, d, J 6.5 Hz), 6.83 (4H, d, J 6.5 Hz), 5.20-5.05 (2H, m), 4.41 (4H, d, J 6.5 Hz), 4.21 (4H, t, J 6.5 Hz), 3.82 (6H, s), 3.64 (4H, s), 3.48 (8H, s), 3.36 (4H, s); ESI MS for C$_{60}$H$_{60}$N$_2$O$_{10}$ calculated 969.1, observed [M+Na]$^+$ 991.3.

Compound S131

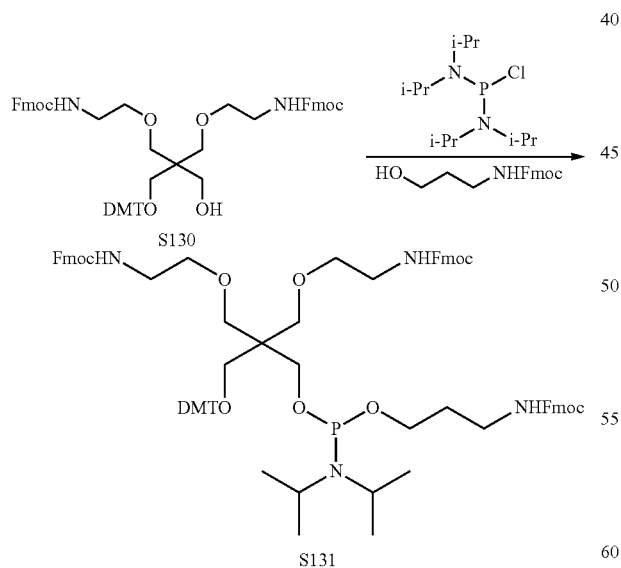

A solution of bis-(N,N-diisopropylamino)-chlorophosphine (0.085 g, 0.32 mmol) in dry CH$_2$Cl$_2$ (1.0 mL) were added dropwise to a solution of 3-Fmoc-amino-propan-1-ol (0.090 g, 0.30 mmol) and N,N-diisopropylethylamine (0.18 mL, 1.05 mmol) in dry CH$_2$Cl$_2$ (3.0 mL) at −78° C. The reaction mixture was warmed to room temperature and stirred for 1.5 h. A solution of compound S130 (0.30 g, 0.30 mmol) in 1.0 mL of dry CH$_2$Cl$_2$ was added, and the resulting mixture was stirred for 10 min. A solution of ETT (0.72 mL, 0.25M in acetonitrile, 0.18 mmol) was added to the reaction mixture, and the resulting mixture was stirred for 3 h. The mixture was diluted with CH$_2$Cl$_2$ (20 mL) and washed with saturated aqueous sodium bicarbonate (20 mL) and brine (20 mL). The organic layer was dried over anhydrous sodium sulfate, and the filtrate was evaporated in vacuum to afford a residue, which was subjected to flash silica gel column purification on a ISCO companion using ethyl acetate/hexane with 3% triethylamine as a co-solvent system (0-30% gradient) to give 0.12 g of product S131 (32%) as a white foam. ESI MS for C$_{84}$H$_{91}$N$_4$O$_{13}$P Calculated 1395.6, Observed 1395.7[M]$^+$; $^{31}$P NMR (202 MHz, CDCl$_3$): δ146.41.

Chiral X-Linkers—Compounds S138, S139, S146 and S147:

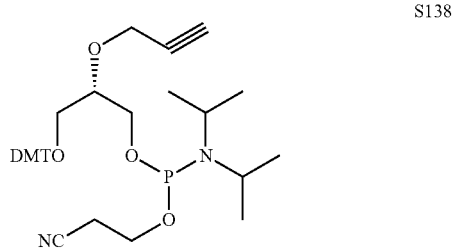

S138

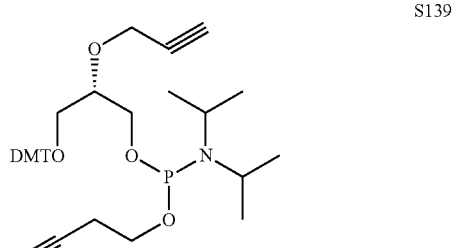

S139

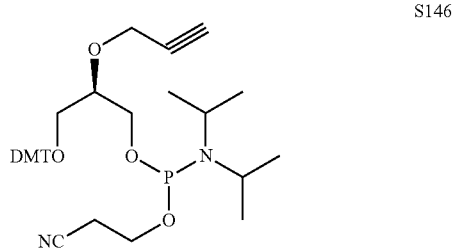

S146

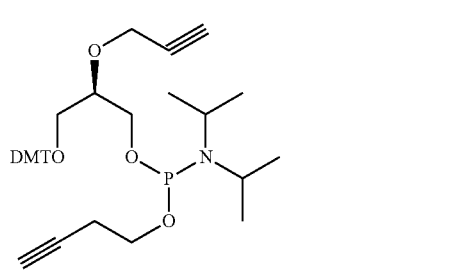

S147

Synthesis of Linkers S138 and S139—General Scheme:

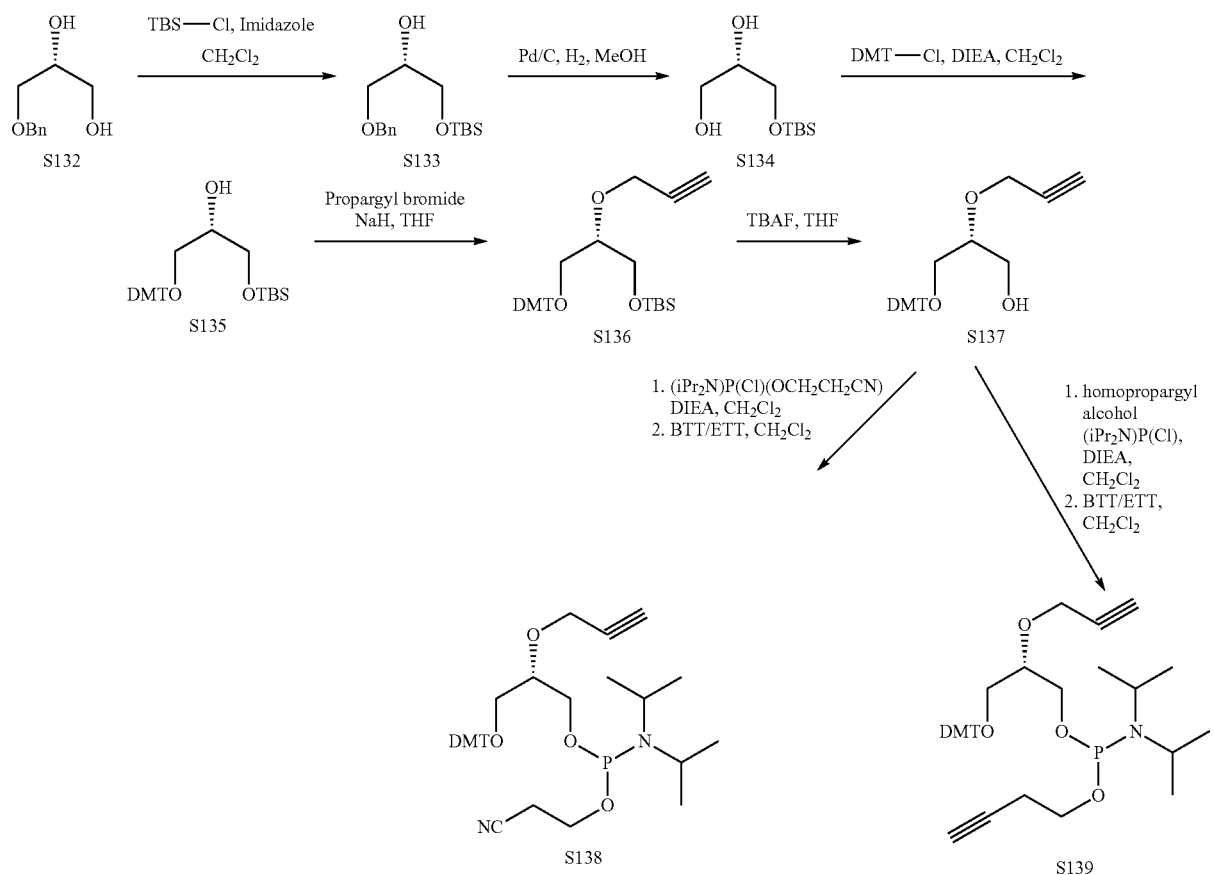

Compound S133

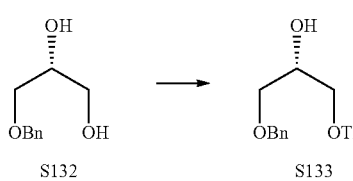

Compound S135

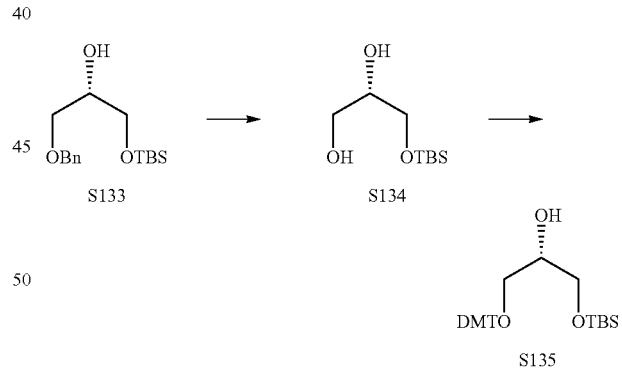

To a solution of (R)-3-Benzyloxy-1,2-propanediol (S132, 4.88 g, 26.78 mmol), Imidazole (3.64 g, 53.56 mmol) in DCM (30 mL) at 0° C. was added a solution of TBDMSCl (TBS-Cl, 4.44 g, 29.46 mmol) in DCM (15 mL) drop wise. The reaction was continued at room temperature for 2 h, after completion of the reaction by TLC, was diluted with DCM, and washed with water. The combined organic layers were washed with brine and dried over anhydrous $Na_2SO_4$, filtered and evaporated to give a residue, which was purified by flash silica gel column using ISCO companion (hexane/ethyl acetate, 0-20%) to give 5.42 g (71%) of the desired compound S133 as a semi solid. $^1$H NMR (500 MHz, $CDCl_3$; ppm): δ7.35-7.7.32 (m, 5H), 4.55 (s, 2H), 3.86-3.84 (m, 1H), 3.69-3.65 (m, 2H), 3.64-3.50 (m, 2H), 2.44 (br, 1H), 0.89 (s, 9H), 0.07 (s, 6H). ESI MS for $C_{16}H_{28}O_3Si$ calculated 296.4, observed $[M+H]^+$ 297.3.

A solution of TBDMS protected compound (S133, 5.6 g, 18.84 mmol), with catalytic amount of Pd in MeOH (40 mL) was stirred at room temperature under $H_2$ atmosphere overnight. After completion of the reaction by TLC, the reaction mixture was quickly filtered through celite bed, washed with methanol, solvent was evaporated, dried on vacuo to give S134 which was used in the next step without further purification with quantitative crude yields.

Compound S135 was prepared using the protocol described for compound S112 in 84% yield as a white solid. $^1$H NMR (500 MHz, $CDCl_3$; ppm): $^1$H NMR (500 MHz, $CDCl_3$; ppm): δ7.42 (d, 2H, J=7.5), 7.33-7.28 (m, 5H), 7.26-7.18 (m, 2H), 6.84-6.80 (m, 4H), 4.14-4.10 (m, 2H), 3.82 (s, 6H), 3.79-3.66 (m, 2H), 3.20-3.14 (m, 1H), 2.41 (d, 1H, J=5.5), 0.85 (s, 9H), 0.038 (d, 6H, J=3.5). ESI MS for $C_{30}H_{40}O_5Si$ calculated 508.7, observed [M+Na]⁺ 531.7.

Compound S137

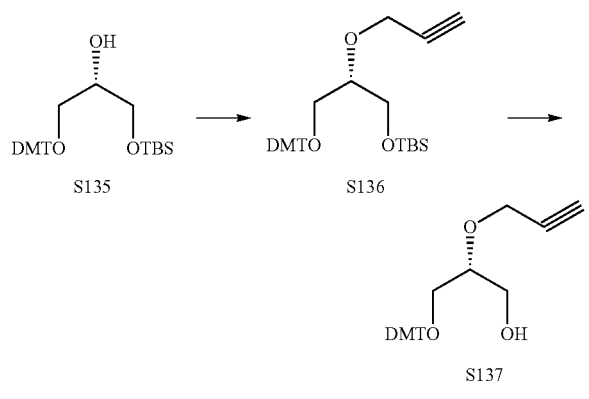

Compound S137 was prepared in two step procedure. The intermediate propargyl protected compound (S136) was prepared using a similar protocol reported for compound S110 in 88% yield as semi solid. ¹H NMR (500 MHz, CDCl₃; ppm): δ7.46 (d, 2H, J=7.5), 7.34-7.33 (m, 3H), 7.32 (m, 2H), 7.28-7.26 (m, 2H), 6.82 (d, 4H, J=7.0) 4.33 (t, 2H, J=2.5), 3.80 (s, 6H), 3.77 (m, 1H), 3.68-3.67 (d, 2H, J=5.5), 3.20-3.18 (m, 2H), 2.38 (m, 1H), 0.83 (s, 9H), 0.02 (d, 6H, J=4.0). ESI MS for $C_{33}H_{42}O_5Si$ calculated 546.7, observed [M+Na]⁺ 569.8.

To a solution of S136 (1.3 g, 2.38 mmol) in THF (10 mL) was added slowly a 1 M solution of TBAF (3.56 mL, 3.56 mmol) at 0° C. and continued the reaction at room temperature for 3 h. After completion of the reaction by TLC, solvent was evaporated, dissolved in ethylacetate and washed with water. The combined organic layers were dried over anhydrous $Na_2SO_4$, filtered and evaporated to give a residue, which was purified by flash silica gel column using ISCO companion (hexane/ethyl acetate, 0-40%) to give 0.82 g (80%) of the desired compound S137 as a semi solid. ¹H NMR (500 MHz, CDCl₃; ppm): δ7.42 (d, 2H, J=7.5), 7.32-7.28 (m, 5H), 7.18-7.16 (m, 2H), 6.84 (d, 4H, J=7.0) 4.33 (m, 2H), 3.80 (s, 6H), 3.79-3.74 (m, 4H), 2.28-3.20 (m, 1H), 2.69 (s, 1H), 2.48-2.42 (dt, 1H, J=2.5). ESI MS for $C_{27}H_{28}O_5$ calculated 432.5, observed [M+Na]⁺ 455.5.

Compound S138

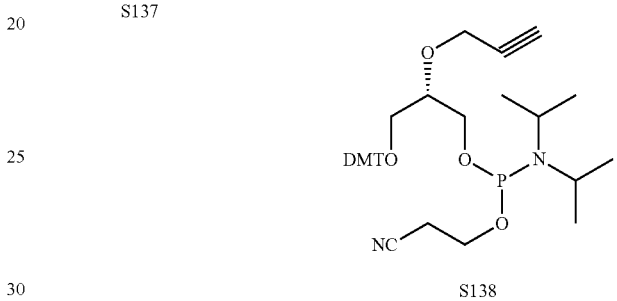

Compound S138 was prepared using the protocol described for compound S113 in 80% yield as a white solid. ³¹P NMR (202 MHz, CDCl₃): δ149.00, 148.91. ESI MS for $C_{36}H_{45}N_2O_6P$ calculated 632.7, observed [M+H]⁺ 633.6.

Synthesis of Linkers S146 and S147—General Scheme:

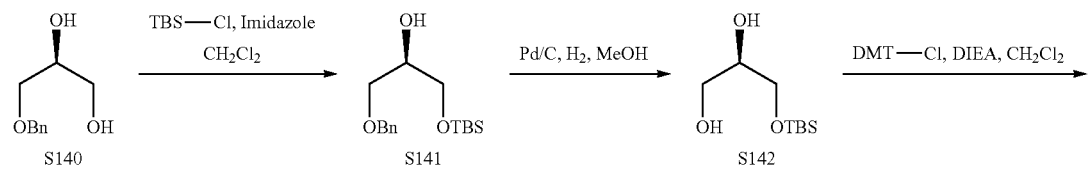

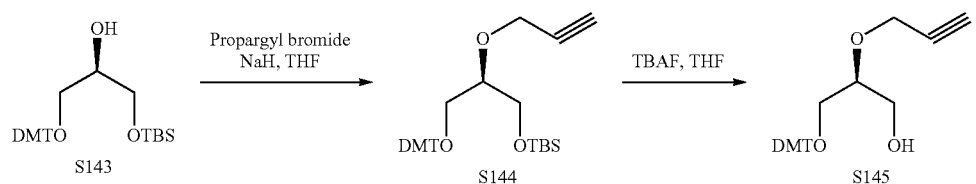

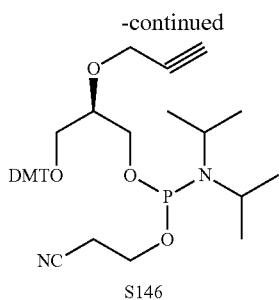

S146

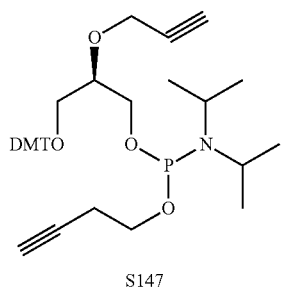

S147

Compound S141

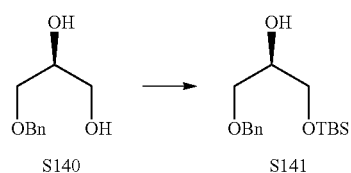 [SMILES: OC[C@H](O)COCc1ccccc1 ; CC(C)(C)[Si](C)(C)OC[C@H](O)COCc1ccccc1 ; "S140" ; "S141"]

Compound S141 was prepared from (S)-3-Benzyloxy-1, 2-propanediol (S140) using the protocol described for compound S133 in 75% yield as a white solid. ESI MS for $C_{16}H_{28}O_3Si$ calculated 296.4, observed $[M+H]^+$ 297.3.

Compound S143

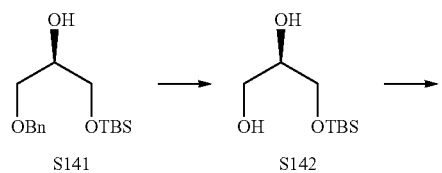

Compound S143 was prepared using the protocol described for compound S135 in 76% yield as a white solid. ESI MS for $C_{30}H_{40}O_5Si$ calculated 508.7, observed $[M+Na]^+$ 531.6.

Compound S145

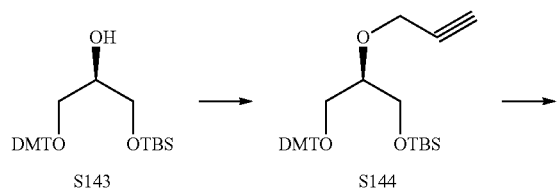

-continued

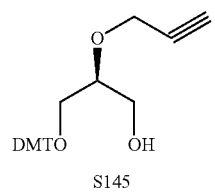

S145

Compound S145 was prepared in two step procedure. First, the intermediate propargyl protected compound (S144) was prepared using the protocol reported for compound S136 in 84% yield as semi solid. $^1$H NMR (500 MHz, CDCl$_3$; ppm): δ7.46 (d, 2H, J=7.5), 7.34-7.33 (m, 3H), 7.32 (m, 2H), 7.28-7.26 (m, 2H), 6.82 (d, 4H, J=7.0) 4.33 (t, 2H, J=2.5), 3.80 (s, 6H), 3.78 (m, 1H), 3.68-3.67 (m, 2H), 3.20-3.18 (m, 2H), 2.39 (t, 1H, J=2.5), 0.83 (s, 9H), 0.02 (d, 6H, J=4.0). ESI MS for $C_{33}H_{42}O_5Si$ calculated 546.7, observed $[M+Na]^+$ 569.6.

Compound S145 was prepared using the protocol described for compound S137 in 86% yield as a white solid. $^1$H NMR (500 MHz, CDCl$_3$; ppm): δ7.44 (d, 2H, J=7.5), 7.31-7.26 (m, 5H), 7.18-7.16 (m, 2H), 6.84-6.82 (d, 4H, J=7.0) 4.33 (m, 2H), 3.80 (s, 6H), 3.77-3.72 (m, 4H), 2.26-3.22 (m, 1H), 2.69 (s, 1H), 2.48-2.42 (dt, 1H, J=2.5). ESI MS for $C_{27}H_{28}O_5$ calculated 432.5, observed $[M+Na]^+$ 455.4.

Compound S146

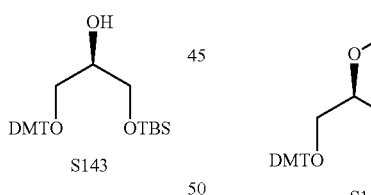

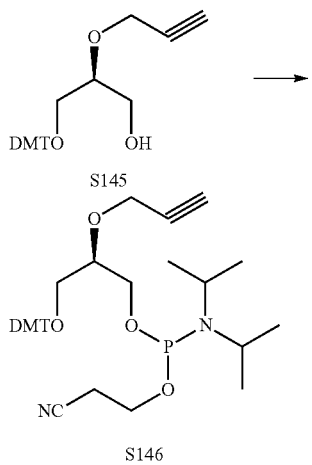

Compound S146 was prepared using the protocol described for compound S113 in 86% yield as a white solid. $^{31}$P NMR (202 MHz, CDCl$_3$): $^{31}$P NMR (202 MHz, CDCl$_3$): δ149.00, 148.90. ESI MS for $C_{36}H_{45}N_2O_6P$ calculated 632.7, observed $[M+H]^+$ 633.7.

Synthesis of Linkers S151 and S152—General Scheme:
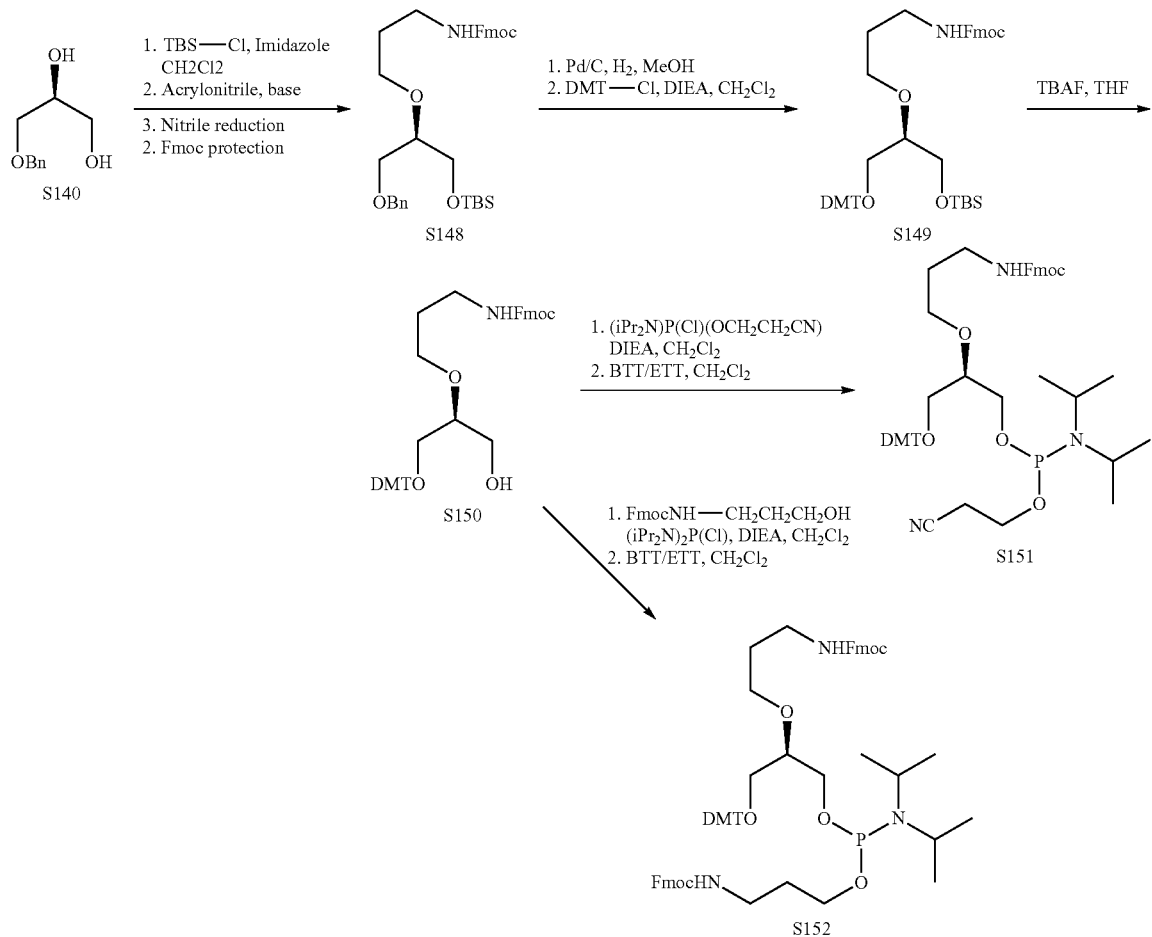
Linkers S156 and S157—General Scheme:
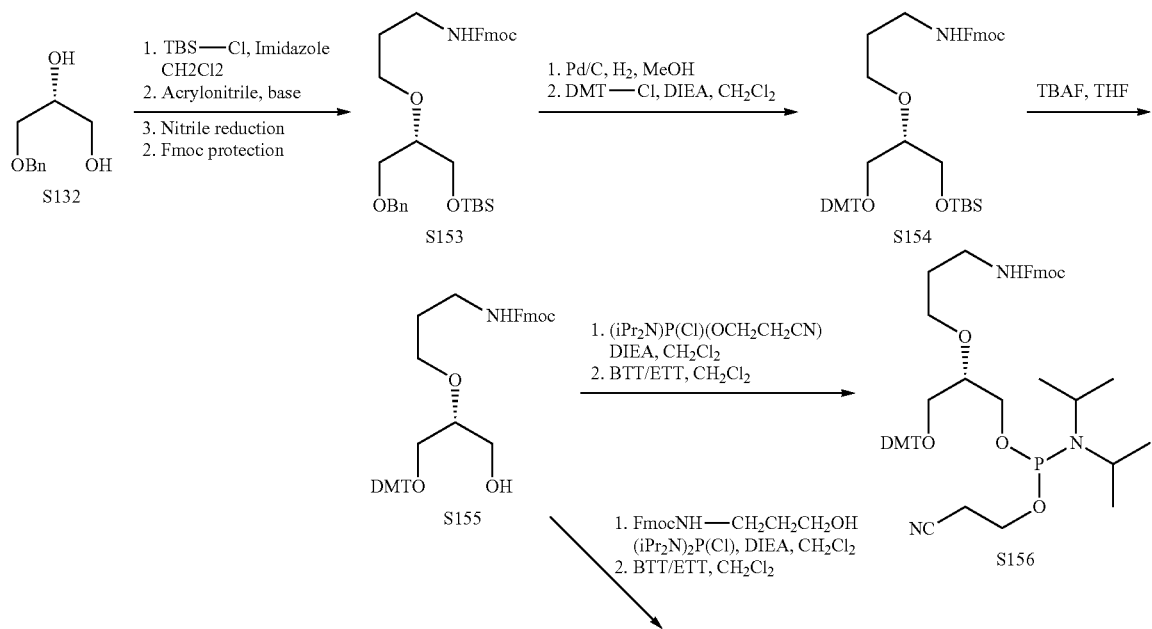

-continued

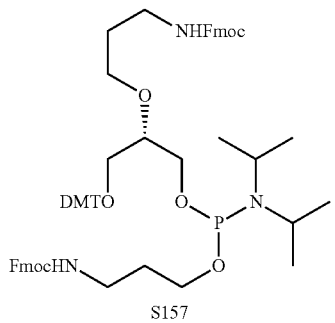

S157

Linkers S151, S152, S156 and S157 can be prepared using reaction conditions described here and also known in the art. For example, compound S140 and S132 can be subjected to a selective TBS protection, acrylonitrile addition, nitrile reduction, Fmoc protection followed by benzyl group removal and DMT protection, TBS removal to give S150 and S155 respectively. These compounds can be converted to amidites S151, S152 and S156, S157 respectively, as shown above.

Phosphoramidite Synthesis
Method 1

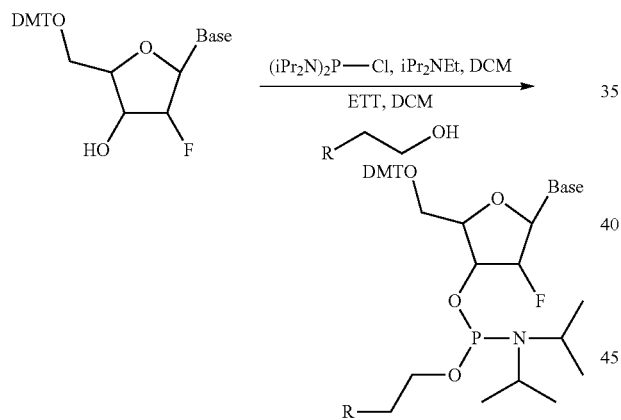

At −78° C., to a solution of appropriately protected nucleoside (20.7 mmol) and N,N-diisopropylethylamine (22.7 mmol) in 100 mL of dry dichloromethane under argon, a solution of bis-(N,N-diisopropylamino)-chlorophosphine (22.7 mmol) in 20 mL of dichloromethane was slowly added. The reaction mixture was allowed to warm to room temperature over 1 hour while stirring was maintained. To this mixture a solution of appropriate alcohol (20.7 mmol) in 15 mL of dry dichloromethane was added, and the resulting mixture was stirred for 10 minutes, at which time a 0.25M ETT solution in acetonitrile (12.42 mmol) was added dropwise. The reaction mixture was stirred for additional 16 h at room temperature. The crude mixture was diluted with 200 mL of dichloromethane and washed sequentially with saturated NaHCO$_3$ solution (50 mL) and brine (50 mL) and then dried over anhydrous Na$_2$SO$_4$. The solvent was evaporated in vacuo, and the resulting mixture was purified by silica gel column chromatography using ethyl acetate/hexane (0-30% gradient on Combi Flash Rf Instrument) to give a diastereomeric mixture of phosphoramidite as a white powder.

Method 2

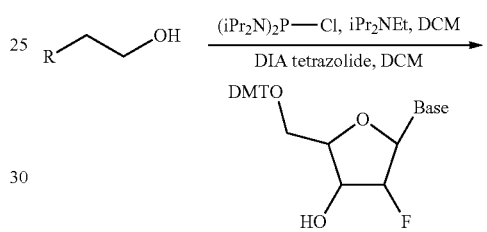

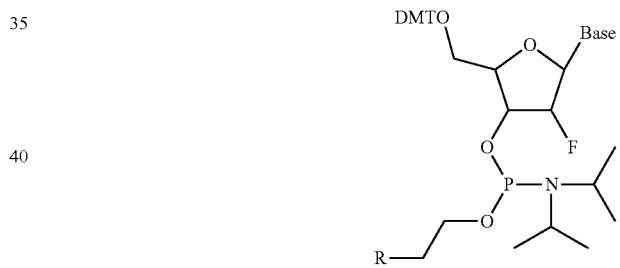

At −78° C., to a solution of an appropriate alcohol (7.46 mmol) and N,N-diisopropylethylamine (7.78 mmol) in dry dichloromethane (15 mL) under argon, a solution of bis-(N, N-diisopropylamino)-chlorophosphine (7.78 mmol) in dichloromethane (5.0 mL) was added. The reaction mixture was allowed to warm to room temperature over 1 h, and the resulting solution was added dropwise to a dichloromethane (15 mL) suspension of appropriately protected nucleoside (3.73 mmol) and diisopropylammonium tetrazolide (7.46 mmol). The reaction continued for additional 16 h at room temperature. The reaction mixture was diluted with 15 mL of dichloromethane and washed sequentially with saturated NaHCO$_3$ solution (10 mL) and brine (10 mL) and then dried over anhydrous Na$_2$SO$_4$. The solvent was evaporated in vacuo, and the mixture was purified by silica gel column chromatography using ethyl acetate/hexane (0-60% gradient on Combi Flash Rf Instrument) to give a diastereomeric mixture of phosphoramidite as a white powder.

Various phosphoramidites were synthesized using the standard synthetic procedures described herein. The prepared phosphoramidites are shown in Table 1.

TABLE 1

| Compound # | Structure | ³¹P NMR (δ, ppm) | Synthesis | Yield (%) |
|---|---|---|---|---|
| U1 | 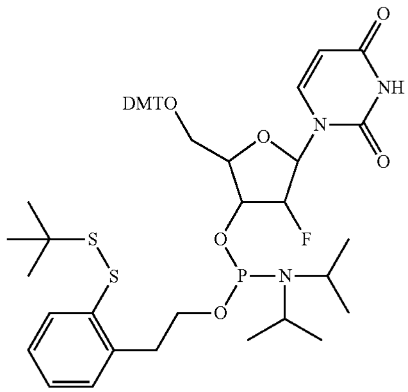 | 154.73 (d, J 8.90 Hz) 154.52 (d, J 7.70 Hz) | Method 1 | 45 |
| U2 | 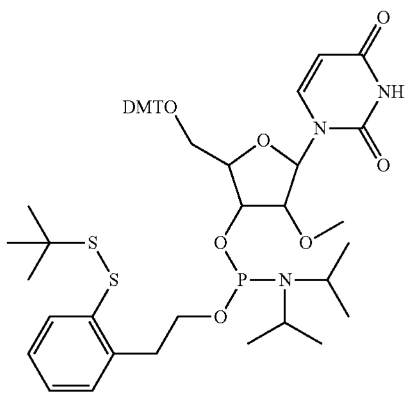 | 149.30 (s) 149.05 (s) | Method 1 | 41 |
| U3 | 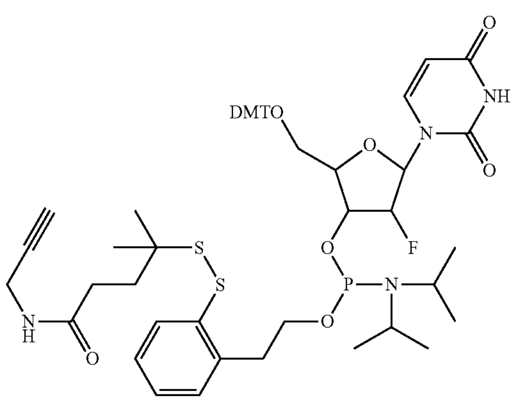 | 154.75 (d, J 5.60 Hz) 154.36 (d, J 10.3 Hz) | Method 1 | 21 |
| U4 | 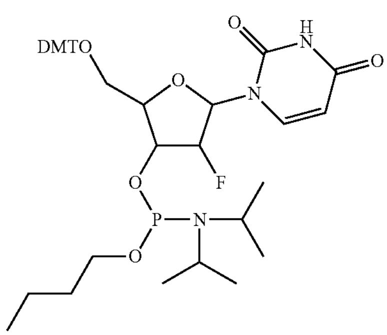 | 154.98 (d, J 8.08 Hz) 154.74 (d, J 8.08 Hz) | Method 1 | 54 |

TABLE 1-continued
| Compound # | Structure | ³¹P NMR (δ, ppm) | Synthesis | Yield (%) |
|---|---|---|---|---|
| U5 | 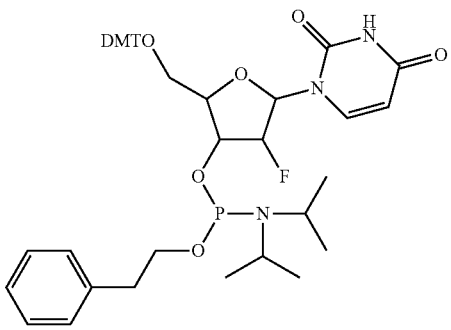 | 154.84 (d, J 12.12 Hz) 154.50 (d, J 8.08 Hz) | Method 1 | 53 |
| U6 | 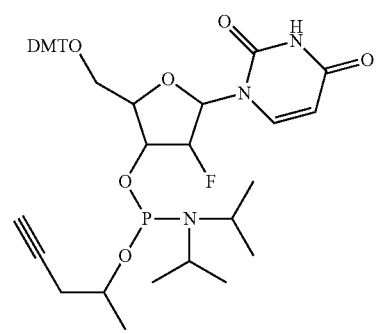 | 154.6 (d, J 6.6 Hz) 154.5 (d, J 8.5 Hz) 154.2 (d, J 9.3 Hz) 152.8 (d, J 10.1 Hz) | Method 1 | 60 |
| U7 | 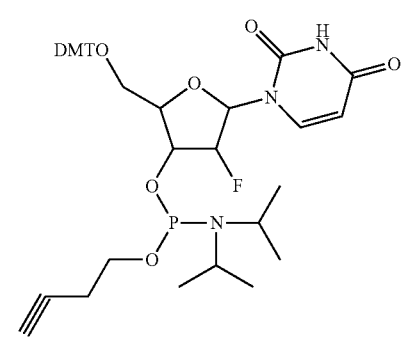 | 155.27 (d, J 6.06 Hz) 155.05 (d, J 8.08 Hz) | Method 1 | 50 |
| U8 | 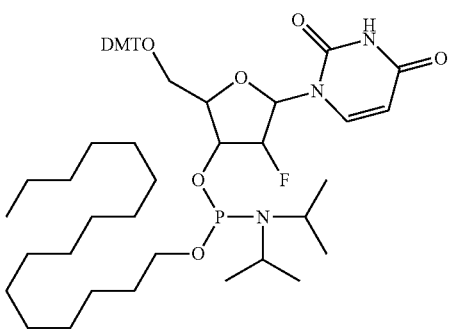 | 155.17 (d, J 8.08 Hz) 154.67 (d, J 10.1 Hz) | Method 1 | 48 |

TABLE 1-continued

| Compound # | Structure | $^{31}$P NMR (δ, ppm) | Synthesis | Yield (%) |
|---|---|---|---|---|
| U9 | 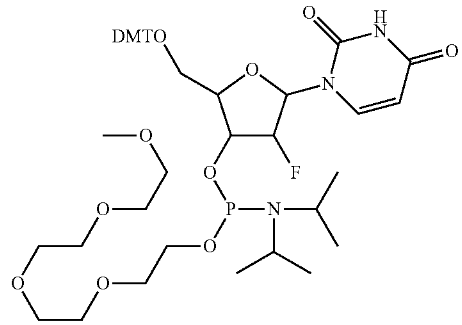 | 155.83 (d, J 6.06 Hz) 155.34 (d, J 10.1 Hz) | Method 1 | 55 |
| U10 | 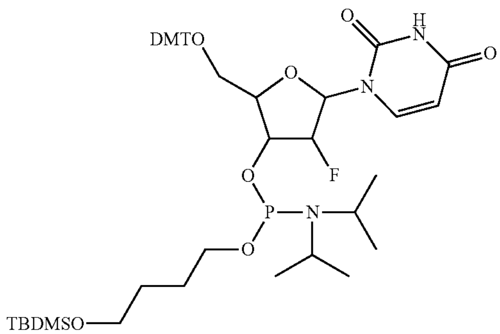 | 155.4 (d, J 7.9 Hz) 154.7 (d, J 9.7 Hz) | Method 1 | 54 |
| C1 | 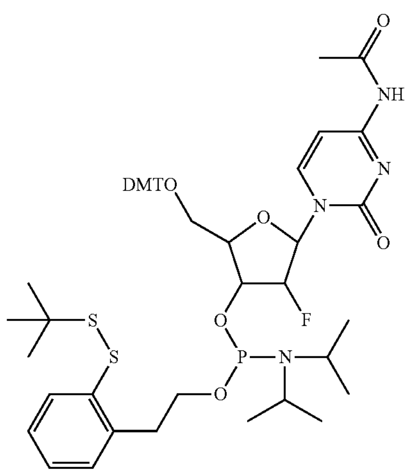 | | Method 1 | |
| C2 | 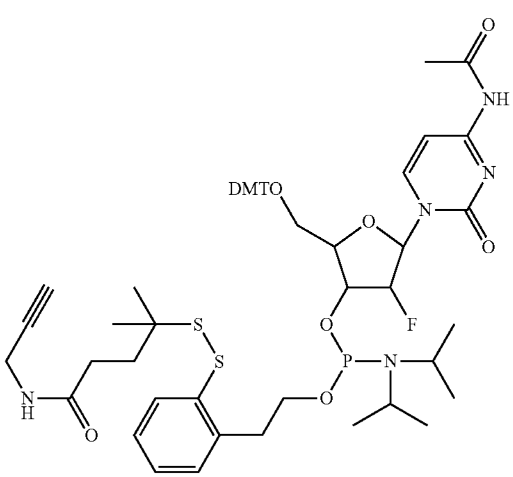 | | Method 1 | |

TABLE 1-continued

| Compound # | Structure | $^{31}$P NMR (δ, ppm) | Synthesis | Yield (%) |
|---|---|---|---|---|
| C3 | 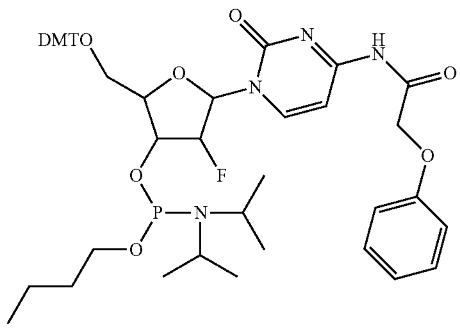 | 154.80 (d, J 8.08 Hz) 154.71 (d, J 6.06 Hz) | Method 1 | 51 |
| C4 | 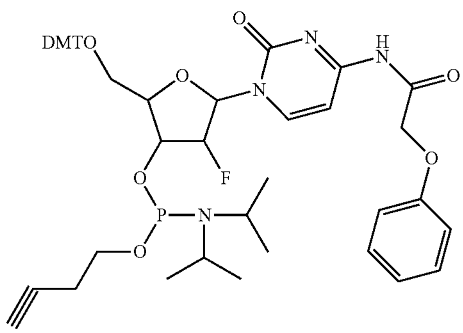 | 155.18 (d, J 6.06 Hz) 154.79 (d, J 8.08 Hz) | Method 1 | 55 |
| C5 | 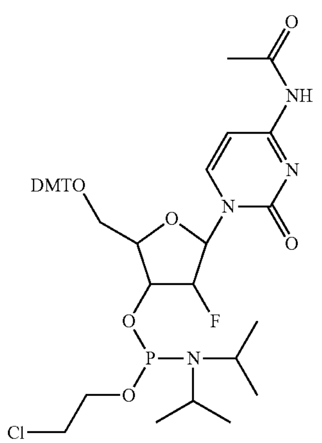 | 151.9 (d, J 6.2 Hz) 151.2 (d, J 8.3 Hz) | Method 1 | 28 |
| C6 | 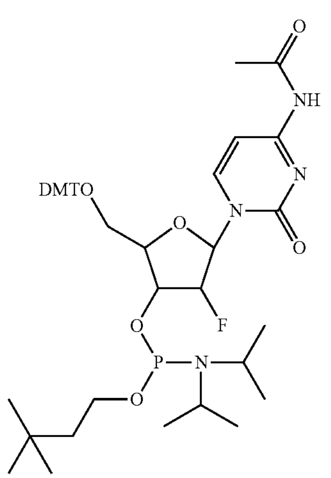 | 149.3 (d, J 6.0 Hz) 149.1 (d, J 8.3 Hz) | Method 1 | 35 |

TABLE 1-continued

| Compound # | Structure | ³¹P NMR (δ, ppm) | Synthesis | Yield (%) |
|---|---|---|---|---|
| C7 | [5'-O-DMT, 2'-F cytidine (N-acetyl) 3'-O-phosphoramidite with cyclohexylmethyl O-substituent and N,N-diisopropylamino] | 149.4 (s)<br>149.1 (d, J 8.3 Hz) | Method 1 | 21 |
| C8 | [5'-O-DMT, 2'-F cytidine (N-acetyl) 3'-O-phosphoramidite with 2-cyclohexylethyl O-substituent and N,N-diisopropylamino] | 149.7 (d, J 8.3 Hz) | Method 1 | 36 |
| C9 | [5'-O-DMT, 2'-F cytidine (N-acetyl) 3'-O-phosphoramidite with hex-3-yn-1-yl O-substituent and N,N-diisopropylamino] | 150.2 (s)<br>150.0 (s) | Method 1 | 27 |

TABLE 1-continued

| Compound # | Structure | ³¹P NMR (δ, ppm) | Synthesis | Yield (%) |
| --- | --- | --- | --- | --- |
| C10 | 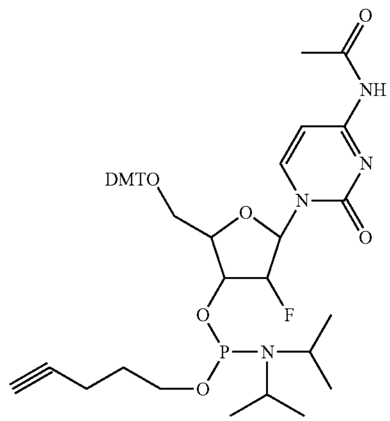 | 150.6 (d, J 8.3 Hz) 150.1 (s) | Method 1 | 37 |
| C11 | 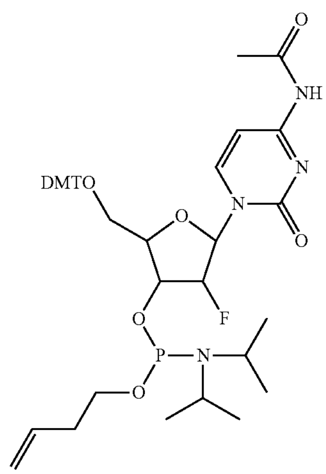 | 149.7 (d, J 8.3 Hz) | Method 1 | 41 |
| C12 | 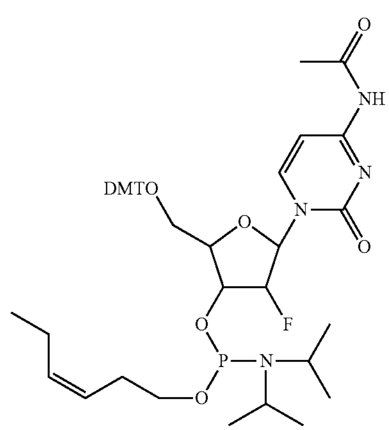 | 149.9 (d, J 8.3 Hz) 149.6 (s) | Method 1 | 48 |

TABLE 1-continued

| Compound # | Structure | ³¹P NMR (δ, ppm) | Synthesis | Yield (%) |
|---|---|---|---|---|
| C13 | 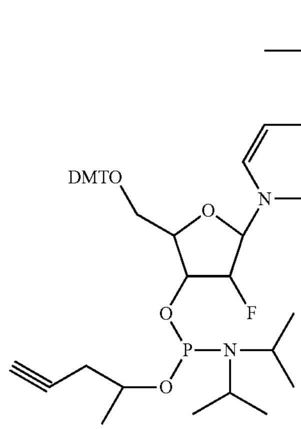 | 149.6 (s) 149.5 (d, J 8.3 Hz) 149.1 (s) 147.8 (s) | Method 1 | 37 |
| C14 | 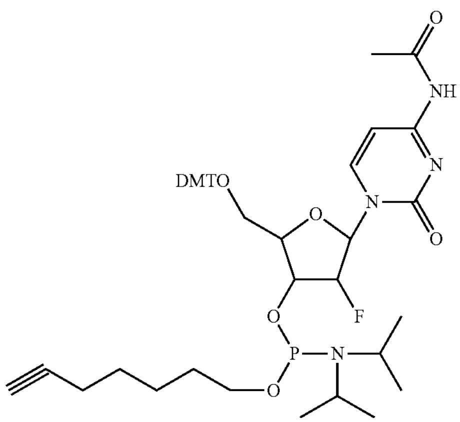 | 150.2 (d, J 8.3 Hz) 149.8 (s) | Method 1 | 14 |
| C15 | 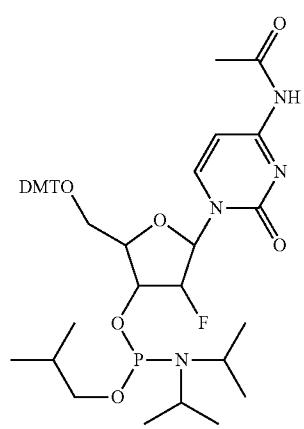 | 150.2 (d, J 8.3 Hz) 150.1 (d, J 6.2 Hz) | Method 1 | 48 |

TABLE 1-continued

| Compound # | Structure | ³¹P NMR (δ, ppm) | Synthesis | Yield (%) |
|---|---|---|---|---|
| C16 | 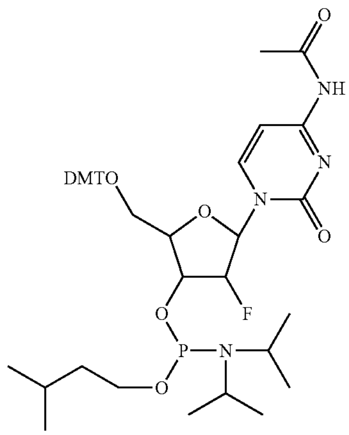 | 150.2 (d, J 10.3 Hz) 149.8 (s) | Method 1 | 47 |
| C17 | 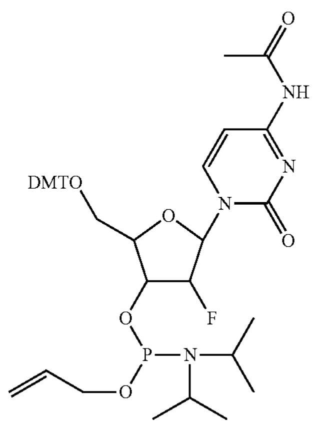 | 150.9 (d, J 8.3 Hz) 150.6 (s) | Method 1 | 52 |
| C18 | 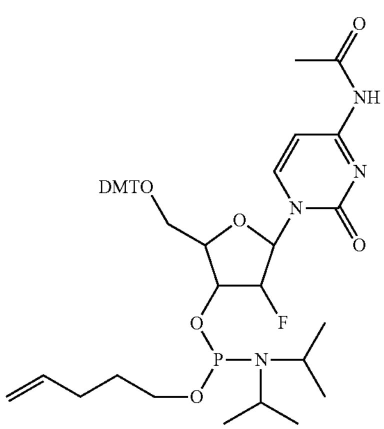 | 150.2 (d, J 6.2 Hz) 149.9 (d, J 4.2 Hz) | Method 1 | 41 |

TABLE 1-continued

| Compound # | Structure | ³¹P NMR (δ, ppm) | Synthesis | Yield (%) |
|---|---|---|---|---|
| C19 | 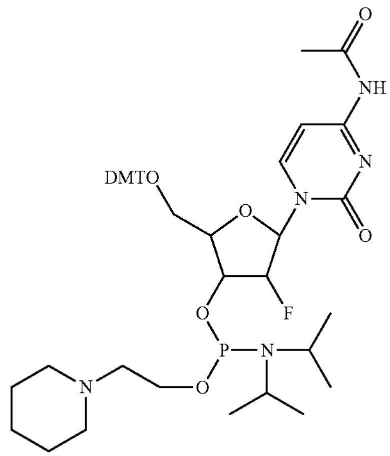 | 150.0 (s)<br>149.5 (s) | Method 1 | 10 |
| C20 | 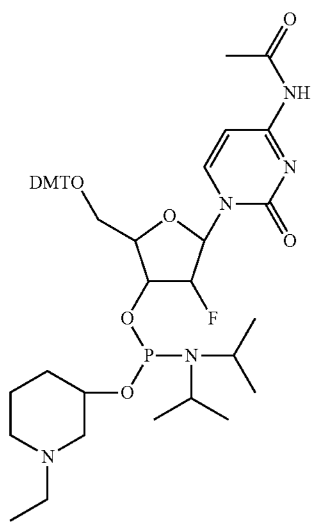 | 149.3 (s)<br>148.8 (s)<br>147.6 (s)<br>146.7 (s) | Method 1 | 4 |
| C21 | 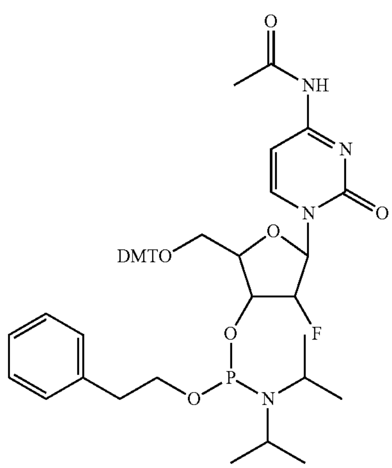 | 149.80 (d, J 8.1 Hz)<br>149.55 (s) | Method 1 | 47 |

TABLE 1-continued
| Compound # | Structure | $^{31}$P NMR (δ, ppm) | Synthesis | Yield (%) |
|---|---|---|---|---|
| C22 | 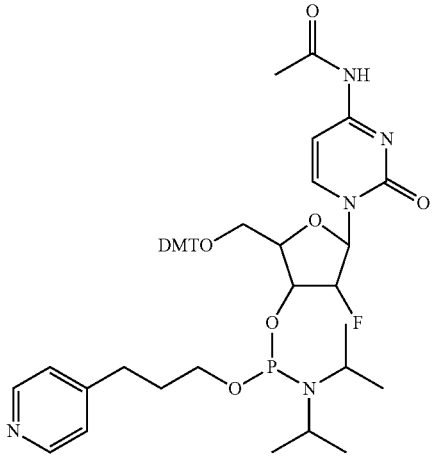 | 150.46 (d, J 8.1 Hz) | Method 1 | 22 |
| A1 | 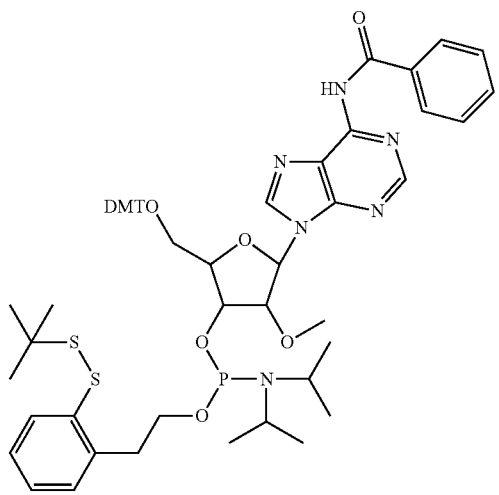 | 154.80 (s) 154.0 (s) | Method 1 | 40 |
| A2 | 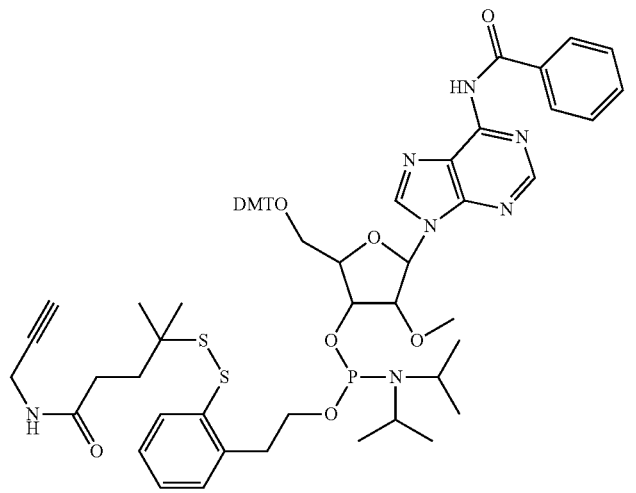 | | Method 1 | |

TABLE 1-continued
| Compound # | Structure | ³¹P NMR (δ, ppm) | Synthesis | Yield (%) |
|---|---|---|---|---|
| A3 | 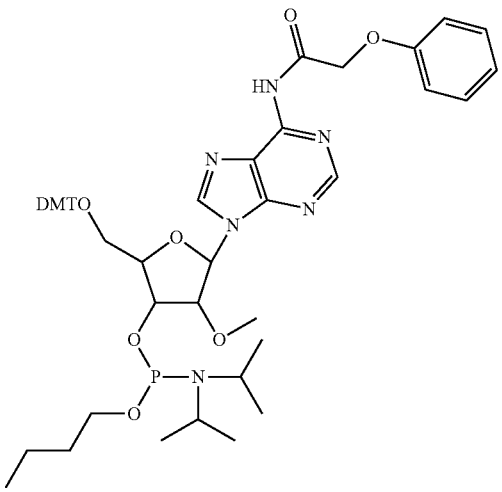 | 154.79 (s)<br>154.01 (s) | Method 1 | 34 |
| A4 | 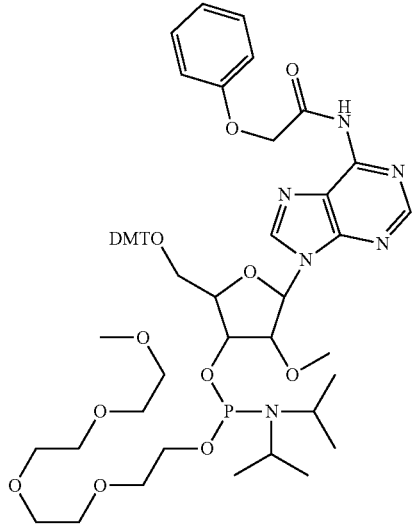 | 155.85 (s)<br>155.09 (s) | Method 1 | 25 |
| A5 | 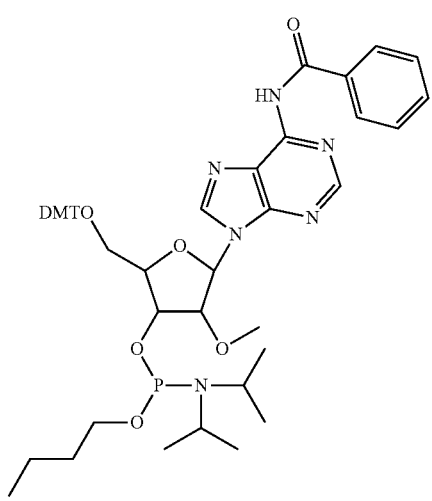 | 154.81 (s)<br>153.99 (s) | Method 1 | 55 |

TABLE 1-continued

| Compound # | Structure | $^{31}$P NMR (δ, ppm) | Synthesis | Yield (%) |
|---|---|---|---|---|
| A6 | 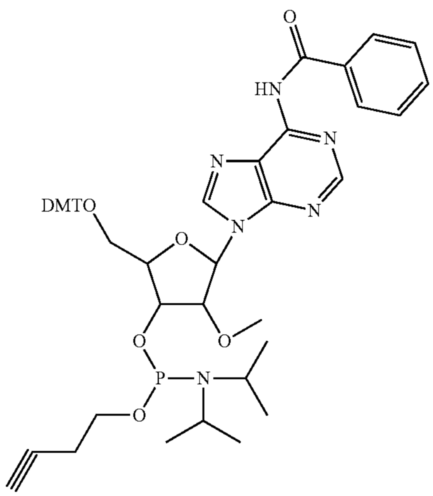 | 150.24 (s) 149.63 (s) | Method 1 | 39 |
| A7 | 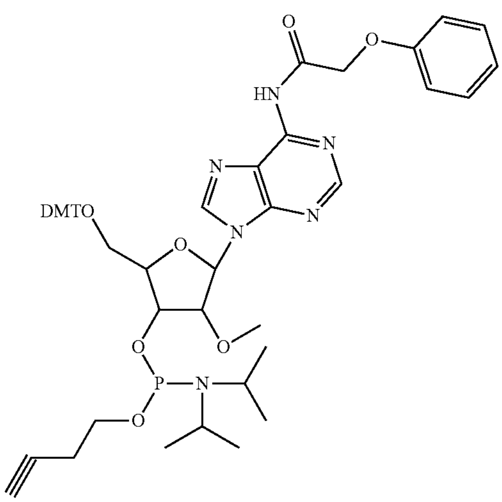 | 155.20 (s) 154.60 (s) | Method 1 | 56 |
| A8 | 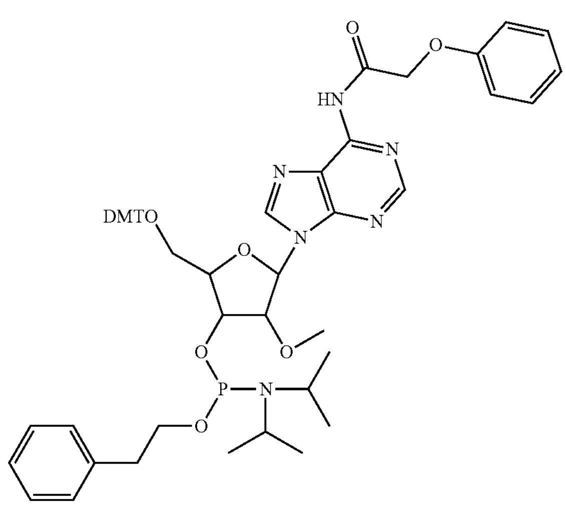 | 155.4 (s) 154.0 (s) | Method 1 | 80 |

TABLE 1-continued

| Compound # | Structure | ³¹P NMR (δ, ppm) | Synthesis | Yield (%) |
|---|---|---|---|---|
| A9 | 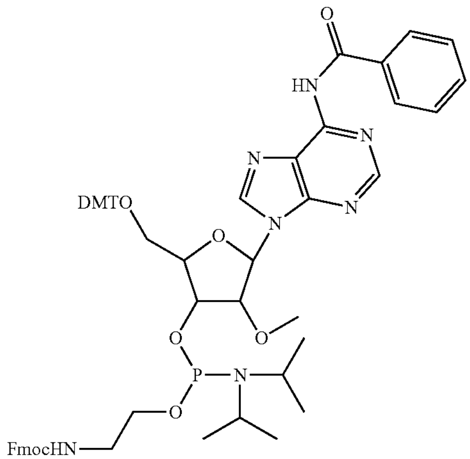 | 151.10 (s) 150.24 (s) | Method 1 | 45 |
| A10 | 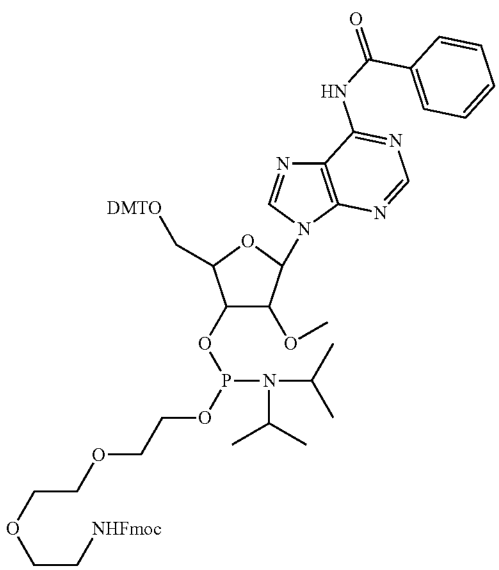 | 150.69 (s) 150.28 (s) | Method 1 | 61 |
| G1 | 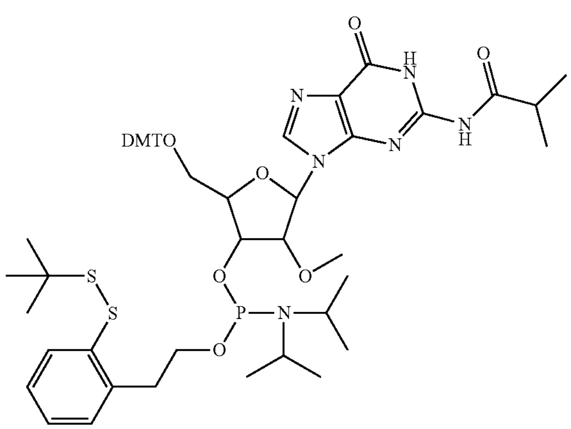 | 150.63 (s) 149.20 (s) | Method 1 | 36 |

TABLE 1-continued

| Compound # | Structure | ³¹P NMR (δ, ppm) | Synthesis | Yield (%) |
|---|---|---|---|---|
| G2 | 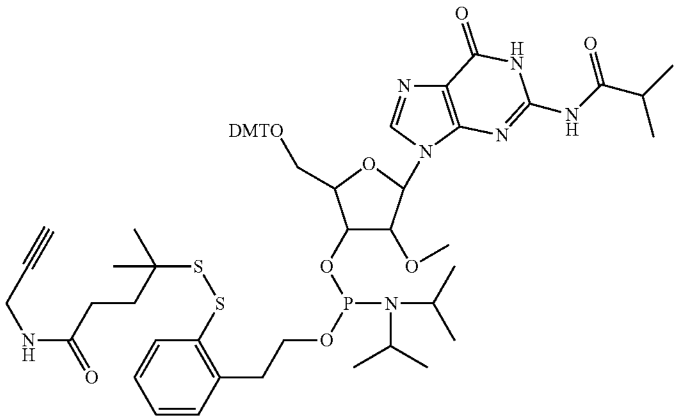 | | Method 2 | |
| G3 | 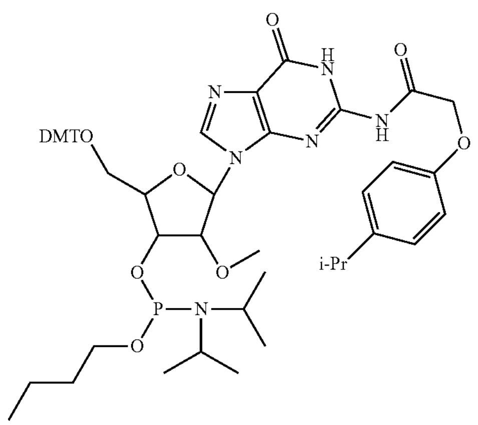 | 154.91 (s)<br>154.36 (s) | Method 2 | 55 |
| G4 | 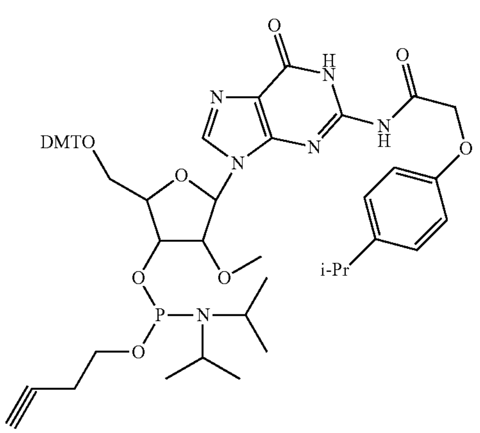 | 155.29 (s)<br>154.85 (s) | Method 2 | 29 |

TABLE 1-continued

| Compound # | Structure | $^{31}P$ NMR (δ, ppm) | Synthesis | Yield (%) |
|---|---|---|---|---|
| G5 | 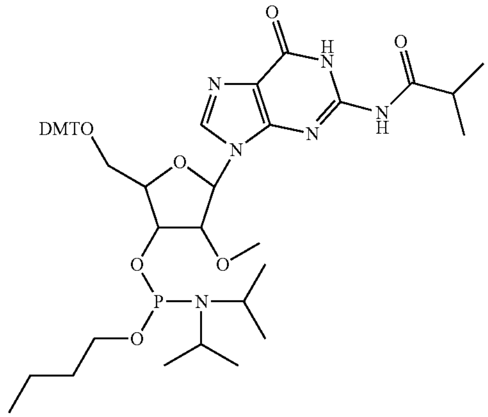 | 154.94 (s) 154.05 (s) | Method 2 | 18 |

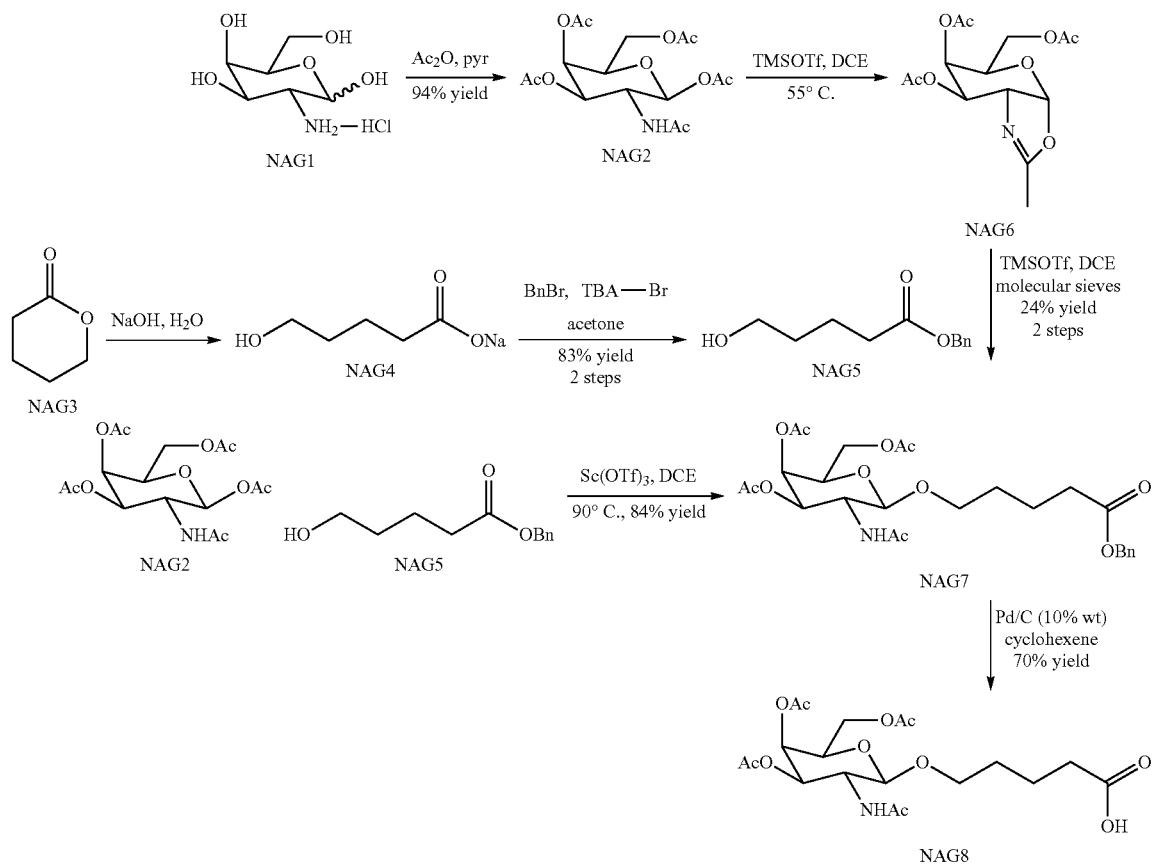

Synthesis of Targeting Moieties
GalNAc (NAG) Ligand Synthesis

Preparation of D-galactosamine pentaacetate (NAG2). D-Galactosamine (25.0 g, 116 mmol) was suspended in anhydrous pyridine (250 mL) and cooled to 0° C. under an inert atmosphere. Acetic anhydride (120 mL, 1160 mmol) was added over the course of 2 h. After stirring overnight, the reaction mixture was concentrated in vacuo. Upon addition of methanol, a white solid precipitated and was collected via filtration to provide the desired product (42.1 g, 93% yield). $^1$H NMR (CDCl$_3$, 500 MHz): δ 5.69 (d, 1H, J 9.0 Hz), 5.40 (m, 1H), 5.37 (d, 1H, J 3.0 Hz), 5.08 (dd, 1H, J 3.0 Hz, 11 Hz), 4.44 (dt, 1H, J 9.5 Hz, 11 Hz), 4.17 (dd, 1H, J7.0 Hz, 11.5 Hz), 4.11 (dd, 1H, J7.0 Hz, 11.5 Hz), 4.01 (t, 1H, J 7.0 Hz), 2.17 (s, 3H), 2.13 (s, 3H), 2.05 (s, 3H), 2.02 (s, 3H), 1.94 (s, 3H), 1.57 (s, 3H)

Preparation of benzyl 5-hydroxy pentanoate (NAG5). A solution of delta-valerolactone (10.0 g, 100 mmol) and NaOH (4.00 g, 100 mmol) in water (100 mL) was stirred overnight at 70° C. The reaction mixture was cooled to room temperature and concentrated in vacuo to give white solid NAG4. This solid was suspended in acetone (100 mL) and refluxed overnight with benzyl bromide (20.5 g, 120 mmol) and tetrabutylammonium bromide (1.61 g, 0.50 mmol). Acetone was removed in vacuo to afford an oily residue, which was dissolved in EtOAc and washed with sat NaHCO$_3$ (aq.) and brine. The organic layer was dried over Na$_2$SO$_4$ and concentrated in vacuo give NAG5 as an oily product (17.1 g, 82% yield). $^1$H NMR (CDCl$_3$, 500 MHz): δ 7.35 (m, 5H), 3.64 (q, 2H, J 6 Hz, 11.5 Hz), 2.41 (t, 2H, J 7.5 Hz), 1.75 (m, 2H), 1.60 (m, 2H), 1.44 (t, 1H, J 6 Hz)

Preparation of benzyloxycarbonylbutyl 2-deoxy-2-N-acetyl-3,4,6-tri-O-acetyl-β-D-galactopyranoside (NAG7)—Method A. Under an inert atmosphere, TMSOTf (8.56 g, 38.4 mmol) was added to a solution of NAG2 (10.0 g, 25.6 mmol) in 1,2-dichloroethane (100 mL) at ambient temperature. The mixture was stirred at 55° C. for 2 h, removed from heat, and stirred overnight. The reaction mixture was poured over ice cold sat NaHCO$_3$ (aq.) and extracted with CH$_2$Cl$_2$. The organic layer was dried over Na$_2$SO$_4$ and concentrated in vacuo to give NAG6 as a syrup. A solution of NAG6 in 1,2-dichloroethane (60 mL) was charged with alcohol NAG5 (8.00 g, 38.4 mmol) and molecular sieves. The mixture was placed under an inert atmosphere, treated with TMSOTf (2.85 g, 12.8 mmol), and stirred overnight at room temperature. The mixture was poured over ice cold sat NaHCO$_3$ (aq.) and extracted with CH$_2$Cl$_2$. The organic layer was dried over Na$_2$SO$_4$ and concentrated in vacuo to give a syrup. This crude material was purified by SiO$_2$ gel chromatography to afford glycoside NAG7 (3.3 g, 24% yield). $^1$H NMR (CDCl$_3$, 500 MHz): δ 7.35 (m, 5H), 5.98 (d, 1H, J7.0 Hz), 5.57 (m, 1H), 5.34 (d, 1H, J 3.0 Hz), 5.25 (dd, 1H, J 3.0 Hz, 11 Hz), 5.10 (s, 2H), 4.63 (d, 1H, J 8.5 Hz), 4.11 (m, 2H), 3.95 (m, 1H), 3.88 (m, 2H), 3.49 (m, 1H), 2.37 (m, 2H), 2.13 (s, 3H), 2.03 (s, 3H), 1.99 (s, 3H), 1.90 (s, 3H), 1.70 (m, 2H), 1.61 (m, 2H)

Preparation of benzyloxycarbonylbutyl 2-deoxy-2-N-acetyl-3,4,6-tri-O-acetyl-β-D-galactopyranoside (NAG7)—Method B. To a solution of NAG2 (5.00 g, 12.8 mmol) and alcohol NAG5 (5.33 g, 25.6 mmol) in 1,2-dichloroethane (50 mL) was added Sc(OTf)$_3$ (0.44 g, 0.90 mmol) in one portion. The mixture was placed under an inert atmosphere and refluxed for 3 h. Upon cooling, the mixture was diluted with CH$_2$Cl$_2$, washed with sat NaHCO$_3$ (aq.), dried over MgSO$_4$, and concentrated in vacuo. Purification by SiO$_2$ gel chromatography afforded glycoside NAG7 (5.53 g, 80% yield).

Preparation of carboxybutyl 2-deoxy-2-N-acetyl-3,4,6-tri-O-acetyl-β-D-galactopyranoside (NAG8). A solution of glycoside NAG7 (1.50 g, 2.41 mmol) in EtOH (25 mL) was degassed under vacuum and purged with argon. The palladium catalyst (10% wt. on activated carbon, 0.50 g) was added in one portion, and the mixture was degassed under vacuum and purged with argon. The heterogeneous mixture was charged with cyclohexene (25 mL) and refluxed for 6 h. Upon cooling, the catalyst was removed by filtration, and the mother liquor was concentrated in vacuo. The crude product was purified by SiO$_2$ gel chromatography to afford NAG8 as a white foam (0.76 g, 70% yield). $^1$H NMR (CDCl$_3$, 500 MHz): δ 5.72 (d, 1H, J 8.5 Hz), 5.35 (d, 1H, J 3.5 Hz), 5.26 (dd, 1H, J 3.5 Hz, 11.5 Hz), 4.67 (d, 1H, J 8.5 Hz), 4.17 (dd, 1H, J 6.5 Hz, 11.5 Hz), 4.12 (dd, 1H, 6.5 Hz, 11.5 Hz), 4.00 (dt, 1H, J 8.5 Hz, 11.5 Hz), 3.92 (m, 2H), 3.53 (m, 1H), 2.39 (m, 2H), 2.15 (s, 3H), 2.05 (s, 3H), 2.01 (s, 3H), 1.97 (s, 3H), 1.71 (m, 2H), 1.65 (m, 2H)

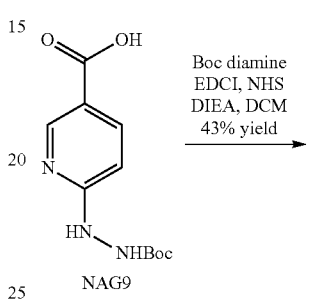

NAG9

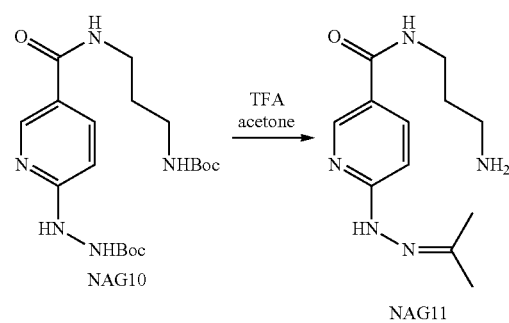

NAG10

NAG11

Preparation of aminopropyl 6-hydrazinonicotamide acetone hydrazone (NAG11). Boc-6-hydrazinonicotinic acid (520 mg, 2.1 mmol) in dichloromethane (20 mL) was treated with EDCl (440 mg, 2.3 mmol), N-hydroxysuccinimide (NHS; 260 mg, 2.3 mmol), Boc-diamine (650 mg, 2.6 mmol), and N,N-diisopropylethylamine (1.1 mL, 6.2 mmol) for 3 h. The reaction was concentrated in vacuo and purified by silica gel chromatography to afford NAG10 (364 mg, 43% yield). $^1$H NMR (CDCl$_3$, 500 MHz): δ 8.55 (br, 1H), 7.93 (d, 2H, J7.5 Hz), 7.45 (br, 1H), 7.12 (br, 1H), 6.62 (d, 1H, J 8.5 Hz), 5.17 (br, 1H), 3.42 (m, 2H), 3.13 (m, 2H), 1.65 (m, 2H), 1.41 (s, 18H). The HyNic acetone hydrazone was formed by treating NAG10 (160 mg, 0.4 mmol) with trifluoroacetic acid (9 mL) and acetone (1 mL) for 1 h. The reaction mixture was concentrated in vacuo and placed on the high vacuum to afford NAG11.

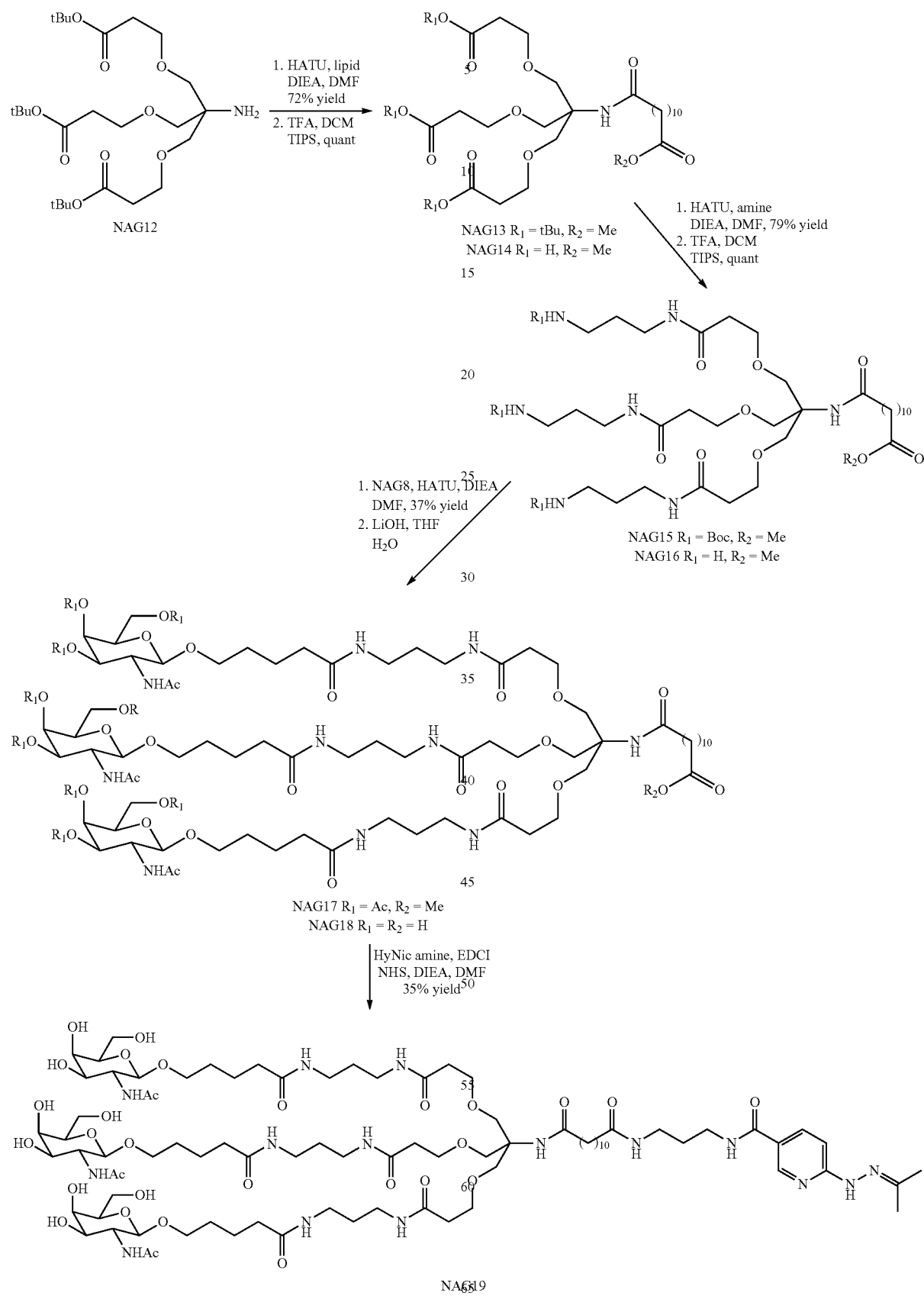

Preparation of tris-(carboxyethoxymethyl)-methylamido-dodecanedioate methyl ester (NAG14). To a solution of dodecanedioic acid methyl ester (211 mg, 0.42 mmol) activated with HATU (122 mg, 0.50 mmol) and N,N-diisopropylethylamine (218 µL, 1.25 mmol) in DMF (2 mL) was added tris-linker NAG12. After 1 h, the reaction mixture was concentrated in vacuo and purified by SiO$_2$ gel chromatography to afford NAG13 (214 mg, 70% yield). MALDI-TOF mass calcd $C_{38}H_{69}NO_{12}$: 731.48, Found: 755.10 [M+Na]. Tris-t-butyl ester NAG13 was hydrolyzed with a TFA:TIPS:DCM (9:0.25:1) cocktail (10.25 mL) for 4 h and concentrated in vacuo to give tris acid NAG14. MALDI-TOF mass calcd $C_{26}H_{45}NO_{12}$: 563.29, Found: 565.33 [M+H].

Preparation of tris-(aminopropanamido-ethoxymethyl)-methylamido-dodecanedioate methyl ester (NAG16). To a solution of tris acid NAG14 (230 mg, 0.41 mmol) activated with HATU (557 mg, 1.35 mmol) and N,N-diisopropylethylamine (470 µL, 2.70 mmol) in DMF (4 mL) was added mono Boc-1,3-diaminopropane (250 mg, 1.44 mmol). After 1 h, the reaction mixture was concentrated in vacuo and purified by SiO$_2$ gel chromatography to afford NAG15 (335 mg, 79% yield). MALDI-TOF mass calcd $C_{50}H_{93}N_7O_{15}$: 1031.67, Found: 1056.40 [M+Na]. Compound NAG15 was treated with a TFA:TIPS:DCM (9:0.25:1) cocktail (10.25 mL) for 1 h and concentrated in vacuo to give tris-amine NAG16. MALDI-TOF mass calcd $C_{35}H_{69}N_7O_9$: 731.51, Found: 733.18 [M+H].

Preparation of tris-GalNAc (NAG18). Monosaccharide NAG8 (192 mg, 0.43 mmol) was treated with HATU (163 mg, 0.43 mmol) and N,N-diisopropylethylamine (150 µL, 0.86 mmol) in DMF (2 mL). After 30 min, a solution of NAG16 (80 mg, 0.11 mmol) in DMF (1 mL) was added, and the mixture was stirred for 1 h. The crude mixture was purified by SiO$_2$ gel chromatography to afford NAG17 (82 mg, 37% yield). Mass calcd $C_{92}H_{150}N_{10}O_{39}$: 2019.00, Found: 2041.85 [M+Na]. The peracetylated trimer GalNAc (82 mg, 0.04 mmol) was hydrolyzed by the treatment with LiOH·H$_2$O (34 mg, 0.81 mmol) in a THF:H$_2$O (3:1) solution (8 mL) to afford NAG18. MALDI-TOF mass calcd $C_{73}H_{130}N_{10}O_{30}$: 1626.89, Found: 1634.52 [M+H].

Preparation of HyNic trimer GalNAc (NAG19). A solution GalNAc trimer NAG18 (32 mg, 0.02 mmol) and HyNic amine NAG11 (20.0 mg, 0.08 mmol) in DMF (1 mL) was treated with EDCl (16.2 mg, 0.08 mmol), NHS (2.5 mg, 0.02 mmol), and N,N-diisopropylethylamine (28 µL, 0.16 mmol) and stirred for 4 h. Upon concentration in vacuo, the crude was dissolved in DMSO and purified by reverse phase HPLC to afford NAG19 (12.6 mg, 35% yield). MALDI-TOF mass calcd $C_{85}H_{147}N_{15}O_{30}$: 1858.04, Found: 1859.83 [M+H].

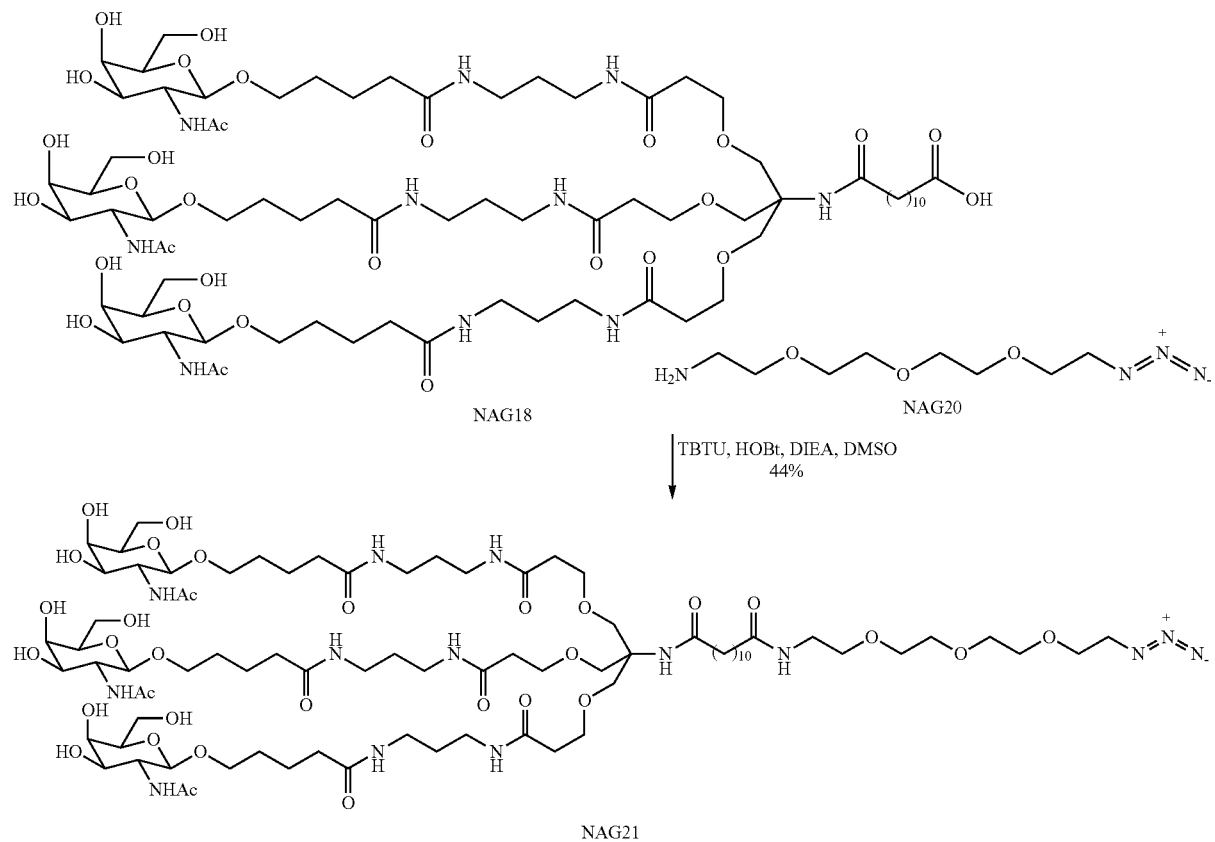

Preparation of azido-Peg3-trimer GalNAc (NAG21). GalNAc trimer carboxylic acid NAG18 (60 mg, 0.03 mmol), azido-Peg3-amine NAG20 (45.6 mg, 0.21 mmol), TBTU (23.8 mg, 0.07 mmol), HOBt (11.5 mg, 0.03 mmol), and N,N-diisopropylethylamine (34 µL) were dissolved in DMSO (0.5 mL) and stirred 2 h. The base was removed in vacuo, and the crude was purified by reverse phase HPLC to afford NAG21 (24 mg, 44%). AP-ESI+ Mass calcd $C_{31}H_{146}N_{14}O_{32}$: 1827.02, Found: 914.8 [M+2H]$^{2+}$

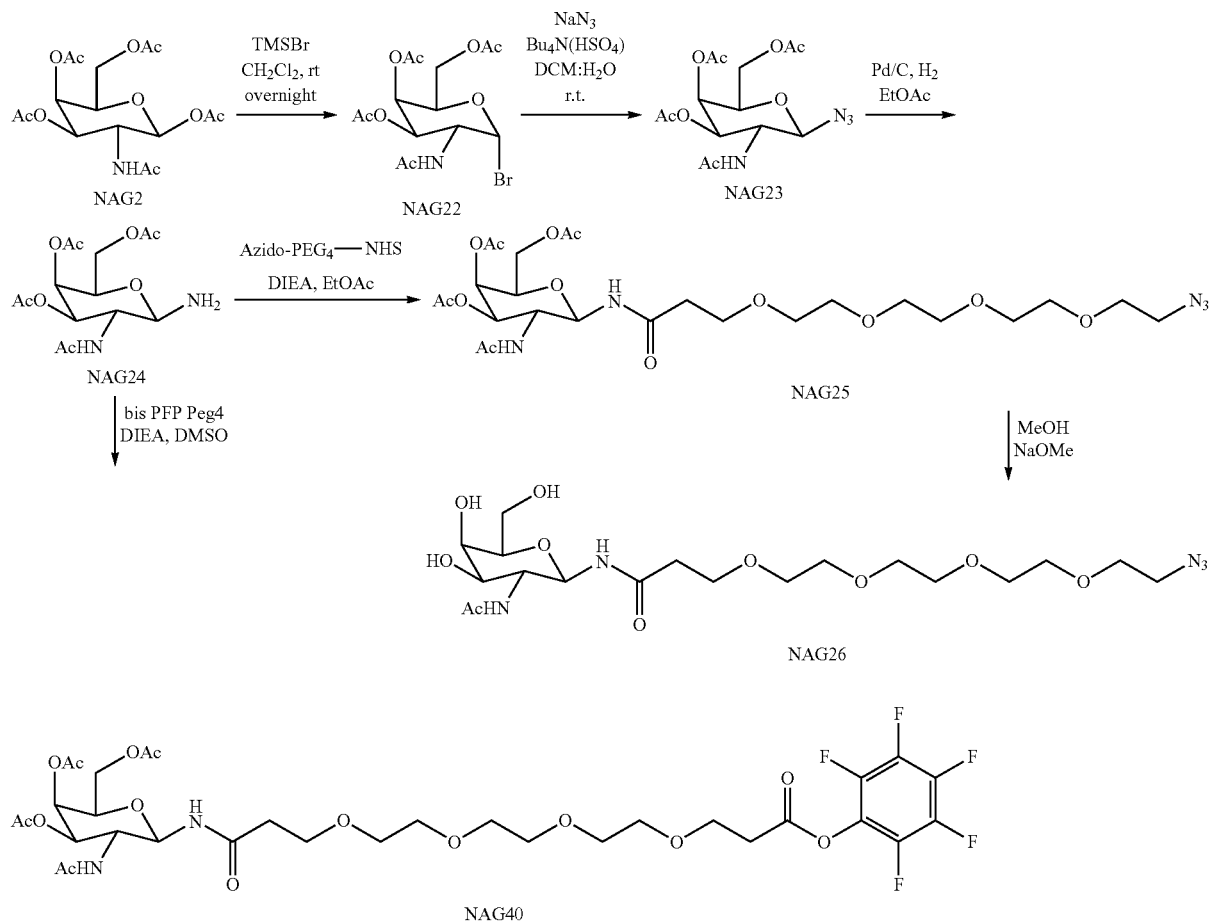

Preparation of 1-bromo-2-deoxy-2-acetamido-3,4,6-tri-O-acetyl-β-D-galactopyranoside (NAG22). To a D-galactosamine pentaacetate (NAG2, 10.0 g, 1 equiv., 25.8 mmol) suspension in DCM (90 ml) at 0° C. in an ice bath under an argon balloon was added bromotrimethylsilane (4.1 mL, 1.2 equiv., 31 mmol) drop wise with stirring. Ice bath was removed after 10 minutes, and the reaction was allowed to stir at room temperature overnight. The reaction progress was monitored by TLC (Hanessian's Stain) using 75% hexanes/ethyl acetate mobile phase. The reaction mixture was concentrated in vacuo, azeotroped with cyclohexane (3×50 mL), dried under high vacuum overnight, and used as is.

Preparation of 1-azido 2-deoxy-2-acetamido-3,4,6-tri-O-acetyl-β-D-galactopyranoside (NAG23). NAG22 (10.6 g, 1.0 equiv., 25.8 mmol) was dissolved in DCM (100 mL). To this solution was added sodium azide (4.86 g, 2.9 equiv., 74.8 mmol) in water (100 mL) and tetrabutylammonium bisulfate (8.32 g, 0.95 equiv., 24.5 mmol). The reaction mixture was stirred vigorously for 1 hour. The reaction progress was monitored by TLC (Hanessian's stain) using 75% hexanes/ethyl acetate mobile phase. The reaction mixture was extracted with DCM (2×50 mL). The organic layer was dried over anhydrous MgSO$_4$ and concentrated in vacuo. The resulting residue was then purified by silica gel flash chromatography (3:1 hexanes:ethyl acetate). $^1$H NMR of the material collected was consistent with the published structure. Observed [M+H]=373.0

Preparation of 1-amino-2-acetamido-1,2-dideoxy-3,4,6-tetra-O-acetyl-β-D-galactopyranose (NAG24). The solution of NAG23 (1.18 g, 3.17 mmol) in ethyl acetate (100 mL) was degassed by evacuation and purging with argon gas (repeated 2×). To this mixture was added the palladium catalyst (10% wt. on activated carbon, ½ microspatula). The stirring heterogeneous reaction mixture was evacuated and purged with H$_2$ (g) (repeated 2×) and stirred overnight at room temperature. HPLC-MS confirmed the formation of the product. At this time, the catalyst was removed by filtration. Concentration of the effluent afforded NAG24, which was used as is in the next step. Observed [M+H]=346.6.

Preparation of 1-amino(15'-azido-tetraethoxy-proprionamide)-2-acetamido-1,2-dideoxy-β-D-galactopyranoside (NAG26). To a solution of NAG24 (3.17 mmol) in dichloromethane (15 mL) was added N,N-diisopropylethylamine (0.55 mL, 3.17 mmol) and azido-PEG4-NHS (1.00 g, 2.57 mmol). The reaction mixture was stirred at room temperature overnight. Reverse phase HPLC revealed the presence of hydrolyzed NHS ester. A solution of HATU (0.49 g, 1.28 mmol) and DIEA (0.55 mL, 3.17 mmol) in DMF (2 mL) was added to assist the acylation. After 1 h, the reaction was diluted with dichloromethane, and washed with sat. NaHCO$_3$ (aq.) and brine. The organic layer was dried over MgSO$_4$ and concentrated in vacuo to afford NAG25. A solution of NAG 25 (~2.57 mmol) in MeOH (50 mL) was placed under Ar (g), and NaOMe (0.5 mL, 25% (w/v) in MeOH) was added. After 2 hrs, HPLC-MS after showed desired product and the reaction was quenched with Dowex H+ resin. The resin was filtered off, and the solvent evaporated in vacuo. The crude product was purified by reverse phase HPLC to afford NAG26 (481 mg, 39% yield). M+H=493.7.

Peg variations of NAG26 with Peg2, Peg6, and Peg8 were synthesized in a similar manner; see Table 2.

TABLE 2

| Compound # | Peg-X | Empirical formula | Mass-spectrometric molecular peak calcd | Mass-spectrometric molecular peak found (ESI +) |
|---|---|---|---|---|
| NAG37 | 2 | $C_{15}H_{27}N_5O_8$ | 405.4 | 406.2 |
| NAG26 | 4 | $C_{19}H_{35}N_5O_{10}$ | 493.5 | 493.7 |
| NAG38 | 6 | $C_{23}H_{43}N_5O_{12}$ | 581.6 | 581.8 |
| NAG39 | 8 | $C_{27}H_{51}N_5O_{14}$ | 669.7 | 670 |

Preparation of 1-amino(3'-propionamide-tris-ethoxy-propionyl-pentafluorophenyl ester)-2-acetamido-1,2-dideoxy-3,4,6-tetra-O-acetyl-β-D-galactopyranose (NAG40). To a solution of NAG24 (1.56 mmol) in DMSO (4 mL) was added bis-PFP-PEG4 (1.00 g, 1.59 mmol) and N,N-diisopropylethylamine (0.28 mL, 2.34 mmol). The reaction mixture was stirred at room temperature for 1 h, and reverse phase HPLC confirmed formation of desired product NAG40. The crude product was purified by reverse phase HPLC to afford NAG40 (0.33 g, 27% yield). ESI MS+ mass calcd $C_{32}H_{41}F_5N_2O_{15}$: 788.2, Found: 789.3 [M+H].

formed and the reaction was cooled to 0° C. A solution of azido-Peg3-amine (0.63 g, 2.91 mmol) in THF (2 mL) was added, and the reaction was stirred for an additional 1 h. Reverse phase HPLC-MS showed formation of compound NAG27. ESI MS+ mass calculated $C_{27}H_{45}N_5O_{13}$: 647.7, Found: 647.8 [M+H]. The precipitate was removed by filtration, and the reaction mixture was concentrated in vacuo to give a thick syrup.

Preparation of [5-(2-{2-[2-(2-azidoethoxy)ethoxy] ethoxy}ethylamino)-5-oxopentanoyl]-2-deoxy-2-N-acetyl-β-D-galactopyranoside (NAG28). Crude NAG27 was dissolved in anhydrous methanol (10 mL) and treated with NaOMe in MeOH (25 wt %, 250 µL). The reaction was stirred overnight at room temperature. At this time, reverse phase HPLC-MS showed consumption of compound NAG27 and formation of compound NAG28. ESI MS+ mass calculated $C_{21}H_{31}N_5O_{10}$: 521.6, Found: 522.3 [M+H]. Dowex H+ resin was added to neutralize the base, the resin was filtered off, and the liquor was concentrated in vacuo to give the crude product, which was purified by reverse phase HPLC to afford compound NAG28 (0.42 g, 36% yield over two steps).

Preparation of ([3-(tert-butoxycarbonylamino)propylamino])-5-oxopentanoyl]-2-deoxy-2-N-acetyl-3,4,6-tri-O-acetyl-β-D-galactopyranoside (NAG29). To a solution of NAG8 (0.29 g, 0.65 mmol) in DMF (3 mL) was treated with HATU (0.25 g, 0.65 mmol) and N,N-diisopropylethylamine (0.34 mL, 1.95 mmol). After 10 min, NH-Boc-1,3-diaminopropane (0.13 g, 0.72 mmol) was added, and the resulting mixture was stirred for 2 h. The mixture was concentrated in vacuo and purified by $SiO_2$ chromatography to provide

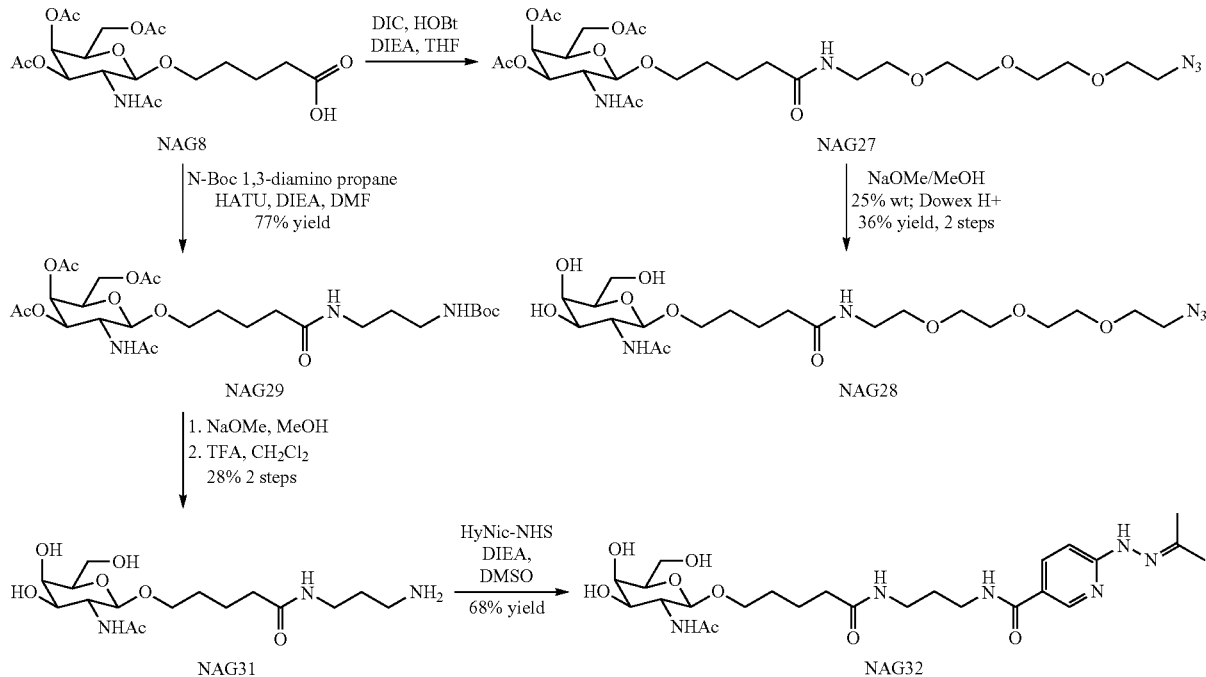

Preparation of [5-(2-{2-[2-(2-azidoethoxy)ethoxy] ethoxy}ethylamino)-5-oxopentanoyl]-2-deoxy-2-N-acetyl-3,4,6-tri-O-acetyl-β-D-galactopyranoside (NAG27). To a solution of NAG8 (1.00 g, 2.24 mmol) in THF (8 mL) was added N,N'-diisoproylcarbodiimide (0.56 g, 4.48 mmol) and HOBt (0.25 g, 2.17 mmol). After 1 h, white precipitate had compound NAG29 (0.30 g, 77% yield). ESI MS+ mass calculated $C_{27}H_{45}N_3O_{12}$: 603.7, Found: 626.8 [M+Na].

Preparation of ([3-(amino)propylamino])-5-oxopentanoyl]-2-deoxy-2-N-acetyl-β-D-galactopyranoside (NAG31). A solution of NAG29 (0.30 g, 0.50 mmol) in anhydrous methanol was treated with NaOMe in MeOH (25 wt %, 50 μL). After 20 min, TLC showed complete consumption of NAG29. Dowex strong H+ resin was added to acidify the reaction and stirred for 30 min. The resin was filtered off and washed with 1% TEA in MeOH and 1 M NaOH (aq). The filtrate was neutralized with 1 M HCl (aq) and concentrated in vacuo to give NAG31 (0.052 g, 28% yield). ESI MS+ mass calculated $C_{16}H_{31}N_3O_7$: 377.4, Found: 377.6 [M+H].

Preparation of ({3-[6-(isopropylidenehydrazino)-nicotinoylamino]propylamino}-5-oxopentanoyl)-2-deoxy-2-N-acetyl-β-D-galactopyranoside (NAG32). A solution NAG31 (0.009 g, 22 μmol) in DMSO (1 mL) was treated with HyNic-sulfo-NHS (0.007 g, 18 μmol) and N,N-diisopropylethylamine (9.4 μL, 54 μmol) for 1 h and purified by reverse phase HPLC to afford NAG32 TFA salt (0.010 g, 68% yield). ESI MS+ mass calculated $C_{25}H_{40}N_6O_8$: 552.6, Found: 554.0 [M+H].

stirring under an argon balloon. The reaction mixture was allowed to stir at room temperature overnight. Completion of the reaction was verified by LC-MS. ESI MS+. The crude product was purified by reverse phase HPLC to afford NAG33 (1.2 g). Mass calcd $C_{21}H_{33}N_5O_{11}$: 531.22, Found: 532.3 [M+H]$^+$.

Preparation of 1-amino-[2-(2-aminoethoxy)ethoxy]propionyl]-2-acetamido-1,2-dideoxy-3,4,6-tetra-0-acetyl-α-D-galactopyranose (NAG34). To NAG33 (1.2 g, 2.3 mmol) dissolved in ethyl acetate (25 mL) was added palladium (10% Pd on activated carbon, 122 mg). Next a hydrogen balloon and vacuum line were inserted. The reaction vessel was evacuated and purged with hydrogen gas (3 cycles). After stirring at room temperature for 1 h, reverse phase HPLC-MS confirmed the formation of the product. Reaction was filtered over a bed of Celite® and washed with EtOAc (3×10 mL). Concentration in vacuo afforded NAG34 in

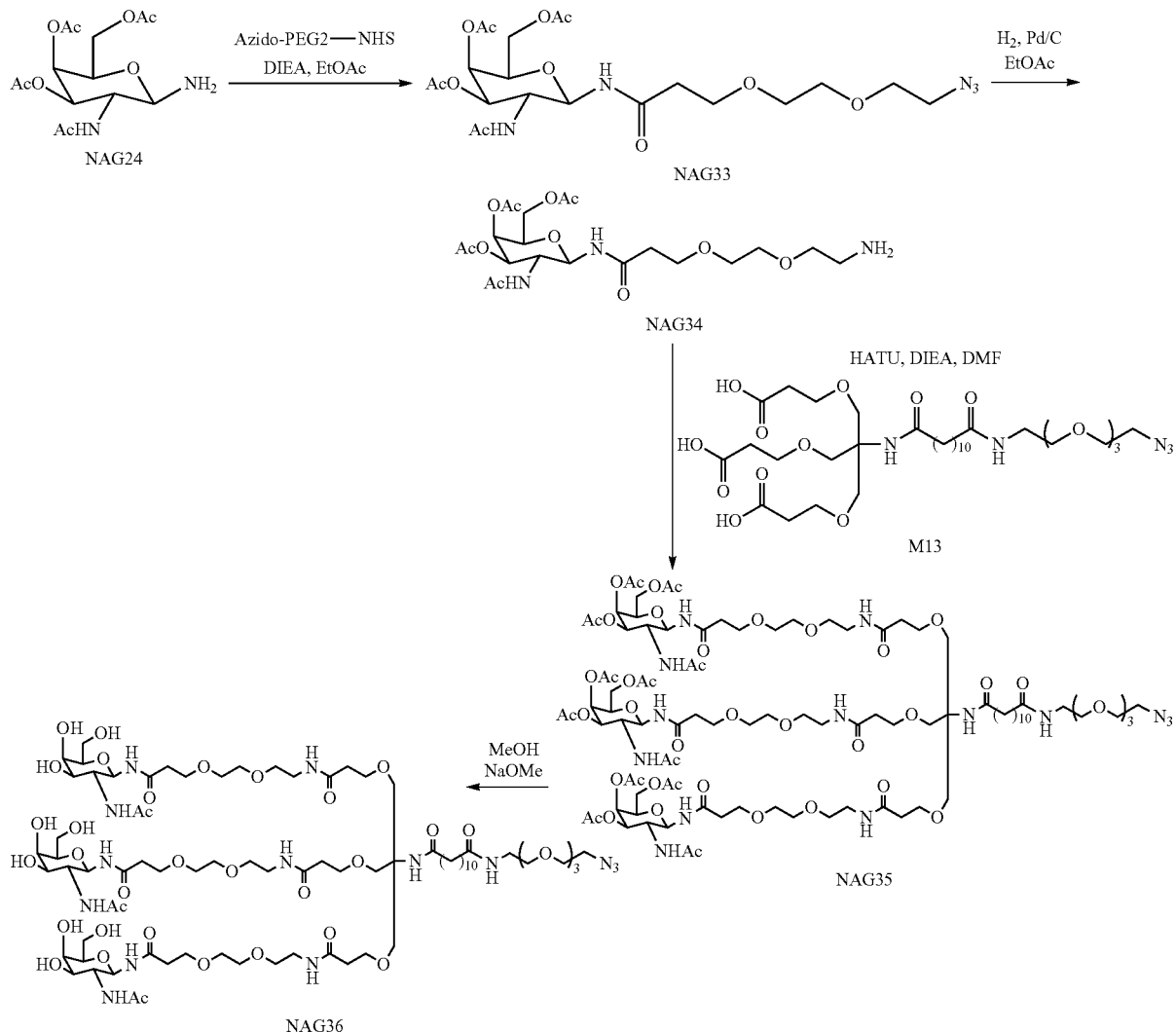

Preparation of 1-amino-(15'-azido-diethyleneglycol propanoyl) 2-acetamido 1,2-dideoxy 3,4,6-tetra-O-acetyl-α-D-galactopyranoside (NAG33). To a solution of NAG24 (2.3 g, 6.7 mmol) in ethyl acetate (90 mL) and N,N-diisopropylethylamine (1.7 mL, 9.9 mmol) was added azido-PEG2-NHS (1.0 g, 3.3 mol) in ethyl acetate (10 mL) dropwise with quantitative yield. ESI MS+ Mass calcd $C_{21}H_{35}N_3O_{11}$: 505.23, Found: 506.3 [M+H]$^+$.

Preparation of peracetylated azido-Peg2-N-GalNAc trimer (NAG36). To the solution of tri-acid linker M13 (52.5 mg, 0.07 mmol) and N,N-diisopropylethylamine (73.2 μL, 0.42 mmol) in DMF (2 mL) was added HATU (119.8 mg, 0.32 mmol) in DMF (2 mL). The reaction was allowed to stir for 10 min at room temperature. Next, NAG34 (159 mg, 0.32 mmol) in DMF (1 mL) was added, and the mixture was stirred overnight at room temperature. LC-MS after 18 h confirmed the formation of the product. Water (10 mL) was added, and the resulting mixture was washed with DCM (3×5 mL). The combined organic layers were dried over $Na_2SO_4$, filtered, and volatiles were removed in vacuo to afford NAG35 (155 mg). ESI MS+ mass calcd $C_{96}H_{158}N_{14}O_{44}$: 2210.5, Found: 1106.8 $[M+2H]^{2+}$. To a solution of NAG35 (155 mg, 70 µmol) in MeOH (5 mL) was added sodium methoxide (25% wt MeOH, 100 µL). The reaction mixture was stirred at room temperature for 1 h under argon balloon. LC-MS after 1 h showed the product formation and the disappearance of starting material. Dowex H+ resin was added to neutralize the reaction mixture. The resin was filtered off, and the volatiles were removed in vacuo. The crude product was purified by reverse phase HPLC to afford NAG36 (10 mg). ESI MS+ Mass calcd $C_{78}H_{140}N_{14}O_{35}$: 1832.96, Found: 917.7 $[M+2H]^{2+}$.

Synthesis of Folate Ligand

Preparation of N-Boc-Peg11 folate (F2). To a solution of folic acid (225 mg, 0.51 mmol) in DMSO (4 mL) was added diisopropylcarbodiimide (80 µL, 0.51 mmol). After stirring for 1.5 h, a solution of Boc-Peg11-diamine (220 mg, 0.34 mmol) in DMSO (1 mL) was added, and the reaction was stirred overnight. Upon addition of water (35 mL) a solid precipitated. The precipitate was collected by filtration and purified by reverse phase HPLC to afford F2 (364 mg, 67% yield). MALDI-TOF mass calcd $C_{48}H_{77}N_9O_{18}$: 1067.54, Found: 1069.89 [M+H].

Preparation of folate-peg 11-HyNic acetone hydrazone (F3). MonoBoc F2 (210 mg, 0.2 mmol) was treated with TFA (9 mL) and acetone (1 mL) for 1.5 h, concentrated in vacuo, and dried under a high vacuum. MALDI-TOF mass calcd $C_{43}H_{69}N_9O_{16}$: 967.48, Found: 969.86 [M+H]. The crude yellowish solid was dissolved in DMSO (200 µL) and treated with a solution of HyNic-NHS ester (10.0 mg, 0.03 mmol) and DIEA (40 µL, 0.23 mmol) for 1.5 h. The crude was purified by RP-HPLC to afford F3 (1.2 mg, 3.5% yield). MALDI-TOF mass calcd $C_{52}H_{73}N_{12}O_{17}$: 1142.56, Found: 1144.03 [M+H].

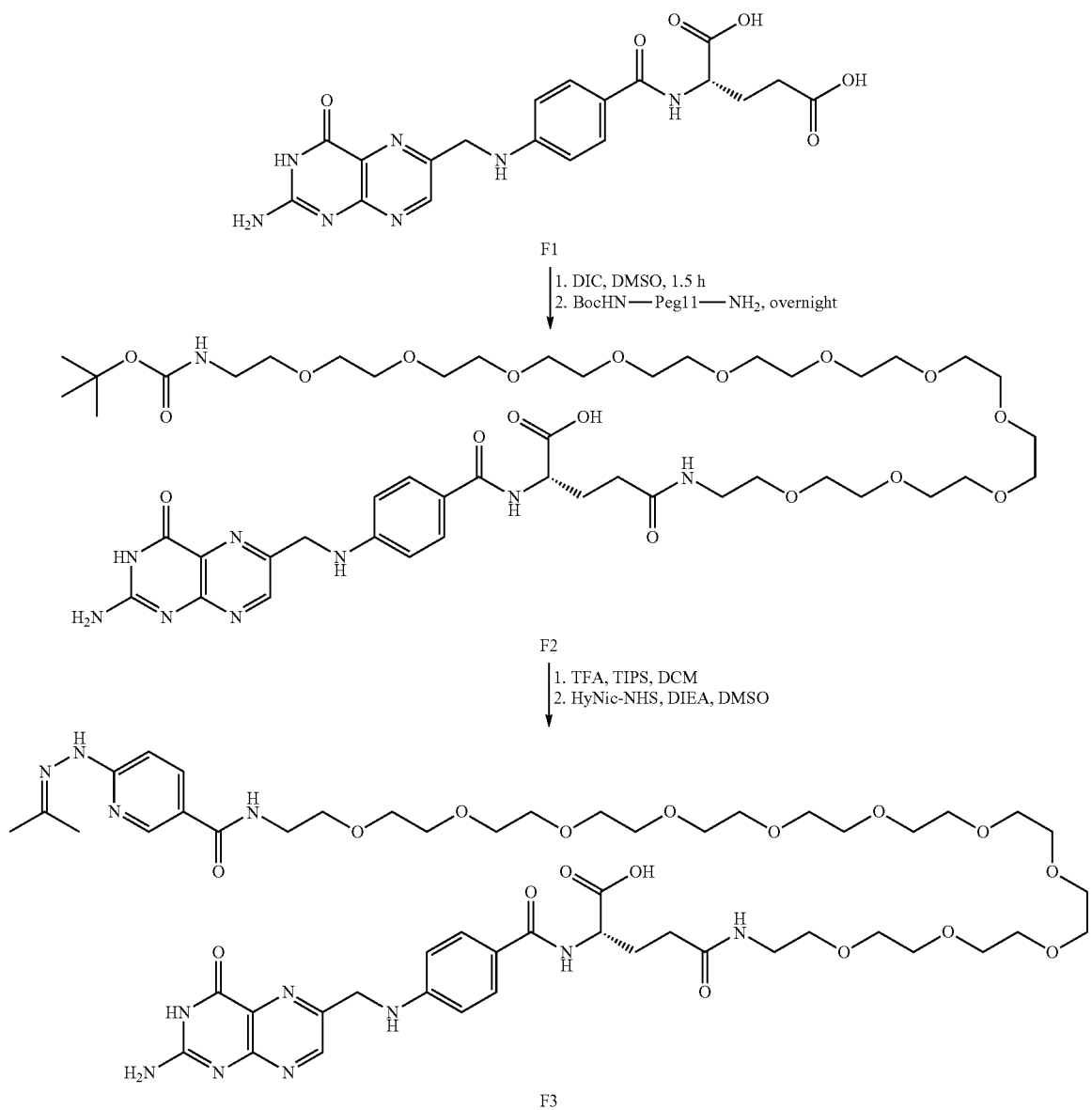

Synthesis of Monovalent Folate Azide

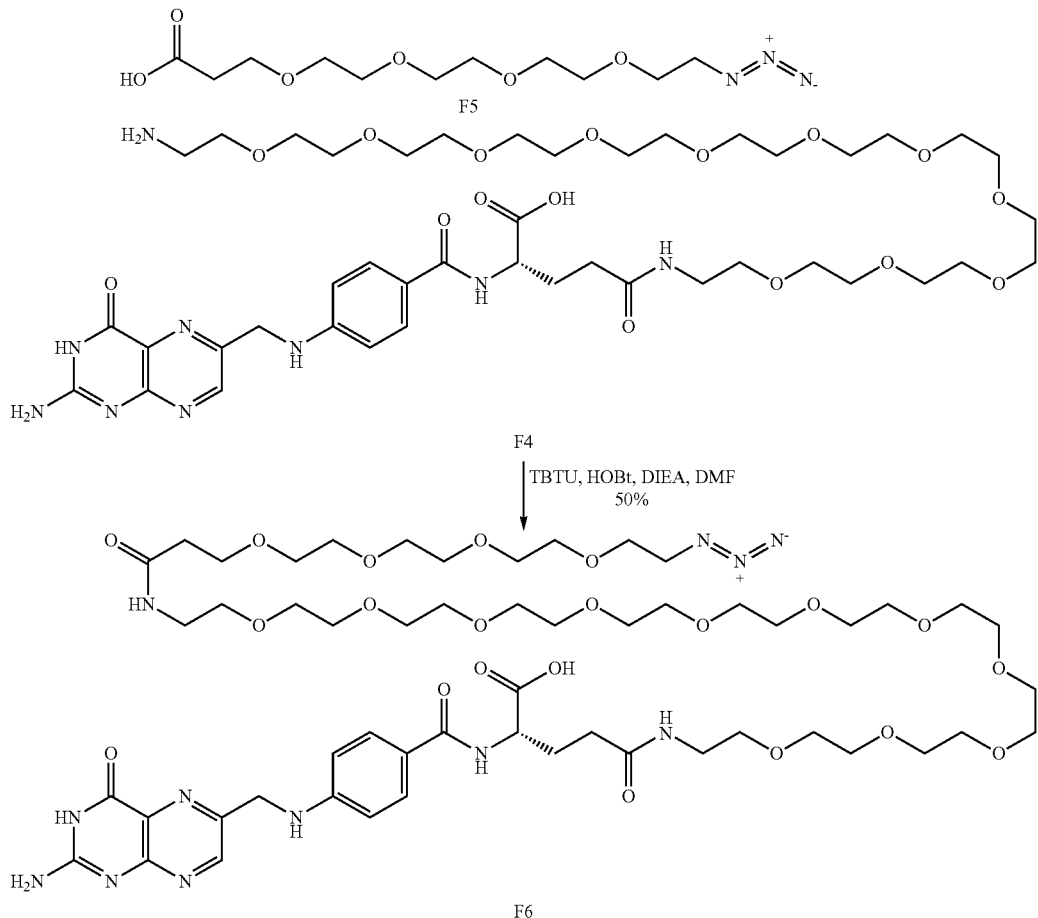

Preparation of azido-Peg4-amido-Peg11 folate (F6). Amino-Peg11 folate F4 (115 mg, 0.12 mmol) in DMSO (1.0 mL) was added to a solution of azido-Peg4 acid (38 mg, 0.13 mmol) activated with TBTU (42 mg, 0.13 mmol), HOBt (20 mg, 0.13 mmol), and DIEA (63 μL, 0.36 mmol) in DMSO (1.0 mL). After 2 h, base was removed in vacuo and the crude purified by RP-HPLC to afford F6 (75 mg, 50%). AP-ESI+ Mass calcd $C_{54}H_{33}N_{12}O_{21}$: 1240.61, Found: 1241.7 $[M+H]^+$, 621.5 $[M+2H]^{2+}$ Synthesis of PSMA Ligands

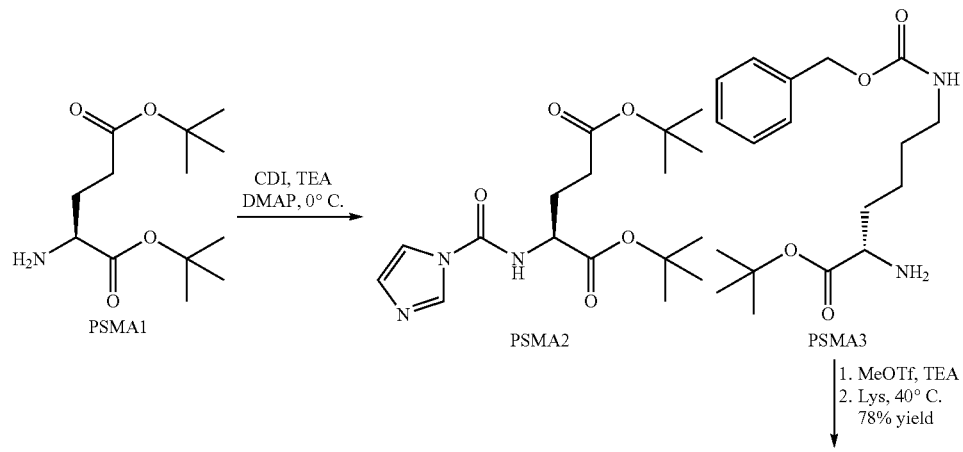

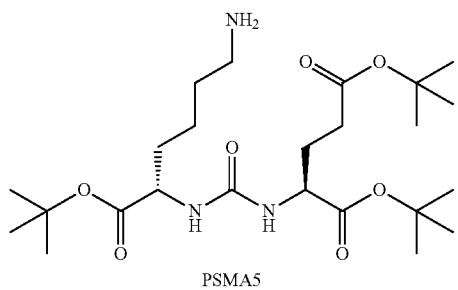

PSMA5

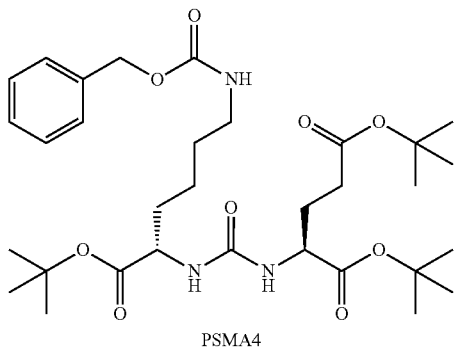

PSMA4

Preparation of Cbz-Lys ureido Glu tris-t-butyl ester (PSMA4). To an ice cold solution of glutamic di-tert-butyl ester (1.06 g, 3.58 mmol), DMAP (27 mg), and TEA (1.25 mL, 8.95 mmol) in $CH_2Cl_2$ (10.0 mL) was added CDI (638 mg, 3.94 mmol) in one portion. After 30 min, the reaction was removed from the ice bath and stirred overnight. The reaction was diluted with $CH_2Cl_2$ and washed with sat. $NaHCO_3$ (aq.), water, and brine. After drying over $Na_2SO_4$, the organic layer was concentrated in vacuo and dried under high vacuum to give PSMA2. A solution of PSMA2 in DCE (10 mL) was cooled to 0° C. and treated sequentially with MeOTf (0.59 g, 3.58 mmol) and TEA (1.00 mL, 7.16 mmol). After 45 min, Cbz-Lys t-butyl ester PSMA3 (1.34 g, 3.58 mmol) in DCE (2 mL) was added, and the mixture was heated at 40° C. After 2 h, the reaction was diluted with $CH_2Cl_2$ and washed with sat. $NaHCO_3$ (aq.), water, and brine. The organic layer was dried over $Na_2SO_4$ and concentrated in vacuo to afford a thick syrup. The crude material was purified through $SiO_2$ gel chromatography to afford PSMA4 (1.73 g, 78%) as a white foam. AP-ESI+ Mass calcd $C_{32}H_{51}N_3O_9$: 621.36, Found: 622.4 $[M+H]^+$, 644.4 $[M+Na]^+$ Preparation of Lys ureido Glu tris-t-butyl ester (PSMA5). A solution of PSMA4 (1.73 g, 2.79 mmol) in EtOAc (100 mL) was degassed by application of vacuum and backfilling with argon. Palladium (10% wt on activated carbon, 0.15 g) was added in one portion, and the mixture was degassed by application of vacuum and backfilling with $H_2$ (g) and stirred for 6 h. The catalyst was removed by filtration, and the mother liquor concentrated in vacuo to give PSMA5 quantitatively. AP-ESI+ Mass calcd $C_{24}H_{45}N_3O_7$: 487.32, Found: 488.4 $[M+H]^+$ Synthesis of Monovalent PSMA Azide (PSMA7)

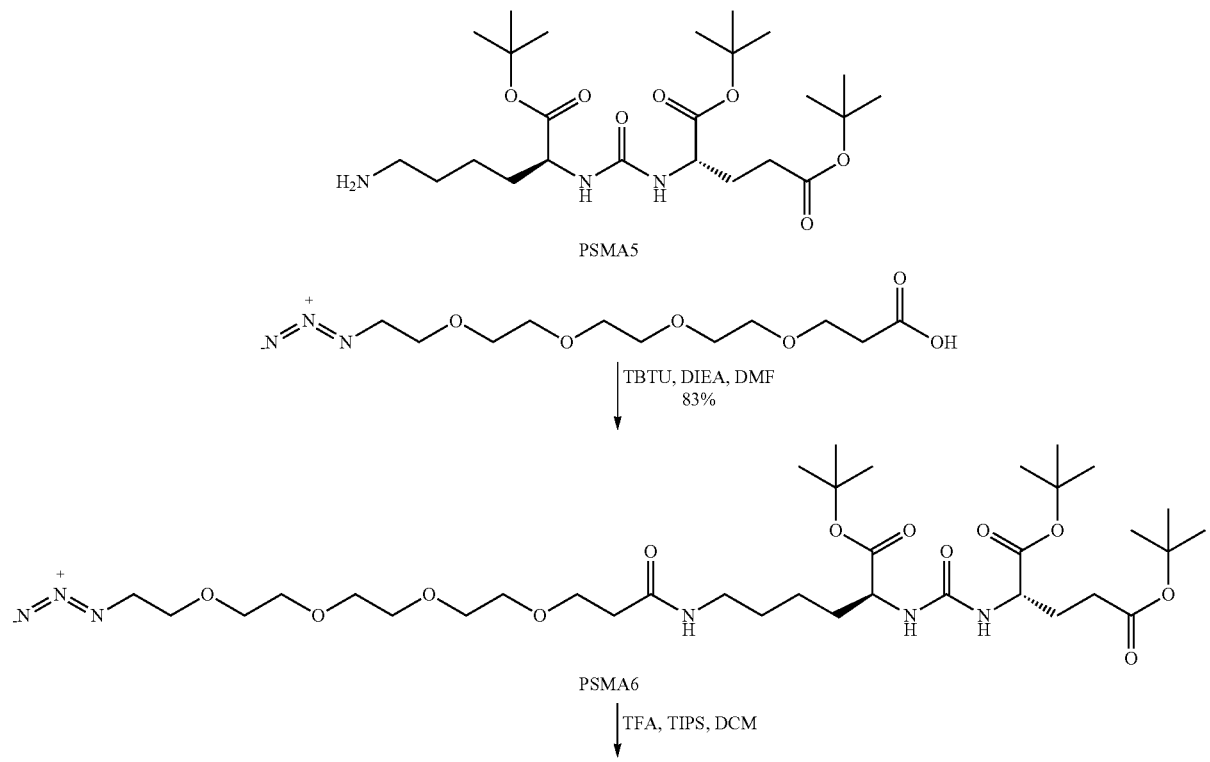

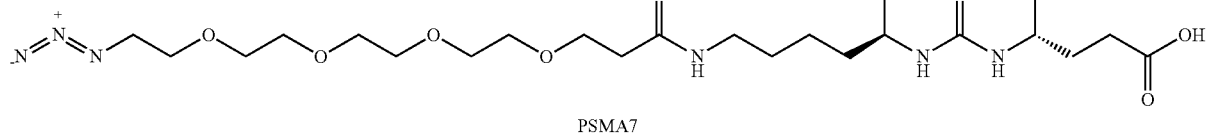

PSMA7

Preparation of azido Peg4 Lys ureido Glu tris-t-butyl ester (PSMA6). Azido Peg4 acid (133 mg, 0.45 mmol) was activated with TBTU (146 mg, 0.45 mmol), HOBt (69 mg, 0.45 mmol), and DIEA (216 μL, 1.24 mmol) in DMF (3.0 mL). After 15 min, a solution of PSMA5 (202 mg, 0.41 mmol) was delivered, and the reaction was stirred at RT for 1.5 h. RP-HPLCMS showed formation of the desired product. The reaction was concentrated in vacuo and purified through $SiO_2$ gel chromatography to afford PSMA6 (257 mg, 83%). AP-ESI+ Mass calcd $C_{35}H_{64}N_6O_{12}$: 760.46, Found: 761.5 $[M+H]^+$, 783.5 $[M+Na]^+$ Preparation of azido Peg4 Lys ureido Glu (PSMA7). Tris-tert-butyl ester PSMA6 (257 mg, 0.34 mmol) was treated with a solution of TFA:TIPS (10 mL, 97.5:2.5, v/v) for 30 min. RP-HPLCMS showed complete conversion to the desired product. The reaction was concentrated in vacuo and purified by RP-HPLC to afford PSMA7 (112 mg, 56%). AP-ESI+ Mass calcd $C_{23}H_{40}N_6O_{12}$: 592.27, Found: 593.3 $[M+H]^+$ Synthesis of Monovalent PSMA HyNic (PSMA10)

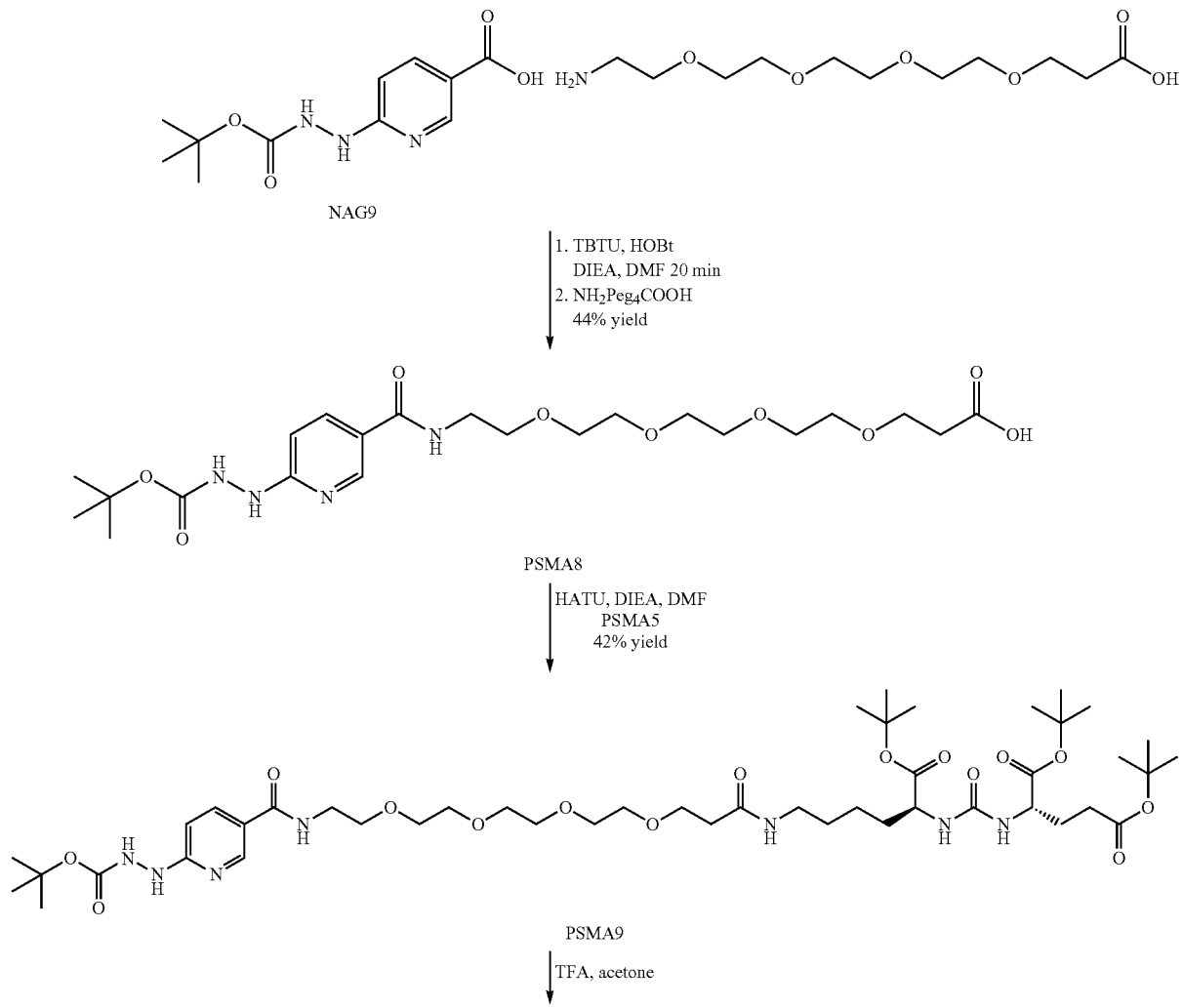

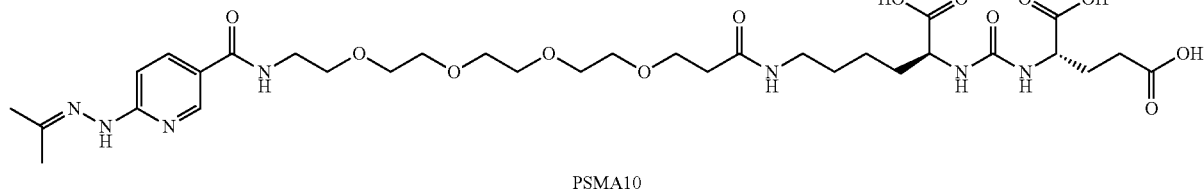

PSMA10

Preparation of N-Boc 4-hydrazino-nicotinamido Peg4 acid (PSMA8). N-Boc 4-hydrazino nicotinic acid NAG9 (137 mg, 0.54 mmol) was treated with TBTU (124 mg, 0.49 mmol), HOBt (83 mg, 0.54 mol), and DIEA (128 μL, 0.74 mmol) in DMF for 20 min. To the activated ester, was added a solution of amino-Peg4-acid (130 mg, 0.49 mmol), and the mixture was stirred for 2 h. The reaction was concentrated in vacuo and purified through SiO$_2$ gel chromatography to afford PSMA8 (107 mg, 44%). AP-ESI+ Mass calcd $C_{22}H_{36}N_4O_9$: 500.25, Found: 501.3 [M+H]$^+$ Preparation of N-Boc 4-hydrazino-nicotinamido Peg4-epsilon-amido lys-alpha-ureido-glu tri-t-butyl ester (PSMA9). PSMA8 (107 mg, 0.21 mmol) was treated with HATU (81 mg, 0.21 mmol) and DIEA (93 μL, 0.53 mmol) in the presence of amine PSMA5 (104 mg, 0.21 mmol) in DMF for 1 h, after which, the reaction was concentrated in vacuo and purified through SiO$_2$ gel chromatography to afford PSMA9 (85 mg, 42%). AP-ESI+ Mass calcd $C_{46}H_{79}N_7O_{15}$: 969.46, Found: 760.6 [M+H]$^+$ Preparation of dimethyl 4-hydrazono nicotinamido Peg4-epsilon-amido lys-alpha-ureido-glu (PSMA10). Tris-t-butyl ester PSMA9 (85 mg, 0.09 mmol) was treated with a solution of TFA:acetone (10 mL, 97.5:2.5, v/v) for 30 min. RP-HPLCMS showed complete conversion to the desired product. The reaction was concentrated in vacuo and purified by RP-HPLC to afford PSMA10 (55 mg, 84%). AP-ESI+ Mass calcd $C_{32}H_{51}N_7O_{13}$: 741.35, Found: 742.4 [M+H]$^+$ Synthesis of Bivalent PSMA Azide (PSMA18)

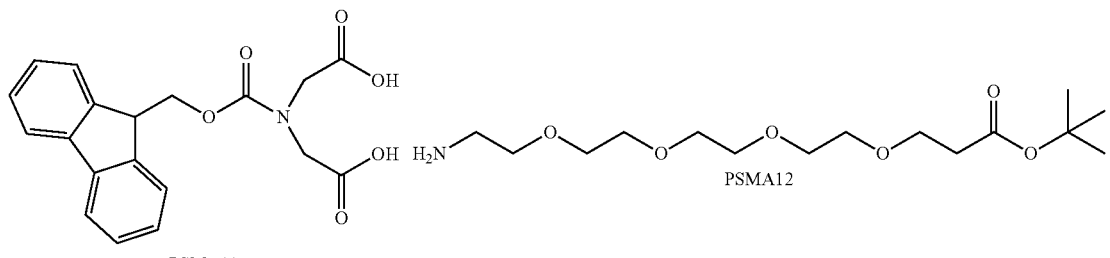

PSMA11    PSMA12

TBTU, HOBt, DIEA, DMF
91%

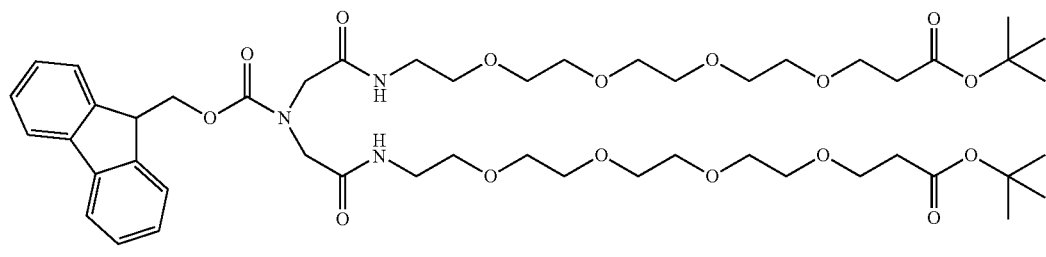

PSMA13

1. TFA, TIPS, DCM
2. PSMA5, HATU, DIEA, 88%

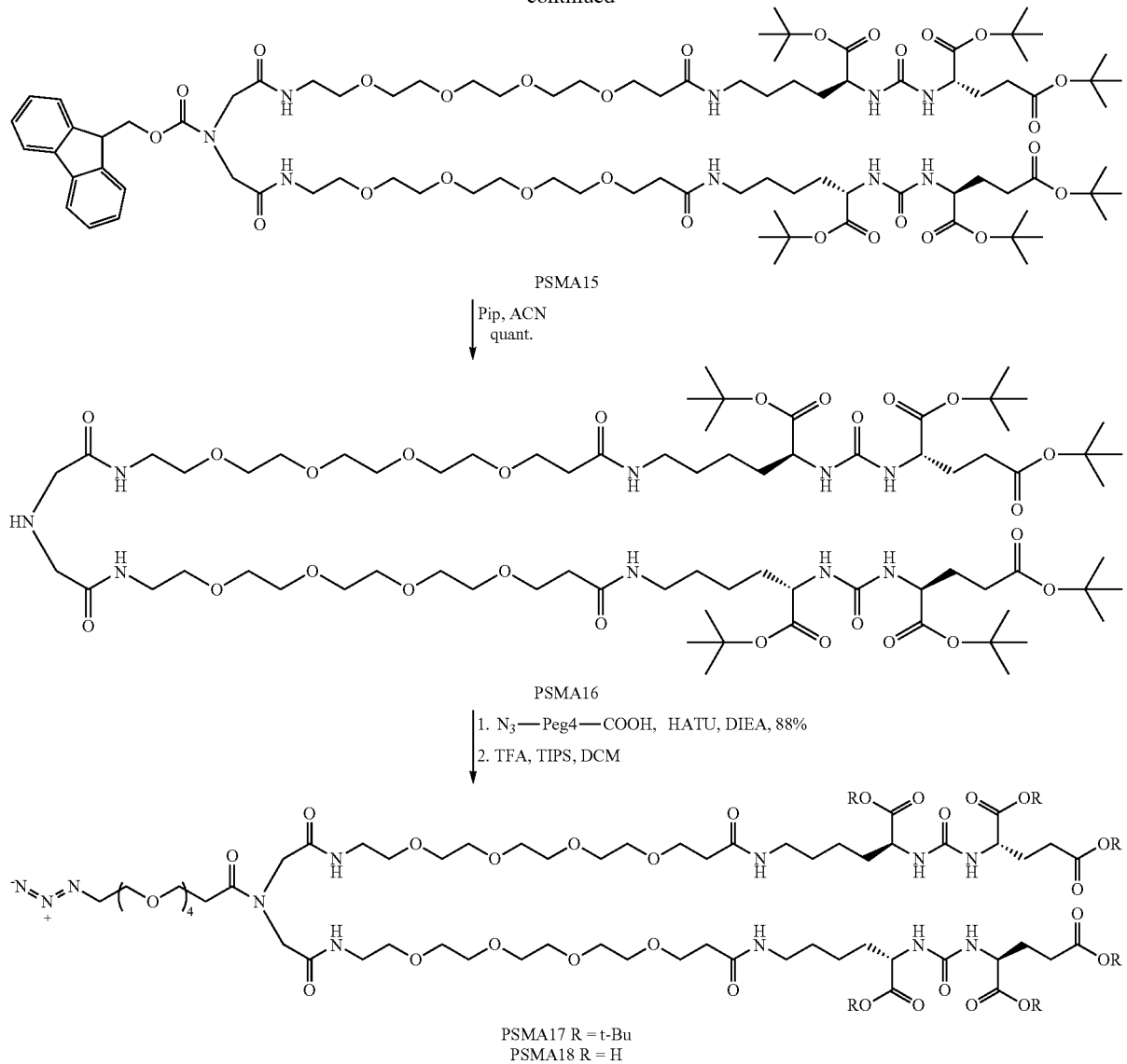

Preparation of N-Fmoc bis-imino-(acetamido-Peg4 t-butyl ester) (PSMA13). N-Fmoc imino diacetic acid, PSMA11, (107 mg, 0.30 mmol) was treated with PSMA12 (212 mg, 0.66 mmol), TBTU (193 mg, 0.60 mmol), HOBt (92 mg, 0.60 mmol), and DIEA (209 μL, 1.20 mmol) in DMF for 2 h. The reaction was concentrated in vacuo and purified through $SiO_2$ gel chromatography to afford PSMA13 (250 mg, 91%). AP-ESI+ Mass calcd $C_{49}H_{75}N_3O_{16}$: 961.51, Found: 962.6 [M+H]$^+$, 984.6 [M+Na]$^+$ Preparation of N-Fmoc bis-imino-(acetamido-Peg4-epsilon-amido lys-alpha-ureido-glu tri-t-butyl ester) (PSMA15). Di-t-butyl ester PMSA13 (250 mg, 0.26 mmol) in DCM (1 mL) was treated with TFA (10 mL) and TIPS (111 μL, 0.54 mmol). After 30 min, the reaction was concentrated in vacuo to afford a syrup, which was washed with hexanes to afford di-acid PSMA14 as a thick syrup. PSMA14 was treated with HATU (198 mg, 0.54 mmol), PSMA5 (292 mg, 0.57 mmol), and DIEA (362 μL, 2.08 mmol) in DMF for 1 h. The reaction was concentrated in vacuo and purified through $SiO_2$ gel chromatography to afford PSMA15 (408 mg, 88%). PSMA14: AP-ESI+ Mass calcd $C_{41}H_{59}N_3O_{16}$: 849.39, Found: 850.5 [M+H]$^+$, 872.5 [M+Na]$^+$. PSMA15: AP-ESI+ Mass calcd $C_{89}H_{145}N_9O_{28}$: 1788.02, Found: 895.3 [M+2H]$^{2+}$, 917.2 [M+2Na]$^{2+}$ Preparation of bis-imino-(acetamido-Peg4-epsilon-amido lys-alpha-ureido-glu tri-t-butyl ester) (PSMA16). N-Fmoc PMSA15 (408 mg, 0.22 mmol) in acetonitrile (10 mL) was treated with piperidine for 30 min. The reaction was concentrated in vacuo, azeotroped with PhMe (3×10 mL), washed with hexanes (3×20 mL), and dried under high vacuum to afford PSMA16. AP-ESI+ Mass calcd $C_{74}H_{135}N_9O_{26}$: 1565.95, Found: 895.3 [M+2H]$^{2+}$, 917.2 [M+2Na]$^{2+}$ Preparation of azido-Peg4-imido-bis-(acetamido-Peg4-epsilon-amido lys-alpha-ureido-glu tri-t-butyl ester) (PSMA17). Amine PMSA16 (172 mg, 0.11 mmol) was added to N$_3$-Peg4-COOH (40 mg, 0.14 mmol) activated with HATU (52 mg, 0.14 mmol) and DIEA (116 μL, 0.66 mmol) in DMF (2 mL). After 1 h, the reaction was concentrated in vacuo and purified by SiO$_2$ gel chromatography to afford PSMA17 (194 mg, 91%). AP-ESI+ Mass calcd C$_{85}$H$_{154}$N$_{12}$O$_{31}$: 1839.08, Found: 895.3 [M+2H]$^{2+}$, 917.2 [M+2Na]$^{2+}$ Preparation of azido-Peg4-imido-bis-(acetamido-Peg4-epsilon-amido lys-alpha-ureido-glu) (PSMA18). Hexa-t-butyl ester PSMA17 (194 mg, 0.10 mmol) was treated with a solution of TFA:acetone (10 mL, 97.5:2.5, v/v) for 30 min. RP-HPLCMS showed complete conversion to the desired product. The reaction was concentrated in vacuo and purified by RP-HPLC to afford PSMA18 (69.4 mg, 44%). AP-ESI+ Mass calcd C$_{61}$H$_{106}$N$_{12}$O$_{31}$: 1502.70, Found: 752.5 [M+2H]$^{2+}$ Synthesis of Bivalent PSMA HyNic (PSMA20)

Preparation of N-Boc 4-hydrazino-nicotinamido Peg$_4$-imido-bis-(acetamido-Peg4-epsilon-amido lys-alpha-ureido-glu tri-t-butyl ester) (PSMA19). Amine PMSA16 (172 mg, 0.11 mmol) was added to PSMA8 (61 mg, 0.12 mmol) activated with HATU (46 mg, 0.12 mmol) and DIEA (116 µL, 0.66 mmol) in DMF (2 mL). After 1 h, the reaction was concentrated in vacuo and purified by SiO$_2$ gel chromatography to afford PSMA19 (201 mg, 89%). AP-ESI+ Mass calcd C$_{96}$H$_{169}$N$_{13}$O$_{34}$: 2048.19, Found: 1025.3 [M+2H]$^{2+}$, 684.0 [M+3H]$^{3+}$ Preparation of dimethyl 4-hydrazono-nicotinamido-Peg$_4$-imido-bis-(acetamido-Peg4-epsilon-amido lys-alpha-ureido-glu) (PSMA20). Hexa-t-butyl ester PSMA19 (201 mg, 0.10 mmol) was treated with a solution of TFA:acetone

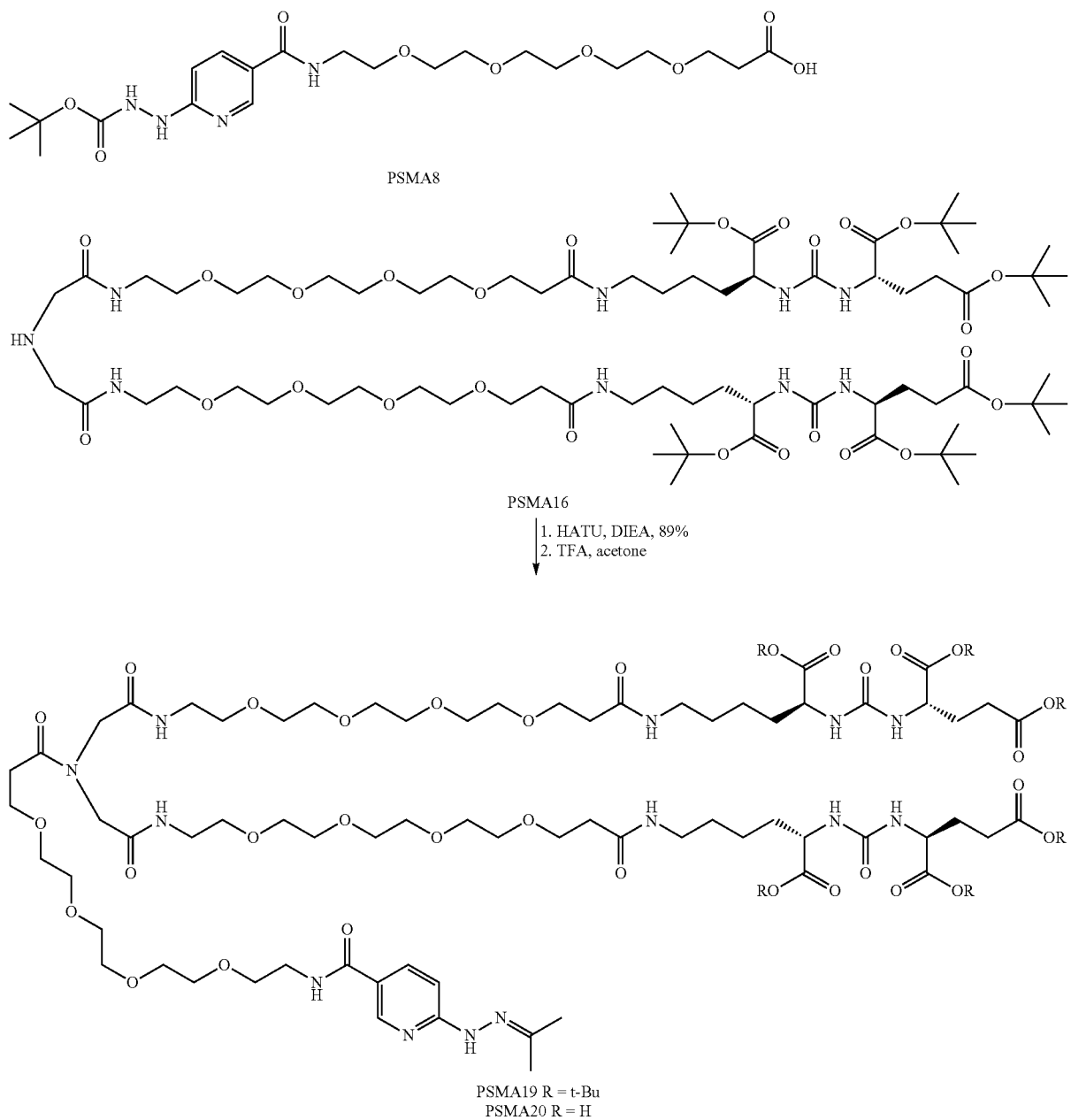

(10 mL, 9:1, v/v) for 60 min. RP-HPLCMS showed complete conversion to the desired product. The reaction was concentrated in vacuo and purified by RP-HPLC to afford PSMA20 (69.4 mg, 44%). AP-ESI+ Mass calcd $C_{70}H_{117}N_{13}O_{32}$: 1651.79, Found: 827.1 $[M+2H]^{2+}$ Synthesis of Mannose Ligand:

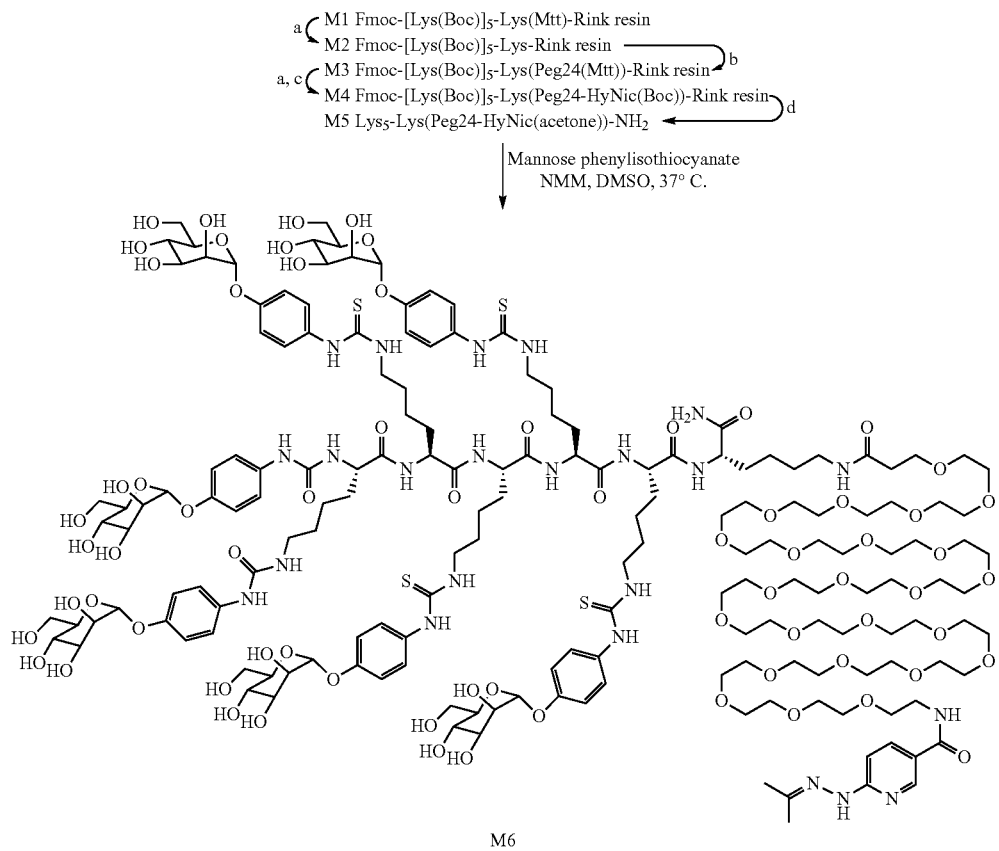

a. 1% TFA, $CH_2Cl_2$
b. HOOC—Peg24—NHMtt, HCTU
c. HyNic(Boc), HCTU;
d. cleavage cocktail Preparation of $Lys_6$-$Peg_{24}$-HyNic (M5). Peptide scaffold was synthesized using standard Fmoc chemistry on a Rink amide resin (0.61 mmol/g) with HCTU coupling and 20% piperidine deprotection. In short, peptide M1 was prepared on an automated synthesizer on a 25 μmol scale. After deprotection of Lys(Mtt), $Peg_{24}$ amino(Mtt) acid was coupled to provide M3. Removal of the Mtt group and subsequent coupling of BocHyNic provided M4. Release of the peptide from the resin using trifluoroacetic acid:triisopropylsilane:water:acetone:dithiothreitol (90:2:2:3:3) and purification by RP-HPLC afforded M5 (7.0 mg). AP-ESI+ Mass calcd $C_{96}H_{185}N_{17}O_{32}$: 2088.33, Found: 1046 m/2z, 698 m/3z, 524 m/4z.

Preparation of $Man_6$-$Lys_6$-$Peg_{24}$-HyNic (M6). Peptide scaffold M5 (7.0 mg) in DMSO (1 mL) was treated with mannose isothiocyanate (8.0 mg) and N-methylmorpholine (NMM; 200 μL). The reaction was stirred for 4 h at 37° C. and purified by RP-HPLC to afford M6 (1.2 mg). MALDI-TOF mass calcd $C_{174}H_{275}N_{23}O_{68}S_6$: 3966.70, Found: 3987.39 [M+Na].

Synthesis of Hexavalent Mannose Azide (M9)

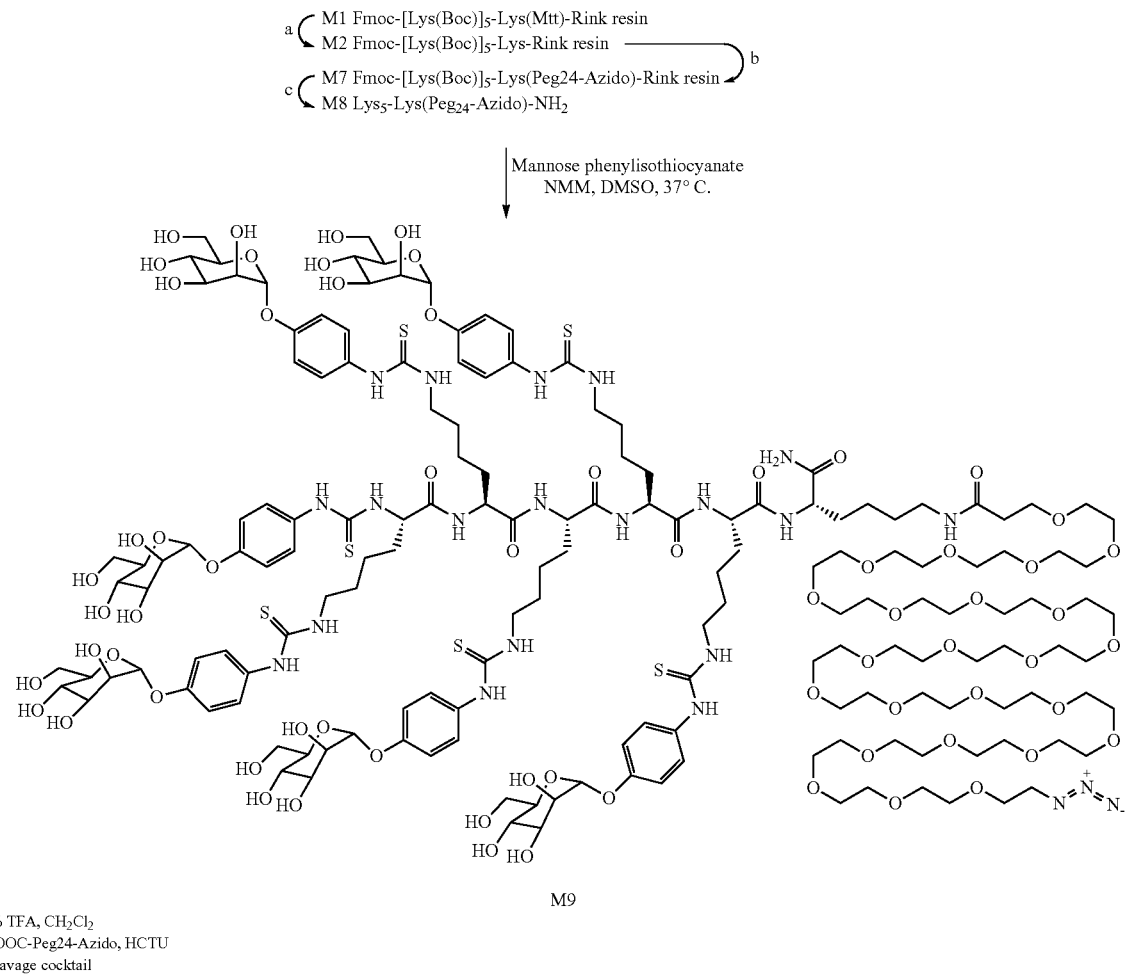

a. 1% TFA, CH$_2$Cl$_2$
b. HOOC-Peg24-Azido, HCTU
c. cleavage cocktail

Preparation of Lys$_6$-Peg$_{24}$-Azide (M8). Peptide scaffold was synthesized using standard Fmoc chemistry on a Rink amide resin (0.61 mmol/g) with HCTU coupling and 20% piperidine deprotection. In short, peptide M1 was prepared on an automated synthesizer on a 100 μmol scale. After deprotection of Lys(Mtt), azido Peg$_{24}$ acid was coupled to provide M7. Release of the peptide from the resin using the cocktail TFA:TIPS:H$_2$O (92.5:2.5:5) afforded M8 (167.0 mg). MALDI-TOF Mass calcd C$_{87}$H$_{174}$N$_{16}$O$_{31}$: 1940.4, Found: 1941.1 Preparation of Man$_6$-Lys$_6$-Peg$_{24}$-Azide (M9). Peptide scaffold M4 (167.0 mg) in DMSO (2 mL) was treated with mannose isothiocyanate and NMM (500 μL). The reaction was stirred at 37° C. and monitored by MALDI-TOF until full conversion to the desired product was achieved (a total of 58 mg of mannose isothyocyanate were added). The final product was purified by RP-HPLC to afford M9 (22 mg). MALDI-TOF mass calcd C$_{165}$H$_{264}$N$_{22}$O$_{67}$S$_6$: 3820.37, Found: 3843.79 [M+Na].

Synthesis of Trivalent Mannose Azide (M15)

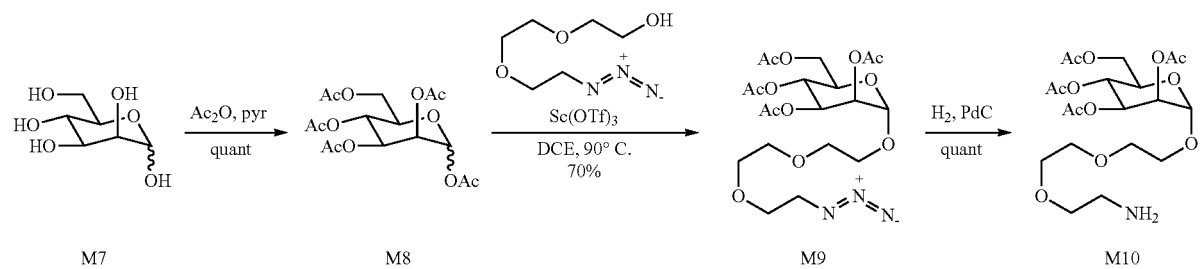

-continued

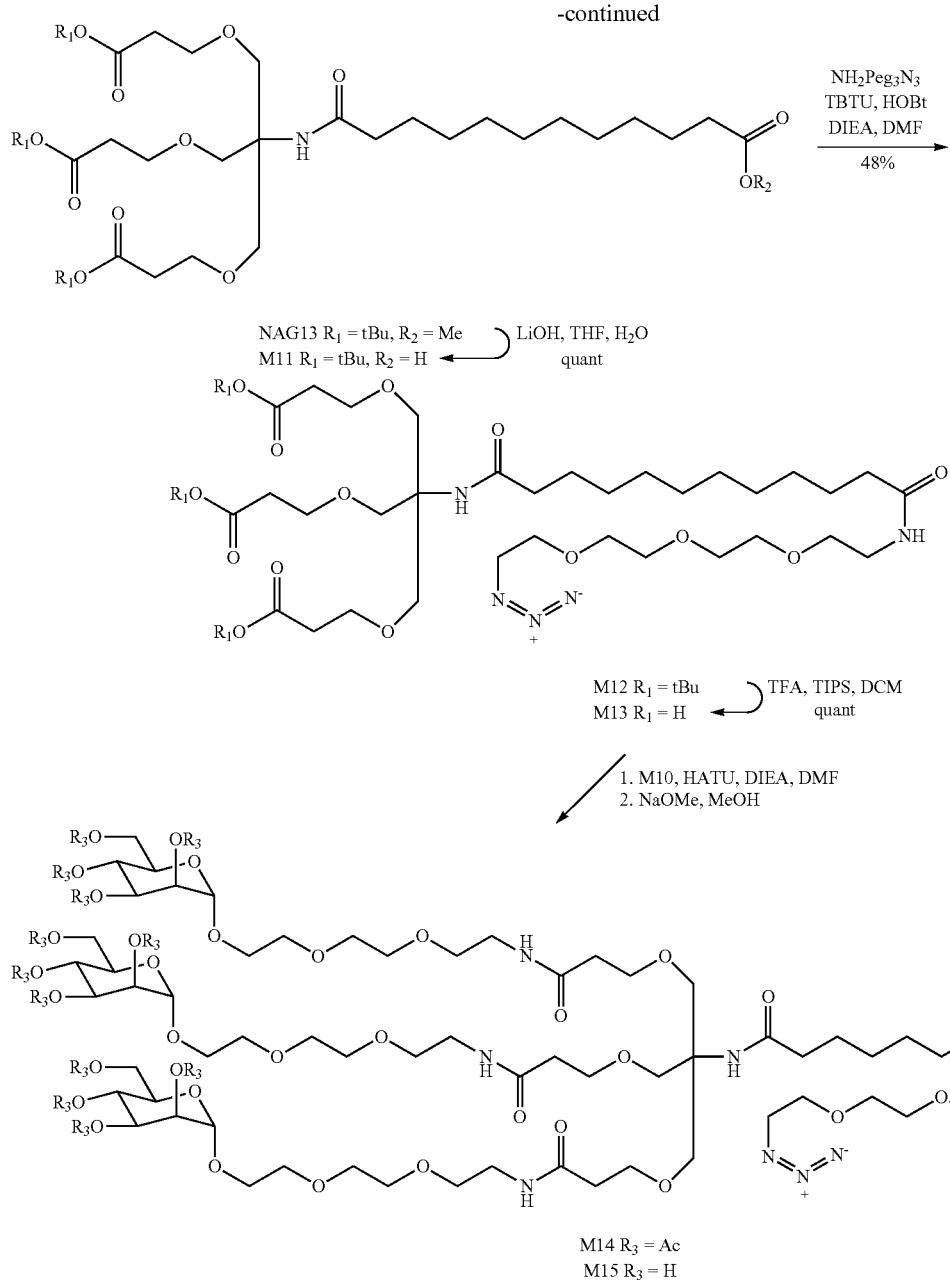

Preparation of azido tri-mannose (M15): D-Mannose was peracetylated by Ac$_2$O in pyridine overnight. Concentration by rotary evaporation followed by azeotroping with PhMe provided the pentaacetate (M8) in quantitative yield. Activation of M8 with Sc(OTf)$_3$ in the presence of commercially available azido Peg$_2$ alcohol afforded azido-Peg$_2$ mannoside (M9), which was hydrogenated quantitatively to amine (M10). Meanwhile, the methyl ester of tris linker (NAG13) was hydrolyzed selectively to afford acid (M11). Coupling of commercially available azido Peg$_3$ amine to M11 by TBTU activation provided azido tris linker (M12). Treatment of tri t-butyl ester M12 with TFA gave tri-acid M13. Coupling of M10 to M13 was mediated by HATU, and the crude mixture was globally de-acetylated to afford azido tri-mannose (M15).

Synthesis of Monovalent Mannose Phosphoramidite (M21)

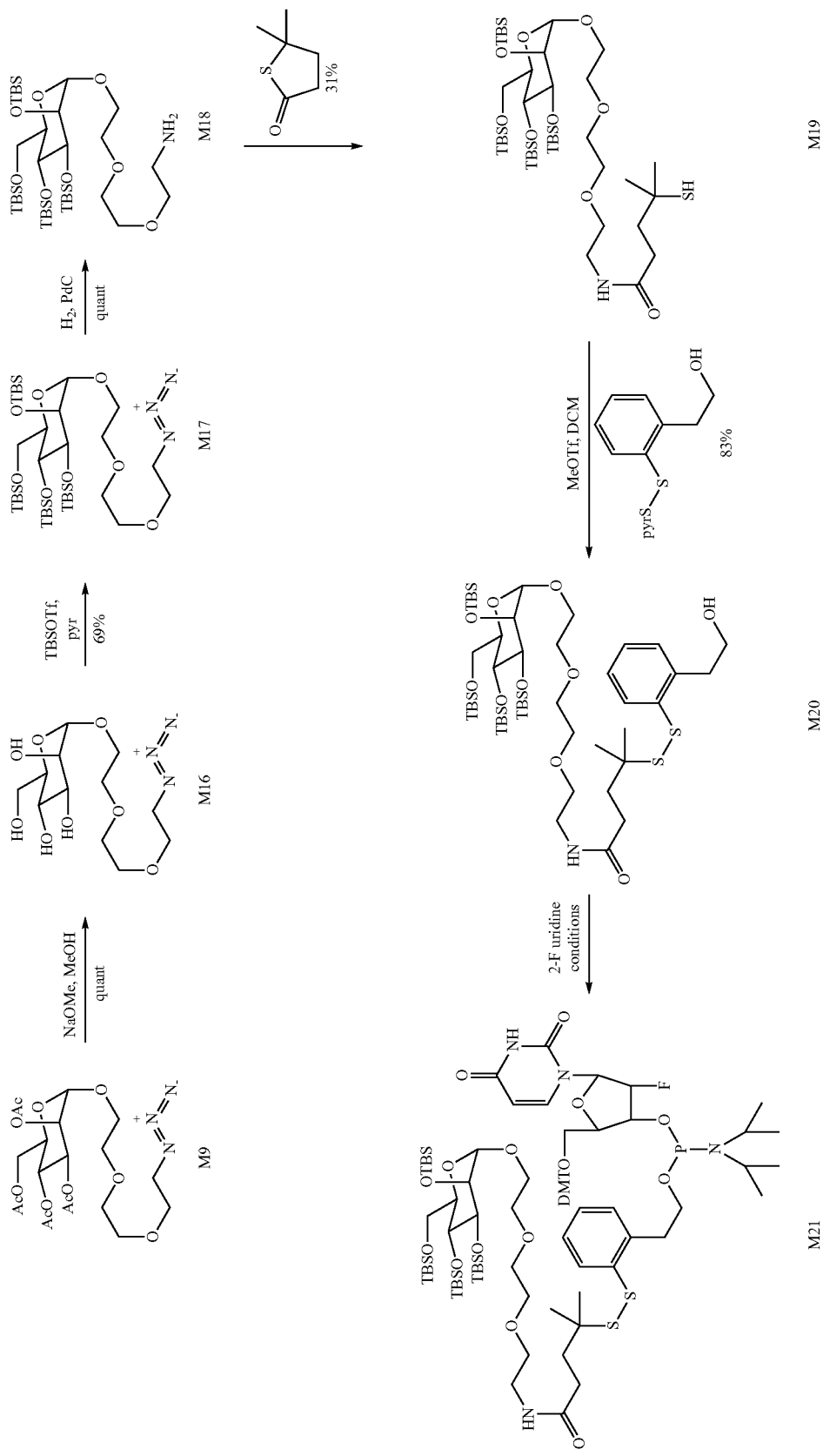

Preparation of mannose disulfide 2-fluoro uridine phosphoramidite (M21): Through standard protection/deprotection chemistry, the acetates of M9 were converted to t-butyl silyl (TBS) M17 through deacetylated intermediate M16. Reduction of azide M17 to amine M18 by hydrogenation facilitated N-acylation with the hindered thiolactone to afford thiol M19. Disulfide M20 was cleanly formed through the addition of aryl mercapto-thiopyridine, which was pre-activated with MeOTf. Phosphoramidite M21 was to be formed in a standard 2-step one-pot manner by the treatment of 2-fluoro uridine with bis(diisopropylamino) chlorophosphine followed by addition of sugar disulfide M20.

Synthesis of Hexavalent Mannose Azide (M30)

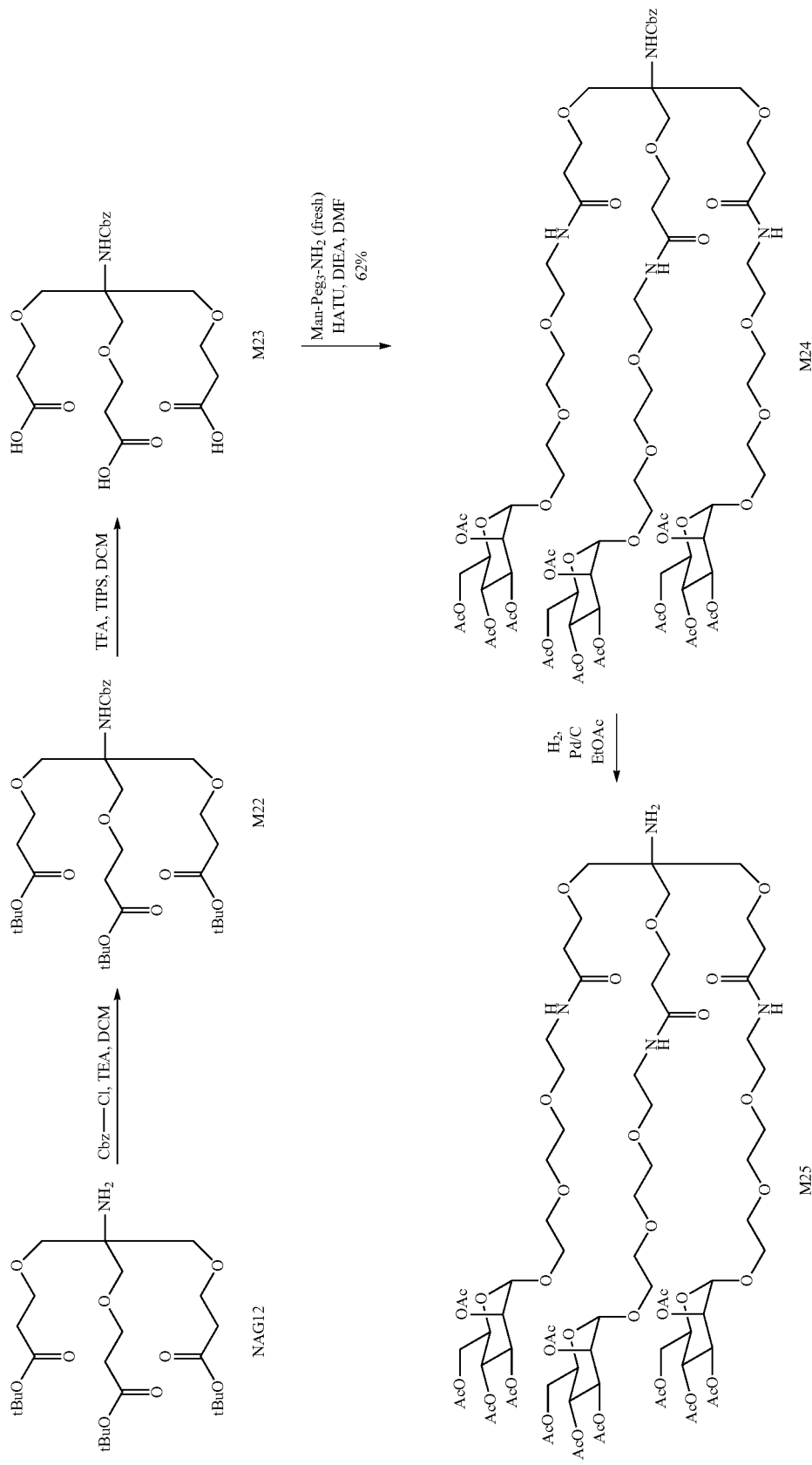

Preparation of N-carbobenzyloxy tris-(t-butoxycarboethoxymethyl)-methylamide (M22): To a solution of NAG12 (3.55 g, 7.02 mmol) in $CH_2Cl_2$ (12 mL) cooled in an ice bath was added Cbz-Cl (35% in PhMe, 7.3 mL) and TEA (3.9 mL). The reaction was warmed to rt and stirred overnight. The mixture was diluted with $CH_2Cl_2$, washed with saturated $NaHCO_3$ (aq), dried over $Na_2SO_4$, and concentrated in vacuo. The crude oil purified by $SiO_2$ chromatography to afford M22 (0.98 g, 22% yield). AP-ESI+ Mass calcd $C_{33}H_{53}NO_{11}$: 639.4, Found: 662.4 [M+Na]$^+$ Preparation of N-carbobenzyloxy tris-((2,3,4,6-tetra-O-acetyl-1-O-α-D-mannopyranosyl)-Peg3-amidoethoxymethyl)-methylamide (M24): Tris-t-butyl ester M22 (0.97 g, 1.51 mmol) and TIPS (0.93 mL, 4.55 mmol) in $CH_2Cl_2$ (5 mL) was treated with TFA (20 mL) for 5 h. The mixture was concentrated in vacuo, the oily residue was washed with hexanes and dried under high vacuum to provide M23. AP-ESI+ Mass calcd $C_{21}H_{29}NO_{11}$: 471.2, Found: 493.9 [M+Na]$^+$ Crude M23 in DMF (5 mL) was cooled on an ice bath and treated with HATU (0.62 g, 1.63) and DIEA (0.65 mL, 3.71 mmol). After stirring for 20 min, a solution of M10 (0.89 g, 1.86 mmol) in DMF (5 mL) was added, and the mixture was warmed to rt and stirred for 3 h. The solvent was removed in vacuo, and the crude was dissolved in EtOAc, washed with saturated $NaHCO_3$ (aq), dried over $Na_2SO_4$, and concentrated in vacuo. Purification by $SiO_2$ chromatography afforded M24 (0.49 g, 62% yield). MALDI-TOF Mass calcd $C_{31}H_{122}N_4O_{44}$: 1854.74, Found: 1850.14

Preparation of tris-((2,3,4,6-tetra-O-acetyl-1-O-α-D-mannopyranosyl)-Peg3-amidoethoxymethyl)-methylamine (M25): A solution of M24 (0.49 g, 0.26 mmol) was dissolved in EtOAc (50 mL) with HOAc (0.2 mL) was degassed by application of vacuum and backfilling with Ar (g). Pd on activated carbon (0.16 g) was added, and the mixture was evacuated and backfilled with $H_2$ (g) thrice. Reaction was stirred for 2 days, catalyst was removed by filtration, and mother liquor concentrated in vacuo to afford M25. AP-ESI+ Mass calcd $C_{73}H_{116}N_4O_{42}$: 1720.7, Found: 1723.42

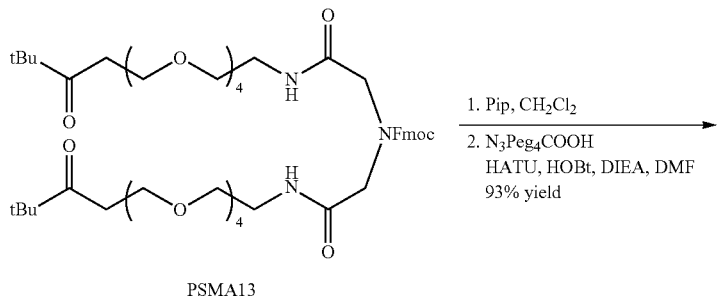

PSMA13

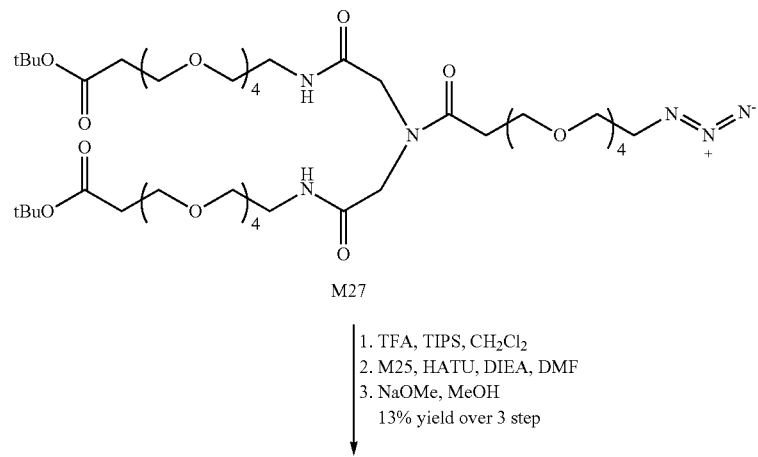

M27

1. TFA, TIPS, $CH_2Cl_2$
2. M25, HATU, DIEA, DMF
3. NaOMe, MeOH

13% yield over 3 step

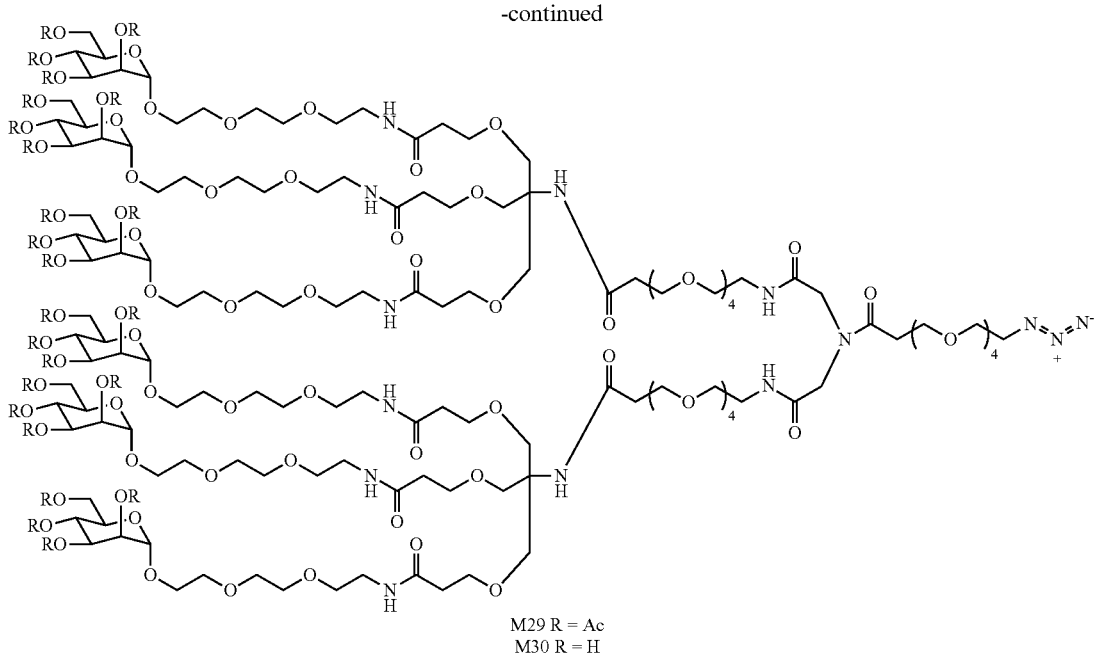

M29 R = Ac
M30 R = H

Preparation of azido-Peg4-imido-bis-(acetamido-Peg4-t-butyl ester) (M27): N-Fmoc PSMA13 (0.72 g, 0.75 mmol) in CH$_2$Cl$_2$ was treated with piperidine (0.75 mL) for 1 h. HPLCMS showed complete conversion to M26, AP-ESI+ Mass calcd C$_{34}$H$_{65}$N$_3$O$_{14}$: 739.4, Found: 740.5 [M+H]$^+$.

The mixture was concentrated in vacuo and azeotroped with PhMe. Crude M26 was reacted with solution of azido Peg4 acid (0.44 g, 1.51 mmol), HATU (0.57 g, 1.51 mmol), and DIEA (0.52 mL) in DMF (5 mL) for 1 h. After solvent removal in vacuo, the crude was dissolved in EtOAc, washed with sat NaHCO$_3$ (aq.), dried over Na$_2$SO$_4$, and concentrated in vacuo. Purification by SiO$_2$ chromatography afforded M27 (0.71 g, 93% yield, 2 steps). AP-ESI+ Mass calcd C$_{45}$H$_{34}$N$_6$O$_{19}$: 1012.6, Found: 1013.6 [M+H]$^+$ Preparation of azido-Peg4-imido-bis-(trimer mannose) (M30): Imido linker M27 (0.69 g, 0.68 mmol) was treated with TIPS (0.28 mL, 1.36 mmol) and TFA (10 mL) to afford tri acid M28; AP-ESI+ Mass calcd C$_{37}$H$_{68}$N$_6$O$_{19}$: 900.5, Found: 900.9 [M+H]$^+$, 922.9 [M+Na]$^+$. Volatiles were removed in vacuo, and M28 dried under high vacuum. Di-acid M28 (82.0 mg, 0.09 mmol) was activated with HATU (75 mg, 0.2 mmol) and DIEA (0.28 mL) in DMF (2 mL) at 0° C. After 30 min, a solution of M25 (0.26 mmol) in DMF (2 ml) was added, and the mixture was warmed toe nd stirred for 2 h. RP-HPLCMS showed complete conversion to M29; Mass calcd C$_{183}$H$_{296}$N$_{14}$O$_{11}$: 4305.84. MALDI-TOF Found: 4303.36 AP-ESI+ Found: 1436.1 [M+3H]$^{3+}$, 1077.3 [M+4H]$^{4+}$. The reaction was diluted with CH$_2$Cl$_2$, washed with sat NaHCO$_3$ (aq.), dried over Na$_2$SO$_4$, and concentrated in vacuo. The crude M29 oil (538 mg) was dissolved in MeOH (20 ml) and was treated with NaOMe (25 wt % in MeOH, 0.5 ml) for 1 h. RP-HPLCMS showed complete conversion to M30. The reaction was quenched by neutralization with Dowex H+ resin. The crude material was purified by HPLC to afford M30 (38.1 mg, 13% yield over 3 steps). Mass calcd C$_{135}$H$_{248}$N$_{14}$O$_{77}$: 297.59, ALDI-TOF Found: 3318.61 [M+Na]$^+$ AP-ESI+ Found: 1100.0 [M+3H]$^{3+}$, 825.3 [M+4H]$^{4+}$.

Example 2. Synthesis of the Polynucleotide Constructs and the Hybridized Polynucleotide Constructs

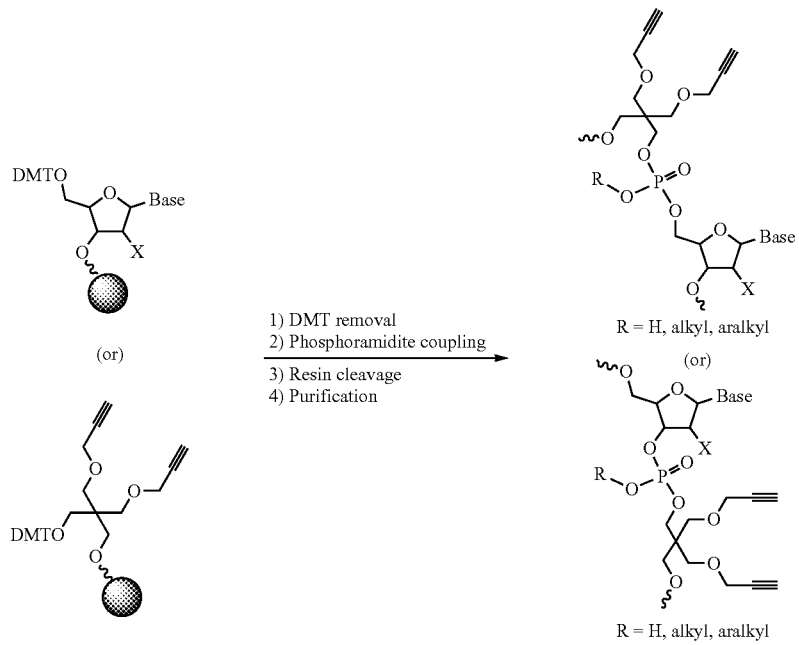

Experimental Details:

All the polynucleotide constructs synthesized were modified at 2'-ribose sugar position with 2'-F and 2'-OMe modifications to improve serum stability and to reduce off-target effects. Automated polynucleotide synthesis (1 µmol scale) was carried out with the following reagents/solvents:

Oxidizer—0.02 M $I_2$ in THF/Pyridine/$H_2O$ (60 s oxidation per cycle)

Deblock—3% Trichloroacetic Acid (2×40 s deblocks per cycle)

Cap Mix A—THF/Pyridine/$Pac_2O$ (60 s capping per cycle)

Cap Mix B—16% Methyl imidazole in THE (60 s capping per cycle)

Sulfurization—0.05 M sulfurizing reagent, 3-((N,N-dimethylaminomethylidene)amino)-3H-1,2,4-dithiazole-5-thione (DDTT), in 60% pyridine/40% acetonitrile (360 s sulfurization per cycle)

Exceptions to standard oligonucleotide synthesis conditions were as follows:

CPG supports with Q-linkers (hydroquinone-O,O'-diacetic acid linker arm) for milder deprotection were used.

All disulfide phosphoramidites were resuspended to a concentration of 100 mM in anhydrous acetonitrile prior to synthesis Phosphoramidite activation was performed with 2.5-fold molar excess of 5-benzylthio-1-H-tetrazole (BTT). Activated phosphoramidites were coupled for 2×3 minute coupling steps per insertion.

Polynucleotide Deprotection and Purification Protocol:

Following automated polynucleotide synthesis, phosphotriester polynucleotides were cleaved and deprotected in 1 mL of 10% diisopropylamine in methanol (10% DIA/MeOH) for 4 h at room temperature. Following the 4 h deprotection, polynucleotide samples were dried by centrifugal evaporation.

When phosphotriester polynucleotides contain standard nucleobase protecting groups (such as A-Bz, C—Ac and G-iBu etc.), following cleavage and deprotection conditions were used: phosphotriester polynucleotides were cleaved and deprotected in 1.0 mL of AMA (1:1 ratio of 36% aq. ammonia and 40% methylamine in methanol) for 2 h at room temperature followed by centrifugal evaporation.

Crude polynucleotide pellets were resuspended in 100 µL of 50% acetonitrile, briefly heated to 65° C., and vortexed thoroughly. Total 100 µL crude polynucleotide samples were injected onto reverse phase HPLC with the following buffers/gradient:

Buffer A=50 mM aqueous triethylammonium acetate (TEAA)

Buffer B=90% acetonitrile

Flow Rate=1 mL/min

Gradient:
0-2 min (100% Buffer A/0% Buffer B)
2-42 min (0% to 60% Buffer B)
42-55 min (60% to 100% Buffer B)

Across the dominant reverse phase HPLC peaks, 0.5 mL fractions were collected and analyzed by MALDI-TOF mass spectrometry to confirm the presence of compounds with the desired mass peaks. Purified fractions containing compounds with the correct mass peaks were frozen and lyophilized. Once dry, fractions were resuspended, combined with corresponding fractions, frozen, and lyophilized to give the final product.

Triester insertions requiring additional deprotection were initially isolated as described above followed by the necessary secondary deprotection steps (see below):

Secondary Deprotection of Phosphotriester Polynucleotide Having Acetal Group

Reverse phase HPLC-purified polynucleotide products were resuspended in 100 μL of 80% formic acid. Reaction was allowed to proceed at room temperature for ~1 h per aldehyde modification. Reaction was monitored by MALDI-TOF mass spectrometry to confirm complete deprotection. Once deprotection was complete, samples were frozen and lyophilized until dry. Lyophilized samples were then resuspended in 1 mL of 20% aqueous acetonitrile and gel-filtered for isolation of the final polynucleotide construct.

Secondary Deprotection of Phosphotriester Polynucleotides Having TBDMS Protection Reverse phase HPLC-purified polynucleotide products were resuspended in 219 μL of anhydrous DMSO, heated briefly to 65° C., and vortexed thoroughly. To the DMSO solution, 31 μL of 6.1 M triethylamine trihydrofluoride (TEA·3HF) was added to give a final concentration of 0.75 M. The reaction was allowed to proceed at room temperature for ~1 h per TBDMS-protected hydroxyl modification. Reaction was monitored by MALDI-TOF mass spectrometry to confirm complete deprotection. Once deprotection was complete, 35 μL of 3 M sodium acetate and 1 mL of butanol were sequentially added. Samples were vortexed thoroughly and placed at −80° C. for 2 h. After 2 h, samples were centrifuged to pellet the polynucleotides. Butanol layer was removed, and the polynucleotide pellet was resuspended in 1 mL of aqueous 20% acetonitrile. Samples were gel-filtered for isolation of the final polynucleotide construct.

Preparation of Hybridized Polynucleotide Constructs

Equal ratio of passenger and guide strands were annealed using standard conditions to provide hybridized polynucleotide constructs in good purity of about 90%, as confirmed by gel electrophoresis.

Stereochemically Enriched Internucleoside Phosphorothioates

Polynucleotide constructs including stereochemically enriched internucleoside phosphorothioates may be prepared as described herein and utilizing methods known in the art for the preparation of stereochemically enriched internucleoside phosphorothioates, e.g., in accordance with the principles described in Oka et al., *Chem. Soc. Rev.*, 40:5829-5843, 2011; Oka et al., *Org. Lett.*, 11:967-970, 2009; and U.S. pre-grant publication Nos. 2013/0184450 and 2015/0197540. Non-limiting examples of the hybridized polynucleotide constructs having one or more stereochemical enriched, internucleoside phosphorothioates are provided in Table 3.

TABLE 3

5'-ggUUAACACCAUUUACUUCAA-3' (SEQ ID NO: 26)(Passenger)
3'-GacCAAUUGUGGUAAAUGAAGuu-5' (SEQ ID NO: 53)(Guide)
OR
5'-ggUUAACACCAUUUACUUCAAX3X3-3' (SEQ ID NO: 26)(Passenger)
3'-GacCAAUUGUGGUAAAUGAAGuu-5' (SEQ ID NO: 53)(Guide)
In these sequence, bold indicates a 2'-fluoro modification, while the rest of the nucleosides are modified to include a 2'-OMe, underlining indicates the point of the attachment of a group carrying one or more auxiliary moieties, UPPER CASE indicates a nucleoside phosphate, lower case indicates a nucleoside phosphorothioate.

| Phosphorothioate(PS) location & Stereochemistry | | | | | | | |
|---|---|---|---|---|---|---|---|
| Passenger strand | | Guide strand | | | | | |
| P1-P2 | P2-P3 | G1-G2 | G2-G3 | G18-G19 | G20-G21 | G21-G22 | G22-G23 |
| R | − | − | − | − | − | − | − |
| S | − | − | − | − | − | − | − |
| − | R | − | − | − | − | − | − |
| − | S | − | − | − | − | − | − |
| R | R | − | − | − | − | − | − |
| S | R | − | − | − | − | − | − |
| R | S | − | − | − | − | − | − |
| S | S | − | − | − | − | − | − |
| − | − | R | − | − | − | − | − |
| − | − | S | − | − | − | − | − |
| − | − | − | R | − | − | − | − |
| − | − | − | S | − | − | − | − |
| − | − | R | R | − | − | − | − |
| − | − | R | S | − | − | − | − |
| − | − | S | R | − | − | − | − |
| − | − | S | S | − | − | − | − |

TABLE 3-continued

5'-ggUUAACACCAUUUACUUCAA-3' (SEQ ID NO: 26)(Passenger)
3'-GacCAAUUGUGGUAAAUGAAGuu-5' (SEQ ID NO: 53)(Guide)
OR
5'-ggUUAACACCAUUUACUUCAAX3X3-3' (SEQ ID NO: 26)(Passenger)
3'-GacCAAUUGUGGUAAAUGAAGuu-5' (SEQ ID NO: 53)(Guide)

In these sequence, bold indicates a 2'-fluoro modification, while the rest of the nucleosides are modified to include a 2'-OMe, underlining indicates the point of the attachment of a group carrying one or more auxiliary moieties, UPPER CASE indicates a nucleoside phosphate, lower case indicates a nucleoside phosphorothioate.

Phosphorothioate(PS) location & Stereochemistry

| Passenger strand | | Guide strand | | | | | |
|---|---|---|---|---|---|---|---|
| P1-P2 | P2-P3 | G1-G2 | G2-G3 | G18-G19 | G20-G21 | G21-G22 | G22-G23 |
| − | − | − | − | R | − | − | − |
| − | − | − | − | S | − | − | − |
| − | − | − | − | − | R | − | − |
| − | − | − | − | − | S | − | − |
| − | − | − | − | R | R | − | − |
| − | − | − | − | R | S | − | − |
| − | − | − | − | S | R | − | − |
| − | − | − | − | S | S | − | − |
| − | − | − | − | − | − | R | − |
| − | − | − | − | − | − | S | − |
| − | − | − | − | − | − | − | R |
| − | − | − | − | − | − | − | S |
| − | − | − | − | − | − | R | R |
| − | − | − | − | − | − | R | S |
| − | − | − | − | − | − | S | R |
| − | − | − | − | − | − | S | S |
| − | − | R | R | − | − | R | R |
| − | − | R | R | − | − | R | S |
| − | − | R | R | − | − | S | R |
| − | − | R | R | − | − | S | S |
| − | − | S | S | − | − | R | R |
| − | − | S | S | − | − | R | S |
| − | − | S | S | − | − | S | R |
| − | − | S | S | − | − | S | S |
| − | − | R | S | − | − | S | S |
| − | − | S | R | − | − | S | S |
| − | − | R | S | − | − | R | R |

In table 3, the numbering of the passenger strand and the number of the guide strand start at the 5'-end; P(n)-P(n+1) indicates the location of the identified stereochemically enriched, phosphorothioate between the nucleoside number (n) and the nucleoside number (n+1) in the passenger strand; G(n)-G(n+1) indicates the location of the identified stereochemically enriched, phosphorothioate between the nucleoside number (n) and the nucleoside number (n+1) in the guide strand; R and S identify the dominant stereochemistry of the identified phosphorus stereogenic center.

Phosphorodithioates

Phosphorodithioate containing polynucleotides can be synthesized using standard polynucleotide synthesis protocols known in the art and disclosed herein (see, e.g., Yang et al., *ACS Chem. Biol.,* 7:1214-1220, 2012; Wu et al., *Nat. Commun.,* 5:3459, 2013). The synthesis may be performed with, e.g., commercially available thiophosphoramidites (e.g., available from Glen Research). Non-limiting examples of thiophosphoraimidites include:

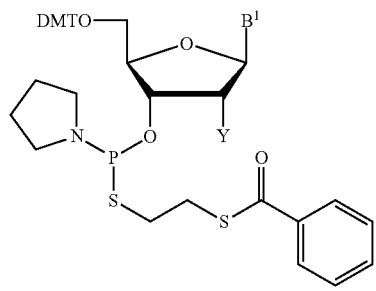

$B^1$=nucleobase;

Y=halogen (e.g., F), optionally substituted $C_{1-6}$ alkoxy (e.g., methoxy or methoxyethoxy), or a protected hydroxyl group.

Representative Examples of Polynucleotide Constructs of the Invention:

In the schemes below, specific nucleoside phosphoramidites used in the syntheses are omitted for clarity.

Linkers X1 and X2

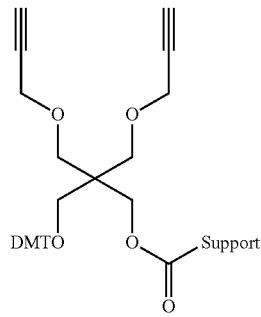

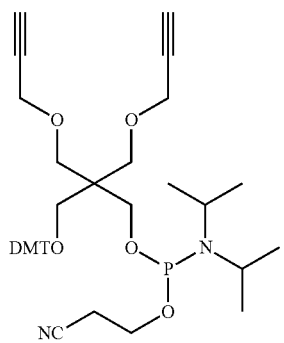
X1

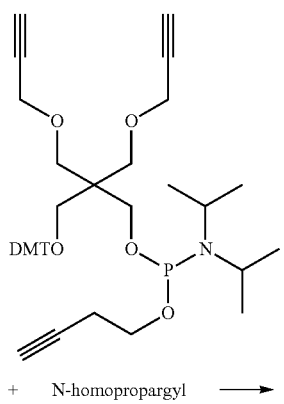
X2

X + N-homopropargyl ⟶

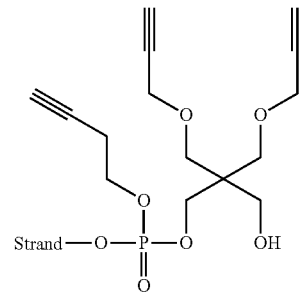

X2 + C3-Cap ⟶

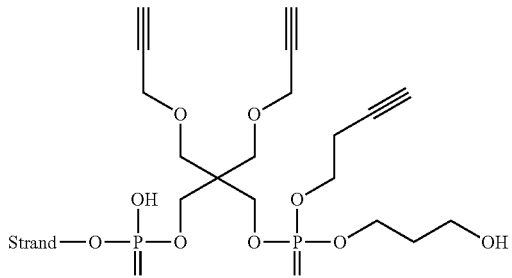

X + X1 ⟶

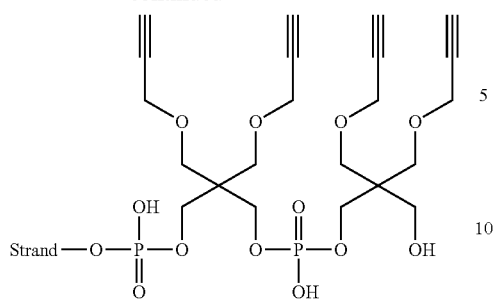
N-homopropargyl = nucleoside (e.g., A, U, C, or G) posphoramidite, where the phosphoramidite phosphorus atom is substituted with homopropargyloxy.
Additional Examples
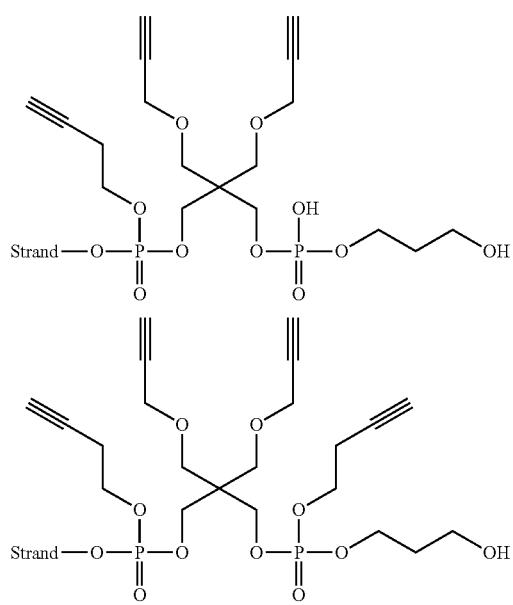
Linkers X3 and X4
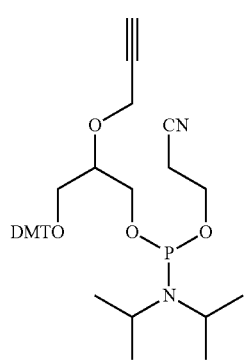
X3
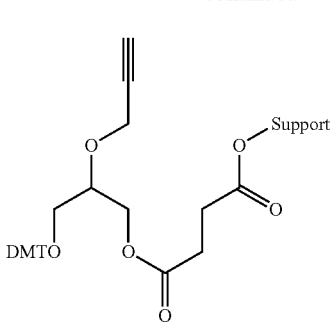
X3a
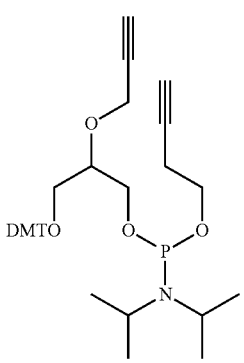
X4
X3a
+
N-homopropargyl
+
N-homopropargyl
→
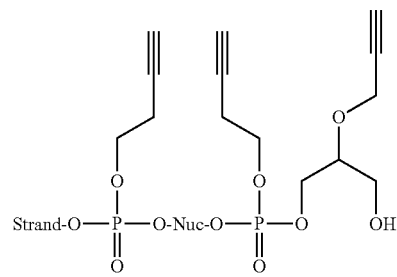
X3
+
X3
+
X3
+
C3-cap
→
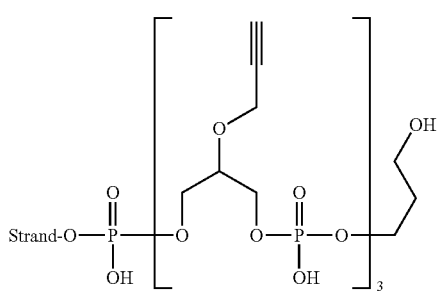
X4
+
N-homopropargyl
+
C3-cap
→

-continued
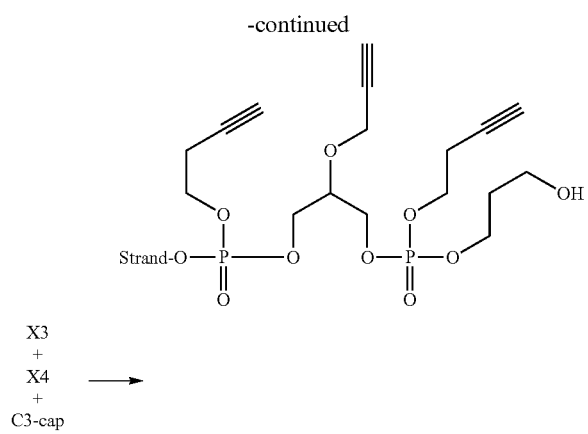
X3
+
X4
+
C3-cap →
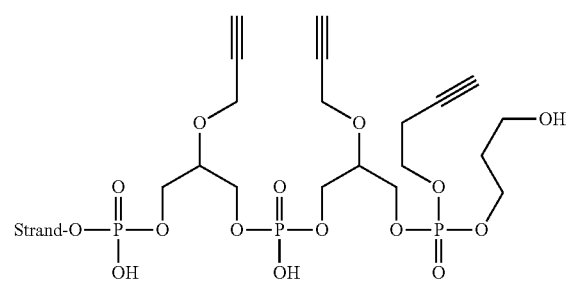
N-homopropargyl = nucleoside (e.g., A, U, C, or G) phosphoramidite, where the phosphoramidite phosphorus atom is substituted with homopropargyloxy.
Nuc = nucleoside.
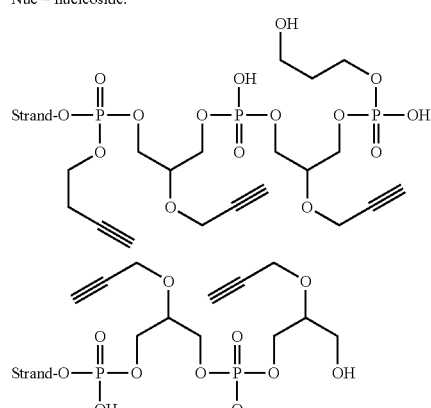
Additional Examples
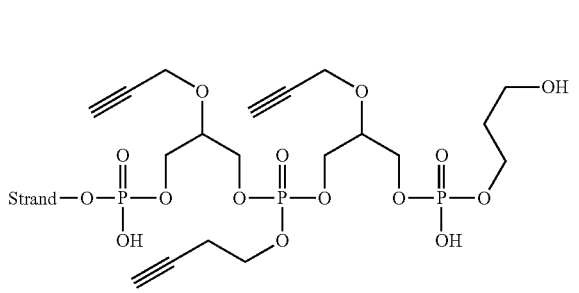
Linkers X5 and X6
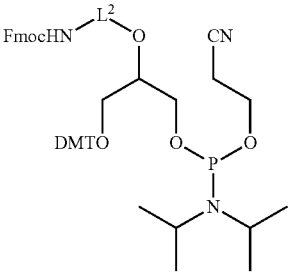
X5
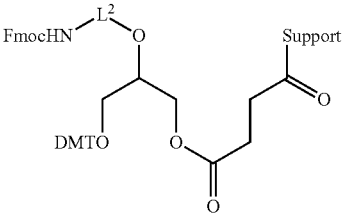
X5a
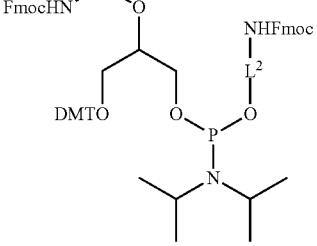
X6
X5a
+
R—L²—NHFmoc →
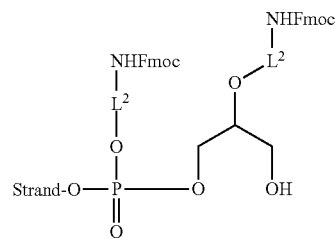
n(X5)
+
C3-cap →
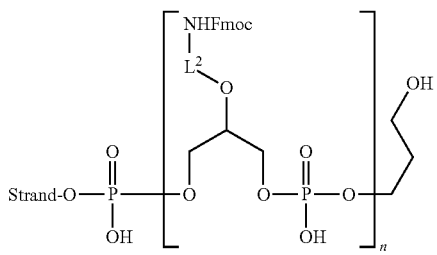
X6
+
R—L²—NHFmoc
+
C3-cap →

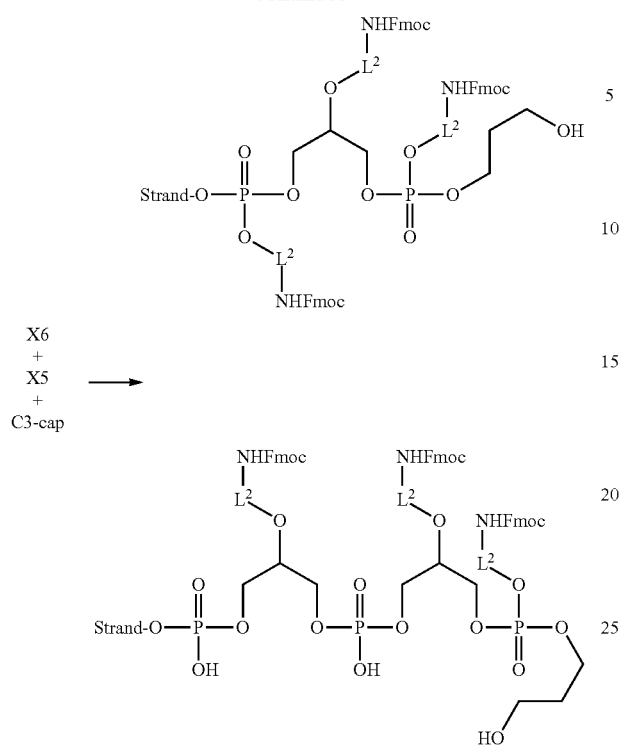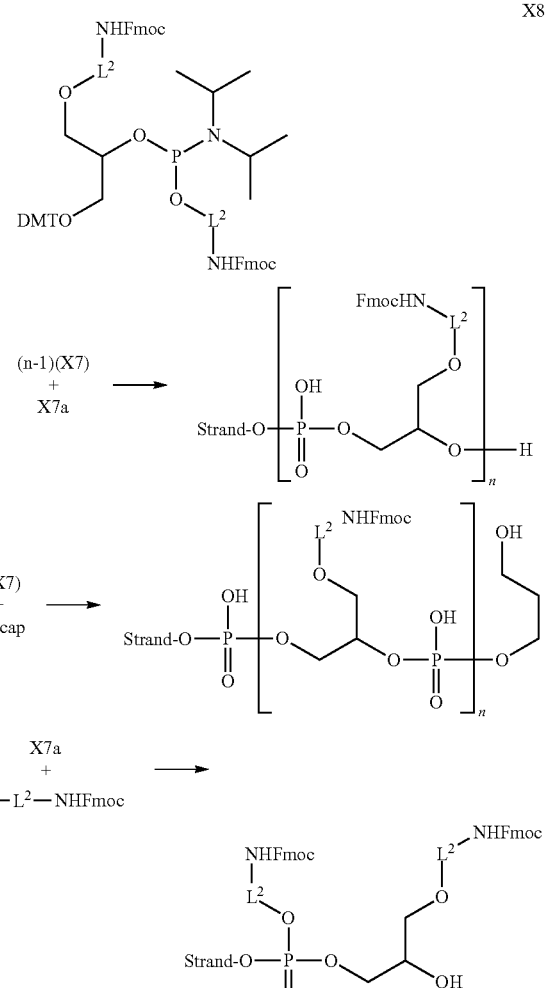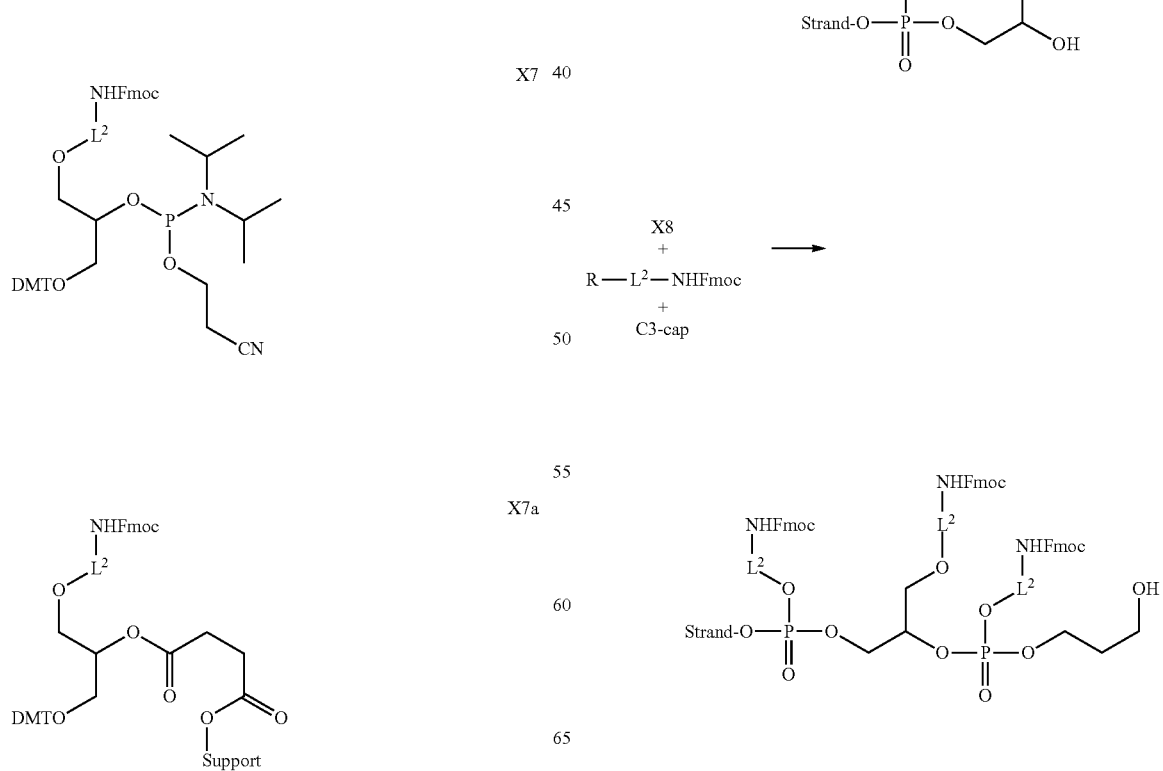

187
-continued

X7 + X8 ⟶

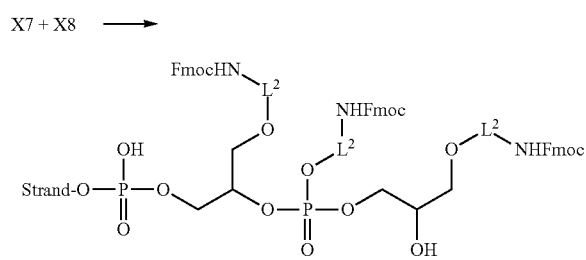

R—L²—NHFmoc = nucleoside (e.g., A, U, C, or G) phosphoramidite, where the phosphorus atom is substituted with —O—L²—NHFmoc, where L² =
—(CH₂)ₘ— or —(CH₂CH₂O)ₘ₁—CH₂CH₂—
n is an integer from 1 to 6
each m is independently an integer from 1 to 20
each m1 is independently an integer from 1 to 10

Linkers X9 and X10

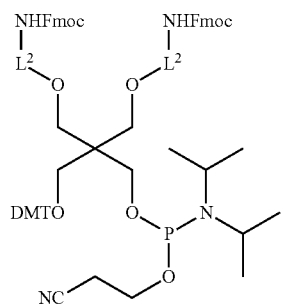

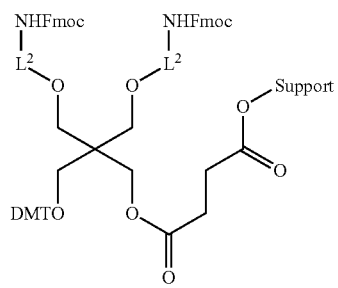

188
-continued

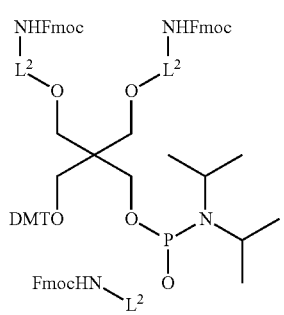

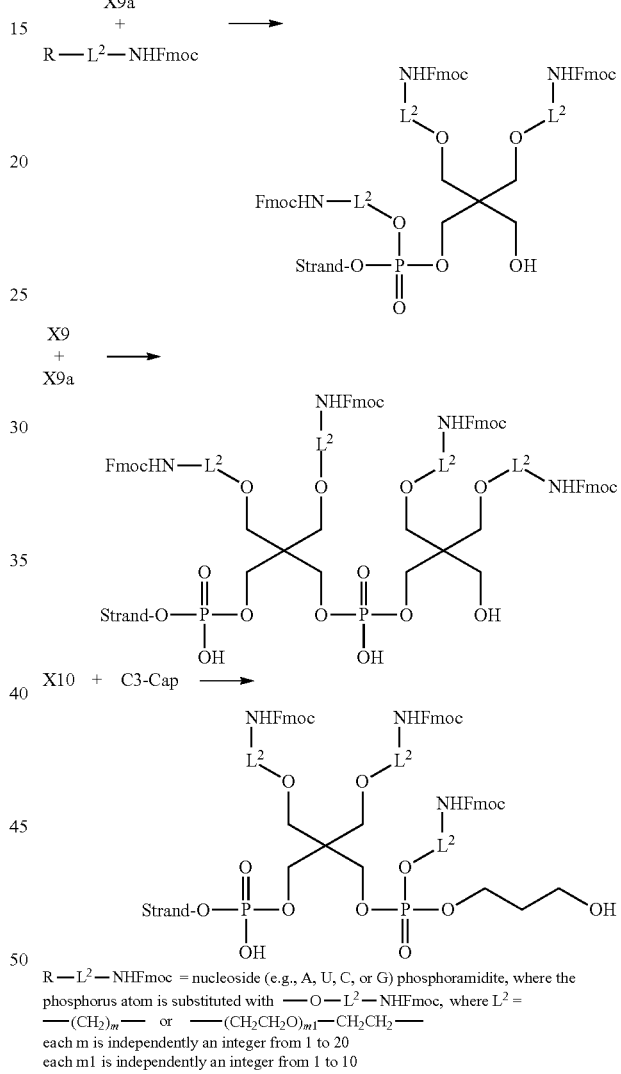

R—L²—NHFmoc = nucleoside (e.g., A, U, C, or G) phosphoramidite, where the phosphorus atom is substituted with —O—L²—NHFmoc, where L² =
—(CH₂)ₘ— or —(CH₂CH₂O)ₘ₁—CH₂CH₂—
each m is independently an integer from 1 to 20
each m1 is independently an integer from 1 to 10

Linkers X11 and X12

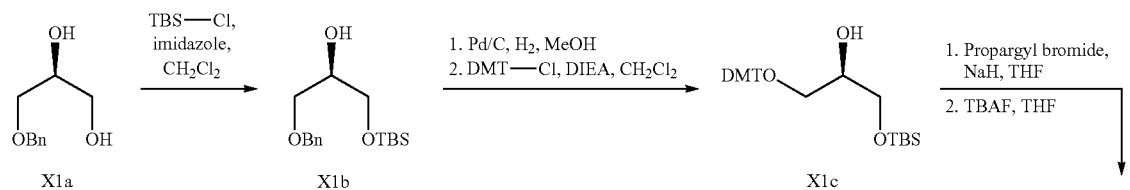

-continued
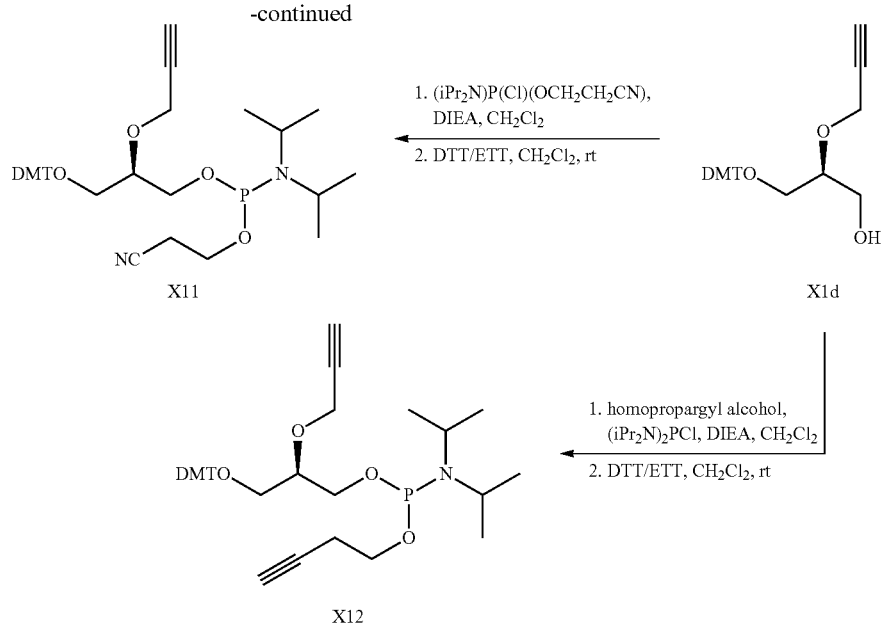
Linkers X13 and X14
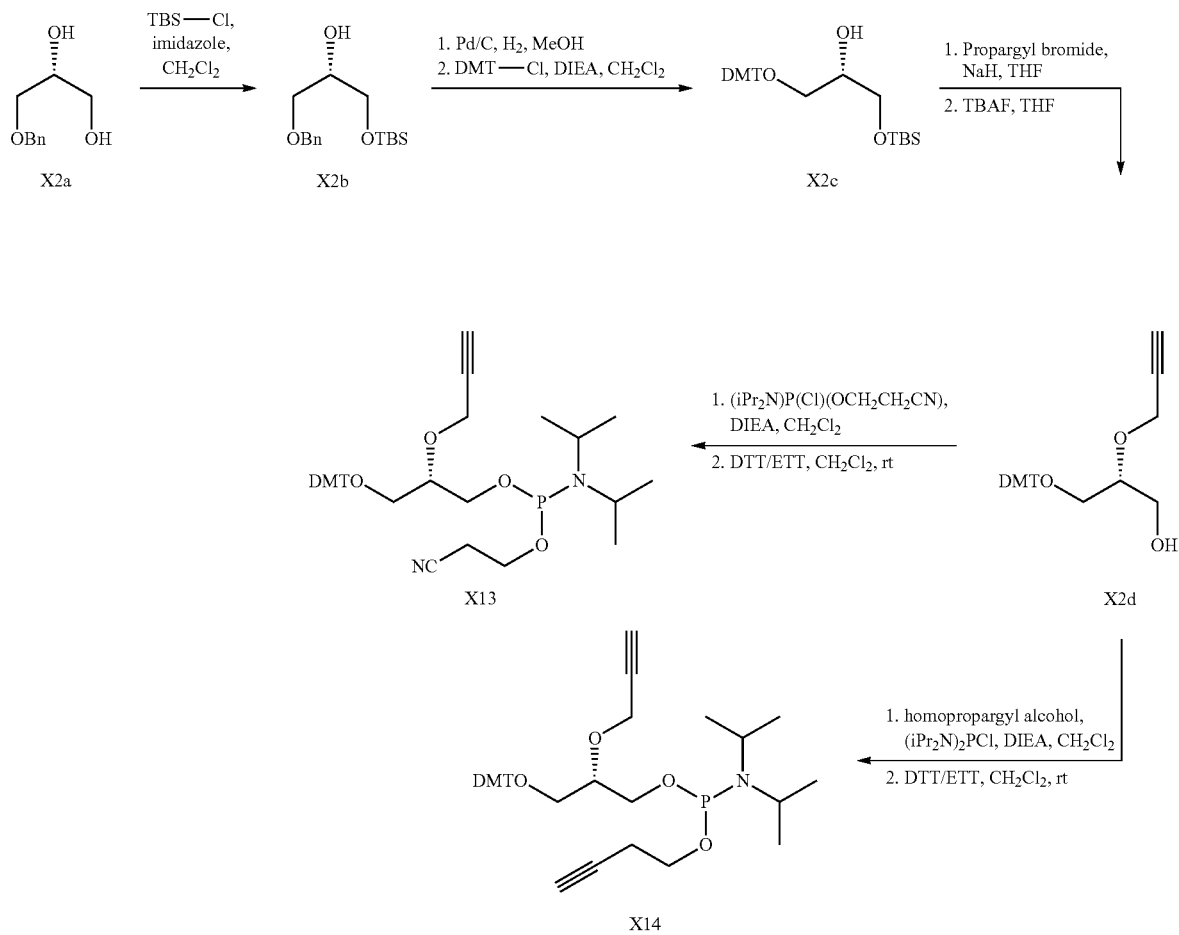

Linkers X15 and X16
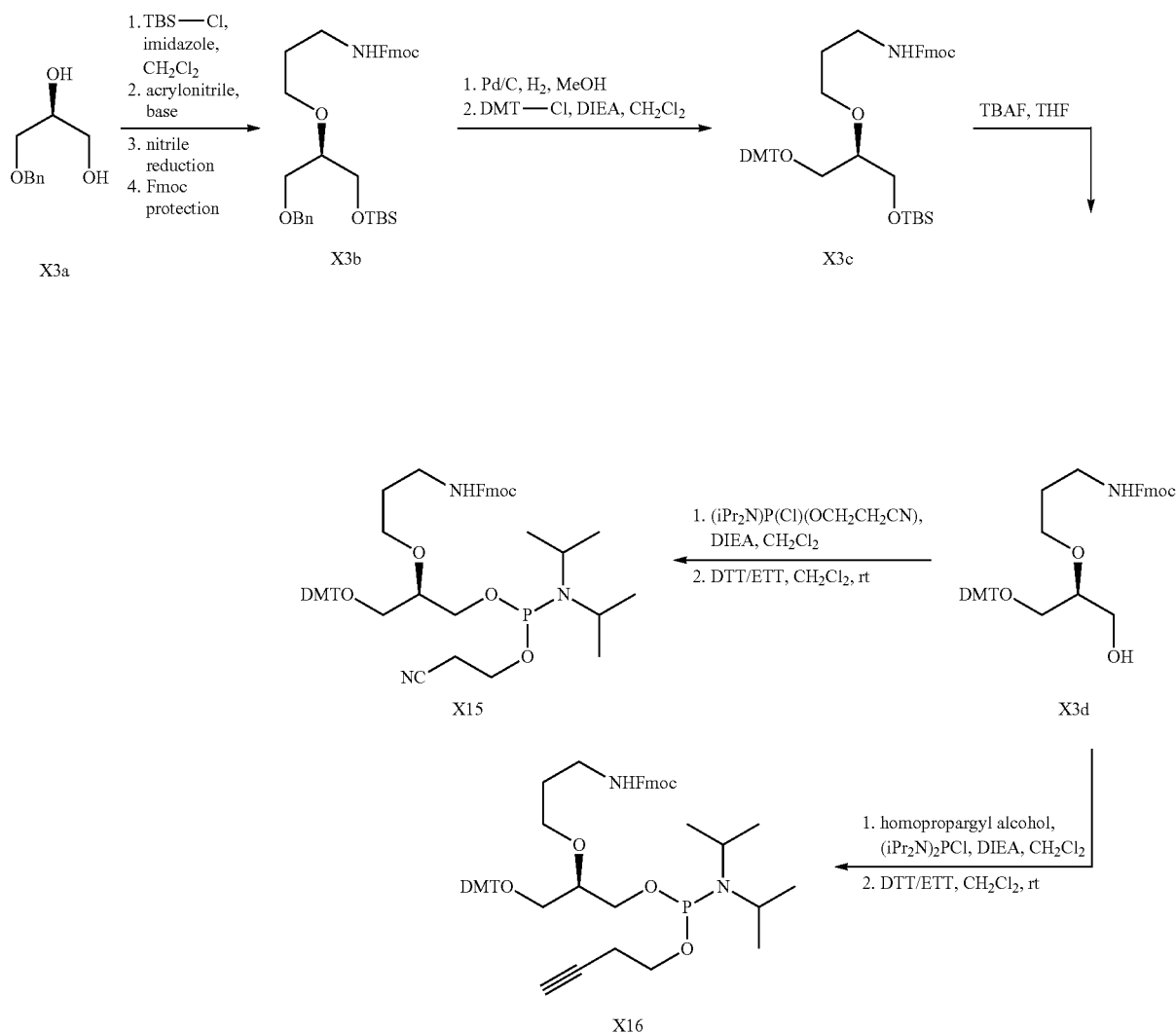
Linkers X17 and X18
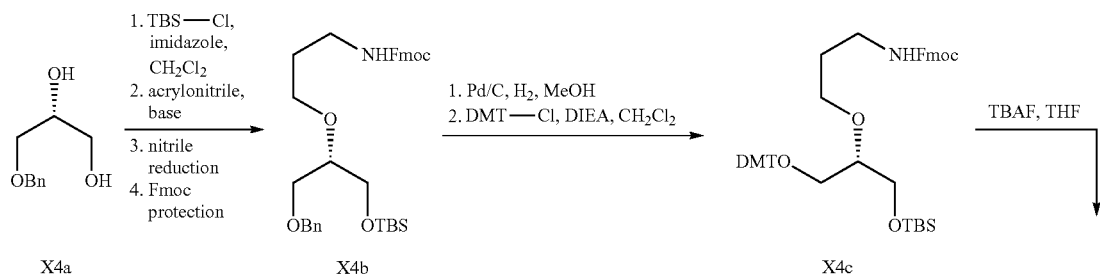

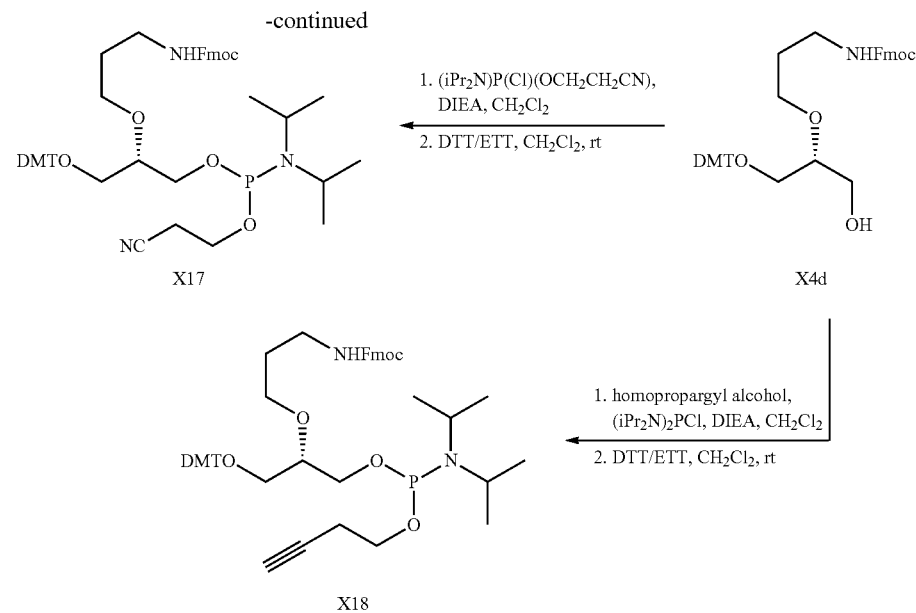

Linkers X11, X12, X13, and X14 can be prepared using reaction conditions known in the art. For example, compound X1a can be subjected to a selective TBS protection, benzyl group removal, followed by alkylation and the TBS group removal to give alcohol X1d, which can then be converted to compounds X11 and X12 under the reaction conditions known in the art for preparation of phosphoramidites. Same experimental conditions can be used to convert compound X2a to compounds X13 and X14. A slightly modified method using X3a and X4a can give compounds X15, X16, X17, and X18.

Other linkers and polynucleotide constructs containing them can be prepared using methods and techniques known in the art. For example, the following structure can be prepared:

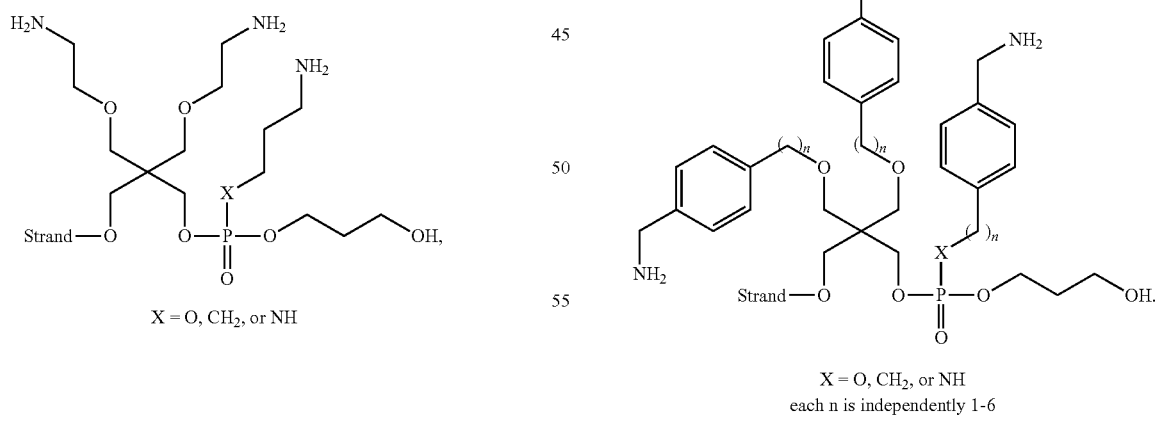

Hybridized Polynucleotide Constructs

The list of prepared hybridized polynucleotide constructs is provided in Table 4.

TABLE 4

| Compound # | Ligand | Target | Strand | Sequences (5'-3') | SEQ ID NO: | Conjugation Linker |
|---|---|---|---|---|---|---|
| Z1 | NAG21 | AT3 | P<br>G | gsgsUuAaCaCCAuUuAcUuCapa<br>usUsgAaGuAaAuggUgUuAaCcsasg | 26<br>53 | Alkynyl |
| Z2 | NAG26 | AT3 | P<br>G | gsgsUuAaCaCCAuUuACpUUpCapa<br>usUsgAaGuAaAuggUgUuAaCcsasg | 26<br>53 | Alkynyl |
| Z3 | NAG21 | AT3 | P<br>G | gsgsUuAaCaCCAuUuACpUUpCapa<br>usUsgAaGuAaAuggUgUuAaCpcsasg | 26<br>53 | Alkynyl |
| Z4 | NAG26 | AT3 | P<br>G | gsgsUuAaCaCCAuUuAcUuCapa<br>usUsgAaGuAaAuggUgUuAaCpcsasg | 26<br>53 | Alkynyl |
| Z5 | NAG21 | TTR | P<br>G | AsasCaGuGuUCUuGcUcUaUapA<br>usUsaUaGaGcAagaAcAcUgUususu | 3<br>50 | Alkynyl |
| Z6 | NAG26 | TTR | P<br>G | AsasCaGuGuUCUuGcUcUaUagA<br>usUsaUaGaGcAagaAcAcUgUpususu | 3<br>50 | Alkynyl |
| Z7 | NAG21 | TTR | P<br>G | AsasCaGuGuUCUuGcUCUanUagA<br>usUsaUaGaGcAagaAcAcUgUususu | 3<br>50 | Alkynyl |
| Z9 | NAG26 | TTR | P<br>G | AsasCaGuGuUCUuGcUCpUapUapA<br>usUsaUaGaGcAagaAcAcUgUpususu | 3<br>50 | Alkynyl |
| Z10 | NAG26 | TTR | P<br>G | AsasCaGuGuUCUuGcUcUaUapAX1<br>usUsaUaGaGcAagaAcAcUgUususu | 3<br>50 | Alkynyl, X1-Linker |
| Z11 | NAG26 | TTR | P<br>G | AsasCaGuGuUCUuGcUcUaUabAX1X1<br>usUsaUaGaGcAagaAcAcUgUususu | 3<br>50 | X1-Linker |
| Z12 | NAG26 | TTR | P<br>G | AsasCaGuGuUCUuGcUcUaUaAX1X1<br>usUsaUaGaGcAagaAcAcUgUususu | 3<br>50 | X1-Linker |
| Z13 | NAG26 | TTR | P<br>G | AsasCaGuGuUCUuGcUcUaUapX1<br>usUsaUaGaGcAagaAcAcUgUususu | 3<br>50 | Alkynyl, X1-Linker |
| Z14 | NAG26 | TTR | P<br>G | AsasCaGuGuUCUuGcUcUaUaaX2n<br>usUsaUaGaGcAagaAcAcUgUususu | 3<br>50 | X2-Linker |
| Z15 | NAG26 | TTR | P<br>G | AsasCaGuGuUCUuGcUcUaUapAX1<br>usUsaUaGaGcAagaAcAcUgUpususu | 3<br>50 | Alkynyl, X1-Linker |
| Z16 | NAG26 | TTR | P<br>G | AsasCaGuGuUCUuGcUcUaUabAX1X1<br>usUsaUaGaGcAagaAcAcUgUpususu | 3<br>50 | X1-Linker |
| Z17 | NAG26 | TTR | P<br>G | AsasCaGuGuUCUuGcUcUaUaAX1X1<br>usUsaUaGaGcAagaAcAcUgUpususu | 3<br>50 | X1-Linker |

TABLE 4-continued

| Compound # | Ligand | Target | Strand | Sequences (5'-3') | SEQ ID NO: | Conjugation Linker |
|---|---|---|---|---|---|---|
| Z18 | NAG26 | TTR | P<br>G | AsasCaGuGuUCUuGcUCuaUaapX1<br>usUsaUaGaGcAagaAcAcUgUpususu | 3<br>50 | Alkynyl, X1-Linker |
| Z19 | NAG26 | TTR | P<br>G | AsasCaGuGuUCUuGcUCuaUaaX2n<br>usUsaUaGaGcAagaAcAcUgUpususu | 3<br>50 | X2-Linker |
| Z20 | NAG26 | AT3 | P<br>G | gsgsUuAaCaCCAuUuAcUuCapaX1<br>usUsgAaGuAaAuggUgUuAaCcsasg | 26<br>53 | Alkynyl, X1-Linker |
| Z21 | NAG26 | AT3 | P<br>G | gsgsUuAaCaCCAuUuAcUuCabaX1X1<br>usUsgAaGuAaAuggUgUuAaCcsasg | 26<br>53 | X1-Linker |
| Z22 | NAG26 | AT3 | P<br>G | gsgsUuAaCaCCAuUuAcUuCaaX1X1<br>usUsgAaGuAaAuggUgUuAaCcsasg | 26<br>53 | X1-Linker |
| Z23 | NAG26 | AT3 | P<br>G | gsgsUuAaCaCCAuUuAcUuCaapX1<br>usUsgAaGuAaAuggUgUuAaCcsasg | 26<br>53 | Alkynyl, X1-Linker |
| Z24 | NAG26 | AT3 | P<br>G | gsgsUuAaCaCCAuUuAcUuCaaX2n<br>usUsgAaGuAaAuggUgUuAaCcsasg | 26<br>53 | X2-Linker |
| Z25 | NAG26 | AT3 | P<br>G | gsgsUuAaCaCCAuUuAcUuCapaX1<br>usUsgAaGuAaAuggUgUuAaCpcsasg | 26<br>53 | Alkynyl, X1-Linker |
| Z26 | NAG26 | AT3 | P<br>G | gsgsUuAaCaCCAuUuAcUuCabaX1X1<br>usUsgAaGuAaAuggUgUuAaCpcsasg | 26<br>53 | X1-Linker |
| Z27 | NAG26 | AT3 | P<br>G | gsgsUuAaCaCCAuUuAcUuCaaX1X1<br>usUsgAaGuAaAuggUgUuAaCpcsasg | 26<br>53 | X1-Linker |
| Z28 | NAG26 | AT3 | P<br>G | gsgsUuAaCaCCAuUuAcUuCaapX1<br>usUsgAaGuAaAuggUgUuAaCpcsasg | 26<br>53 | Alkynyl, X1-Linker |
| Z29 | NAG26 | AT3 | P<br>G | gsgsUuAaCaCCAuUuAcUuCaaX2n<br>usUsgAaGuAaAuggUgUuAaCpcsasg | 26<br>53 | X2-Linker |
| Z30 | NAG37 | TTR | P<br>G | AsasCaGuGuUCUuGcUCuaUaaX2n<br>usUsaUaGaGcAagaAcAcUgUpususu | 3<br>50 | X2-Linker |
| Z31 | NAG38 | TTR | P<br>G | AsasCaGuGuUCUuGcUCuaUaaX2n<br>usUsaUaGaGcAagaAcAcUgUpususu | 3<br>50 | X2-Linker |
| Z32 | NAG39 | TTR | P<br>G | AsasCaGuGuUCUuGcUCuaUaaX2n<br>usUsaUaGaGcAagaAcAcUgUpususu | 3<br>50 | X2-Linker |
| Z33 | NAG26 | TTR | P<br>G | AsasCaGuGuUCUuGcUCuaUaATpTp<br>usUsaUaGaGcAagaAcAcUgUpususu | 4<br>50 | Alkynyl |
| Z34 | NAG26 | PCSK9 | P<br>G | UsusUuCuAgAcCuGuUuUgCuUX2n<br>asAsgCaAaAcAgGuCuAgAaapasGsu | 61<br>5 | X2-Linker |

TABLE 4-continued

| Compound # | Ligand | Target | Strand | Sequences (5'-3') | SEQ ID NO: | Conjugation Linker |
|---|---|---|---|---|---|---|
| Z35 | NAG26 | PCSK9 | P<br>G | CsasAgCaGaCAUuUaUCUuUuUX2n<br>asAsaAaGaUaAaugUgCuUpgsCsu | 15<br>2 | X2-Linker |
| Z36 | NAG26 | PCSK9 | P<br>G | CsusAgAcCuGUUuUgCuUuUgUX2n<br>asCsaAaGcCaAaacAgCuapgsAsa | 22<br>10 | X2-Linker |
| Z37 | NAG26 | PCSK9 | P<br>G | CsusAgAcCuGUUuUgcuuuuguX2n<br>asCsaAaagCaAaacAgGucuapgsasa | 22<br>10 | X2-Linker |
| Z38 | NAG26 | AT3 | P<br>G | gsgsUuAaCaCCAuUuAcUuCaaTpTpTp<br>usUsgAaGuAaAuggUgUuAaCpcsasg | 27<br>53 | Alkynyl |
| Z39 | NAG26 | AT3 | P<br>G | gsgsUuAaCaCCAuUuAcUuCaaX3X3X3<br>usUsgAaGuAaAuggUgUuAaCpcsasg | 26<br>53 | X3-Linker |
| Z40 | NAG26 | AT3 | P<br>G | gsgsUuAaCaCCAuUuAcUuCaapX3X3<br>usUsgAaGuAaAuggUgUuAaCpcsasg | 26<br>53 | Alkynyl, X3-Linker |
| Z41 | NAG26 | AT3 | P<br>G | gsgsUuAaCaCCAuUuAcUuCaapX3<br>usUsgAaGuAaAuggUgUuAaCpcsasg | 26<br>53 | Alkynyl, X3-Linker |
| Z42 | NAG26 | AT3 | P<br>G | gsgsUuAaCaCCAuUuAcUuCaaX4X4n<br>usUsgAaGuAaAuggUgUuAaCpcsasg | 26<br>53 | X4-Linker |
| Z43 | NAG26 | AT3 | P<br>G | gsgsUuAaCaCCAuUuAcUuCaaX3X4n<br>usUsgAaGuAaAuggUgUuAaCpcsasg | 26<br>53 | X3-Linker, X4-Linker |
| Z44 | NAG26 | AT3 | P<br>G | gsgsUuAaCaCCAuUuAcUuCaapX4n<br>usUsgAaGuAaAuggUgUuAaCpcsasg | 26<br>53 | Alkynyl, X4-Linker |
| Z45 | NAG26 | AT3 | P<br>G | gsgsUuAaCaCCAuUuAcUuCaaX2n<br>usUsgAaGuAaAuggUgUuAaCpcsasg | 26<br>53 | X2-Linker |
| Z46 | NAG26 | AT3 | P<br>G | gsgsUuAaCaCCAuUuAcUuCaaX2n<br>usUsgAaGuAaAuggUgUuAaCbcsasg | 26<br>53 | X2-Linker |
| Z47 | NAG26 | TTR | P<br>G | AsasCaGuGuUCUuGcUcUaUaaX2n<br>usUsaUaGaGcAagaAcAcUguususu | 3<br>50 | X2-Linker |
| Z48 | NAG26 | TTR | P<br>G | AsasCaGuGuUCUuGcUcUaUaaX2n<br>usUsaUaGaGcAagaAcAcUgUPususu | 3<br>50 | X2-Linker |
| Z49 | NAG26 | TTR | P<br>G | AsasCaGuGuUCUuGcUcUaUaaX2n<br>usUsaUaGaGcAagaAcAcUguususu | 3<br>50 | X2-Linker |
| Z50 | NAG26 | TTR | P<br>G | AsasCaGuGuUCUuGcUcUaUaaX2n<br>usUsaUaGaGcAagaAcAcUbususu | 3<br>50 | X2-Linker |
| Z51 | NAG26 | TTR | P<br>G | AsasCaGuGuUCUuGcUcUaUaaX2n<br>usUsaUaGaGcAagaAcAcUguususu | 3<br>50 | X2-Linker |

TABLE 4-continued

| Compound # | Ligand | Target | Strand | Sequences (5'-3') | SEQ ID NO: | Conjugation Linker |
|---|---|---|---|---|---|---|
| Z52 | NAG26 | AT3 | P<br>G | gggsUuAcCaCCAuUuAcUuCaakX5X5<br>usUsgAaGuAaAuggUgUuAaCpcsasg | 26<br>53 | Amide, X5-Linker |
| Z53 | NAG26 | AT3 | P<br>G | gggsUuAcCaCCAuUuAcUuCaaeX5X5<br>usUsgAaGuAaAuggUgUuAaCpcsasg | 26<br>53 | Amide, X5-Linker |
| Z54 | NAG26 | AT3 | P<br>G | gggsUuAcCaCCAuUuAcUuCaak1X5X5<br>usUsgAaGuAaAuggUgUuAaCpcsasg | 26<br>53 | Amide, X5-Linker |
| Z55 | NAG26 | AT3 | P<br>G | gggsUuAcCaCCAuUuAcUuCaapX3X3<br>usUsGaAguAaAuggUgUuAaccsasg | 26<br>53 | Homopropargyl, X3-Linker |
| Z56 | NAG26 | AT3 | P<br>G | gsgsuuaacaCCAuuuacuucaapX3X3<br>usUsGaAgUaAaAuggUgUuAaccsasg | 26<br>53 | Homopropargyl, X3-Linker |
| Z57 | NAG26 | AT3 | P<br>G | gsgsuuaaCaCCauuuacuucaapX3X3<br>usUsGaAGuAaAuAuGgUgUUAaccsasg | 26<br>53 | Homopropargyl, X3-Linker |
| Z58 | NAG26 | AT3 | P<br>G | gsgsuuaaCaCcAuUuAcuucaapX3X3<br>usUsGaAcuAaAuGgUgUuAaCcsasg | 26<br>53 | Homopropargyl, X3-Linker |
| Z59 | NAG26 | AT3 | P<br>G | gsgsuuaacaCCAuuuacuucaapX3X3<br>usUsgaaguAaAucguGuUaaccsasg | 26<br>53 | Homopropargyl, X3-Linker |
| Z60 | NAG26 | AT3 | P<br>G | gsgsuuaaCaCCAuuuacuucaapX3X3<br>usUsgaagUaaauggGuUaaccsasg | 26<br>53 | Homopropargyl, X3-Linker |
| Z61 | NAG26 | AT3 | P<br>G | gsgsuuaaCaCCAuuuacuucaapX3X3<br>usUsgaaGuAauggUguuaaccsasg | 26<br>53 | Homopropargyl, X3-Linker |
| Z62 | NAG26 | AT3 | P<br>G | gsgsuuaaCaCCAuuuacuucaapX3X3<br>usUsgaaguaauggUgUuaaccsasg | 26<br>53 | Homopropargyl, X3-Linker |
| Z63 | NAG26 | AT3 | P<br>G | gsgsuuaacaCCAuuuacuucaapX3X3<br>usUsgaaguaaauGguuaaccsasg | 26<br>53 | Homopropargyl, X3-Linker |
| Z64 | NAG26 | AT3 | P<br>G | gggsUuAcCaCCAuUuAcUuCacX2n<br>usUsgAaGuAaAuggUgUuAaCpcsasg | 28<br>53 | X2-Linker |
| Z65 | NAG26 | AT3 | P<br>G | gggsUuAcCaCCAuUuAcUuCagX2n<br>usUsgAaGuAaAuggUgUuAaCpcsasg | 29<br>53 | X2-Linker |
| Z66 | NAG26 | AT3 | P<br>G | gggsUuAcCaCCAuUuAcUuCauX2n<br>usUsgAaGuAaAuggUgUuAaCpcsasg | 30<br>53 | X2-Linker |
| Z67 | None | TTR | P<br>G | AsasCaGuGuUCUuGcUcUaUaaX2n<br>usUsaUaGaGcAagaAcAcUgUpususu | 3<br>50 | X2-Linker |
| Z67A | NAG26 | TTR | P<br>G | AsasCaGuGuUCUuGcUcUaUaaX2n<br>usUsaUaGaGcAagaAcAcUgUpususu | 3<br>50 | X2-Linker |

TABLE 4-continued

| Compound # | Ligand | Target | Strand | Sequences (5'-3') | SEQ ID NO: | Conjugation Linker |
|---|---|---|---|---|---|---|
| Z68 | NAG26 | AT3 | P<br>G | gsgsUuAaCaCCAuUuAcUuCaaX2n<br>P1usUsgAaGuAaAuggUgUuAaCpcsasg | 26<br>53 | X2-Linker |
| Z69 | NAG26 | AT3 | P<br>G | gsgsUuAaCaCCAuUuAcUuCaaX2n<br>p2usUsgAaGuAaAuggUgUuAaCpcsasg | 26<br>53 | X2-Linker |
| Z70 | NAG26 | AT3 | P<br>G | gsgsUuAaCaCCAuUuAcUuCaaX2n<br>P3usUsgAaGuAaAuggUgUuAaCpcsasg | 26<br>53 | X2-Linker |
| Z71 | NAG26 | AT3 | P<br>G | gsgsUuAaCaCCAuUuAcUuCaaX2n<br>p4usUsgAaGuAaAuggUgUuAaCpcsasg | 26<br>53 | X2-Linker |
| Z72 | NAG26 | AT3 | P<br>G | gsgsUuAaCaCCAuUuAcUuCaaX2n<br>usUsgAaGuAaAuggUgUuAaCpcsasg | 26<br>53 | X2-Linker |
| Z73 | NAG26 | AT3 | P<br>G | gsgsUuAaCaCCAuUuAcUuCaaX2n<br>usUsgAX3aGuAaAuggUgUuAaCpcsasg | 26<br>53 | X2-Linker |
| Z74 | NAG26 | AT3 | P<br>G | gsgsUuAaCaCCAuUuAcUuCaaX2n<br>usUsgAaX3GuAaAuggUgUuAaCpcsasg | 26<br>53 | X2-Linker |
| Z75 | NAG26 | AT3 | P<br>G | gsgsUuAaCaCCAuUuAcUuCaaX2n<br>usUsgAaGX3uAaAuggUgUuAaCpcsasg | 26<br>53 | X2-Linker |
| Z76 | NAG26 | AT3 | P<br>G | gsgsUuAaCaCCAuUuAcUuCaaX2n<br>usUsgAagnuAaAuggUgUuAaCpcsasg | 26<br>53 | X2-Linker |
| Z77 | NAG26 | AT3 | P<br>G | gsgsUuAaCaCCAuUuAcUuCaap**X3R*X3S***<br>usUsgAaGuAaAuggUgUuAaCpcsasg | 26<br>53 | Homopropargyl, Chiral X3-Linker |
| Z78 | NAG26 | AT3 | P<br>G | gsgsUuAaCaCCAuUuAcUuCaap**X3S*X3S***<br>usUsgAaGuAaAuggUgUuAaCpcsasg | 26<br>53 | Homopropargyl, Chiral X3-Linker |
| Z79 | NAG26 | AT3 | P<br>G | gsgsUuAaCaCCAuUuAcUuCaap**X3R*X3S***<br>usUsgAaGuAaAuggUgUuAaCpcsasg | 26<br>53 | Homopropargyl, Chiral X3-Linker |
| Z80 | NAG26 | AT3 | P<br>G | gsgsUuAaCaCCAuUuAcUuCaap**X3S*X3R***<br>usUsgAaGuAaAuggUgUuAaCpcsasg | 26<br>53 | Homopropargyl, Chiral X3-Linker |
| Z81 | NAG26 | AT3 | P<br>G | gsgsUuAaCaCCAuUuAcUuCaapX3X3R*<br>usUsgAaGuAaAuggUgUuAaCpcsasg | 26<br>53 | Homopropargyl, Chiral X3-Linker |
| Z82 | NAG26 | AT3 | P<br>G | gsgsUuAaCaCCAuUuAcUuCaapX3X3S*<br>usUsgAaGuAaAuggUgUuAaCpcsasg | 26<br>53 | Homopropargyl, Chiral X3-Linker |
| Z83 | NAG26 | AT3 | P<br>G | gsgsUuAaCaCCAuUuAcUuCaap**X3R*X3**<br>usUsgAaGuAaAuggUgUuAaCpcsasg | 26<br>53 | Homopropargyl, Chiral X3-Linker |
| Z84 | NAG26 | AT3 | P<br>G | gsgsUuAaCaCCAuUuAcUuCaap**X3S*X3**<br>usUsgAaGuAaAuggUgUuAaCpcsasg | 26<br>53 | Homopropargyl, Chiral X3-Linker |

TABLE 4-continued

| Compound # | Ligand | Target | Strand | Sequences (5'-3') | SEQ ID NO: | Conjugation Linker |
|---|---|---|---|---|---|---|
| Z85 | NAG26 | AT3 | P<br>G | gsgsUuAaCaCCAuUuAcUuCaaX2n<br>usUsgAaGuAaAuggUgUuAacCsaS*g | 26<br>53 | X2-Linker |
| Z86 | NAG26 | AT3 | P<br>G | gsgsUuAaCaCCAuUuAcUuCaaX2n<br>usUsgAaGuAaAuggUgUuAaCcS*asg | 26<br>53 | X2-Linker |
| Z87 | NAG26 | AT3 | P<br>G | gsgsUuAaCaCCAuUuAcUuCaaX2n<br>usUsgAaGuAaAuggUgUuAaCcS*aS*g | 26<br>53 | X2-Linker |
| Z88 | NAG26 | AT3 | P<br>G | gsgsUuAaCaCCAuUuAcUuCaaX2n<br>usS*UsgAaGuAaAuggUgUuAaCcsasg | 26<br>53 | X2-Linker |
| Z89 | NAG26 | AT3 | P<br>G | gsgsuuaacaCcAuuuacuucaaX2n<br>usUsgaaguaaauGgUguuaaccsasg | 26<br>53 | X2-Linker |
| Z90 | NAG26 | AT3 | P<br>G | gsgsuuaaCaCcAuuuacuucaaX2n<br>usUsgaaguaaauGgUguuaaccsasg | 26<br>53 | X2-Linker |
| Z91 | NAG40 | AT3 | P<br>G | gsgsUuAaCaCCAuUuAcUuCaaX2NH₂n<br>usUsgAaGuAaAuggUgUuAaCcsasg | 26<br>53 | X2-NH2 Linker |
| Z92 | NAG40 | AT3 | P<br>G | gsgsuuaaCaCcAuuuacuucaaX2NH₂n<br>usUsgaaguaaauGgUguuaaCcsasg | 26<br>53 | X2-NH2 Linker |
| Z93 | NAG26 | AT3 | P<br>G | gsgsuuaaCaCcAuuuacuucaaX2n<br>usUsgaaguaaauGgUuaaccsusc | 26<br>53 | X2-Linker |
| Z94 | NAG26 | AT3 | P<br>G | csgsuuaaCaCcAuuuacuucaaX2n<br>usUsgaaguaaauGgUuaaccgsusc | 21<br>55 | X2-Linker |
| Z95 | NAG26 | AT3 | P<br>G | cscsuuaaCaCcAuuuacuucaaX2n<br>usUsgaaguaaauGgUuaaggsusc | 20<br>56 | X2-Linker |
| Z96 | NAG26 | AT3 | P<br>G | cscsauuaCaCcAuuuacuucaaX2n<br>usUsgaaguaaauGgUuauggsusc | 18<br>57 | X2-Linker |
| Z97 | NAG26 | AT3 | P<br>G | cscsaaaaCaCcAuuuacuucaaX2n<br>usUsgaaguaaauGgUuuuggsusc | 17<br>58 | X2-Linker |
| Z98 | NAG26 | AT3 | P<br>G | gsgsuuaaCaCcAuuuacuucaaX2n<br>usUsgaaguaaauGgUuaaccsasg | 26<br>53 | X2-Linker |
| Z99 | NAG26 | AT3 | P<br>G | gsgsuuaaCaCcAuuuacuucaaX2n<br>usUsgaaguaaauGgUuaaccsasg | 26<br>53 | X2-Linker |
| Z100 | NAG26 | AT3 | P<br>G | gsgsuuaaCaCcAuuuacuucaaX2n<br>usUsgaaguaaauGgUuaaggsusc | 26<br>53 | X2-Linker |
| Z101 | NAG26 | AT3 | P<br>G | cscsuuaaCaCcAuuuacuucaaX2n<br>usUsgaaguaaauGgUuaaggsusc | 20<br>56 | X2-Linker |

TABLE 4-continued

| Compound # | Ligand | Target | Strand | Sequences (5'-3') | SEQ ID NO: | Conjugation Linker |
|---|---|---|---|---|---|---|
| Z102 | NAG26 | AT3 | P<br>G | cscsauaaCaCcAuuuacuucaaX2n<br>usUsgaaguaaauGgUguauggsusc | 18<br>57 | X2-Linker |
| Z103 | NAG26 | AT3 | P<br>G | cscsaaaaCaCcAuuuacuucaaX2n<br>usUsgaaguaaauGgUguuuggsusc | 17<br>58 | X2-Linker |
| Z104 | NAG26 | AT3 | P<br>G | gS*tgsuuaaCaCcAuuuacuucaaX2n<br>usUsgaaguaaauGgUguaaccsasg | 26<br>53 | X2-Linker |
| Z105 | NAG26 | AT3 | P<br>G | gggS*tuuaaCaCcAuuuacuucaaX2n<br>usUsgaaguaaauGgUguaaccsasg | 26<br>53 | X2-Linker |
| Z106 | NAG26 | AT3 | P<br>G | gS*gS*tuuaaCaCcAuuuacuucaaX2n<br>usUsgaaguaaauGgUguaaccsasg | 26<br>53 | X2-Linker |
| Z107 | NAG26 | AT3 | P<br>G | gsgsuuaaCaCcAuuuacuucaaX2n<br>usUsgaaguaaauGgUguaaccsaS*g | 26<br>53 | X2-Linker |
| Z108 | NAG26 | AT3 | P<br>G | gsgsuuaaCaCcAuuuacuucaaX2n<br>usUsgaaguaaauGgUguaaccS*asg | 26<br>53 | X2-Linker |
| Z109 | NAG26 | AT3 | P<br>G | gsgsuuaaCaCcAuuuacuucaaX2n<br>usUsgaaguaaauGgUguaaccS*aS*g | 26<br>53 | X2-Linker |
| Z110 | NAG26 | AT3 | P<br>G | gsgsuuaaCaCcAuuuacuucuuS*caaX2n<br>usUsgaaguaaauGgUguaaccsasg | 26<br>53 | X2-Linker |
| Z111 | NAG26 | AT3 | P<br>G | gsgsuuaaCaCcAuuuacuucuuS*aaX2n<br>usUsgaaguaaauGgUguaaccsasg | 26<br>53 | X2-Linker |
| Z112 | NAG26 | AT3 | P<br>G | gsgsuuaaCaCcAuuuacuucaS*aX2n<br>usUsgaaguaaauGgUguaaccsasg | 26<br>53 | X2-Linker |
| Z113 | NAG26 | AT3 | P<br>G | gsgsuuaaCaCcAuuuacuucaS*X2n<br>usUsgaaguaaauGgUguaaccsasg | 26<br>53 | X2-Linker |
| Z114 | NAG26 | AT3 | P<br>G | gsgsuuaaCaCcAuuuacuucaS*aS*X2n<br>usUsgaaguaaauGgUguaaccag | 26<br>53 | X2-Linker |
| Z115 | NAG26 | AT3 | P<br>G | gsgsuuCuGgUuaacaccauuuX2n<br>asAsugguuaaCcAgAaccsasg | 31<br>8 | X2-Linker |
| Z116 | NAG26 | AT3 | P<br>G | csusgguuCuGgUuaacaccauuuX2n<br>asAsugguuaaCcAgAaccagsgsg | 24<br>9 | X2-Linker |
| Z117 | NAG26 | AT3 | P<br>G | ususcuGgUuAacaccauuuaX2n<br>usAsaaugguuaaCcAgaasCsc | 51<br>35 | X2-Linker |
| Z118 | NAG26 | AT3 | P<br>G | gsgsuucuGgUuAacaccauuuaX2n<br>usAsaaugguuuaAcCAgaaccsasg | 32<br>36 | X2-Linker |

TABLE 4-continued

| Compound # | Ligand | Target | Strand | Sequences (5'-3') | SEQ ID NO: | Conjugation Linker |
|---|---|---|---|---|---|---|
| Z119 | NAG26 | AT3 | P<br>G | uscsugGuUaAcaccauuuaaX2n<br>usUsaaaugugutUaAcCagasasc | 44<br>47 | X2-Linker |
| Z120 | NAG26 | AT3 | P<br>G | gsusucugGuUaAcaccauuuaaX2n<br>usUsaaauggutUaAcCagaacScsa | 34<br>48 | X2-Linker |
| Z121 | NAG26 | AT3 | P<br>G | usgsguUaAcAccauuuacuuX2n<br>asAsguaaauggtUaAccasgsa | 46<br>6 | X2-Linker |
| Z122 | NAG26 | AT3 | P<br>G | uscsugguUaAcAccauuuacuuX2n<br>aaAsguaaauggutUaAccagasasc | 45<br>7 | X2-Linker |
| Z123 | NAG26 | AT3 | P<br>G | gsgsuuUaCaCcauuuacuuaX2n<br>usAsaguaaauggUgUuAaccsasg | 25<br>39 | X2-Linker |
| Z124 | NAG26 | AT3 | P<br>G | csusgguUaCaCcauuuacuuaX2n<br>usAsaguaaauggUgUuAaccagsasa | 23<br>40 | X2-Linker |
| Z125 | NAG26 | AT3 | P<br>G | ususaaCaCcAuuuacuucaaX2n<br>usUsgaaguaaauGgUguaaSesc | 49<br>52 | X2-Linker |
| Z126 | NAG26 | AT3 | P<br>G | gsgsuuaaCaCcAuuuacuucaaX2n<br>usUsgaaguaaauGgUuaaccasasg | 26<br>53 | X2-Linker |
| Z127 | NAG26 | AT3 | P<br>G | usasacAcCaUuuacuucaaX2n<br>usUsugaaguaaaUgGuuaasa | 37<br>59 | X2-Linker |
| Z128 | NAG26 | AT3 | P<br>G | gsusuaacAcCaUuuacuucaaaX2n<br>usUsugaaguaaaUgGuUuaacscsa | 33<br>60 | X2-Linker |
| Z129 | NAG26 | AT3 | P<br>G | ascsaCcaUuUacuucaaggaX2n<br>usCsscuugaaguaaAaUgGugususa | 11<br>42 | X2-Linker |
| Z130 | NAG26 | AT3 | P<br>G | usasacaCcaUuUacuucaaggaX2n<br>usCsscuugaaguaaAaUgCuguuasasc | 38<br>43 | X2-Linker |
| Z131 | NAG26 | AT3 | P<br>G | cscsauUaCUucaagggccuX2n<br>asGsgcccuugaaGuAaAuggsusg | 19<br>13 | X2-Linker |
| Z132 | NAG26 | AT3 | P<br>G | csasuuUaCuUcaagggccuaX2n<br>usAsggcccuugaAgUaAaugsgsu | 16<br>41 | X2-Linker |
| Z133 | NAG26 | AT3 | P<br>G | asusuuAcUuCaagggccuguX2n<br>asCsaggcccuugAaGuAaausgsg | 14<br>12 | X2-Linker |
| Z134 | NAG26 | AT3 | P<br>G | uscsugGuUaAcaccauuuaaX2n<br>usUsaaaugugutUaAcCsagasasc | 44<br>47 | X2-Linker |
| Z135 | NAG26 | AT3 | P<br>G | uscsugGuUaAcaccauuuaaX2n<br>usUsaaauggugutUaAccagasasc | 44<br>47 | X2-Linker |

TABLE 4-continued

| Compound # | Ligand | Target | Strand | Sequences (5'-3') | SEQ ID NO: | Conjugation Linker |
|---|---|---|---|---|---|---|
| Z136 | NAG26 | AT3 | P<br>G | usgsguUaAcAccauuuacuuX2n<br>asAsguaaaugguGuUaAsccasgsa | 46<br>6 | X2-Linker |
| Z137 | NAG26 | AT3 | P<br>G | usgsguUaAcAccauuuacuuX2n<br>asAsguaaauugguGuUaaccasgsa | 46<br>6 | X2-Linker |
| Z138 | NAG26 | AT3 | P<br>G | usgsguUsaAcAccauuuacuuX2n<br>asAsguaaauugguGuUaAccasgsa | 46<br>6 | X2-Linker |
| Z139 | NAG26 | AT3 | P<br>G | usgsguuaAcAccauuuacuuX2n<br>asAsguaaauugguGuUaAccasgsa | 46<br>6 | X2-Linker |
| Z140 | NAG26 | AT3 | P<br>G | usgsguUsaAcAccauuuacuuX2n<br>asAsguaaauugguGuUaAsccasgsa | 46<br>6 | X2-Linker |
| Z141 | NAG26 | AT3 | P<br>G | usgsguuaAcAccauuuacuuX2n<br>asAsguaaauugguGuUaaccasgsa | 46<br>6 | X2-Linker |
| Z142 | NAG26 | AT3 | P<br>G | UsgsGuUaACAcCaUuUaCuUX2n<br>asAsguaAaUgGuguUaAcCasgsa | 45<br>7 | X2-Linker |
| Z143 | NAG26 | AT3 | P<br>G | UscsUgGuUaAcACcaUuUaCuUX2n<br>asAsgUaAaUgGuguUaAcCaGasasc | 45<br>7 | X2-Linker |
| Z144 | NAG26 | AT3 | P<br>G | gsgsUuAaCaCCAuUuAcUuCaaX2n<br>uR*UsgAaGuAaAuggUgUuAcCpcsasg | 26<br>53 | X2-Linker |
| Z145 | NAG26 | AT3 | P<br>G | gsgsUuAaCaCCAuUuAcUuCaaX2n<br>uS*US*gAaGuAaAuggUgUuAaCpcsasg | 26<br>53 | X2-Linker |
| Z146 | NAG26 | AT3 | P<br>G | gsgsUuAaCaCCAuUuAcUuCaaX2n<br>uS*UsgAaGuAaAuggUgUuAaCcsasg | 26<br>53 | X2-Linker |
| Z147 | NAG26 | AT3 | P<br>G | gsgsUuAaCaCCAuUuAcUuCaaX2n<br>usUS*gAaGuAaAuggUgUuAaCcsasg | 26<br>53 | X2-Linker |
| Z148 | NAG26 | AT3 | P<br>G | gsgsUuAaCaCCAuUuAcUuCaaX2n<br>usUR*gAaGuAaAuggUgUuAaCcsasg | 26<br>53 | X2-Linker |
| Z149 | NAG26 | AT3 | P<br>G | gsgsUuAaCaCCAuUuAcUuCaaX2n<br>uS*US*gAaGuAaAuggUgUuAaCcsasg | 26<br>53 | X2-Linker |
| Z150 | NAG26 | AT3 | P<br>G | gsgsUuAaCaCCAuUuAcUuCaaX2n<br>uS*UR*gAaGuAaAuggUgUuAaCcsasg | 26<br>53 | X2-Linker |
| Z151 | NAG26 | AT3 | P<br>G | gsgsUuAaCaCCAuUuAcUuCaaX2n<br>uR*US*gAaGuAaAuggUgUuAaCcsasg | 26<br>53 | X2-Linker |
| Z152 | NAG26 | AT3 | P<br>G | gsgsUuAaCaCCAuUuAcUuCaaX2n<br>usUsgAaGuAaAuggUgUuAaCcS*asg | 26<br>53 | X2-Linker |

TABLE 4-continued

| Compound # | Ligand | Target | Strand | Sequences (5'-3') | SEQ ID NO: | Conjugation Linker |
|---|---|---|---|---|---|---|
| Z153 | NAG26 | AT3 | P<br>G | gsgsUuAcAcaCCAuUuAcUuCaaX2n<br>usUsgAaGuAaAuggUgUuAaCcR*asg | 26<br>53 | X2-Linker |
| Z154 | NAG26 | AT3 | P<br>G | gsgsUuAcAcaCCAuUuAcUuCaaX2n<br>usUsgAaGuAaAuggUgUuAaCcsaS*g | 26<br>53 | X2-Linker |
| Z155 | NAG26 | AT3 | P<br>G | gsgsUuAcAcaCCAuUuAcUuCaaX2n<br>usUsgAaGuAaAuggUgUuAaCcsaR*g | 26<br>53 | X2-Linker |
| Z156 | NAG26 | AT3 | P<br>G | gsgsUuAcAcaCCAuUuAcUuCaaX2n<br>usUsgAaGuAaAuggUgUuAaCcS*aS*g | 26<br>53 | X2-Linker |
| Z157 | NAG26 | AT3 | P<br>G | gsgsUuAcAcaCCAuUuAcUuCaaX2n<br>usUsgAaGuAaAuggUgUuAaCcS*aR*g | 26<br>53 | X2-Linker |
| Z158 | NAG26 | AT3 | P<br>G | gsgsUuAcAcaCCAuUuAcUuCaaX2n<br>usUsgAaGuAaAuggUgUuAaCcR*aS*g | 26<br>53 | X2-Linker |
| Z159 | NAG26 | AT3 | P<br>G | gsgsUuAcAcaCCAuUuAcUuCaaX2n<br>usUsgAaGuAaAuggUgUuAaCcR*aR*g | 26<br>53 | X2-Linker |
| Z160 | NAG26 | AT3 | P<br>G | gsgsUuAcAcaCCAuUuAcUuCaaX2n<br>uR*UR*gAaGuAaAuggUgUuAaCcR*aR*g | 26<br>53 | X2-Linker |
| Z161 | NAG26 | AT3 | P<br>G | gsgsUuAcAcaCCAuUuAcUuCaaX2n<br>uR*UR*gAaGuAaAuggUgUuAaCcR*aS*g | 26<br>53 | X2-Linker |
| Z162 | NAG26 | AT3 | P<br>G | gsgsUuAcAcaCCAuUuAcUuCaaX2n<br>uR*UR*gAaGuAaAuggUgUuAaCcS*aR*g | 26<br>53 | X2-Linker |
| Z163 | NAG26 | AT3 | P<br>G | gsgsUuAcAcaCCAuUuAcUuCaaX2n<br>uR*UR*gAaGuAaAuggUgUuAaCcS*aS*g | 26<br>53 | X2-Linker |
| Z164 | NAG26 | AT3 | P<br>G | gsgsUuAcAcaCCAuUuAcUuCaaX2n<br>uS*US*gAaGuAaAuggUgUuAaCcR*aR*g | 26<br>53 | X2-Linker |
| Z165 | NAG26 | AT3 | P<br>G | gsgsUuAcAcaCCAuUuAcUuCaaX2n<br>uS*US*gAaGuAaAuggUgUuAaCcR*aS*g | 26<br>53 | X2-Linker |
| Z166 | NAG26 | AT3 | P<br>G | gsgsUuAcAcaCCAuUuAcUuCaaX2n<br>uS*US*gAaGuAaAuggUgUuAaCcS*aR*g | 26<br>53 | X2-Linker |
| Z167 | NAG26 | AT3 | P<br>G | gsgsUuAcAcaCCAuUuAcUuCaaX2n<br>uS*US*gAaGuAaAuggUgUuAaCcS*aS*g | 26<br>53 | X2-Linker |
| Z168 | NAG26 | AT3 | P<br>G | gsgsUuAcAcaCCAuUuAcUuCaaX2n<br>uR*US*gAaGuAaAuggUgUuAaCcS*aS*g | 26<br>53 | X2-Linker |
| Z169 | NAG26 | AT3 | P<br>G | gsgsUuAcAcaCCAuUuAcUuCaaX2n<br>uS*UR*gAaGuAaAuggUgUuAaCcS*aS*g | 26<br>53 | X2-Linker |

TABLE 4-continued

| Compound # | Ligand | Target | Strand | Sequences (5'-3') | SEQ ID NO: | Conjugation Linker |
|---|---|---|---|---|---|---|
| Z170 | NAG26 | AT3 | P | gsgsUuAaCaCCAuUuAcUuCaaX2n | 26 | X2-Linker |
|  |  |  | G | uR*US*gAaGuAaAuggUgUuAaCcR*aR*g | 53 |  |
| Z171 | NAG26 | AT3 | P | gsgsUuAaCaCCAuUuAcUuCaaX2n | 26 | X2-Linker |
|  |  |  | G | uS*UR*gAaGuAaAuggUgUuAaCcR*aR*g | 53 |  |
| Z172 | NAG26 | AT3 | P | gR*gR*UuAaCaCCAuUuAcUuCaaX2n | 26 | X2-Linker |
|  |  |  | G | uR*UR*gAaGuAaAuggUgUuAaCcR*aR*g | 53 |  |
| Z173 | NAG26 | AT3 | P | gR*gR*UuAaCaCCAuUuAcUuCaaX2n | 26 | X2-Linker |
|  |  |  | G | uR*US*gAaGuAaAuggUgUuAaCcR*aR*g | 53 |  |
| Z174 | NAG26 | AT3 | P | gR*gR*UuAaCaCCAuUuAcUuCaaX2n | 26 | X2-Linker |
|  |  |  | G | uR*UR*gAaGuAaAuggUgUuAaCcR*aR*g | 53 |  |
| Z175 | NAG26 | AT3 | P | gR*gR*UuAaCaCCAuUuAcUuCaaX2n | 26 | X2-Linker |
|  |  |  | G | uR*UR*gAaGuAaAuggUgUuAaCcR*aR*g | 53 |  |
| Z176 | NAG26 | AT3 | P | gR*gR*UuAaCaCCAuUuAcUuCaaX2n | 26 | X2-Linker |
|  |  |  | G | uS*UR*gAaGuAaAuggUgUuAaCcS*aS*g | 53 |  |
| Z177 | NAG26 | AT3 | P | gR*gR*UuAaCaCCAuUuAcUuCaaX2n | 26 | X2-Linker |
|  |  |  | G | uS*UR*gAaGuAaAuggUgUuAaCcS*aS*g | 53 |  |
| Z178 | NAG26 | AT3 | P | gR*gR*UuAaCaCCAuUuAcUuCaaX2n | 26 | X2-Linker |
|  |  |  | G | uR*UR*gAaGuAaAuggUgUuAaCcS*aS*g | 53 |  |
| Z179 | NAG26 | AT3 | P | gR*gR*UuAaCaCCAuUuAcUuCaaX2n | 26 | X2-Linker |
|  |  |  | G | uS*US*gAaGuAaAuggUgUuAaCcS*aS*g | 53 |  |
| Z180 | NAG26 | AT3 | P | gR*gR*UuAaCaCCAuUuAcUuCaaX2n | 26 | X2-Linker |
|  |  |  | G | uS*US*gAaGuAaAuggUgUuAaCcR*aS*g | 53 |  |
| Z181 | NAG26 | AT3 | P | gR*gR*UuAaCaCCAuUuAcUuCaaX2n | 26 | X2-Linker |
|  |  |  | G | uR*US*gAaGuAaAuggUgUuAaCcS*aR*g | 53 |  |
| Z182 | NAG26 | AT3 | P | gR*gR*UuAaCaCCAuUuAcUuCaaX2n | 26 | X2-Linker |
|  |  |  | G | uR*UR*gAaGuAaAuggUgUuAaCcS*aS*g | 53 |  |
| Z183 | NAG26 | AT3 | P | gR*gR*UuAaCaCCAuUuAcUuCaaX2n | 26 | X2-Linker |
|  |  |  | G | uS*US*gAaGuAaAuggUgUuAaCcS*aS*g | 53 |  |
| Z184 | NAG26 | AT3 | P | gR*gR*UuAaCaCCAuUuAcUuCaaX2n | 26 | X2-Linker |
|  |  |  | G | uR*US*gAaGuAaAuggUgUuAaCcR*aR*g | 53 |  |
| Z185 | NAG26 | AT3 | P | gS*gR*UuAaCaCCAuUuAcUuCaaX2n | 26 | X2-Linker |
|  |  |  | G | uS*UR*gAaGuAaAuggUgUuAaCcS*aR*g | 53 |  |
| Z186 | NAG26 | AT3 | P | gS*gS*UuAaCaCCAuUuAcUuCaaX2n | 26 | X2-Linker |
|  |  |  | G | uR*UR*gAaGuAaAuggUgUuAaCcR*aR*g | 53 |  |

TABLE 4-continued

| Compound # | Ligand | Target | Strand | Sequences (5'-3') | SEQ ID NO: | Conjugation Linker |
|---|---|---|---|---|---|---|
| Z187 | NAG26 | AT3 | P<br>G | gS*gR*UuAaCaCCAuUuAcUuCaaX2n<br>uR*UR*gAaGuAaAuggUgUuAaCcS*aR*g | 26<br>53 | X2-Linker |
| Z188 | NAG26 | AT3 | P<br>G | gS*gR*UuAaCaCCAuUuAcUuCaaX2n<br>uR*UR*gAaGuAaAuggUgUuAaCcR*aS*g | 26<br>53 | X2-Linker |
| Z189 | NAG26 | AT3 | P<br>G | gS*gR*UuAaCaCCAuUuAcUuCaaX2n<br>uS*US*gAaGuAaAuggUgUuAaCcR*aS*g | 26<br>53 | X2-Linker |
| Z190 | NAG26 | AT3 | P<br>G | gS*gR*UuAaCaCCAuUuAcUuCaaX2n<br>uS*US*gAaGuAaAuggUgUuAaCcS*aR*g | 26<br>53 | X2-Linker |
| Z191 | NAG26 | AT3 | P<br>G | gS*gR*UuAaCaCCAuUuAcUuCaaX2n<br>uS*UR*gAaGuAaAuggUgUuAaCcS*aS*g | 26<br>53 | X2-Linker |
| Z192 | NAG26 | AT3 | P<br>G | gS*gR*UuAaCaCCAuUuAcUuCaaX2n<br>uS*US*gAaGuAaAuggUgUuAaCcR*aS*g | 26<br>53 | X2-Linker |
| Z193 | NAG26 | AT3 | P<br>G | gS*gR*UuAaCaCCAuUuAcUuCaaX2n<br>uS*US*gAaGuAaAuggUgUuAaCcS*aR*g | 26<br>53 | X2-Linker |
| Z194 | NAG26 | AT3 | P<br>G | gS*gR*UuAaCaCCAuUuAcUuCaaX2n<br>uS*US*gAaGuAaAuggUgUuAaCcS*aS*g | 26<br>53 | X2-Linker |
| Z195 | NAG26 | AT3 | P<br>G | gS*gR*UuAaCaCCAuUuAcUuCaaX2n<br>uS*US*gAaGuAaAuggUgUuAaCcR*aR*g | 26<br>53 | X2-Linker |
| Z196 | NAG26 | AT3 | P<br>G | gR*gS*UuAaCaCCAuUuAcUuCaaX2n<br>uR*UR*gAaGuAaAuggUgUuAaCcR*aR*g | 26<br>53 | X2-Linker |
| Z197 | NAG26 | AT3 | P<br>G | gR*gS*UuAaCaCCAuUuAcUuCaaX2n<br>uS*UR*gAaGuAaAuggUgUuAaCcR*aR*g | 26<br>53 | X2-Linker |
| Z198 | NAG26 | AT3 | P<br>G | gR*gS*UuAaCaCCAuUuAcUuCaaX2n<br>uR*US*gAaGuAaAuggUgUuAaCcR*aR*g | 26<br>53 | X2-Linker |
| Z199 | NAG26 | AT3 | P<br>G | gR*gS*UuAaCaCCAuUuAcUuCaaX2n<br>uR*US*gAaGuAaAuggUgUuAaCcR*aR*g | 26<br>53 | X2-Linker |
| Z200 | NAG26 | AT3 | P<br>G | gR*gS*UuAaCaCCAuUuAcUuCaaX2n<br>uR*UR*gAaGuAaAuggUgUuAaCcR*aS*g | 26<br>53 | X2-Linker |
| Z201 | NAG26 | AT3 | P<br>G | gR*gS*UuAaCaCCAuUuAcUuCaaX2n<br>uS*US*gAaGuAaAuggUgUuAaCcS*aS*g | 26<br>53 | X2-Linker |
| Z202 | NAG26 | AT3 | P<br>G | gR*gS*UuAaCaCCAuUuAcUuCaaX2n<br>uS*US*gAaGuAaAuggUgUuAaCcS*aS*g | 26<br>53 | X2-Linker |
| Z203 | NAG26 | AT3 | P<br>G | gR*gS*UuAaCaCCAuUuAcUuCaaX2n<br>uS*US*gAaGuAaAuggUgUuAaCcS*aS*g | 26<br>53 | X2-Linker |

TABLE 4-continued

| Compound # | Ligand | Target | Strand | Sequences (5'-3') | SEQ ID NO: | Conjugation Linker |
|---|---|---|---|---|---|---|
| Z204 | NAG26 | AT3 | P<br>G | gR*gS*UuAaCaCCAuUuAcUuCaaX2n<br>uS*US*gAaGuAaAuggUgUuAaCcR*aS*g | 26<br>53 | X2-Linker |
| Z205 | NAG26 | AT3 | P<br>G | gR*gS*UuAaCaCCAuUuAcUuCaaX2n<br>uS*US*gAaGuAaAuggUgUuAaCcS*aR*g | 26<br>53 | X2-Linker |
| Z206 | NAG26 | AT3 | P<br>G | gR*gS*UuAaCaCCAuUuAcUuCaaX2n<br>uR*UR*gAaGuAaAuggUgUuAaCcS*aS*g | 26<br>53 | X2-Linker |
| Z207 | NAG26 | AT3 | P<br>G | gR*gS*UuAaCaCCAuUuAcUuCaaX2n<br>uS*US*gAaGuAaAuggUgUuAaCcR*aR*g | 26<br>53 | X2-Linker |
| Z208 | NAG26 | AT3 | P<br>G | gS*gS*UuAaCaCCAuUuAcUuCaaX2n<br>uR*UR*gAaGuAaAuggUgUuAaCcR*aR*g | 26<br>53 | X2-Linker |
| Z209 | NAG26 | AT3 | P<br>G | gS*gS*UuAaCaCCAuUuAcUuCaaX2n<br>uS*UR*gAaGuAaAuggUgUuAaCcS*aR*g | 26<br>53 | X2-Linker |
| Z210 | NAG26 | AT3 | P<br>G | gS*gS*UuAaCaCCAuUuAcUuCaaX2n<br>uR*US*gAaGuAaAuggUgUuAaCcR*aS*g | 26<br>53 | X2-Linker |
| Z211 | NAG26 | AT3 | P<br>G | gS*gS*UuAaCaCCAuUuAcUuCaaX2n<br>uR*UR*gAaGuAaAuggUgUuAaCcS*aR*g | 26<br>53 | X2-Linker |
| Z212 | NAG26 | AT3 | P<br>G | gS*gS*UuAaCaCCAuUuAcUuCaaX2n<br>uR*UR*gAaGuAaAuggUgUuAaCcR*aS*g | 26<br>53 | X2-Linker |
| Z213 | NAG26 | AT3 | P<br>G | gS*gS*UuAaCaCCAuUuAcUuCaaX2n<br>uS*US*gAaGuAaAuggUgUuAaCcS*aS*g | 26<br>53 | X2-Linker |
| Z214 | NAG26 | AT3 | P<br>G | gS*gS*UuAaCaCCAuUuAcUuCaaX2n<br>uS*US*gAaGuAaAuggUgUuAaCcS*aS*g | 26<br>53 | X2-Linker |
| Z215 | NAG26 | AT3 | P<br>G | gS*gS*UuAaCaCCAuUuAcUuCaaX2n<br>uS*UR*gAaGuAaAuggUgUuAaCcS*aS*g | 26<br>53 | X2-Linker |
| Z216 | NAG26 | AT3 | P<br>G | gS*gS*UuAaCaCCAuUuAcUuCaaX2n<br>uS*US*gAaGuAaAuggUgUuAaCcS*aS*g | 26<br>53 | X2-Linker |
| Z217 | NAG26 | AT3 | P<br>G | gS*gS*UuAaCaCCAuUuAcUuCaaX2n<br>uS*US*gAaGuAaAuggUgUuAaCcS*aR*g | 26<br>53 | X2-Linker |
| Z218 | NAG26 | AT3 | P<br>G | gS*gS*UuAaCaCCAuUuAcUuCaaX2n<br>uR*UR*gAaGuAaAuggUgUuAaCcR*aR*g | 26<br>53 | X2-Linker |
| Z219 | NAG26 | AT3 | P<br>G | gS*gS*UuAaCaCCAuUuAcUuCaaX2n<br>uS*US*gAaGuAaAuggUgUuaaccS*aR*g | 26<br>53 | X2-Linker |
| Z220 | NAG26 | AT3 | P<br>G | gR*gR*UuAaCaCCAuUuAcUuCaaX2n<br>uR*US*gaaguaaauGgUuaaccS*aR*g | 26<br>53 | X2-Linker |

TABLE 4-continued

| Compound # | Ligand | Target | Strand | Sequences (5'-3') | SEQ ID NO: | Conjugation Linker |
|---|---|---|---|---|---|---|
| Z221 | NAG26 | AT3 | P<br>G | gsgsuuaaCaCcAuuuacuucaaX2n<br>uR*UR*gaaguaaauGgUuaaccS*aS*g | 26<br>53 | X2-Linker |
| Z222 | NAG26 | AT3 | P<br>G | gsgsuuaaCaCcAuuuacuucaaX2n<br>uR*UR*gaaguaaauGgUuaaccS*aR*g | 26<br>53 | X2-Linker |
| Z223 | NAG26 | AT3 | P<br>G | gsgsuuaaCaCcAuuuacuucaaX2n<br>usUsgaaguaaauGgUuaaccsasc | 26<br>62 | X2-Linker |
| Z224 | NAG26 | PCSK9 | P<br>G | uR*uR*uugcUuUuGuaacuugaaaX2n<br>uR*UR*ucaaguuacAaAaGcaaaaS*cS*a | 63<br>64 | X2-Linker |
| Z225 | NAG26 | PCSK9 | P<br>G | uR*uS*uugcUuUuGuaacuugaaaX2n<br>uR*UR*ucaaguuacAaAaGcaaaaS*cR*a | 63<br>64 | X2-Linker |
| Z226 | NAG26 | PCSK9 | P<br>G | gR*uR*uuugUaGcAuuuuuauuaaX2n<br>usUsaauaaaaauGcUaCaaaaccc | 65<br>66 | X2-Linker |
| Z227 | NAG26 | PCSK9 | P<br>G | gR*uS*uuugUaGcAuuuuuauuaaX2n<br>usUsaauaaaaauGcUaCaaaaccc | 65<br>66 | X2-Linker |
| Z228 | NAG26 | PCSK9 | P<br>G | gsusuuugUaGcAuuuuuauuaaX2n<br>uR*UR*aauaaaaauGcUaCaaaacS*cS*c | 65<br>66 | X2-Linker |
| Z229 | NAG26 | PCSK9 | P<br>G | gsusuuugUaGcAuuuuuauuaaX2n<br>uR*UR*aauaaaaauGcUaCaaaacR*cS*c | 65<br>66 | X2-Linker |
| Z230 | NAG26 | PCSK9 | P<br>G | gR*uR*uuugUaGcAuuuuuauuaaX2n<br>uR*UR*aauaaaaauGcUaCaaaacS*cS*c | 65<br>66 | X2-Linker |
| Z231 | NAG26 | PCSK9 | P<br>G | gR*uS*uuugUaGcAuuuuuauuaaX2n<br>uR*UR*aauaaaaauGcUaCaaaacR*cS*c | 65<br>66 | X2-Linker |
| Z232 | NAG26 | PCSK9 | P<br>G | gR*uR*uuugUaGcAuuuuuauuaaX2n<br>uR*UR*aauaaaaauGcUaCaaaacS*cS*c | 65<br>66 | X2-Linker |
| Z233 | NAG26 | PCSK9 | P<br>G | gR*uS*uuugUaGcAuuuuuauuaaX2n<br>uR*UR*aauaaaaauGcUaCaaaacR*cS*c | 65<br>66 | X2-Linker |
| Z234 | NAG26 | AT3 | P<br>G | gsgsUuAaCaCCAuUuAcUuCaaX2n<br>usUsgAX3GuAaAuggUgUuAaCcsasg | 26<br>67 | X2-Linker |
| Z235 | NAG26 | AT3 | P<br>G | gsgsUuAaCaCCAuUuAcUuCaaX2n<br>usUsgAaX3uAaAuggUgUuAaCcsasg | 26<br>68 | X2-Linker |
| Z236 | NAG26 | AT3 | P<br>G | gsgsUuAaCaCCAuUuAcUuCaaX2n<br>usUsgAaCX3AaAuggUgUuAaCcsasg | 26<br>69 | X2-Linker |
| Z237 | None | TTR | P<br>G | AsasCaGuGuUCUuGcUcUaUaA<br>usUsaUX3GaGcAagaAcAcUgUsusu | 3<br>70 | None |

TABLE 4-continued

| Compound # | Ligand | Target | Strand | Sequences (5'-3') | SEQ ID NO: | Conjugation Linker |
|---|---|---|---|---|---|---|
| Z238 | None | TTR | P<br>G | AsasCaGuGuUCUuGcUCuUaUaA<br>usUaUaCX3GcAagaCaCuGuUususu | 3<br>71 | None |
| Z239 | None | PCSK9 | P<br>G | UsusGcUuUgUAaCuUgAaGaU<br>asUscUX3CaAgUuacAaAaGcAasasa | 72<br>73 | None |
| Z240 | None | PCSK9 | P<br>G | UsusGcUuUgUAaCuUgAaGaU<br>asUscUucX3AgUuacAaAaGcAasasa | 72<br>74 | None |
| Z241 | None | PCSK9 | P<br>G | GscsUuUuGuAACuUgAaGaUaU<br>asUsaUX3UuCaAguuAcAaAaGcsasa | 75<br>76 | None |
| Z242 | None | PCSK9 | P<br>G | GscsUuUuGuAACuUgAaGaUaU<br>asUsaUcUX3CaAguuAcAaAaGcsasa | 75<br>77 | None |
| Z243 | None | PCSK9 | P<br>G | UsasAcUuGaAGAuAuUuAuUcU<br>asGsaAX3AaAuAucuUCaAgUuascsa | 78<br>79 | None |
| Z244 | None | PCSK9 | P<br>G | UsasAcUuGaAGAuAuUuAuUcU<br>asGsaAuX3AuAucuUCaAgUuUascsa | 78<br>80 | None |
| Z245 | None | PCSK9 | P<br>G | GsusUuUgUaGCAuUuUuAuUaA<br>usUsaAX3AaAaAugcUaCaAaAcscsc | 65<br>81 | None |
| Z246 | None | PCSK9 | P<br>G | GsusUuUgUaGCAuUuUuAuUaA<br>usUsaAuX3AaAugcUaCaAaAcscsc | 65<br>82 | None |
| Z247 | None | PCSK9 | P<br>G | UsusGuAgCaUUUuUaUuAaUaU<br>asUsaUX3AaUaAaaaUgCuAcAasasa | 83<br>84 | None |
| Z248 | None | PCSK9 | P<br>G | UsusGuAgCaUUUuUaUuAaUaU<br>asUsaUuX3UaAaaaUgCuAcAasasa | 83<br>85 | None |
| Z249 | NAG26 | AT3 | P<br>G | gsgsUuAaCaCCAuUuAcUuCaaX2n<br>usUsgaX3sGuAaAuggUgUuAaCcsasg | 26<br>67 | X2-Linker |
| Z250 | NAG26 | AT3 | P<br>G | gsgsUuAaCaCCAuUuAcUuCaaX2n<br>usUsgaX3GuAaAuggUgUuAaCcsasg | 26<br>67 | X2-Linker |
| Z251 | NAG26 | AT3 | P<br>G | gsgsUuAaCaCCAuUuAcUuCaaX2n<br>usUsgasX3GuAaAuggUgUuAaCcsasg | 26<br>67 | X2-Linker |
| Z252 | NAG26 | AT3 | P<br>G | gsgsUuAaCaCCAuUuAcUuCaaX2n<br>usUsgasX3GuAaAuggUgUuAaCcsasg | 26<br>67 | X2-Linker |
| Z253 | NAG26 | AT3 | P<br>G | gsgsUuAaCaCCAuUuAcUuCaaX2n<br>usUsgasX3sGuAaAuggUgUuAaCcsasg | 26<br>67 | X2-Linker |
| Z254 | NAG26 | AT3 | P<br>G | gsgsUuAaCaCCAuUuAcUuCaaX2n<br>usUsgaaGX3sAaAuggUgUuAaCcsasg | 26<br>69 | X2-Linker |

TABLE 4-continued

| Compound # | Ligand | Target | Strand | Sequences (5'-3') | SEQ ID NO: | Conjugation Linker |
|---|---|---|---|---|---|---|
| Z255 | NAG26 | AT3 | P<br>G | gsgsUuAaCaCCAuUuAcUuCaaX2n<br>usUsgAaggX3AaAuggUgUuAaCcsasg | 26<br>69 | X2-Linker |
| Z256 | NAG26 | AT3 | P<br>G | gsgsUuAaCaCCAuUuAcUuCaaX2n<br>usUsgAagsX3sAaAuggUgUuAaCcsasg | 26<br>69 | X2-Linker |
| Z257 | NAG26 | AT3 | P<br>G | gsgsUuAaCaCCAuUuAcUuCaaX2n<br>usUsgAagpX3GuAaAuggUgUuAaCcsasg | 26<br>67 | X2-Linker |
| Z258 | NAG26 | AT3 | P<br>G | gsgsUuAaCaCCAuUuAcUuCaaX2n<br>usUsgAX4GuAaAuggUgUuAaCcsasg | 26<br>67 | X2-Linker |
| Z259 | NAG26 | AT3 | P<br>G | gsgsUuAaCaCCAuUuAcUuCaaX2n<br>usUsgapX4GuAaAuggUgUuAaCcsasg | 26<br>67 | X2-Linker |
| Z260 | NAG26 | AT3 | P<br>G | gsgsUuAaCaCCAuUuAcUuCaaX2n<br>usUsgAagpX3AaAuggUgUuAaCcsasg | 26<br>69 | X2-Linker |
| Z261 | NAG26 | AT3 | P<br>G | gsgsUuAaCaCCAuUuAcUuCaaX2n<br>usUsgAacX4AaAuggUgUuAaCcsasg | 26<br>69 | X2-Linker |
| Z262 | NAG26 | AT3 | P<br>G | gsgsUuAaCaCCAuUuAcUuCaaX2n<br>usUsgAagpX4AaAuggUgUuAaCcsasg | 26<br>69 | X2-Linker |
| Z263 | NAG26 | AT3 | P<br>G | gsgsUuAaCaCCAuUuAcUuCaaX2n<br>usUsgIaGuAaAuggUgUuAaCcsasg | 26<br>86 | X2-Linker |
| Z264 | NAG26 | AT3 | P<br>G | gsgsUuAaCaCCAuUuAcUuCaaX2n<br>usUsgAIGuAaAuggUgUuAaCcsasg | 26<br>87 | X2-Linker |
| Z265 | NAG26 | AT3 | P<br>G | gsgsUuAaCaCCAuUuAcUuCaaX2n<br>usUsgAaIuAaAuggUgUuAaCcsasg | 26<br>88 | X2-Linker |
| Z266 | NAG26 | AT3 | P<br>G | gsgsuuaaCaCCAuuuacuucaaX2n<br>usUsgIaguaaauGgUguuaaccsasg | 26<br>86 | X2-Linker |
| Z267 | NAG26 | AT3 | P<br>G | gsgsuuaaCaCCAuuuacuucaaX2n<br>usUsgaIguaaauGgUguuaaccsasg | 26<br>87 | X2-Linker |
| Z268 | NAG26 | AT3 | P<br>G | gsgsuuaaCaCCAuuuacuucaaX2n<br>usUsgaaIuaaauGgUguuaaccsasg | 26<br>88 | X2-Linker |
| Z269 | NAG26 | AT3 | P<br>G | gsgsuuaaCaCCAuuuacuucaaX2n<br>usUsgsIaguaaauGgUguuaaccsasg | 26<br>86 | X2-Linker |
| Z270 | NAG26 | AT3 | P<br>G | gsgsuuaaCaCCAuuuacuucaaX2n<br>usUsgIsaguaaauGgUguuaaccsasg | 26<br>86 | X2-Linker |
| Z271 | NAG26 | AT3 | P<br>G | gsgsuuaaCaCCAuuuacuucaaX2n<br>usUsgsIsaguaaauGgUuaaccsasg | 26<br>86 | X2-Linker |

TABLE 4-continued

| Compound # | Ligand | Target Strand | Sequences (5'-3') | SEQ ID NO: | Conjugation Linker |
|---|---|---|---|---|---|
| Z272 | NAG26 | AT3 | P<br>G | gsgsuuaacaccauuuacuucaaX2n<br>usUsgasIguaaauGgUgUuaaccsasg | 26<br>87 | X2-Linker |
| Z273 | NAG26 | AT3 | P<br>G | gsgsuuaaCaCcAuuuacuucaaX2n<br>usUsgasIsguaaauGgUgUuaaccsasg | 26<br>87 | X2-Linker |
| Z274 | NAG26 | AT3 | P<br>G | gsgsuuaaCaCcAuuuacuucaaX2n<br>usUsgasIsguaaauGgUgUuaaccsasg | 26<br>87 | X2-Linker |
| Z275 | NAG26 | AT3 | P<br>G | gsgsuuaaCaCcAuuuacuucaaX2n<br>usUsgaasIuaaauGgUgUuaaccsasg | 26<br>88 | X2-Linker |
| Z276 | NAG26 | AT3 | P<br>G | gggsuuaaCaCcAuuuacuucaaX2n<br>usUsgaaIsuaaauGgUgUuaaccsasg | 26<br>88 | X2-Linker |
| Z277 | NAG26 | AT3 | P<br>G | gsgsuuaaCaCcAuuuacuucaaX2n<br>usUsgaasIsuaaauGgUgUuaaccsasg | 26<br>88 | X2-Linker |

Figure 8A:
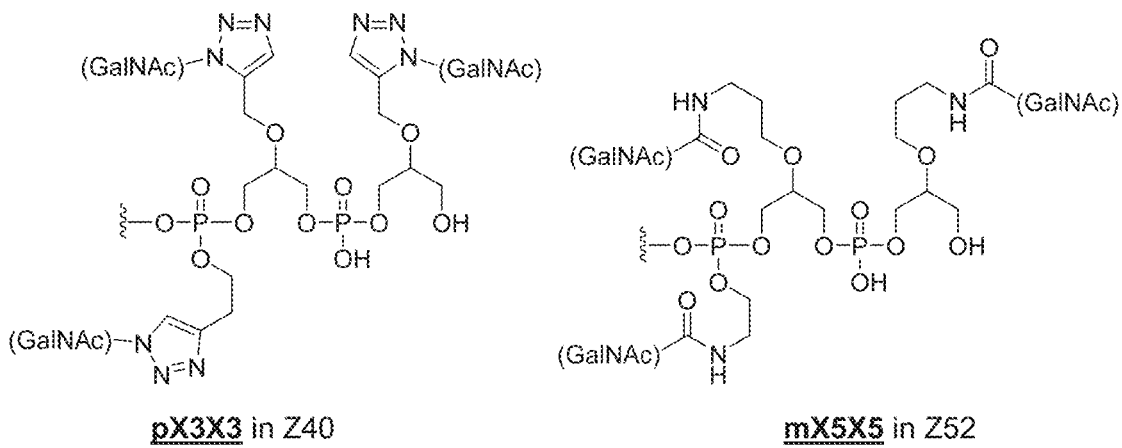
FIG. 8A is a chart showing the structures of the conjugation sites of the passenger strands in Z40, Z52, Z53, and Z54.
Figure 8A:
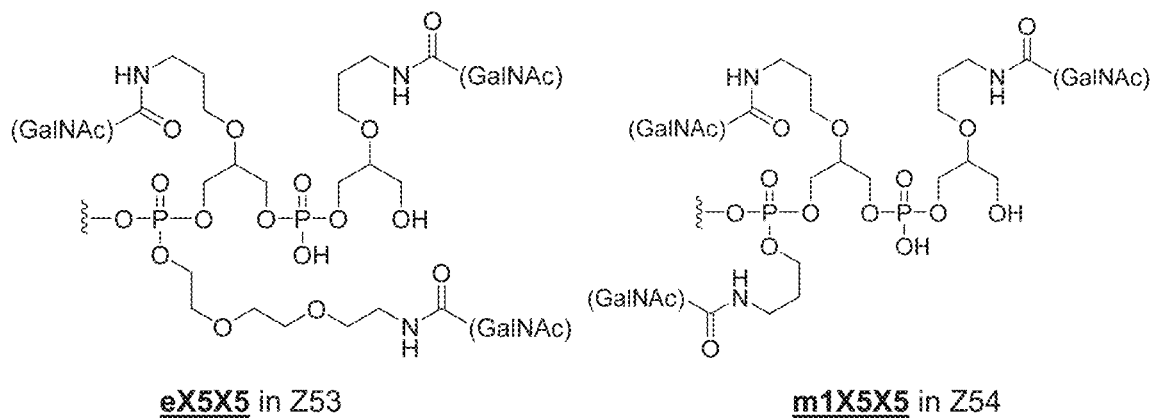
Figure 8A:
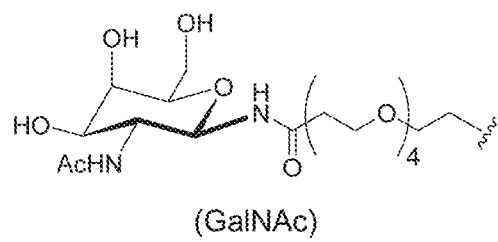
Figure 8B:
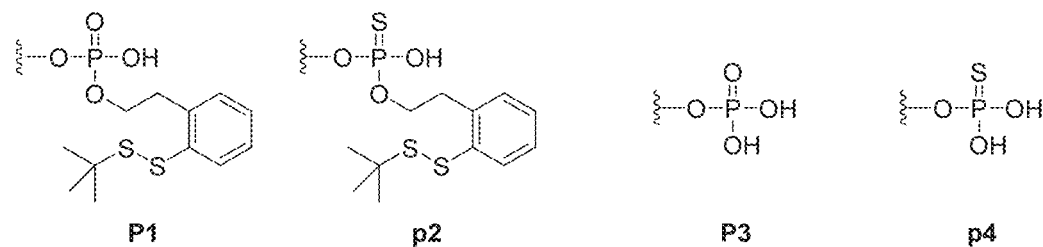
FIG. 8B is a chart showing the structures of P1, p2, P3, and p4, as well the structures of X1, X2, X3, X4, X5, and X2-$NH_2$ prior to ligand conjugation.
Figure 8B:
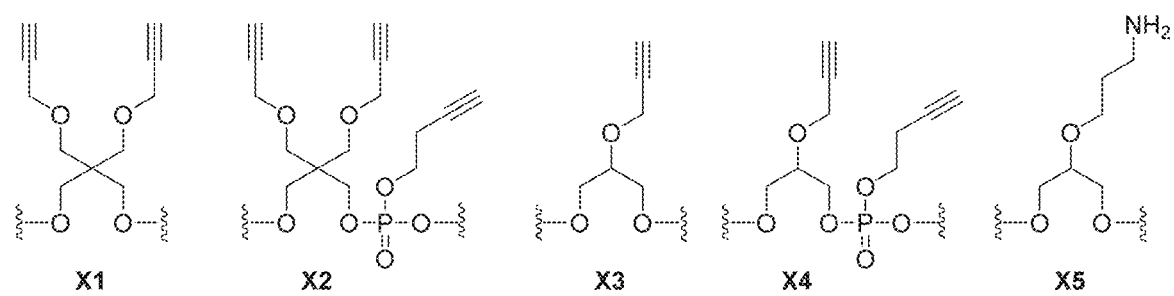
Figure 8B:
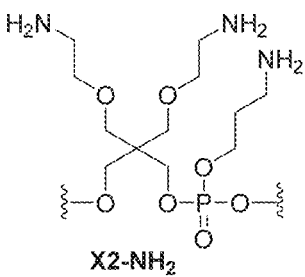
Figure 9:
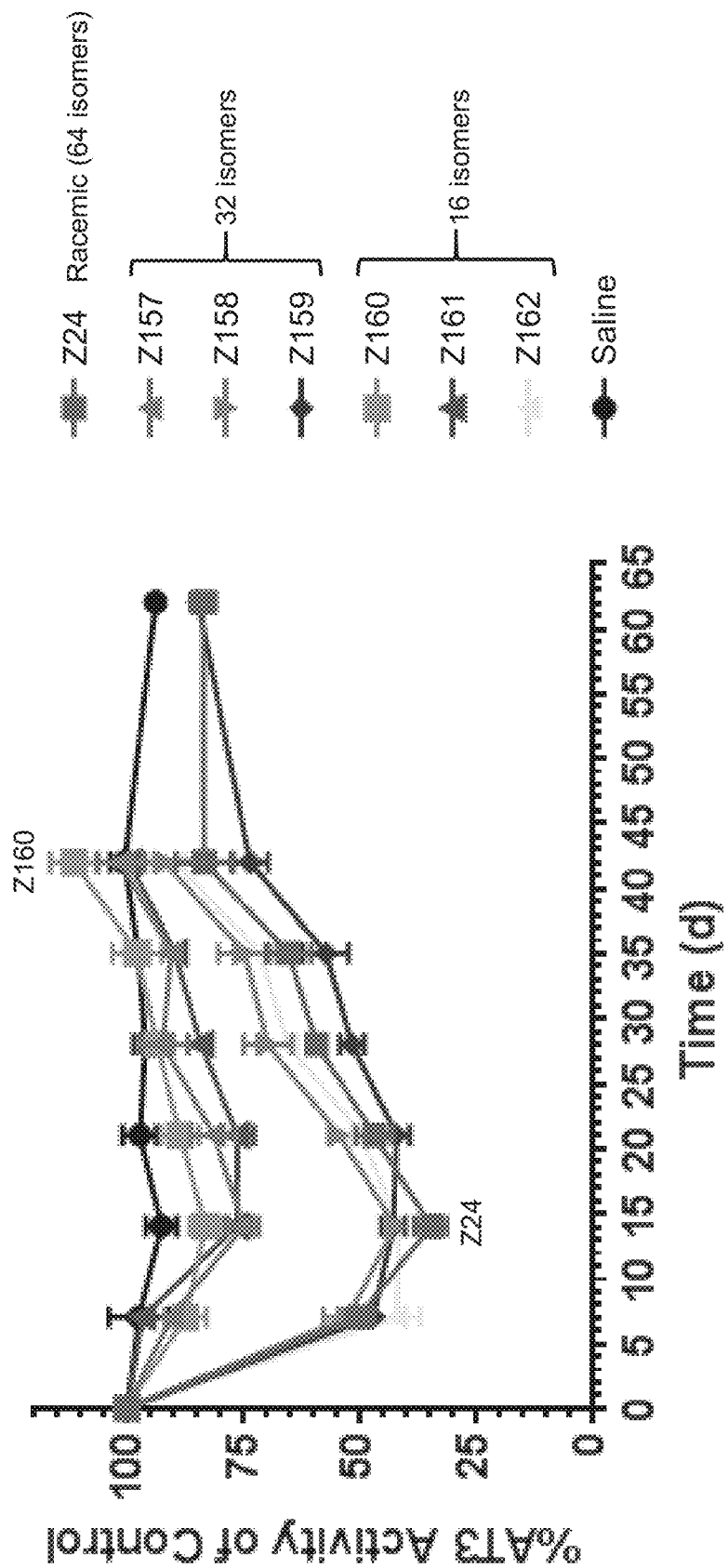
FIG. 9 is a chart showing AT3 activity in mice measured at predetermined time periods after a single 0.25 mg/kg subcutaneous dosing of the mice with the tested compositions.

In Table 4, UNDERLINE represents the conjugation site; UPPER CASE represents a 2'-fluoro-2'-deoxyribose; lower case represents a 2'-methoxy-2'-deoxyribose; p represents a homopropargyl phosphotriester; italics represents 2-(t-butyl-dithio)phenyl-ethyl phosphotriester; s represents phosphorothioate; n represents 3' C3-OH group; b represents n-butyl phosphotriester; e represents 2-aminoethyl-diethylene glycol phosphotriester; k represents 2-aminoethyl phosphotriester; k1 represents 2-aminopropyl phosphotriester; U represents uridine having a 3'-carbon bonded to 2-(t-butyl-dithio)phenyl-ethyl phosphotriester P represents phenethyl phosphotriester; R\* is Rp chiral internucleoside phosphorothioate; S\* is Sp chiral internucleoside phosphorothioate; I is 2'-OMe inosine nucleoside; the structures of P1, p2, P3, and p4 are shown in FIG. 8B; and the structures of X1, X2, X3, X4, X5, and X2-NH2 prior to ligand conjugation are shown in FIG. 8B.

Conjugation Methods
Click Reaction
Copper-THPTA Complex Preparation

A 5 mM aqueous solution of copper sulfate pentahydrate ($CuSO_4 \cdot 5H_2O$) and a 10 mM aqueous solution of tris(3-hydroxypropyltriazolylmethyl)amine (THPTA) were mixed 1:1 (v/v) (1:2 molar ratio) and allowed to stand at room temperature for 1 hour. This complex can be used to catalyze Huisgen cycloaddition, e.g., as shown in the general conjugation schemes below.

General Procedure (100 nM Scale):

To a solution of 710 µL of water and 100 µL tert-butanol (10% of final volume) in a 1.7 mL Eppendorf tube was added 60 µL of the copper-THPTA complex followed by 50 µL of a 2 mM solution of the oligo, 60 µL of a 20 mM aqueous sodium ascorbate solution and 20 µL of a 10 mM solution of GalNAc-azide. After thorough mixing the solution was allowed to stand at room temperature for 1 hour. Completion of the reaction was confirmed by gel analysis.

The reaction mixture was added to a screw cap vial containing 5-10 fold molar excess of SiliaMetS® TAAcONa (resin bound EDTA sodium salt). The mixture was stirred for 1 hour. This mixture was then eluted through an Illustra™ Nap™-10 column Sephadex™. The resulting solution was then frozen and lyophilized overnight.

Amidation

Conjugation through amidation may be performed under the amidation reaction conditions known in the art. See, e.g., Aaronson et al., Bioconjugate Chem. 22:1723-1728, 2011.

General Procedure (100 nmol Scale):

100 µL of a 1 mM stock solution of $X2-NH_2$ ssRNA in 50% acetonitrile were mixed with 9 µL of a 100 mM stock solution of GalNAc-PFP. Solution was diluted to 195 µL total volume with water, and 5 µL of diisopropylethylamine was added. Reaction was allowed to proceed at RT for 30 minutes followed by urea denaturing gel analysis and MALDI-TOF mass spectrometry to confirm complete conjugation. Once completion of the conjugation reaction was confirmed, 200 µL reaction solution was diluted to 1 mL with water and purified over Illustra™ NAP-10 column. The NAP-10 eluent was then frozen and lyophilized, followed by quantification and siRNA duplexing.

General Conjugation Schemes
Conjugation Through Click Reaction 1 where each of n and q is independently 0 or 1;

m is an integer from 0 to 5;

R is H or —$(CH_2)_3$—OH;

each R' is independently H or propargyl;

each R" is independently H or —$(CH_2)$-(1,2,3-triazol-1,4-diyl)-(Linker)-$(AM)_p$;

each $R^A$ is H or propargyl, provided that at least one $R^A$ is propargyl;

each $R^B$ is H or —$(CH_2)$-(1,2,3-triazol-1,4-diyl)-(Linker)-$(AM)_p$;

each AM is independently an auxiliary moiety (e.g., GalNAc or Mannose);

each p is independently an integer from 1 to 6; and each Linker is independently a multivalent linker (e.g., -$Q^2([-Q^3-Q^4-Q^5]_s-Q^6-T)_p$, where $Q^2$ is a linear group (e.g., $[-Q^3-Q^4-Q^5]_s-$), if p is 1, or a branched group (e.g., $[-Q^3-Q^4-Q^5]_s-Q^7([-Q^3-Q^4-Q^5]_s-(Q^7)_{p1})_{p2}$, where p1 is 0 or 1, p2 is 0, 1, 2, or 3), if p is an integer from 2 to 6;

each $Q^3$ and $Q^6$ is independently absent, —CO—, —NH—, —O—, —S—, —OC(O)—, —COO—, —NHC(O)—, —C(O)NH—, —$CH_2$—, —$CH_2NH$—, —$NHCH_2$—, —$CH_2O$—, or —$OCH_2$—;

each $Q^4$ is independently absent, optionally substituted $C_{1-12}$ alkylene, optionally substituted $C_{2-12}$ alkenylene, optionally substituted $C_{2-12}$ alkynylene, or optionally substituted $C_{2-12}$ heteroalkylene;

each $Q^5$ is independently absent, —CO—, —NH—, —O—, —S—, —$CH_2$—, —C(O)O—, —OC(O)—, —C(O)NH—, —NH—C(O)—, —NH—$CH(R^a)$—C(O)—, or —C(O)—$CH(R^a)$—NH—; and each $R^a$ is independently H or an amino acid side chain).

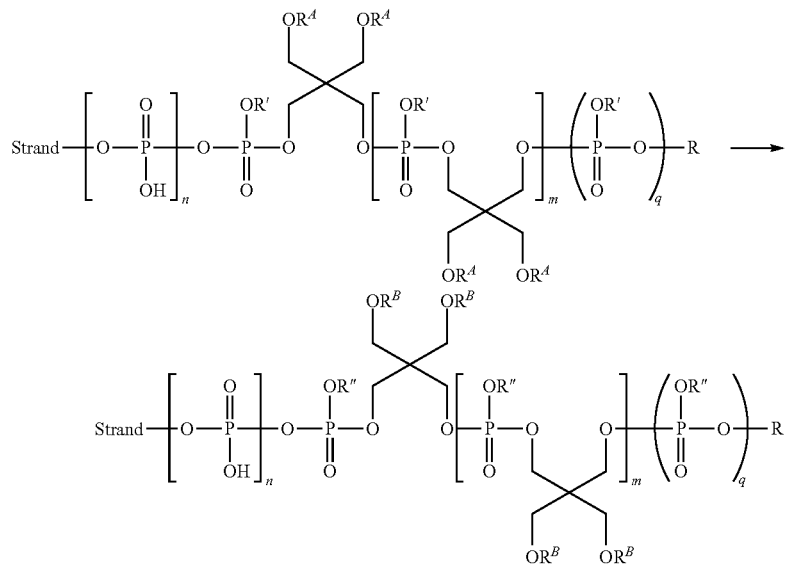

Conjugation Through Click Reaction 2

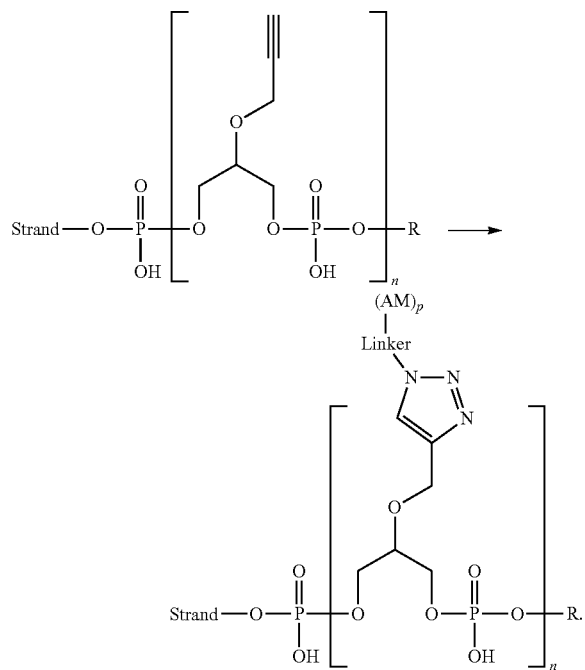

where
n is an integer from 1 to 6;
each p is independently an integer from 1 to 6;
each AM is independently an auxiliary moiety (e.g., a targeting moiety (e.g., GalNAc or mannose));
R is H or —$(CH_2)_3$—OH; and
each Linker is independently a multivalent linker (e.g., -$Q^2([-Q^3-Q^4-Q^5]_s-Q^6-T)_p$, where
$Q^2$ is a linear group (e.g., $[-Q^3-Q^4-Q^5]_s-$), if p is 1, or a branched group (e.g., $[-Q^3-Q^4-Q^5]_s-Q^7([-Q^3-Q^4-Q^5]_s-(Q^7)_{p1})_{p2}$, where p1 is 0 or 1, p2 is 0, 1, 2, or 3), if p is an integer from 2 to 6; each s is independently an integer from 0 to 20, where the repeating units are same or different;
each $Q^3$ and $Q^6$ is independently absent, —CO—, —NH—, —O—, —S—, —OC(O)—, —COO—, —NHC(O)—, —C(O)NH—, —$CH_2$—, —$CH_2NH$—, —$NHCH_2$—, —$CH_2O$—, or —$OCH_2$—;
each $Q^4$ is independently absent, optionally substituted $C_{1-12}$ alkylene, optionally substituted $C_{2-12}$ alkenylene, optionally substituted $C_{2-12}$ alkynylene, or optionally substituted $C_{2-12}$ heteroalkylene;
each $Q^5$ is independently absent, —CO—, —NH—, —O—, —S—, —$CH_2$—, —C(O)O—, —OC(O)—, —C(O)NH—, —NH—C(O)—, —NH—CH($R^a$)—C(O)—, or —C(O)—CH($R^a$)—NH—; and
each $R^a$ is independently H or an amino acid side chain; provided that at least one of $Q^3$, $Q^4$, and $Q^5$ is present).

Conjugation Through Amidation 1

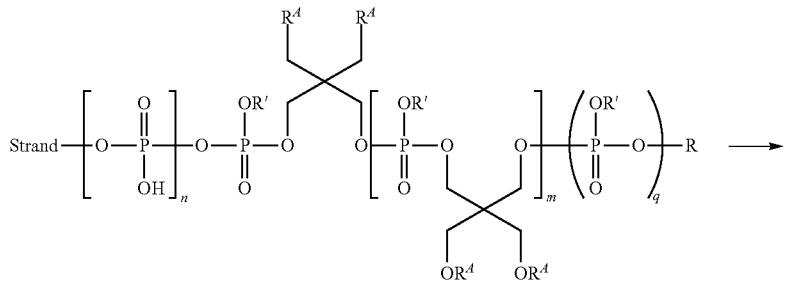

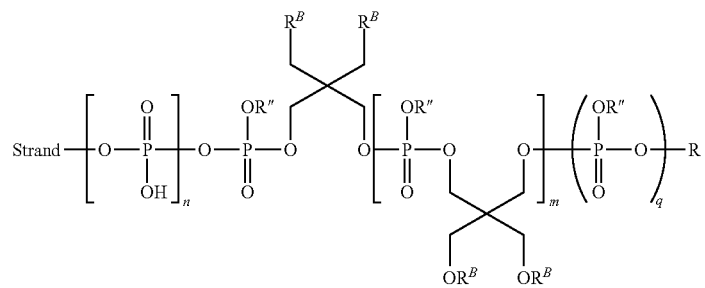

where each of n and q is independently 0 or 1;

m is an integer from 0 to 5;

R is H, —(CH$_2$)$_3$—OH, or —(CH$_2$)$_3$—O-Sol, where Sol is solid support;

each R' is independently H or -(Linker1)-NHR$^{PG}$;

each R" is independently H or -(Linker1)-NH—C(O)-(Linker)-(AM)$_q$;

each R$^A$ is H or -(Linker1)-NHR$^{PG}$, provided that at least one R$^A$ is -(Linker1)-NHR$^{PG}$;

each R$^B$ is H or -(Linker1)-NH—C(O)-(Linker)-(AM)$_q$;

each R$^{PG}$ is independently H or an N-protecting group;

each AM is independently an auxiliary moiety (e.g., GalNAc or mannose);

each p is independently an integer from 1 to 6;

each Linker is independently a multivalent linker (e.g., -Q$^2$([-Q$^3$-Q$^4$-Q$^5$]$_s$-Q$^6$-T)$_p$, where Q$^2$ is a linear group (e.g., [-Q$^3$-Q$^4$-Q$^5$]$_s$-), if p is 1, or a branched group (e.g., [-Q$^3$-Q$^4$-Q$^5$]$_s$-Q$^7$([-Q$^3$-Q$^4$-Q$^5$]$_s$-(Q$^7$)$_{p1}$)$_{p2}$, where p1 is 0 or 1, p2 is 0, 1, 2, or 3), if p is an integer from 2 to 6; each s is independently an integer from 0 to 20, where the repeating units are same or different;

each Q$^3$ and each Q$^6$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—;

each Q$^4$ is independently absent, optionally substituted C$_{1-12}$ alkylene, optionally substituted C$_{2-12}$ alkenylene, optionally substituted C$_{2-12}$ alkynylene, optionally substituted C$_{2-12}$ heteroalkylene, or optionally substituted C$_{1-9}$ heterocyclylene;

each Q$^5$ is independently absent, —CO—, —NH—, —O—, —S—, —SO$_2$—, —CH$_2$—, —C(O)O—, —OC(O)—, —C(O)NH—, —NH—C(O)—, —NH—CH(R$^a$)—C(O)—, or —C(O)—CH(R$^a$)—NH—; and each R$^a$ is independently H or an amino acid side chain;

provided that at least one of Q$^3$, Q$^4$, and Q$^5$ is present);

and each Linker1 is [-Q$^3$-Q$^4$-Q$^5$]$_s$-, provided that at least one of Q$^3$, Q$^4$, and Q$^5$ is present.

Conjugation Through Amidation 1

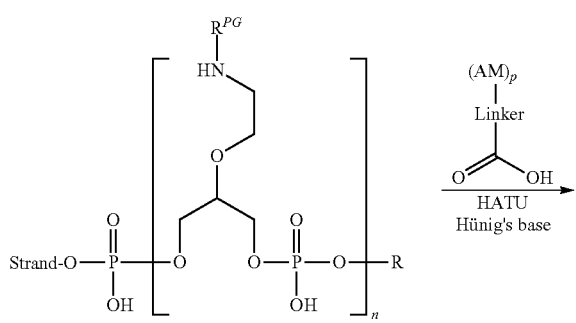

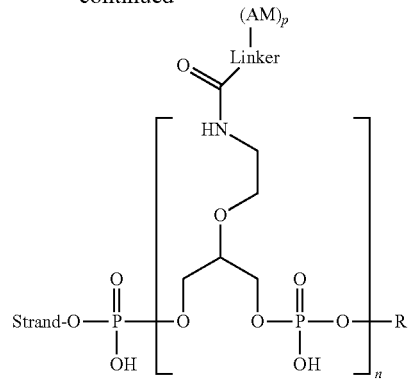

where n is an integer from 1 to 6;

each p is independently an integer from 1 to 6;

R$^{PG}$ is H or N-protecting group (e.g., Fmoc), where all R$^{PG}$ groups are replaced with —C(O)-(Linker)-(AM)$_p$;

R is H, —(CH$_2$)$_3$—OH, or —(CH$_2$)$_3$—O-Sol, where Sol is solid support;

each AM is independently an auxiliary moiety (e.g., GalNAc or mannose); and each Linker is independently a multivalent linker (e.g., -Q$^2$([-Q$^3$-Q$^4$-Q$^5$]$_s$-Q$^6$-T)$_p$, where Q$^2$ is a linear group (e.g., [-Q$^3$-Q$^4$-Q$^5$]$_s$-), if p is 1, or a branched group (e.g., [-Q$^3$-Q$^4$-Q$^5$]$_s$-Q$^7$([-Q$^3$-Q$^4$-Q$^5$]$_s$-(Q$^7$)$_{p1}$)$_{p2}$, where p1 is 0 or 1, p2 is 0, 1, 2, or 3), if p is an integer from 2 to 6; each s is independently an integer from 0 to 20, where the repeating units are same or different;

each Q$^3$ and each Q$^6$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—;

each Q$^4$ is independently absent, optionally substituted C$_{1-12}$ alkylene, optionally substituted C$_{2-12}$ alkenylene, optionally substituted C$_{2-12}$ alkynylene, optionally substituted C$_{2-12}$ heteroalkylene, or optionally substituted C$_{1-9}$ heterocyclylene;

each Q$^5$ is independently absent, —CO—, —NH—, —O—, —S—, —SO$_2$—, —CH$_2$—, —C(O)O—, —OC(O)—, —C(O)NH—, —NH—C(O)—, —NH—CH(R$^a$)—C(O)—, or —C(O)—CH(R$^a$)—NH—; and each R$^a$ is independently H or an amino acid side chain).

Conjugation through amidation may be performed both in solution phase and on solid support. When R$^{PG}$ is an N-protecting group (e.g., Fmoc), the protected amine may be treated with an N-protecting group removing agent known in the art for the deprotection of the N-protecting group that is R$^{PG}$ to give an intermediate, in which R$^{PG}$ is H.

The auxiliary moiety can be GalNAc. The bonding between GalNAc and Linker may be through the anomeric carbon atom of GalNAc. In particular, the anomeric carbon atom of GalNAc along with the cyclic oxygen atom can be a part of a hemiaminal (e.g., when the anomeric carbon atom of GalNAc is bonded to the nitrogen atom of an amide functional group present in the Linker).

GalNAc-Linker-COOH may have the following structure:

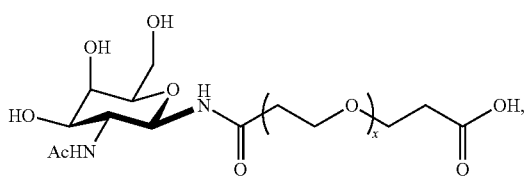

where x is an integer from 0 to 20 (e.g., x is an integer from 0 to 10 or from 2 to 10 (e.g., x is 2, 4, 6, or 8)).

In another exemplary conjugation through amidation a PFP ester, e.g., NAG40 may be conjugated to the conjugation moiety in a polynucleotide construct of the invention.

Example 3. Experiments Assessing the in Vitro and in Vivo Activity of the Hybridized Polynucleotide Constructs In Vitro Experiments Primary mouse hepatocytes were isolated using the standard two-step collagenase perfusion technique (Li et. al. *Methods Mol. Biol.*, 633:185-196; 2010). Briefly, a 6-10 week old female $C_{57}$/B16 mouse was anesthetized by intraperitoneal injection of a mixture of ketamine (80-100 mg/kg)/xylazine (5-10 mg/kg). The abdominal cavity was then exposed, and the visceral vena cava was cannulated using a 22 G needle. The hepatic vein was severed, and the liver was immediately perfused for 5-10 min using a solution of phosphate-buffered saline (PBS) containing 0.5 mM ETDA. This solution was immediately switched to a solution of collagenase (100 IU/mL) in Dulbecco's Modified Eagle's Medium (DMEM, Gibco) for another 5-10 min. At the end of perfusion, the liver was removed, and the hepatocytes were collected in DMEM containing 10% fetal bovine serum at 4° C. The cells were then filtered through a 70 μm sterile filter, washed three times in the same solution, and cell viability was assessed using Trypan Blue staining. Cells were then seeded in 96-well plates coated with 0.1% rat tail collagen or 2% matrigel and incubated for 3-4 hours at 37° C. in a 5% $CO_2$ incubator. Test compounds were then added to cells and incubated at 37° C. in a 5% $CO_2$ incubator. At the end of the incubation period, the cells were lysed, the mRNA was isolated, and the expression of the target gene was measured by qPCR and normalized to a house-keeping gene using standard protocols. The data for this experiment are in Table 5.

Transfection Experiment

To assess the in vitro activity of siRNA duplexes, the indicated cell types were grown in recommended media conditions (i.e. DMEM or similar media supplemented with 10% fetal bovine serum (FBS), 100 μg/ml of streptomycin, and 100 U/ml of penicillin) at 37° C. under 5% $CO_2$. Prior to transfection, cells were plated in 96-well microtiter plates at a density of $1 \times 10^4$ cells per well and allowed to adhere overnight. Cells were treated with siRNA packaged and delivered by Lipofectamine RNAiMax (Life Technologies) according to manufacturer's recommendations at concentration of 100 nM in full-log descending dose response. At the end of the incubation period, the cells were lysed, the mRNA was isolated, and the expression of the target gene was measured by qPCR and normalized to a house-keeping gene using standard protocols. The data for this experiment are in Table 8.

Free-Uptake Experiment

Primary non-human hepatocytes from Bioreclamation-IVT were thawed and plated on collagen-coated 96-well plates at a density of 70,000 cells per well and allowed to adhere for 4 hours at 37° C. in a 5% $CO_2$ incubator. After 4 hours, hepatocytes were treated with conjugated siRNA in the absence of transfection reagents (free uptake). Cells were treated with compound concentrations starting at 1 μM with a full-log descending dilution. At the end of the incubation period, the cells were lysed, the mRNA was isolated, and the expression of the target gene was measured by qPCR and normalized to a house-keeping gene using standard protocols. The data for this experiment are in Tables 6 and 8.

In Vivo Experiments

Test compounds were administered to female C57B16 mice via either subcutaneous or intravenous (lateral tail vein) injection (200 μL; 3 mice/treatment). At the appropriate time point post injection, mice were sacrificed and blood samples were collected by cardiac puncture. Approximately 50-100 mg piece of liver sample was collected and was immediately frozen in liquid nitrogen. Total mRNA was isolated from liver homogenates using standard protocols and the expression of target gene was quantitated by qPCR and normalized to a house-keeping gene using standard protocols.

In another format, blood was collected from mice at different time points post-dosing using sodium citrate as an anticoagulant. Plasma AT3 protein was measured using a commercially available chromogenic assay that assesses the heparin cofactor activity of AT3 using an anti-factor Xa method.

The in vitro and in vivo experimental results are provided in FIGS. 1-7 and 9-20 and in Tables 5-8.

TABLE 5

| Compound # | Target | In vitro primary mouse hepatocytes (IC50, nM) | In vivo activity; Remaining AT3/TTR plasma activity as % vehicle control Mean (SEM) | | | Dose |
|---|---|---|---|---|---|---|
| | | | Day 7 | Day 21 | Day 35 | |
| Z1 | AT3 | 0.36 | 37.2 (2.3) | | | 0.5 mg/kg, day 0 |
| Z2 | AT3 | 1.57 | 29.8 (4.3) | | | |
| Z3 | AT3 | 1.62 | 31.1 (1.0) | | | |
| Z4 | AT3 | 0.33 | 33.3 (3.7) | | | |
| Z5 | TTR | 0.002 | 33.4 (2.1) | 60.6 (3.1) | 85.5 (4.8) | 0.5 mg/kg, day 0 |
| Z6 | TTR | 0.006 | 16.6 (2.1) | 41.9 (4.2) | 71.9 (0.4) | |
| Z7 | TTR | 0.04 | 34.9 (3) | 81.1 (3.5) | 85.6 (8.1) | |
| Z9 | TTR | 0.04 | 32.0 (2.3) | 58.9 (3.9) | 86.8 (7.5) | |
| Z10 | TTR | 0.07 | 21.6 (3.6) | 43.5 (4.0) | 76.6 (9.1) | 0.5 mg/kg, day0 |
| Z11 | TTR | 0.02 | 18.3 (1.4) | 46.6 (3.6) | 74.7 (5.5) | |

TABLE 5-continued

| Compound # | Target | In vitro primary mouse hepatocytes (IC50, nM) | In vivo activity; Remaining AT3/TTR plasma activity as % vehicle control Mean (SEM) | | | Dose |
|---|---|---|---|---|---|---|
| | | | Day 7 | Day 21 | Day 35 | |
| Z12 | TTR | 0.08 | 23.6 (1.9) | 49.4 (2.0) | 84.9 (2.0) | |
| Z13 | TTR | 0.1 | 16.4 (1.8) | 56.4 (5.8) | 85.9 (5.9) | |
| Z14 | TTR | 0.17 | 14.3 (1.2) | 42.7 (6.1) | 77.5 (3.1) | |
| Z15 | TTR | 0.06 | 11.9 (2.4) | 23.8 (10.1) | 59.9 (8.3) | |
| Z16 | TTR | 0.04 | 15.7 (2.8) | 27.3 (6.6) | 68.0 (9.4) | |
| Z17 | TTR | 0.17 | 7.4 (0.4) | 10.6 (0.4) | 37.3 (3.2) | |
| Z18 | TTR | 0.1 | 9.5 (0.5) | 16.6 (1.0) | 52.4 (3.7) | |
| Z19 | TTR | 0.1 | 9.1 (2.9) | 10.5 (0.1) | 46.9 (4.3) | |
| Z20 | AT3 | 1.5 | 43.2 (0.7) | 37.0 (1.3) | 53.9 (2.8) | 0.4 mg/kg, day 0 |
| Z21 | AT3 | 0.4 | 37.5 (1.2) | 25.0 (0.7) | 36.9 (3.0) | |
| Z22 | AT3 | 1.8 | 41.6 (1.1) | 32.7 (1.3) | 41.1 (3.2) | |
| Z23 | AT3 | 2.8 | 40.1 (0.9) | 25.3 (3.1) | 38.6 (2.8) | |
| Z24 | AT3 | 2.9 | 29.5 (3.7) | 24.2 (1.2) | 39.8 (4.1) | |
| Z25 | AT3 | 1 | 45.7 (5.0) | 29.6 (3.3) | 37.2 (3.7) | |
| Z26 | AT3 | 0.7 | 43.5 (4.1) | 26.4 (3.9) | 35.2 (1.8) | |
| Z27 | AT3 | 1.9 | 36.6 (1.4) | 26.1 (3.2) | 40.8 (4.5) | |
| Z28 | AT3 | 4.5 | 36.4 (0.7) | 21.4 (1.1) | 29.7 (2.3) | |
| Z29 | AT3 | 4.6 | 39.2 (1.0) | 28.0 (3.6) | 30.8 (1.7) | |
| Z30 | TTR | 0.1 | 17.7 (1.2) | 28.0 (3.6) | 56.0 (10.7) | 0.5 mg/kg, day 0 |
| Z31 | TTR | 0.9 | 23.9 (1.6) | 42.1 (3.8) | 62.8 (5.6) | |
| Z32 | TTR | 1.6 | 15.0 (1.9) | 24.6 (2.7) | 62.0 (7.3) | |
| Z38 | AT3 | — | 56.9 (2.3) | 70.0 (2.9) | 96.3 (2.1) | 0.5 mg/kg, day 0 |
| Z39 | AT3 | 4.9 | 27.8 (2.2) | 30.6 (1.8) | | |
| Z40 | AT3 | 4.5 | 18.6 (3.6) | 16.1 (1.5) | | |
| Z41 | AT3 | 2.2 | 27.6 (2.1) | 23.8 (2.3) | | |
| Z42 | AT3 | 1.3 | 34.8 (1.4) | 36.3 (4.0) | | |
| Z43 | AT3 | 3.7 | 32.3 (3.4) | 42.7 (2.9) | | |
| Z44 | AT3 | 3.7 | 31.1 (3.8) | 26.5 (3.2) | | |
| Z45 | AT3 | 5.8 | 19.1 (1.7) | | | |
| Z46 | AT3 | 3 | 21.1 (0.9) | | | |
| Z47 | TTR | 0.06 | 11.2 (3.5) | | | |
| Z48 | TTR | 0.1 | 11.9 (0.5) | | | |
| Z49 | TTR | 0.1 | 17.4 (4.3) | | | |
| Z50 | TTR | 0.1 | 10.4 (1.5) | | | |
| Z51 | TTR | 0.1 | 12.8 (1.1) | | | |
| Z52 | AT3 | | 84.3 (5.5) | 90.7 (5.5) | | |
| Z53 | AT3 | | 65.5 (0.6) | 64.9 (1.5) | | |
| Z54 | AT3 | | 46.1 | 49 | | 0.25 mg/kg, day 0 |
| Z55 | AT3 | | 75.7 | 79.6 | | 0.25 mg/kg, day 0 |
| Z56 | AT3 | | 67.2 | 68.3 | | |
| Z57 | AT3 | | 80.3 | 92.7 | | |
| Z58 | AT3 | | 80.1 | 83.6 | | |
| Z59 | AT3 | | 95.7 | 88.3 | | |
| Z60 | AT3 | | 90.9 | 89.7 | | |
| Z61 | AT3 | | 67.1 | 79.2 | | |
| Z62 | AT3 | | 61.2 | 65 | | |
| Z63 | AT3 | | 70.9 | 71.8 | | |
| Z64 | AT3 | | | 38.7 (5.7) | 50.3 (7.6) | 0.25 mg/kg, day 0 |
| Z65 | AT3 | | | 36.2 (3.5) | 49.9 (3.3) | |
| Z66 | AT3 | | | 50.1 (0.6) | 69.6 (2.2) | |
| Z67 | TTR | | | | | |
| Z68 | AT3 | | 50.2 (3.6) | 51.9 (2.8) | 67.2 (3.2) | 0.25 mg/kg, day 0 |
| Z69 | AT3 | | 86 (5.0) | 82.1 (0.8) | 89.3 (3.7) | |
| Z70 | AT3 | | 57.9 (0.2) | 54.6 (2.8) | 62.9 (3.4) | |
| Z71 | AT3 | | 52.3 (6.2) | 49.6 (3.1) | 66 (5.8) | |
| Z72 | AT3 | 7.9 | | | | |
| Z73 | AT3 | >1000 | | | | |
| Z74 | AT3 | >1000 | | | | |
| Z75 | AT3 | >1000 | | | | |
| Z76 | AT3 | >1000 | | | | |
| Z77 | AT3 | | 79.5 (1.2) | 79.4 (2.1) | | 0.25 mg/kg, day 0 |
| Z78 | AT3 | | 76 (6.3) | 63.9 (5.0) | | |
| Z79 | AT3 | | 85.8 (6.3) | 72.1 (5.5) | | |
| Z80 | AT3 | | 89 (4.8) | 74.8 (1.9) | | |
| Z81 | AT3 | | 79.6 (2.9) | 70.5 (2.5) | | |
| Z82 | AT3 | | 90.1 (3.1) | 74.7 (0.6) | | |
| Z83 | AT3 | | 87.7 (4.3) | 80.9 (6.0) | | |
| Z84 | AT3 | | 72.1 (6.7) | 63.8 (11.2) | | |
| Z85 | AT3 | | 43.2 (3.1) | 54.3 (1.5) | 66.7 (1.2) | 0.25 mg/kg, day 0 |
| Z86 | AT3 | | 59.8 (5.3) | 61.8 (3.5) | 59.3 (8.5) | |
| Z87 | AT3 | | 61.8 (1.9) | 87.6 (5.0) | | |
| Z88 | AT3 | | 82.5 (0.9) | 89.9 (2.8) | | |

TABLE 5-continued

| Compound # | Target | In vitro primary mouse hepatocytes (IC50, nM) | In vivo activity; Remaining AT3/TTR plasma activity as % vehicle control Mean (SEM) | | | Dose |
|---|---|---|---|---|---|---|
| | | | Day 7 | Day 21 | Day 35 | |
| Z89 | AT3 | | 44.2 (2.8) | 46.8 (6.7) | 64.7 (3.5) | |
| Z90 | AT3 | 4.5 | 42.9 (3.5) | 41.7 (2.2) | 52.2 (3.8) | |
| Z91 | AT3 | | 60.2 (2.6) | 74.8 (2.2) | | 0.25 mg/kg, day 0 |
| Z92 | AT3 | | 52.6 (3.2) | 51.7 (3.0) | | |
| Z93 | AT3 | 4 | 71.3 (2.7) | 72.8 (0.6) | | |
| Z94 | AT3 | 1.6 | 62.3 (0.3) | 63.7 (1.1) | | |
| Z95 | AT3 | 1.1 | 75.2 (1.9) | 80.4 (1.8) | | |
| Z96 | AT3 | 3.3 | 81.4 (5.5) | 94.2 (1.2) | | |
| Z97 | AT3 | 1.7 | 101.3 (2.0) | 102.6 (3.6) | | |
| Z98 | AT3 | | 36.9 (4.7) | 23.5 (1.8) | | 0.25 mg/kg, day 0 |
| Z99 | AT3 | | 45.1 (2.1) | 32.8 (1.6) | | |
| Z100 | AT3 | | 41.8 (1.1) | 33.9 (3.2) | | |
| Z101 | AT3 | | 68.3 (5.8) | 67.1 (3.6) | | |
| Z102 | AT3 | | 74.4 (3.1) | 73.0 (2.4) | | |
| Z103 | AT3 | | 91.4 (1.5) | 95.0 (3.2) | | |
| Z104 | AT3 | | 43.6 (2.5) | 43.3 (1.8) | 45.0 (5.5) | 0.25 mg/kg, day 0 |
| Z105 | AT3 | | 32.2 (3.4) | 42.3 (3.1) | 49.1 (5.7) | |
| Z106 | AT3 | | | | | |
| Z107 | AT3 | | 51.3 (3.5) | 49.9 (1.5) | 55.3 (1.8) | |
| Z108 | AT3 | | 45.8 (4.7) | 38.9 (4.1) | 49.5 (2.1) | |
| Z109 | AT3 | | 37.5 (1.2) | 37.0 (3.2) | 52.6 (4.4) | |
| Z110 | AT3 | | 32.9 (0.7) | 38.9 (2.4) | 50.6 (1.5) | |
| Z111 | AT3 | | 48.8 (1.6) | 57.6 (2.0) | 79.6 (1.9) | |
| Z112 | AT3 | | 42.6 (6.1) | 40.8 (7.2) | 50.4 (6.6) | |
| Z113 | AT3 | | 44.1 (3.4) | 44.1 (3.4) | 58.8 (2.4) | |
| Z114 | AT3 | | 42.9 (4.5) | 56.1 (4.1) | 64.3 (4.2) | |
| Z115 | AT3 | | 101.5 (2.0) | | | 0.25 mg/kg, day 0 |
| Z116 | AT3 | | 93.2 (6.7) | | | |
| Z117 | AT3 | | 116.1 (5.0) | | | |
| Z118 | AT3 | | 107.0 (8.8) | | | |
| Z119 | AT3 | | 82.0 (6.6) | | | |
| Z120 | AT3 | | 59.2 (2.7) | | | |
| Z121 | AT3 | | 70.7 (4.0) | | | |
| Z122 | AT3 | | | | | |
| Z123 | AT3 | | 101.3 (9.6) | | | |
| Z124 | AT3 | | 115.4 (1.2) | | | |
| Z125 | AT3 | | 87.8 (8.6) | | | |
| Z126 | AT3 | | 60.0 (4.7) | | | |
| Z127 | AT3 | | 88.3 (7.7) | | | |
| Z128 | AT3 | | 87.2 (2.9) | | | |
| Z129 | AT3 | | 96.1 (4.9) | | | |
| Z130 | AT3 | | 117.8 (4.1) | | | |
| Z131 | AT3 | | 108.0 (3.6) | | | |
| Z132 | AT3 | | 115.9 (4.0) | | | |
| Z133 | AT3 | | 106.6 (4.0) | | | |

TABLE 6

| | In Vitro, Free-Uptake Murine Hepatocytes (% Remaining AT3 Expression) | | |
|---|---|---|---|
| Compound # | 1 nM | 3.3 nM | 10 nM |
| Z24 | 77.8 | 38.2 | 15.0 |
| Z144 | 100.8 | 107.9 | 27.0 |
| Z145 | 103.5 | 55.1 | 26.5 |
| Z146 | 105.1 | 64.8 | 34.5 |
| Z147 | 89.6 | 62.4 | 27.2 |
| Z148 | 99.5 | 62.8 | 32.5 |
| Z149 | 100.7 | 92.5 | 64.0 |
| Z150 | 96.4 | 60.6 | 22.0 |
| Z151 | 88.6 | 52.8 | 20.2 |
| Z152 | 87.5 | 43.3 | 16.0 |
| Z153 | 105.1 | 73.2 | 30.8 |
| Z154 | 79.4 | 43.2 | 16.7 |
| Z155 | 113.8 | 86.7 | 48.2 |
| Z156 | 108.2 | 75.9 | 41.8 |
| Z157 | 67.5 | 28.7 | 11.4 |
| Z158 | 109.3 | 75.8 | 38.7 |
| Z159 | 103.9 | 61.6 | 32.8 |
| Z160 | 103.0 | 74.2 | 33.6 |
| Z161 | 106.1 | 54.8 | 24.8 |
| Z162 | 98.2 | 62.3 | 32.0 |
| Z163 | 62.9 | 27.9 | 12.8 |
| Z164 | 124.8 | 135.0 | 124.8 |
| Z165 | 133.1 | 104.1 | 67.0 |
| Z166 | 121.2 | 100.6 | 73.1 |
| Z167 | 91.0 | 50.3 | 22.7 |
| Z168 | 88.1 | 44.0 | 18.0 |
| Z169 | 60.8 | 25.9 | 11.4 |
| Z170 | 99.3 | 60.4 | 28.1 |
| Z171 | 141.2 | 137.8 | 97.5 |
| Z172 | 98.6 | 57.3 | 33.6 |
| Z174 | 98.1 | 47.6 | 24.1 |
| Z175 | 81.1 | 43.9 | 19.3 |
| Z176 | 78.8 | 49.1 | 27.7 |
| Z178 | 63.7 | 30.1 | 18.9 |

TABLE 6-continued

In Vitro, Free-Uptake Murine Hepatocytes
(% Remaining AT3 Expression)

| Compound # | 1 nM | 3.3 nM | 10 nM |
|---|---|---|---|
| Z182 | 67.7 | 29.8 | 18.2 |
| Z187 | 93.9 | 52.3 | 26.0 |
| Z194 | 57.1 | 26.5 | 15.7 |
| Z196 | 104.5 | 63.7 | 30.0 |
| Z198 | 91.7 | 50.2 | 24.9 |
| Z199 | 90.7 | 48.1 | 21.8 |
| Z200 | 92.0 | 55.2 | 31.4 |
| Z202 | 59.1 | 25.7 | 12.4 |
| Z206 | 48.2 | 18.6 | 9.6 |
| Z209 | 66.8 | 39.5 | 23.0 |
| Z210 | 63.7 | 34.9 | 20.7 |
| Z211 | 64.1 | 37.5 | 21.4 |
| Z212 | 68.0 | 36.1 | 22.6 |
| Z214 | 43.0 | 25.0 | 14.4 |
| Z218 | 42.0 | 20.2 | 14.5 |
| Z184 | 92.8 | 68.4 | 38.8 |
| Z186 | 94.2 | 57.0 | 32.7 |
| Z188 | 93.5 | 62.7 | 35.8 |
| Z190 | 93.9 | 55.1 | 23.6 |

TABLE 7

| Compound # | Phosphorothioate Stereochemical Identity | | | | | | In Vivo, 0.25 mg/kg Single Dose Mouse Studies (% Remaining AT3 Expression) | | | | | | | |
|---|---|---|---|---|---|---|---|---|---|---|---|---|---|---|
| | P1 | P2 | G22 | G21 | G2 | G1 | Day 7 | Day 14 | Day 21 | Day 28 | Day 35 | Day 42 | Day 49 | Day 56 | Day 63 |
| Z24 | R/S | R/S | R/S | R/S | R/S | R/S | 49.7 | 43.8 | 50.9 | 62.5 | 64.7 | ND | 81.8 | x | x |
| Z144 | R/S | R/S | R/S | R/S | R/S | R | 50.6 | 49.9 | 55.8 | 64.1 | 65.8 | ND | 79.0 | x | x |
| Z145 | R/S | R/S | R/S | R/S | R | R | 45.9 | 54.9 | 52.1 | 57.7 | 70.8 | ND | 88.7 | x | x |
| Z146 | R/S | R/S | R/S | R/S | R/S | S | 90.6 | 75.0 | 81.3 | 92.4 | 90.6 | 101.3 | x | x | x |
| Z147 | R/S | R/S | R/S | R/S | S | R/S | 52.5 | 42.3 | 54.5 | 69.8 | 74.8 | 91.8 | x | x | x |
| Z148 | R/S | R/S | R/S | R/S | R | R/S | 47.0 | 42.7 | 42.1 | 51.7 | 57.3 | 73.5 | ND | ND | 84.8 |
| Z149 | R/S | R/S | R/S | R/S | S | S | 87.5 | 83.1 | 88.6 | 93.6 | 97.9 | 111.3 | x | x | x |
| Z150 | R/S | R/S | R/S | R/S | R | S | 96.6 | 76.5 | 76.4 | 84.2 | 89.7 | 99.4 | x | x | x |
| Z151 | R/S | R/S | R/S | R/S | S | R | 42.0 | 41.5 | 49.5 | 59.8 | 71.5 | 89.6 | x | x | x |
| Z152 | R/S | R/S | R/S | S | R/S | R/S | 50.1 | 49.1 | 59.9 | 63.5 | 65.6 | ND | 73.7 | ND | 81.2 |
| Z153 | R/S | R/S | R/S | R | R/S | R/S | 53.0 | 56.1 | 73.9 | 78.8 | 76.7 | ND | 87.5 | ND | 99.1 |
| Z154 | R/S | R/S | S | R/S | R/S | R/S | 59.8 | 42.9 | 63.2 | 63.5 | 66.9 | ND | 76.6 | ND | 91.5 |
| Z155 | R/S | R/S | R | R/S | R/S | R/S | 63.3 | 53.8 | 72.7 | 73.5 | 79.0 | ND | 84.6 | ND | 84.0 |
| Z156 | R/S | R/S | S | S | R/S | R/S | 57.9 | 44.5 | 59.5 | 59.7 | 65.0 | ND | 72.7 | ND | 84.8 |
| Z157 | R/S | R/S | R | S | R/S | R/S | 53.0 | 36.8 | 58.2 | 61.3 | 67.9 | ND | 79.2 | ND | 93.7 |
| Z158 | R/S | R/S | S | R | R/S | R/S | 59.2 | 61.5 | 72.6 | 72.2 | 84.5 | ND | 83.1 | ND | 90.1 |
| Z159 | R/S | R/S | R | R | R/S | R/S | 64.8 | 64.4 | 76.9 | 90.8 | 101.0 | x | x | x | x |
| Z160 | R/S | R/S | R | R | R | R | 54.1 | 56.5 | 66.4 | 70.0 | 83.0 | x | x | x | x |
| Z161 | R/S | R/S | R | S | R | R | 47.1 | 52.1 | 53.6 | 58.2 | 71.8 | 78.0 | 77.2 | 85.2 | x |
| Z162 | R/S | R/S | R | S | R | R | 45.6 | 47.5 | 44.6 | 49.4 | 56.8 | 59.1 | 57.5 | 67.5 | x |
| Z163 | R/S | R/S | S | S | R | R | 40.7 | 36.5 | 37.3 | 42.7 | 47.6 | 54.9 | 57.6 | 71.6 | x |
| Z164 | R/S | R/S | R | R | S | S | 105.7 | 107.0 | 105.3 | x | x | x | x | x | x |
| Z165 | R/S | R/S | S | R | S | S | 102.2 | 96.6 | 104.0 | x | x | x | x | x | x |
| Z166 | R/S | R/S | R | S | S | S | 92.5 | 89.4 | 90.9 | x | x | x | x | x | x |
| Z167 | R/S | R/S | S | S | S | S | 92.1 | 99.6 | 99.3 | x | x | x | x | x | x |
| Z168 | R/S | R/S | S | S | S | R | 57.3 | 54.1 | 59.7 | 73.4 | 84.0 | x | x | x | x |
| Z169 | R/S | R/S | S | S | R | S | 75.4 | 74.0 | 76.0 | 84.6 | 92.3 | x | x | x | x |
| Z170 | R/S | R/S | R | R | S | R | 56.4 | 66.8 | 70.1 | 83.8 | 102.1 | x | x | x | x |
| Z171 | R/S | R/S | R | R | R | R | 96.7 | 89.3 | 95.1 | x | x | x | x | x | x |
| Z182 | R | R | R | R | S | R | 67.3 | 43.6 | 59.8 | 73.4 | 76.4 | x | x | x | x |
| Z174 | R | R | R | R | S | R | 69.5 | 55.1 | 72.6 | 90.0 | 100.7 | x | x | x | x |
| Z175 | R | R | R | S | R | R | 57.4 | 23.8 | 33.4 | 49.6 | 54.4 | 56.8 | 66.8 | 70.1 | 88 |
| Z176 | R | R | S | R | R | R | 61.1 | 39.9 | 49.7 | 61.7 | 69.1 | 70.5 | 74.6 | 80.8 | 92 |
| Z178 | R | R | S | S | S | R | 60.2 | 36.0 | 53.6 | 75.9 | 79.2 | x | x | x | c |
| Z182 | R | S | R | S | R | R | 57.2 | 25.4 | 33.6 | 49.8 | 56.5 | 61.8 | 78.3 | 77.3 | 84 |
| Z187 | S | R | R | S | R | R | 71.5 | 40.8 | 43.1 | 66.5 | 62.6 | 64.5 | 79.1 | 76.5 | 80 |
| Z194 | S | R | S | R | R | R | 71.5 | 45.9 | 55.9 | 65.0 | 72.8 | 78.9 | 85.0 | 83.2 | 94.5 |
| Z196 | R | S | R | R | R | R | 74.2 | 57.0 | 68.0 | 95.1 | 98.5 | x | x | x | x |
| Z198 | R | S | R | R | S | R | 73.9 | 63.8 | 69.2 | 94.1 | 94.8 | x | x | x | x |
| Z199 | R | S | S | R | R | R | 6.14 | 27.3 | 38.5 | 45.4 | 56.4 | 61.3 | 71.0 | 67.1 | 73.8 |
| Z200 | R | S | S | R | R | R | 60.1 | 41.7 | 45.6 | 66.8 | 82.7 | x | x | x | x |
| Z202 | R | S | S | S | S | R | 52.8 | 30.3 | 43.2 | 59.4 | 77.7 | x | x | x | x |
| Z206 | R | S | S | R | R | R | 60.0 | 32.5 | 38.8 | 50.2 | 60.1 | 65.1 | 70.4 | 80.4 | 86.8 |
| Z208 | S | S | R | R | R | R | 57.5 | 56.8 | 57.4 | 80.2 | 87.3 | x | x | x | x |
| Z210 | S | S | R | R | R | R | 58.0 | 58.7 | 72.0 | 89.8 | 93.4 | x | x | x | x |
| Z211 | S | S | R | S | R | R | 53.6 | 37.0 | 35.4 | 52.9 | 56.8 | 61.8 | 75.4 | 79.3 | 85.5 |
| Z212 | S | S | R | S | R | R | 57.8 | 47.0 | 45.1 | 61.8 | 72.7 | 85.4 | 85.1 | 84.5 | 100 |
| Z214 | S | S | S | S | S | R | 57.1 | 45.1 | 44.4 | 59.4 | 76.6 | 74.7 | 84.8 | 85.4 | 92.3 |
| Z218 | S | S | S | S | R | R | 62.3 | 43.0 | 41.3 | 49.5 | 57.5 | 57.6 | 71.4 | 72.5 | 81.2 |
| Z184 | S | R | R | R | R | R | 62.4 | 59.8 | 84.5 | 81.7 | x | x | x | x | x |
| Z186 | S | R | R | R | S | R | 58.5 | 65.4 | 85.8 | 83.1 | x | x | x | x | x |
| Z188 | S | R | S | R | R | R | 53.6 | 55.9 | 69.7 | 71.9 | x | x | x | x | x |

TABLE 7-continued

| Compound | Phosphorothioate Stereochemical Identity | | | | | | In Vivo, 0.25 mg/kg Single Dose Mouse Studies (% Remaining AT3 Expression) | | | | | | | | |
|---|---|---|---|---|---|---|---|---|---|---|---|---|---|---|---|
| # | P1 | P2 | G22 | G21 | G2 | G1 | Day 7 | Day 14 | Day 21 | Day 28 | Day 35 | Day 42 | Day 49 | Day 56 | Day 63 |
| Z190 | S | R | S | S | S | R | 52.5 | 50.7 | 61.5 | 67.9 | x | x | x | x | x |
| Z220 | R | R | R | S | S | R | 55.2 | 49.2 | 56.1 | 67.9 | 84 | x | 100 | x | x |
| Z221 | R/S | R/S | S | S | R | R | 42.2 | 33.4 | 35.2 | 44.3 | 51.7 | x | 67.4 | 69.4 | 72.8 |
| Z222 | R/S | R.S | R | S | R | R | 43 | 34.2 | 35.4 | 43.1 | 54.4 | x | 57.3 | 66.3 | 60.4 |

In Table 7, column P1 provides the P-stereochemical identity for the phosphorothioate bonded to the 3'-carbon atom of the first nucleoside in the passenger strand; column P2 provides the P-stereochemical identity for the phosphorothioate bonded to the 3'-carbon atom of the second nucleoside in the passenger strand; column G22 provides the P-stereochemical identity for the phosphorothioate bonded to the 3'-carbon atom of the twenty-second nucleoside in the guide strand; column G21 provides the P-stereochemical identity for the phosphorothioate bonded to the 3'-carbon atom of the twenty-first nucleoside in the guide strand; column G2 provides the P-stereochemical identity for the phosphorothioate bonded to the 3'-carbon atom of the second nucleoside in the guide strand; and column G1 provides the P-stereochemical identity for the phosphorothioate bonded to the 3'-carbon atom of the first nucleoside in the guide strand.

TABLE 8

| Compound | | Primary Murine Hepatocytes (Transfection) | | | | Primary Murine Heptocytes (Free Uptake) | HeLa Cells (Transfection) |
|---|---|---|---|---|---|---|---|
| # | Target | 0.05 nM | 0.5 nM | 5 nM | IC50 (nM) | IC50 (pM) | IC50 (pM) |
| Z24 | AT3 | | | | | 2.1 | |
| Z234 | AT3 | | | | | 1.4 | |
| Z235 | AT3 | | | | | 5.5 | |
| Z236 | AT3 | | | | | 1.3 | |
| Z67A | TTR | | | | 2 | | |
| Z237 | TTR | | | | | 2.2 | |
| Z238 | TTR | | | | | 2.3 | |
| Z239 | PCSK9 | | | | | | 71 |
| Z240 | PCSK9 | | | | | | 695 |
| Z241 | PCSK9 | | | | | | 242 |
| Z242 | PCSK9 | | | | | | 92 |
| Z243 | PCSK9 | | | | | | 54 |
| Z244 | PCSK9 | | | | | | 57 |
| Z245 | PCSK9 | | | | | | 1505 |
| Z246 | PCSK9 | | | | | | 70 |
| Z247 | PCSK9 | | | | | | 265 |
| Z248 | PCSK9 | | | | | | 940 |
| Z249 | AT3 | | | | | | |
| Z250 | AT3 | | | | | | |
| Z251 | AT3 | | | | | | |
| Z252 | AT3 | | | | | | |
| Z253 | AT3 | | | | | | |
| Z254 | AT3 | | | | | | |
| Z255 | AT3 | | | | | | |
| Z256 | AT3 | | | | | | |
| Z257 | AT3 | | | | | | |
| Z258 | AT3 | | | | | | |
| Z259 | AT3 | | | | | | |
| Z260 | AT3 | | | | | | |
| Z261 | AT3 | | | | | | |
| Z262 | AT3 | | | | | | |
| Z90 | AT3 | | | | | 4.5 | |
| Z263 | AT3 | | | | | 4.1 | |
| Z264 | AT3 | | | | | 4.1 | |
| Z265 | AT3 | | | | | 1.7 | |
| Z266 | AT3 | | | | | 4.9 | |
| Z267 | AT3 | | | | | 5.5 | |
| Z268 | AT3 | | | | | 7.9 | |
| Z269 | AT3 | | | | | | |
| Z270 | AT3 | | | | | | |
| Z271 | AT3 | | | | | | |
| Z272 | AT3 | | | | | | |
| Z273 | AT3 | | | | | | |
| Z274 | AT3 | | | | | | |
| Z275 | AT3 | | | | | | |
| Z276 | AT3 | | | | | | |
| Z277 | AT3 | | | | | | |

TABLE 9

| Compound # | In vivo, 0.25 mg/kg, single dose mouse studies (% remaining AT3 expression) | | | | | | | |
|---|---|---|---|---|---|---|---|---|
| | Day 7 | Day 14 | Day 21 | Day 28 | Day 35 | Day 42 | Day 49 | Day 56 | Day 63 |
| Z24 | 49.7 | 43.8 | 50.9 | 62.5 | 64.7 | ND | 81.8 | x | x |
| Z152 | 50.1 | 49.1 | 59.9 | 63.5 | 65.6 | ND | 73.7 | ND | 81.2 |
| Z153 | 53.0 | 56.1 | 73.9 | 78.8 | 76.7 | ND | 87.5 | ND | 99.1 |
| Z154 | 59.8 | 42.9 | 63.2 | 63.5 | 66.9 | ND | 76.6 | ND | 91.5 |
| Z155 | 63.3 | 53.8 | 72.7 | 73.5 | 79.0 | ND | 84.6 | ND | 84.0 |
| Z156 | 57.9 | 44.5 | 59.5 | 59.7 | 65.0 | ND | 72.7 | ND | 84.8 |
| Z157 | 53.0 | 36.8 | 58.2 | 61.3 | 67.9 | ND | 79.2 | ND | 93.7 |
| Z158 | 59.2 | 61.5 | 72.6 | 72.2 | 84.5 | ND | 83.1 | ND | 90.1 |

Figure 10:
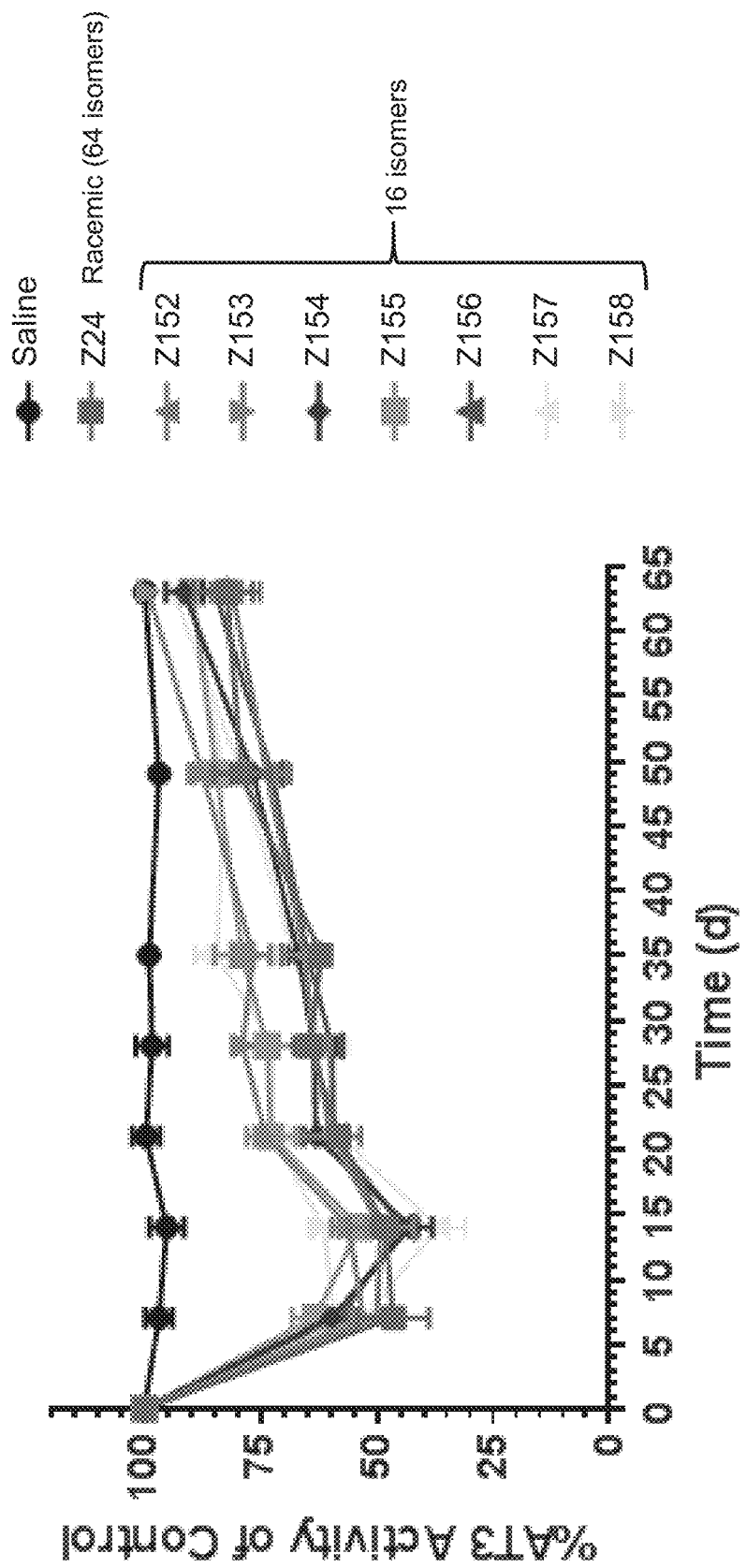
FIG. 10 is a chart showing AT3 activity in mice measured at predetermined time periods after a single 0.25 mg/kg subcutaneous dosing of the mice with the tested compositions.

The data from Table 9 are shown in FIG. 10.

TABLE 10

| Compound # | In vivo, 0.25 mg/kg, single dose mouse studies (% remaining AT3 expression) | | | | | | | |
|---|---|---|---|---|---|---|---|---|
| | Day 7 | Day 14 | Day 21 | Day 28 | Day 35 | Day 42 | Day 49 | Day 56 | Day 63 |
| Z24 | 49.7 | 43.8 | 50.9 | 62.5 | 64.7 | ND | 81.8 | x | x |
| Z159 | 64.8 | 64.4 | 76.9 | 90.8 | 101.0 | x | x | x | x |
| Z160 | 54.1 | 56.5 | 66.4 | 70.0 | 83.0 | x | x | x | x |
| Z161 | 47.1 | 52.1 | 53.6 | 58.2 | 71.8 | 78.0 | 77.2 | 85.2 | x |
| Z162 | 45.6 | 47.5 | 44.6 | 49.4 | 56.8 | 59.1 | 57.5 | 67.5 | x |
| Z163 | 40.7 | 36.5 | 37.3 | 42.7 | 47.6 | 54.9 | 57.6 | 71.6 | x |
| Z164 | 105.7 | 107.0 | 105.3 | x | x | x | x | x | x |
| Z165 | 102.2 | 96.6 | 104.0 | x | x | x | x | x | x |
| Z166 | 92.5 | 89.4 | 90.9 | x | x | x | x | x | x |
| Z167 | 92.1 | 99.6 | 99.3 | x | x | x | x | x | x |
| Z168 | 57.3 | 54.1 | 59.7 | 73.4 | 84.0 | x | x | x | x |
| Z169 | 75.4 | 74.0 | 76.0 | 84.6 | 92.3 | x | x | x | x |
| Z170 | 56.4 | 66.8 | 70.1 | 83.8 | 102.1 | x | x | x | x |
| Z171 | 96.7 | 89.3 | 95.1 | x | x | x | x | x | x |

Figure 11:
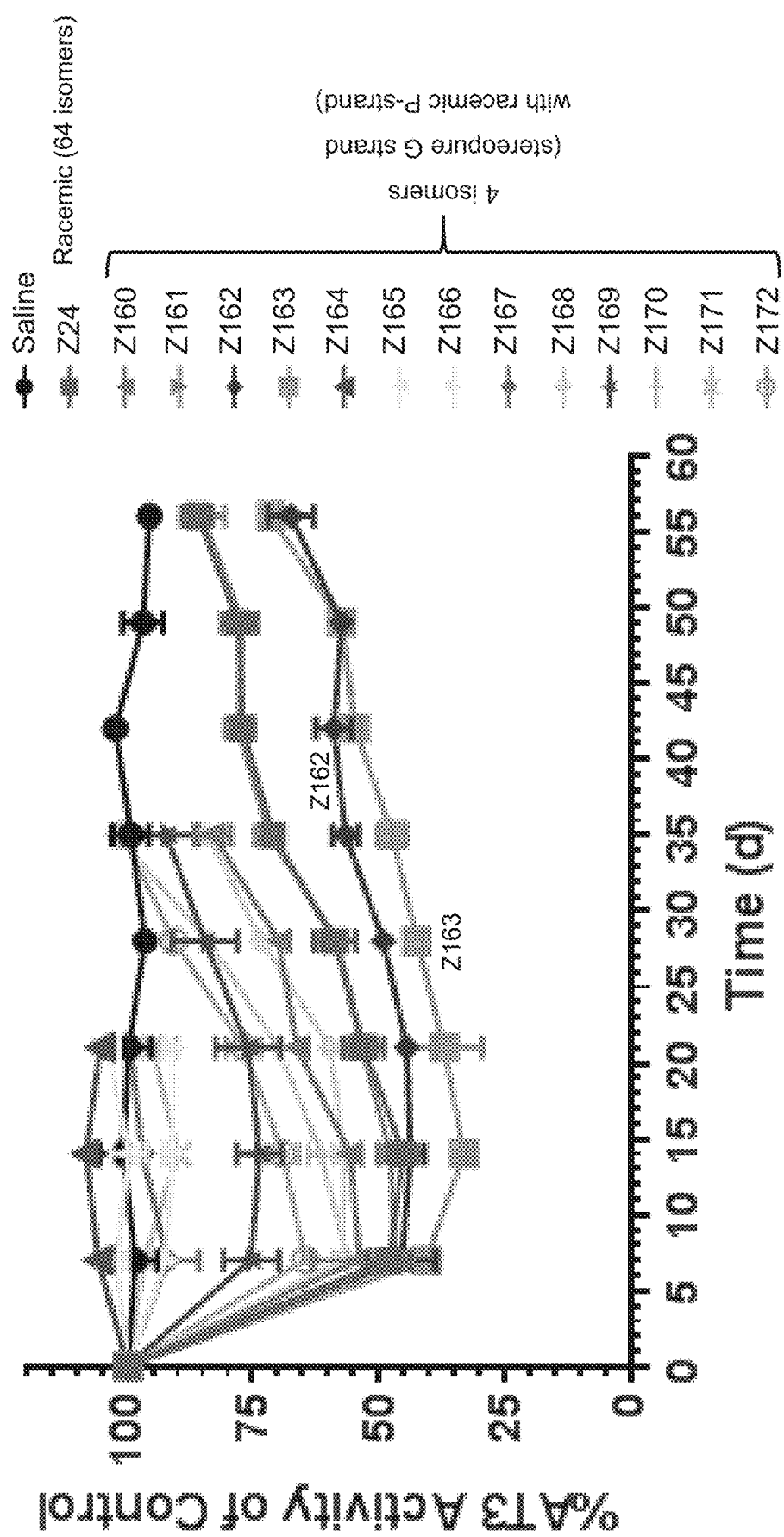
FIG. 11 is a chart showing AT3 activity in mice measured at predetermined time periods after a single 0.25 mg/kg subcutaneous dosing of the mice with the tested compositions.

The data from Table 10 are shown in FIG. 11.

TABLE 11

| Compound # | In vivo, 0.25 mg/kg, single dose mouse studies (% remaining AT3 expression) | | | | | | | |
|---|---|---|---|---|---|---|---|---|
| | Day 7 | Day 14 | Day 21 | Day 28 | Day 35 | Day 42 | Day 49 | Day 56 | Day 63 |
| Z24 | 49.7 | 43.8 | 50.9 | 62.5 | 64.7 | ND | 81.8 | x | x |
| Z172 | 67.3 | 43.6 | 59.8 | 73.4 | 76.34 | x | x | x | x |
| Z174 | 69.5 | 55.1 | 72.6 | 90.0 | 100.7 | x | x | x | x |
| Z175 | 57.4 | 23.8 | 33.4 | 49.6 | 54.4 | 56.8 | 66.8 | 70.1 | 88 |
| Z176 | 61.1 | 39.9 | 49.7 | 61.7 | 69.1 | 70.5 | 74.6 | 80.8 | 92 |
| Z178 | 60.2 | 36.0 | 53.6 | 75.9 | 79.2 | x | x | x | x |
| Z182 | 57.2 | 25.4 | 33.6 | 49.8 | 56.5 | 61.8 | 78.3 | 77.3 | 84 |
| Z187 | 71.5 | 40.8 | 43.1 | 66.5 | 62.6 | 64.5 | 79.1 | 76.5 | 80 |
| Z194 | 71.5 | 45.9 | 55.9 | 65.0 | 72.8 | 78.9 | 85.0 | 83.2 | 94.5 |
| Z196 | 74.2 | 57.0 | 68.0 | 95.1 | 98.5 | x | x | x | x |
| Z198 | 73.9 | 63.8 | 69.2 | 94.1 | 94.8 | x | x | x | x |
| Z199 | 61.4 | 27/3 | 38.5 | 45.4 | 56.4 | 61.3 | 71.0 | 67.1 | 73.8 |
| Z200 | 60.1 | 41.7 | 45.6 | 66.8 | 82.7 | x | x | x | x |
| Z202 | 52.8 | 30.3 | 43.2 | 59.4 | 77.7 | x | x | x | x |
| Z206 | 60.0 | 32.5 | 38.8 | 50.2 | 60.1 | 65.1 | 70.4 | 80.4 | 86.8 |
| Z208 | 57.5 | 56.8 | 57.4 | 80.2 | 87.3 | x | x | x | x |
| Z210 | 58.0 | 58.7 | 72.0 | 89.8 | 93.4 | x | x | x | x |
| Z211 | 53.6 | 37.0 | 35.4 | 52.9 | 56.8 | 61.8 | 75.4 | 79.3 | 85.5 |
| Z212 | 57.8 | 47.0 | 45.1 | 61.8 | 72.7 | 75.4 | 85.1 | 84.5 | 100 |
| Z214 | 57.1 | 45.1 | 44.4 | 59.4 | 76.6 | 74.7 | 84.8 | 85.4 | 92.3 |
| Z218 | 62.3 | 43.0 | 41.3 | 49.5 | 57.5 | 57.6 | 71.4 | 72.5 | 81.2 |

Figure 12:
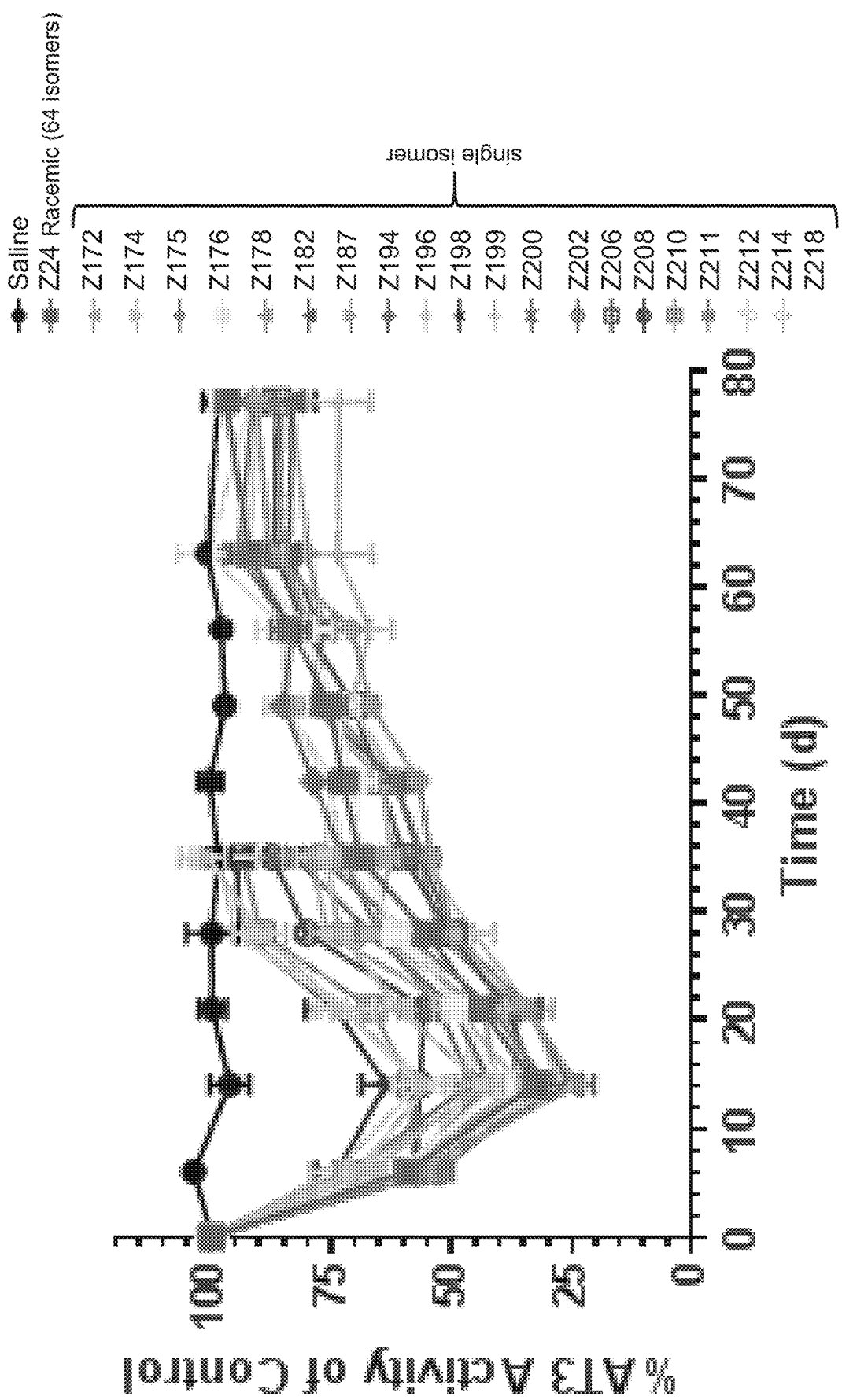
FIG. 12 is a chart showing AT3 activity in mice measured at predetermined time periods after a single 0.25 mg/kg subcutaneous dosing of the mice with the tested compositions.

The data from Table 11 are shown in FIG. 12.

TABLE 12

| Compound # | In vivo, 0.25 mg/kg, single dose mouse studies (% remaining AT3 expression) | | | | | | | | |
|---|---|---|---|---|---|---|---|---|---|
| | Day 7 | Day 14 | Day 21 | Day 28 | Day 35 | Day 42 | Day 49 | Day 56 | Day 63 |
| Z24 | 49.7 | 43.8 | 50.9 | 62.5 | 64.7 | ND | 81.8 | x | x |
| Z184 | 62.4 | 59.8 | 84.5 | 81.7 | x | x | x | x | x |
| Z186 | 58.5 | 65.4 | 85.8 | 83.1 | x | x | x | x | x |
| Z188 | 53.6 | 55.9 | 69.7 | 71.9 | x | x | x | x | x |
| Z190 | 52.5 | 50.7 | 61.5 | 67.9 | x | x | x | x | x |

Figure 13:
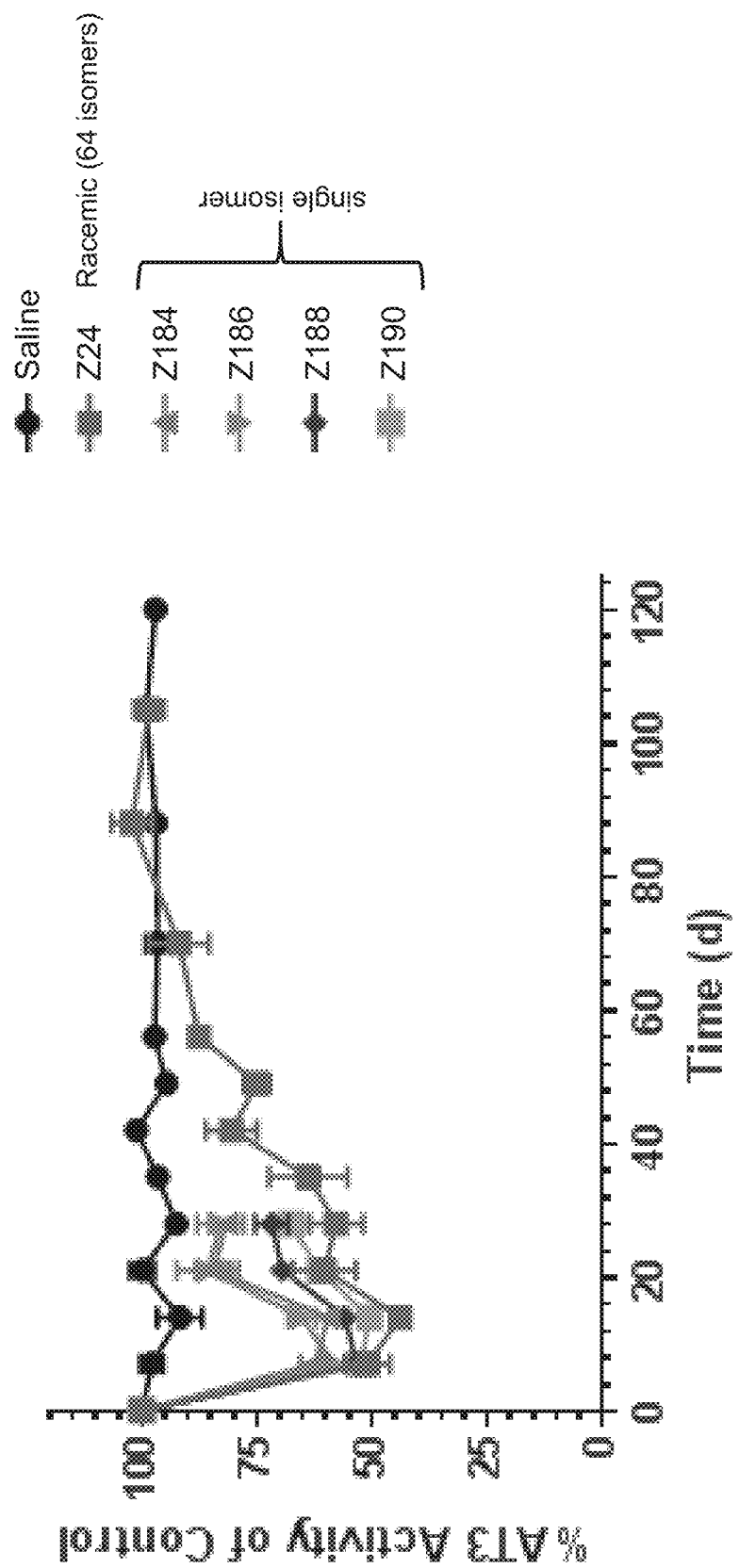
FIG. 13 is a chart showing AT3 activity in mice measured at predetermined time periods after a single 0.25 mg/kg subcutaneous dosing of the mice with the tested compositions.

The data from Table 12 are shown in FIG. 13.

TABLE 13

| Compound # | In vivo, 0.25 mg/kg, single dose mouse studies (% remaining AT3 expression) | | | | | | | | |
|---|---|---|---|---|---|---|---|---|---|
| | Day 7 | Day 14 | Day 21 | Day 28 | Day 35 | Day 42 | Day 49 | Day 56 | Day 63 |
| Z24 | 49.7 | 43.8 | 50.9 | 62.5 | 64.7 | ND | 81.8 | x | x |
| Z175 | 57.4 | 23.8 | 33.4 | 49.6 | 54.4 | 56.8 | 66.8 | 70.1 | 88 |
| Z182 | 57.2 | 25.4 | 33.6 | 49.8 | 56.5 | 61.8 | 78.3 | 77.3 | 84 |
| Z199 | 61.4 | 27.3 | 38.5 | 45.4 | 56.4 | 61.3 | 71.0 | 67.1 | 73.8 |
| Z206 | 60.0 | 32.5 | 38.8 | 50.2 | 60.1 | 65.1 | 70.4 | 80.4 | 86.8 |
| Z211 | 53.6 | 37.0 | 35.4 | 52.9 | 56.8 | 61.8 | 75.4 | 79.3 | 85.5 |
| Z218 | 62.3 | 43.0 | 41.3 | 49.5 | 57.5 | 57.6 | 71.4 | 72.5 | 81.2 |

Figure 14:
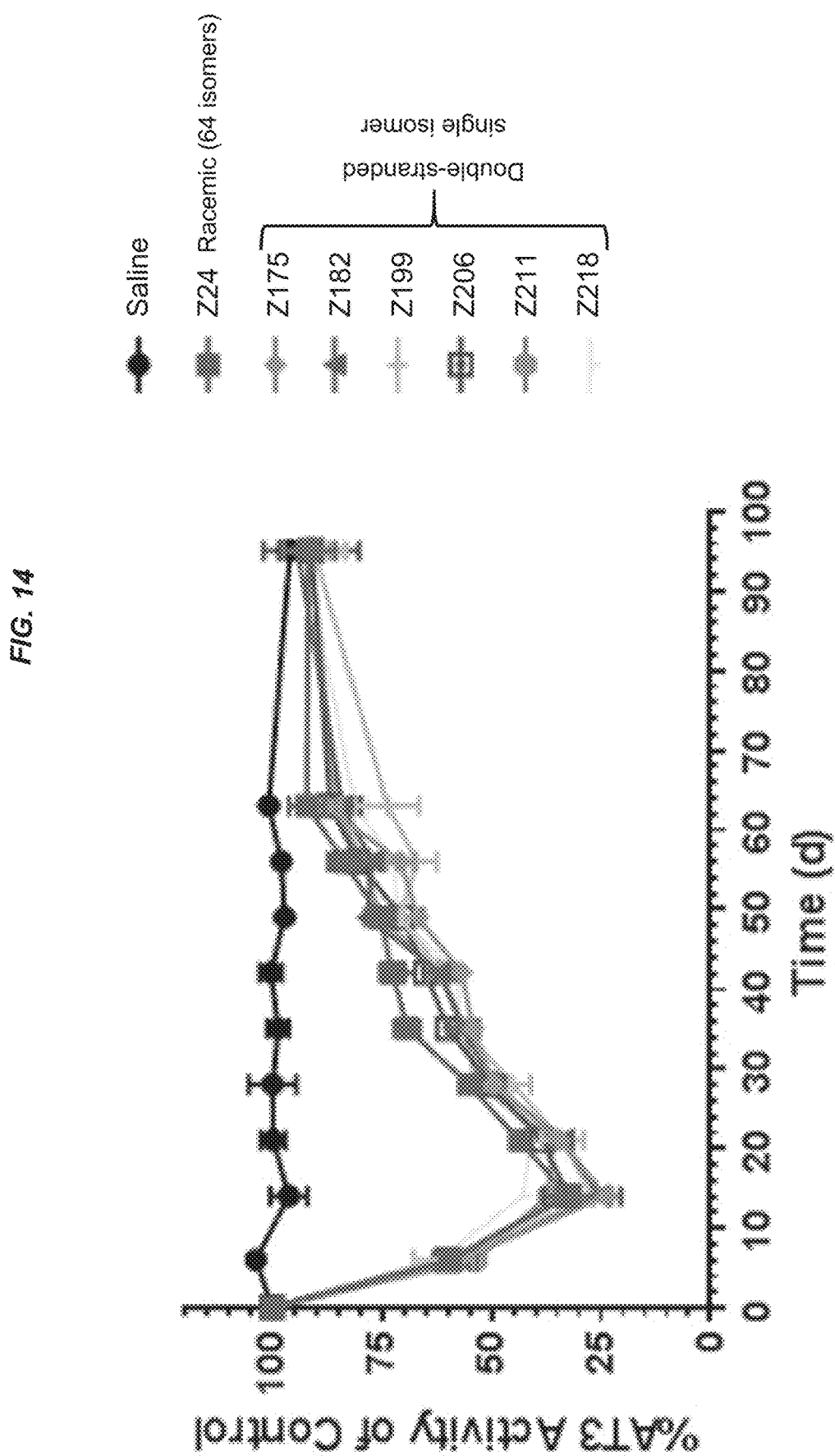
FIG. 14 is a chart showing AT3 activity in mice measured at predetermined time periods after a single 0.25 mg/kg subcutaneous dosing of the mice with the tested compositions.
Figure 15:
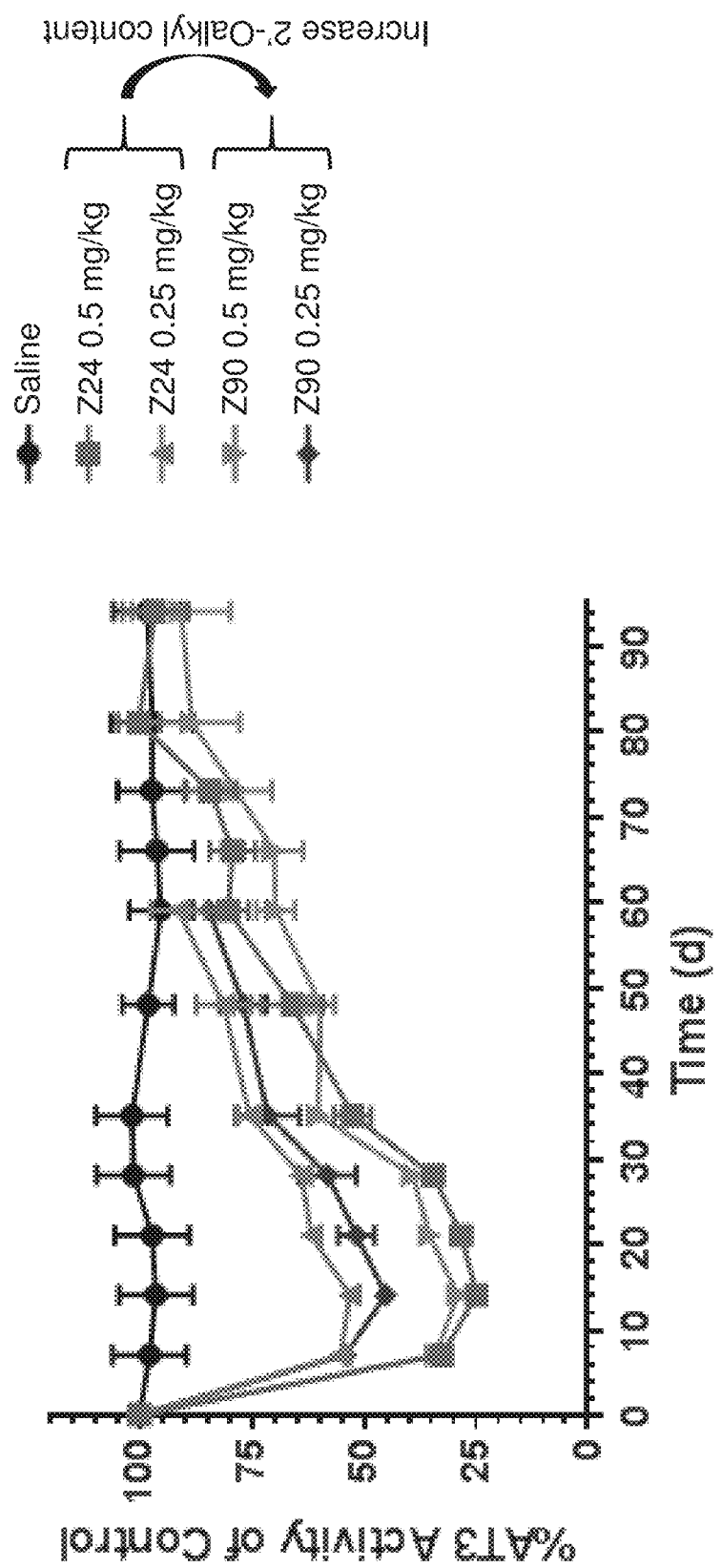
FIG. 15 is a chart showing AT3 activity in mice measured at predetermined time periods after a single 0.25 mg/kg or 0.5 mg/kg subcutaneous dosing of the mice with the tested compositions.
Figure 16:
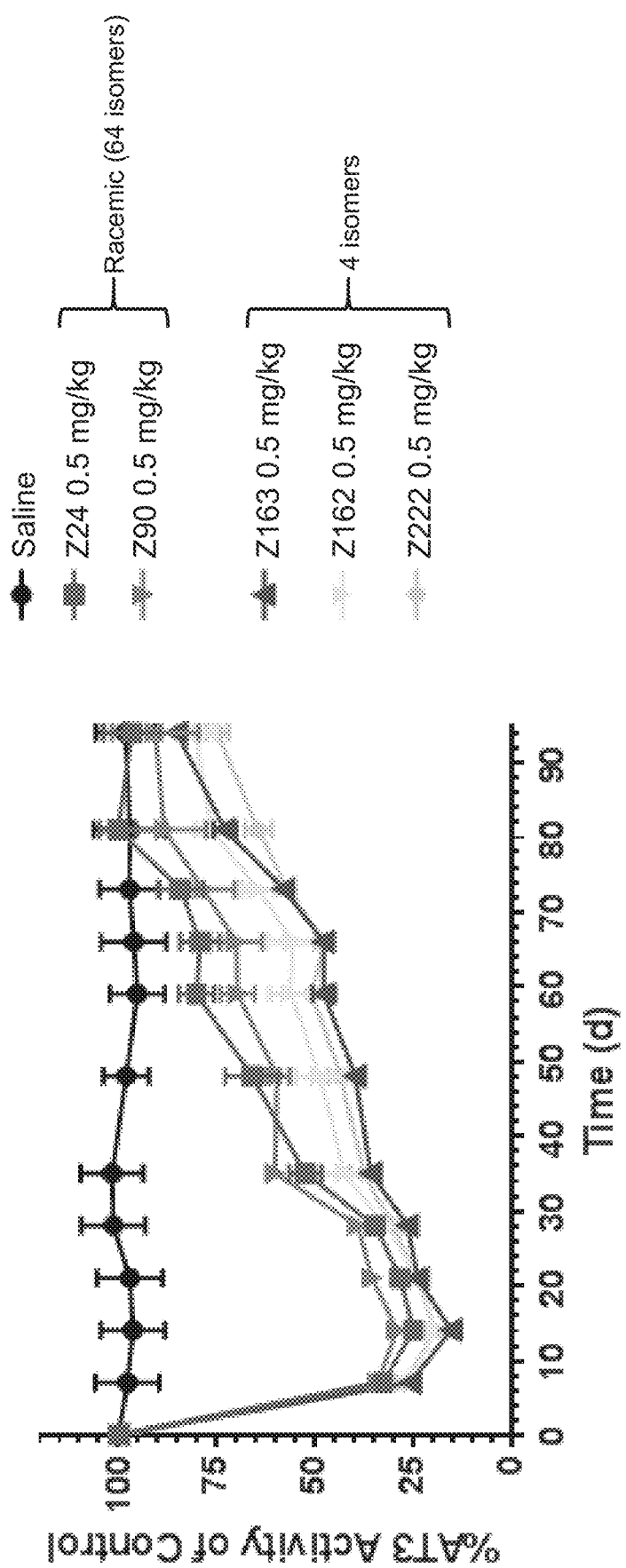
FIG. 16 is a chart showing AT3 activity in mice measured at predetermined time periods after a single 0.5 mg/kg subcutaneous dosing of the mice with the tested compositions.

The data from Table 13 are shown in FIG. 14.

TABLE 14

| | In vivo, 0.25 mg/kg, single dose mouse studies (% remaining AT3 expression) | | | | | | | | | |
|---|---|---|---|---|---|---|---|---|---|---|
| Compound # | Day 7 | Day 14 | Day 21 | Day 28 | Day 35 | Day 42 | Day 48 | Day 59 | Day 66 | Day 73 | Dose (mg/kg) |
| Z24 | 32.6 | 24.9 | 28.3 | 34.7 | 52.6 | ND | 66.0 | 80.3 | 80.0 | 84.2 | 0.5 |
| Z90 | 34.0 | 29.1 | 35.5 | 39.1 | 60.2 | ND | 60.0 | 70.0 | 70.2 | 78.5 | 0.5 |
| Z162 | 52.2 | 39.4 | 39.5 | 49.0 | 58.7 | ND | 71.2 | 72.3 | 67.1 | 81.1 | 0.25 |
| Z163 | 44.6 | 33.2 | 38.2 | 43.3 | 55.3 | ND | 57.3 | 67.7 | 67.0 | 78.2 | 0.25 |
| Z222 | 43.0 | 34.2 | 35.4 | 43.1 | 54.4 | ND | 57.3 | 66.3 | 60.4 | 64.4 | 0.25 |

Figure 17:
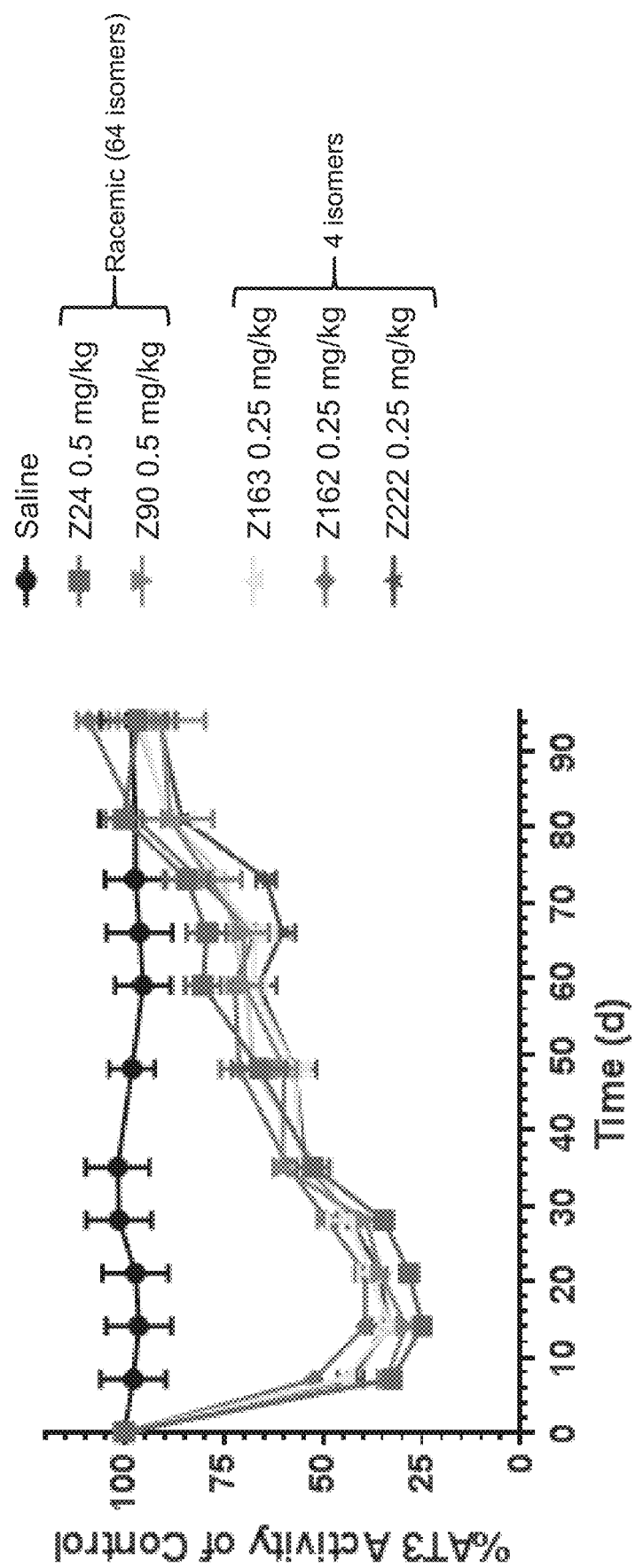
FIG. 17 is a chart showing AT3 activity in mice measured at predetermined time periods after a single 0.25 mg/kg or 0.5 mg/kg subcutaneous dosing of the mice with the tested compositions.
Figure 18:
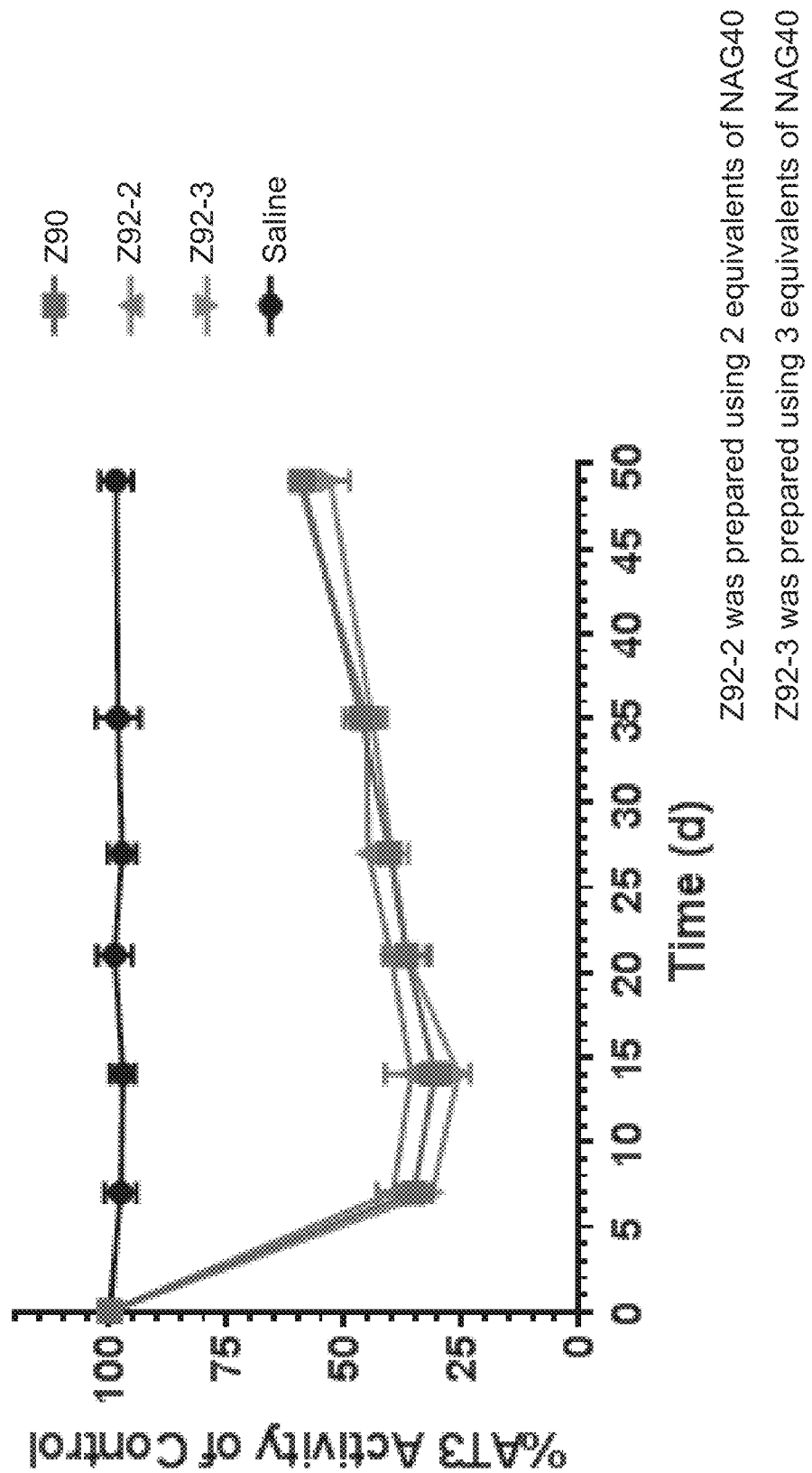
FIG. 18 is a chart showing AT3 activity in mice measured at predetermined time periods after a single 0.25 mg/kg subcutaneous dosing of the mice with the tested compositions. Z92-2 was prepared using two equivalent of NAG40. Z92-3 was prepared using three equivalents of NAG40.

The data from Table 14 are shown in FIG. 17.

OTHER EMBODIMENTS

The invention is further described by the following enumerated items.

1. A polynucleotide construct comprising a strand bonded to at least one group of formula (I):

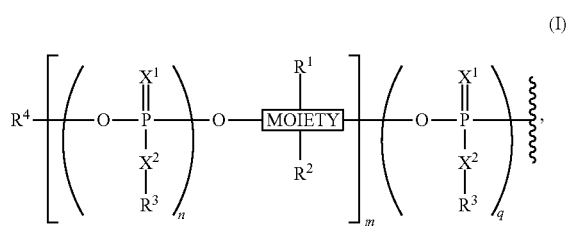

(I)

or a salt thereof, or a stereoisomer thereof,
wherein
each $X^1$ is independently O or S;
each $X^2$ is independently O, S, NH, or a bond;
MOIETY is optionally substituted $C_{2-10}$ alkane-tetrayl or a group $-M^1-M^2-M^3-$, wherein each $M^1$ and each $M^3$ is independently absent or optionally substituted $C_{1-6}$ alkylene, and $M^2$ is optionally substituted $C_{3-9}$ heterocycle-tetrayl, optionally substituted $C_{6-10}$ arene-tetrayl, or optionally substituted $C_{3-8}$ cycloalkane-tetrayl;
each $R^1$ and each $R^2$ is independently H, optionally substituted $C_{1-16}$ alkyl, optionally substituted $C_{2-16}$ heteroalkyl, a conjugation moiety, or -LinkA$(-T)_p$, provided that at least one $R^1$ or at least one $R^2$ is a conjugation moiety or -LinkA$(-T)_p$;
each $R^3$ is independently H, optionally substituted $C_{1-16}$ alkyl, optionally substituted $C_{2-16}$ heteroalkyl, optionally substituted $C_{2-16}$ alkenyl, optionally substituted $C_{2-16}$ alkynyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl, a conjugation moiety, or -LinkA$(-T)_p$;
$R^4$ is H, optionally substituted $C_{1-6}$ alkyl, -LinkA$(-T)_p$, or -Sol;
each LinkA is independently a multivalent linker, at least one the multivalent linker comprising —C(O)—N(H)— bonded to T;
each T is independently an auxiliary moiety;
Sol is a solid support;
m is an integer from 1 to 6;
each n is independently 0 or 1;
each p is independently an integer from 1 to 6; and
q is an integer from 0 to 3;
wherein the polynucleotide construct comprises no more than one Sol; and wherein, when the at least one group of formula (I) is bonded to an internucleoside phosphate, internucleoside phosphorothioate, or internucleoside phosphorodithioate, q is 0.

2. A polynucleotide construct comprising a strand bonded to at least one group of formula (I):

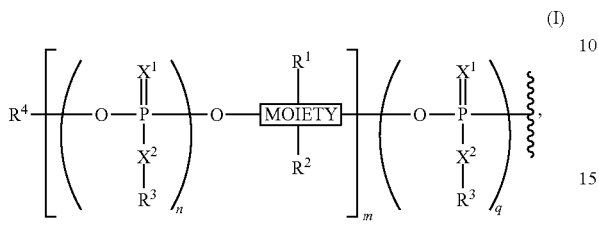

or a salt thereof, or a stereoisomer thereof,
wherein
each $X^1$ is independently O or S;
each $X^2$ is independently O, S, NH, or a bond;
MOIETY is optionally substituted $C_{2-10}$ alkane-tetrayl or a group -$M^1$-$M^2$-$M^3$-, wherein each $M^1$ and each $M^3$ is independently absent or optionally substituted $C_{1-6}$ alkylene, and $M^2$ is optionally substituted $C_{3-9}$ heterocycle-tetrayl, optionally substituted $C_{6-10}$ arene-tetrayl, or optionally substituted $C_{3-8}$ cycloalkane-tetrayl;
each $R^1$ and each $R^2$ is independently H, optionally substituted $C_{1-6}$ alkyl, optionally substituted $C_{2-16}$ heteroalkyl, a conjugation moiety, or -LinkA(-T)$_p$, provided that at least one $R^1$ or at least one $R^2$ is a conjugation moiety or -LinkA(-T)$_p$;
each $R^3$ is independently H, optionally substituted $C_{1-16}$ alkyl, optionally substituted $C_{2-16}$ heteroalkyl, optionally substituted $C_{2-16}$ alkenyl, optionally substituted $C_{2-16}$ alkynyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl, a conjugation moiety, or -LinkA(-T)$_p$;
$R^4$ is H, optionally substituted $C_{1-6}$ alkyl, -LinkA(-T)$_p$, or -Sol;
each LinkA is independently a multivalent linker;
each T is independently an auxiliary moiety;
Sol is solid support;
m is an integer from 1 to 6;
each n is independently 0 or 1;
each p is independently an integer from 1 to 6; and
q is an integer from 0 to 3;
wherein the polynucleotide construct comprises no more than one Sol;
wherein, when the at least one group of formula (I) is bonded to an internucleoside phosphate, internucleoside phosphorothioate, or internucleoside phosphorodithioate, q is 0; and
wherein the strand comprises at least one nucleoside substituted at position 2 with optionally substituted $C_{1-6}$ alkoxy, optionally substituted $C_{2-12}$ alkoxyalkyl, halogen, or cyano.

3. The polynucleotide construct of item 1 or 2, or a salt thereof, or a stereoisomer thereof, wherein at least one -LinkA(-T)$_p$ is of formula (II):

wherein
each s is independently an integer from 0 to 20, wherein the repeating units are same or different;

$Q^1$ is a conjugation linker;
$Q^2$ is a linear group, if p is 1, or a branched group, if p is an integer from 2 to 6;
each $Q^3$ and each $Q^6$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—;
each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, optionally substituted $C_{6-10}$ arylene, optionally substituted $C_{1-9}$ heteroarylene, or optionally substituted $C_{1-9}$ heterocyclylene (e.g., each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene);
each $Q^5$ is independently absent, —CO—, —NH—, —O—, —S—, —SO$_2$—, —CH$_2$—, —C(O)O—, —OC(O)—, —C(O)NH—, —NH—C(O)—, —NH—CH($R^a$)—C(O)—, or —C(O)—CH($R^a$)—NH—; and
each $R^a$ is independently H or an amino acid side chain;
provided that at least one of $Q^3$, $Q^4$, and $Q^5$ is present.

4. The polynucleotide construct of item 3, or a salt thereof, or a stereoisomer thereof, wherein each -LinkA(-T)$_p$ is independently of formula (II).

5. The polynucleotide construct of item 3 or 4, or a salt thereof, or a stereoisomer thereof, wherein $Q^1$ is —O-$Q^L$-$Q^C$-, wherein $Q^L$ is optionally substituted $C_{2-12}$ heteroalkylene or optionally substituted $C_{1-12}$ alkylene, and $Q^C$ is (i) optionally substituted $C_{2-12}$ heteroalkylene comprising —C(O)—N(H)—, —N(H)—C(O)—, —S(O)$_2$—N(H)—, or —N(H)—S(O)$_2$—; (ii) optionally substituted $C_{1-12}$ heterocyclylene; (iii) optionally substituted $C_{1-12}$ thioheterocyclylene; (iv) cyclobut-3-ene-1,2-dione-3,4-diyl; or (v) pyrid-2-yl hydrazone.

6. The polynucleotide construct of item 3 or 4, or a salt thereof, or a stereoisomer thereof, wherein $Q^1$ comprises:

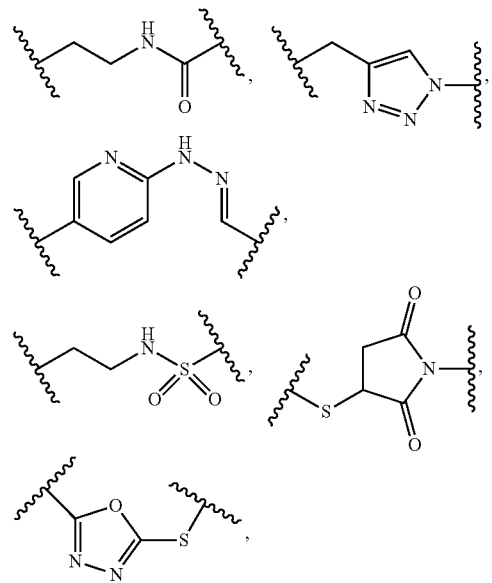

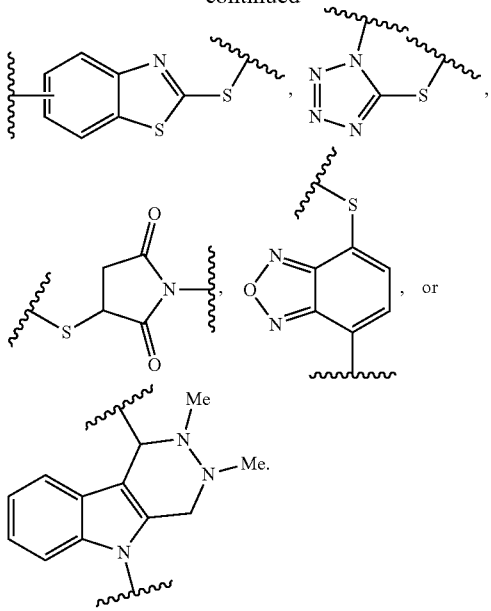

7. The polynucleotide construct of any one of items 3 to 6, or a salt thereof, or a stereoisomer thereof, wherein p is 1, and $Q^2$ is a linear group of formula $-[Q^3-Q^4-Q^5]_s-$.

8. The polynucleotide construct of any one of items 3 to 6, or a salt thereof, or a stereoisomer thereof, wherein p is an integer from 2 to 6, and $Q^2$ is a branched group of formula $-[Q^3-Q^4-Q^5]_s-Q^7(-[Q^3-Q^4-Q^5]_s-(Q^7)_{p1})_{p2}$, wherein $Q^7$ is optionally substituted $C_{1-6}$ alkane-triyl, optionally substituted $C_{1-6}$ alkane-tetrayl, optionally substituted $C_{2-6}$ heteroalkane-triyl, or optionally substituted $C_{2-6}$ heteroalkane-tetrayl;
wherein
p1 is 0 or 1;
p2 is 0, 1, 2, or 3;
wherein,
when p1 is 0, LinkA is a trivalent or tetravalent linker, and,
when p1 is 1, LinkA is a tetravalent, pentavalent, or hexavalent linker.

9. The polynucleotide construct of any one of items 1 to 8, or a salt thereof, or a stereoisomer thereof, wherein at least one T is a targeting moiety.

10. The polynucleotide construct of any one of items 1 to 9, or a salt thereof, or a stereoisomer thereof, wherein at least one T is an asialoglycoprotein receptor ligand, mannose, folate, prostate specific membrane antigen (PSMA), or an antibody or an antigen-binding fragment thereof.

11. The polynucleotide construct of item 10, or a salt thereof, or a stereoisomer thereof, wherein at least one T is the asialoglycoprotein receptor ligand.

12. The polynucleotide construct of item 11, or a salt thereof, or a stereoisomer thereof, wherein at least one T is N-acetyl galactosamine.

13. The polynucleotide construct of item 12, or a salt thereof, or a stereoisomer thereof, wherein N-acetyl galactosamine comprises an anomeric carbon bonded to LinkA, wherein the anomeric carbon is part of a hemiaminal group.

14. The polynucleotide construct of item 13, or a salt thereof, or a stereoisomer thereof, wherein the anomeric carbon of N-acetyl galactosamine is bonded to an amide nitrogen atom.

15. The polynucleotide construct of any one of items 1 to 14, or a salt thereof, or a stereoisomer thereof, wherein at least one T is a cell penetrating peptide.

16. The polynucleotide construct of any one of items 1 to 15, or a salt thereof, or a stereoisomer thereof, wherein at least one T is an endosomal escape moiety.

17. The polynucleotide construct of any one of items 1 to 16, or a salt thereof, or a stereoisomer thereof, wherein the at least one group of formula (I) is linked to a nucleoside that is one of five 5'- or five 3'-terminal nucleosides.

18. The polynucleotide construct of any one of items 1 to 17, or a salt thereof, or a stereoisomer thereof, wherein the strand is bonded to 1, 2, 3, or 4 groups of formula (I), wherein the groups of formula (I) are same or different.

19. The polynucleotide construct of any one of items 1 to 18, or a salt thereof, or a stereoisomer thereof, wherein the strand comprises at least one non-bioreversible, internucleoside phosphotriester.

20. The polynucleotide construct of item 19, or a salt thereof, or a stereoisomer thereof, wherein the at least one non-bioreversible, internucleoside phosphotriester is a phosphate, phosphorothioate, or phosphorodithioate that is substituted with a substituent selected independently from the group consisting of optionally substituted $C_{2-16}$ alkyl; optionally substituted $C_{3-16}$ alkenyl; optionally substituted $C_{3-16}$ alkynyl; optionally substituted $C_{3-8}$ cycloalkyl; optionally substituted $C_{3-8}$ cycloalkenyl; optionally substituted ($C_{3-8}$ cycloalkyl)-$C_{1-4}$-alkyl; optionally substituted ($C_{3-8}$ cycloalkenyl)-$C_{1-4}$-alkyl; optionally substituted $C_{6-14}$ aryl; optionally substituted ($C_{6-14}$ aryl)-$C_{1-4}$-alkyl; optionally substituted $C_{1-9}$ heteroaryl having 1 to 4 heteroatoms selected from N, O, and S; optionally substituted ($C_{1-9}$ heteroaryl)-$C_{1-4}$-alkyl having 1 to 4 heteroatoms selected from N, O, and S; optionally substituted $C_{2-9}$ heterocyclyl having 1 to 4 heteroatoms selected from N, O, and S, wherein the heterocyclyl does not comprise an S—S bond; optionally substituted ($C_{2-9}$ heterocyclyl)-$C_{1-4}$-alkyl having 1 to 4 heteroatoms selected from N, O, and S, wherein the heterocyclyl does not comprise an S—S bond; and a group of the following structure:

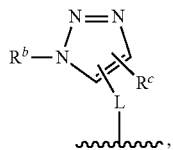

wherein
L is $C_{2-6}$ alkylene;
$R^b$ is optionally substituted $C_{2-6}$ alkyl; optionally substituted $C_{6-14}$ aryl; optionally substituted ($C_{6-14}$ aryl)-$C_{1-4}$-alkyl; optionally substituted $C_{3-8}$ cycloalkyl; optionally substituted ($C_{3-8}$ cycloalkyl)-$C_{1-4}$-alkyl; optionally substituted $C_{1-9}$ heteroaryl having 1 to 4 heteroatoms selected from the group consisting of N, O, and S; optionally substituted ($C_{1-9}$ heteroaryl)-$C_{1-4}$-alkyl having 1 to 4 heteroatoms selected from the group consisting of N, O, and S;

optionally substituted C$_{2-9}$ heterocyclyl having 1 to 4 heteroatoms selected from the group consisting of N, O, and S, wherein the heterocyclyl does not comprise an S—S bond; optionally substituted (C$_{2-9}$ heterocyclyl)-C$_{1-4}$-alkyl having 1 to 4 heteroatoms selected from N, O, and S, wherein the heterocyclyl does not comprise an S—S bond; and a poly(ethylene glycol) terminated with —OH, C$_1$. 6 alkoxy, or —COOH; and R$^c$ is H or C$_{1-6}$ alkyl.

21. The polynucleotide construct of item 20, or a salt thereof, or a stereoisomer thereof, wherein the at least one non-bioreversible, internucleoside phosphotriester is a phosphate, phosphorothioate, or phosphorodithioate substituted with a substituent that is C$_{2-16}$ alkyl,

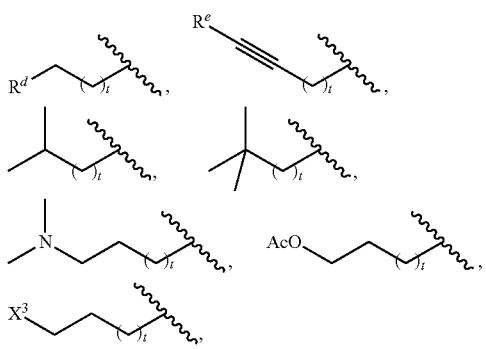

or a group formed by cycloaddition reaction of

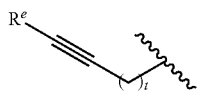

with an azido-containing substrate,
wherein
t is an integer from 1 to 6;
R$^d$ is optionally substituted C$_6$ aryl; optionally substituted C$_{4-5}$ heteroaryl that is a six member ring comprising 1 or 2 nitrogen atoms; or optionally substituted C$_{4-5}$ heterocyclyl that is a six member ring comprising 1 or 2 nitrogen atoms;
R$^e$ is H or C$_{1-6}$ alkyl;
X$^3$ is a halogen, —COOR$^5$, or —CONR$^6$$_2$, wherein each of R$^5$ and R$^6$ is independently H, optionally substituted C$_{1-6}$ alkyl, optionally substituted C$_{6-14}$ aryl, optionally substituted C$_{1-9}$ heteroaryl, or optionally substituted C$_{2-9}$ heterocyclyl; and
the azido-containing substrate is

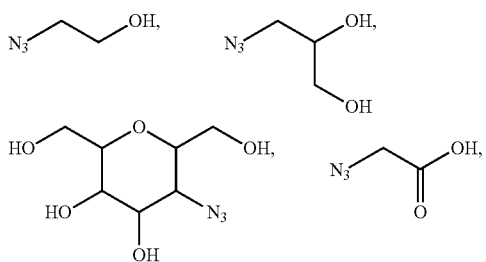

-continued

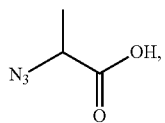

N$_3$-PEG-OH, N$_3$-PEG-COOH,

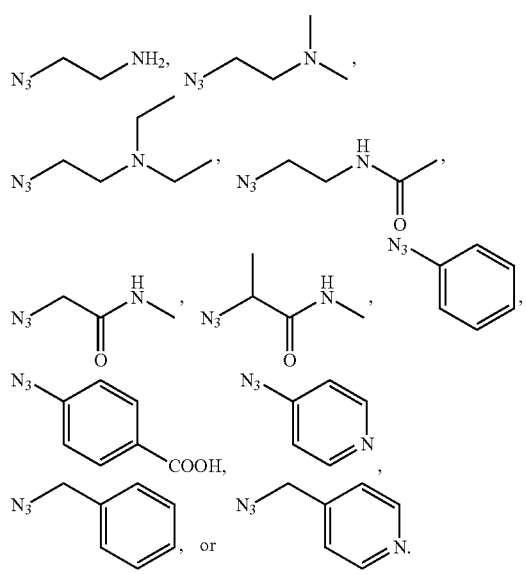

22. The polynucleotide construct of any one of items 19 to 21, or a salt thereof, or a stereoisomer thereof, wherein the strand comprises from 1 to 5 of the non-bioreversible, internucleoside phosphotriesters.
23. The polynucleotide construct of any one of items 19 to 22, or a salt thereof, or a stereoisomer thereof, wherein one of the non-bioreversible, internucleoside phosphotriesters connects the second nucleoside and the third nucleoside of the strand.
24. The polynucleotide construct of any one of items 19 to 23, or a salt thereof, or a stereoisomer thereof, wherein one of the non-bioreversible, internucleoside phosphotriesters connects the fifth nucleoside and the sixth nucleoside of the strand.
25. The polynucleotide construct of any one of items 19 to 24, or a salt thereof, or a stereoisomer thereof, wherein one of the non-bioreversible, internucleoside phosphotriesters connects the seventeenth nucleoside and the eighteenth nucleoside of the strand.
26. The polynucleotide construct of any one of items 19 to 25, or a salt thereof, or a stereoisomer thereof, wherein one of the non-bioreversible, internucleoside phosphotriesters connects the nineteenth nucleoside and the twentieth nucleoside of the strand.
27. The polynucleotide construct of any one of items 19 to 26, or a salt thereof, or a stereoisomer thereof, wherein one of the non-bioreversible, internucleoside phosphotriesters connects the twentieth nucleoside and the twenty-first nucleoside of the strand.
28. The polynucleotide construct of any one of items 19 to 22, or a salt thereof, or a stereoisomer thereof, wherein the at least one non-bioreversible, internucleoside phosphotriester connects two consecutive nucleosides that are two of six 5'- or six 3'-terminal nucleosides of the strand.

29. The polynucleotide construct of any one of items 19 to 28, or a salt thereof, or a stereoisomer thereof, wherein the strand comprises one or more internucleoside phosphonates.

30. The polynucleotide construct of item 29, or a salt thereof, or a stereoisomer thereof, wherein the one or more internucleoside phosphonates connects two consecutive nucleosides that are two of six 5'- or six 3'-terminal nucleosides of the strand.

31. The polynucleotide construct of any one of items 1 to 30, or a salt thereof, or a stereoisomer thereof, wherein the strand comprises 19 or more nucleosides.

32. The polynucleotide construct of any one of items 1 to 31, or a salt thereof, or a stereoisomer thereof, wherein the strand comprises fewer than 100 nucleosides.

33. The polynucleotide construct of item 32, or a salt thereof, or a stereoisomer thereof, wherein the strand comprises fewer than 50 nucleosides.

34. The polynucleotide construct of item 33, or a salt thereof, or a stereoisomer thereof, wherein the strand comprises fewer than 32 nucleosides.

35. The polynucleotide construct of any one of items 1 to 34, or a salt thereof, or a stereoisomer thereof, wherein the strand comprises at least one 2'-modified nucleoside.

36. The polynucleotide construct of item 35, or a salt thereof, or a stereoisomer thereof, wherein all nucleosides in the strand are independently 2'-modified nucleosides.

37. The polynucleotide construct of any one of items 1 to 36, or a salt thereof, or a stereoisomer thereof, wherein the strand is interrupted by at least one internucleoside, abasic spacer.

38. The polynucleotide construct of claim 37, or a salt thereof, or a stereoisomer thereof, wherein at least one internucleoside, abasic spacer is of formula (III):

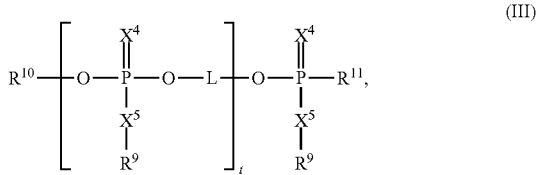

(III)

wherein
L is a sugar analogue;
each $X^4$ is independently O or S;
each $X^5$ is independently O, S, NH, or a bond;
each $R^9$ is independently H, optionally substituted $C_{1-6}$ alkyl, optionally substituted $C_{2-6}$ alkenyl, optionally substituted $C_{2-6}$ alkynyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl, -LinkA(-T)$_p$, or a conjugation moiety;
each LinkA is independently a multivalent linker (e.g., including —C(O)—N(H)—);
each T is independently an auxiliary moiety;
$R^{10}$ is a bond to a 3'-carbon atom of a nucleoside (x) in the strand;
$R^{11}$ is a bond to a 5'-oxygen atom of a nucleoside (x+t+1) in the strand;
p is an integer from 1 to 6; and
t is an integer from 1 to 6.

39. A polynucleotide construct comprising a strand interrupted by at least one internucleoside, abasic spacer of formula (III):

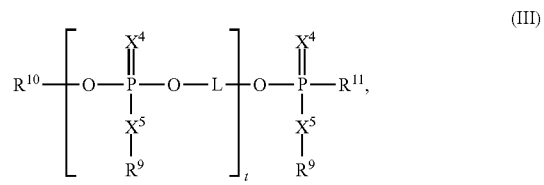

(III)

wherein
L is a sugar analogue;
each $X^4$ is independently O or S;
each $X^5$ is independently O, S, NH, or a bond;
each $R^9$ is independently H, optionally substituted $C_{1-6}$ alkyl, optionally substituted $C_{2-6}$ alkenyl, optionally substituted $C_{2-6}$ alkynyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl, -LinkA(-T)$_p$, or a conjugation moiety;
each LinkA is independently a multivalent linker (e.g., including —C(O)—N(H)—);
each T is independently an auxiliary moiety;
$R^{10}$ is a bond to a 3'-carbon atom of a nucleoside (x) in the strand;
$R^{11}$ is a bond to a 5'-oxygen atom of a nucleoside (x+t+1) in the strand;
p is an integer from 1 to 6; and
t is an integer from 1 to 6.

40. The polynucleotide construct of item 39, or a salt thereof, or a stereoisomer thereof, wherein t is 1.

41. The polynucleotide construct of item 39 or 40, or a salt thereof, or a stereoisomer thereof, wherein $R^9$ is H.

42. The polynucleotide construct of any one of items 39 to 41, or a salt thereof, or a stereoisomer thereof, wherein $X^4$ is O.

43. The polynucleotide construct of any one of items 39 to 41, or a salt thereof, or a stereoisomer thereof, wherein $X^4$ is S.

44. The polynucleotide construct of any one of items 39 to 43, or a salt thereof, or a stereoisomer thereof, wherein $X^5$ is O.

45. The polynucleotide construct of any one of items 39 to 44, or a salt thereof, or a stereoisomer thereof, wherein (x) is 2, 3, 4, or 5.

46. The polynucleotide construct of any one of items 39 to 45, or a salt thereof, or a stereoisomer thereof, wherein (x) is 13, 14, 15, or 16.

47. The polynucleotide construct of any one of items 39 to 46, or a salt thereof, or a stereoisomer thereof, wherein the construct comprises only 1 or only 2 internucleoside, abasic spacers.

48. The polynucleotide construct of any one of items 39 to 47, or a salt thereof, or a stereoisomer thereof, wherein the strand comprises at least one 2'-modified nucleoside.

49. The polynucleotide construct of item 48, or a salt thereof, or a stereoisomer thereof, wherein all nucleosides in the strand are independently 2'-modified nucleosides.

50. The polynucleotide construct of item 48, or a salt thereof, or a stereoisomer thereof, wherein at least 80% of nucleosides in the strand are 2'-modified nucleosides.

51. The polynucleotide construct of item 50, or a salt thereof, or a stereoisomer thereof, wherein each 2'-modified nucleoside is independently a 2'-alkoxy nucleoside.
52. The polynucleotide construct of item 48, or a salt thereof, or a stereoisomer thereof, wherein at least one of the second, twelfth, fourteenth, and sixteenth nucleosides in the strand is a 2'-fluoro nucleoside.
53. The polynucleotide construct of item 52, or a salt thereof, or a stereoisomer thereof, wherein the second, twelfth, fourteenth, and sixteenth nucleosides in the strand are all independently 2'-fluoro nucleosides.
54. A polynucleotide construct comprising a strand, wherein the second, twelfth, fourteenth, and sixteenth nucleosides in the strand are all independently 2'-fluoro nucleosides.
55. The polynucleotide construct of any one of items 52 to 54, or a salt thereof, or a stereoisomer thereof, wherein the remaining nucleosides are 2'-alkoxy nucleosides.
56. The polynucleotide construct of any one of items 52 to 55, or a salt thereof, or a stereoisomer thereof, wherein the remaining nucleosides are 2'-methoxy nucleosides.
57. The polynucleotide construct of any one of items 39 to 56, or a salt thereof, or a stereoisomer thereof, wherein the strand comprises a seed region comprising a hypoxanthine nucleobase-containing nucleoside (e.g., inosine).
58. A polynucleotide construct, or a salt thereof, or a stereoisomer thereof, comprising a strand comprising a seed region comprising a hypoxanthine nucleobase-containing nucleoside (e.g., inosine).
59. The polynucleotide construct of item 57 or 58, or a salt thereof, or a stereoisomer thereof, wherein the hypoxanthine nucleobase-containing nucleoside is the second nucleoside in the strand.
60. The polynucleotide construct of item 57 or 58, or a salt thereof, or a stereoisomer thereof, wherein the hypoxanthine nucleobase-containing nucleoside is the third nucleoside in the strand.
61. The polynucleotide construct of item 57 or 58, or a salt thereof, or a stereoisomer thereof, wherein the hypoxanthine nucleobase-containing nucleoside is the fourth nucleoside in the strand.
62. The polynucleotide construct of item 57 or 58, or a salt thereof, or a stereoisomer thereof, wherein the hypoxanthine nucleobase-containing nucleoside is the fifth nucleoside in the strand.
63. The polynucleotide construct of item 57 or 58, or a salt thereof, or a stereoisomer thereof, wherein the hypoxanthine nucleobase-containing nucleoside is the sixth nucleoside in the strand.
64. The polynucleotide construct of any one of items 39 to 63, or a salt thereof, or a stereoisomer thereof, wherein the strand comprises at least one stereochemically enriched phosphorothioate.
65. A polynucleotide construct, or a salt thereof, or a stereoisomer thereof, comprising a strand comprising at least one stereochemically enriched phosphorothioate.
66. The polynucleotide construct of item 64 or 65, or a salt thereof, or a stereoisomer thereof, wherein the strand comprises only 1, 2, 3, or 4 stereochemically enriched phosphorothioate.
67. The polynucleotide construct of any one of items 64 to 66, or a salt thereof, or a stereoisomer thereof, wherein at least one (e.g., one or two) stereochemically enriched phosphorothioate is disposed between two consecutive nucleosides that are two of six 5-terminal nucleosides of the strand.
68. The polynucleotide construct of any one of items 64 to 67, or a salt thereof, or a stereoisomer thereof, wherein at least one (e.g., one or two) stereochemically enriched phosphorothioate is disposed between two consecutive nucleosides that are two of six 3-terminal nucleosides of the strand.
69. The polynucleotide construct of any one of items 64 to 68, or a salt thereof, or a stereoisomer thereof, wherein (i) one stereochemically enriched phosphorothioate is covalently bonded between the first nucleoside and the second nucleoside within the strand.
70. The polynucleotide construct of any one of items 64 to 68, or a salt thereof, or a stereoisomer thereof, wherein (i) one stereochemically enriched phosphorothioate is covalently bonded between the second nucleoside and the third nucleoside within the strand.
71. The polynucleotide construct of any one of items 64 to 70, or a salt thereof, or a stereoisomer thereof, wherein one stereochemically enriched phosphorothioate is covalently bonded between the twenty-first nucleoside and the twenty-second nucleoside within the strand.
72. The polynucleotide construct of any one of items 64 to 71, or a salt thereof, or a stereoisomer thereof, wherein one stereochemically enriched phosphorothioate is covalently bonded between the twenty-second nucleoside and the twenty-third nucleoside within the strand.
73. The polynucleotide construct of any one of items 64 to 72, or a salt thereof, or a stereoisomer thereof, wherein the stereochemically enriched phosphorothioate has $R_P$ stereochemical identity.
74. The polynucleotide construct of any one of items 64 to 73, or a salt thereof, or a stereoisomer thereof, wherein the stereochemically enriched phosphorothioate has $S_P$ stereochemical identity.
75. The polynucleotide construct of any one of items 39 to 74, or a salt thereof, or a stereoisomer thereof, wherein the strand comprises 19 or more nucleosides.
76. The polynucleotide construct of any one of items 39 to 75, or a salt thereof, or a stereoisomer thereof, wherein the strand comprises fewer than 100 nucleosides.
77. The polynucleotide construct of item 76, or a salt thereof, or a stereoisomer thereof, wherein the strand comprises fewer than 50 nucleosides.
78. The polynucleotide construct of item 77, or a salt thereof, or a stereoisomer thereof, wherein the strand comprises fewer than 32 nucleosides.
79. A hybridized polynucleotide construct comprising a passenger strand and a guide strand loadable into a RISC complex, wherein the guide strand is the polynucleotide construct of any one of items 39 to 78, or a salt thereof, or a stereoisomer thereof.
80. A hybridized polynucleotide construct comprising a passenger strand and a guide strand loadable into a RISC complex, wherein the passenger strand is the polynucleotide construct of any one of items 1 to 38, or a salt thereof, or a stereoisomer thereof.
81. A hybridized polynucleotide construct comprising a passenger strand and a guide strand loadable into a RISC complex; wherein at least one of the strands comprises at least one phosphorodithioate or at least one stereochemically enriched internucleoside phosphorothioate; and wherein at least one of the strands is bonded to at least one group of formula (I):

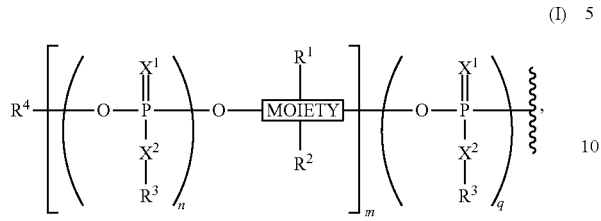

or a salt thereof, or a stereoisomer thereof,
wherein
each $X^1$ is independently O or S;
each $X^2$ is independently O, S, NH, or a bond;
MOIETY is optionally substituted $C_{2-10}$ alkane-tetrayl or a group $-M^1-M^2-M^3-$, wherein each $M^1$ and each $M^3$ is independently absent or optionally substituted $C_{1-6}$ alkylene, and $M^2$ is optionally substituted $C_{3-9}$ heterocycle-tetrayl, optionally substituted $C_{6-10}$ arene-tetrayl, or optionally substituted $C_{3-8}$ cycloalkane-tetrayl;
each $R^1$ and each $R^2$ is independently H, optionally substituted $C_{1-16}$ alkyl, optionally substituted $C_{2-16}$ heteroalkyl, a conjugation moiety, or -LinkA(-T)$_p$, provided that at least one $R^1$ or at least one $R^2$ is a conjugation moiety or -LinkA(-T)$_p$;
each $R^3$ is independently H, optionally substituted $C_{1-16}$ alkyl, optionally substituted $C_{2-16}$ heteroalkyl, optionally substituted $C_{2-16}$ alkenyl, optionally substituted $C_{2-16}$ alkynyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl, a conjugation moiety, or -LinkA(-T)$_p$;
$R^4$ is H, optionally substituted $C_{1-6}$ alkyl, -LinkA(-T)$_p$, or -Sol;
each LinkA is independently a multivalent linker;
each T is independently an auxiliary moiety;
Sol is solid support;
m is an integer from 1 to 6;
each n is independently 0 or 1;
each p is independently an integer from 1 to 6; and
q is an integer from 0 to 3;
wherein the hybridized polynucleotide construct comprises no more than one Sol; and
wherein, when the at least one group of formula (I) is bonded to an internucleoside phosphate, internucleoside phosphorothioate, or internucleoside phosphorodithioate, q is 0.

82. A hybridized polynucleotide construct comprising a passenger strand and a guide strand loadable into a RISC complex; wherein at least one of the strands comprises at least one 2'-modified nucleoside; and wherein at least one of the strands is bonded to at least one group of formula (I):

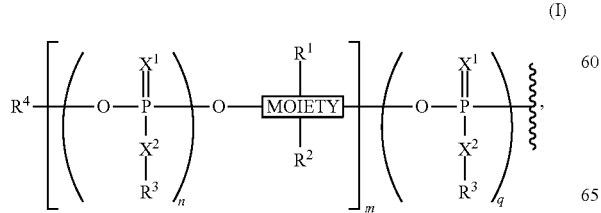

or a salt thereof, or a stereoisomer thereof,
wherein
each $X^1$ is independently O or S;
each $X^2$ is independently O, S, NH, or a bond;
MOIETY is optionally substituted $C_{2-10}$ alkane-tetrayl or a group $-M^1-M^2-M^3-$, wherein each $M^1$ and each $M^3$ is independently absent or optionally substituted $C_{1-6}$ alkylene, and $M^2$ is optionally substituted $C_{3-9}$ heterocycle-tetrayl, optionally substituted $C_{6-10}$ arene-tetrayl, or optionally substituted $C_{3-8}$ cycloalkane-tetrayl;
each $R^1$ and each $R^2$ is independently H, optionally substituted $C_{1-16}$ alkyl, optionally substituted $C_{2-16}$ heteroalkyl, a conjugation moiety, or -LinkA(-T)$_p$, provided that at least one $R^1$ or at least one $R^2$ is a conjugation moiety or -LinkA(-T)$_p$;
each $R^3$ is independently H, optionally substituted $C_{1-16}$ alkyl, optionally substituted $C_{2-16}$ heteroalkyl, optionally substituted $C_{2-16}$ alkenyl, optionally substituted $C_{2-16}$ alkynyl, optionally substituted ($C_{1-9}$ heterocyclyl)-$C_{1-6}$-alkyl, optionally substituted ($C_{6-10}$ aryl)-$C_{1-6}$-alkyl, optionally substituted ($C_{3-8}$ cycloalkyl)-$C_{1-6}$-alkyl, a conjugation moiety, or -LinkA(-T)$_p$;
$R^4$ is H, optionally substituted $C_{1-6}$ alkyl, -LinkA(-T)$_p$, or -Sol;
each LinkA is independently a multivalent linker;
each T is independently an auxiliary moiety;
Sol is solid support;
m is an integer from 1 to 6;
each n is independently 0 or 1;
each p is independently an integer from 1 to 6; and
q is an integer from 0 to 3;
wherein the hybridized polynucleotide construct comprises no more than one Sol; and
wherein, when the at least one group of formula (I) is bonded to an internucleoside phosphate, internucleoside phosphorothioate, or internucleoside phosphorodithioate, q is 0.

83. The hybridized polynucleotide construct of item 81 or 82, or a salt thereof, or a stereoisomer thereof, wherein at least one -LinkA(-T)$_p$ is of formula (II):

wherein
each s is independently an integer from 0 to 20, wherein the repeating units are same or different;
$Q^1$ is a conjugation linker;
$Q^2$ is a linear group, if p is 1, or a branched group, if p is an integer from 2 to 6;
each $Q^3$ and each $Q^6$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—;
each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, optionally substituted $C_{6-10}$ arylene, optionally substituted $C_{1-9}$ heteroarylene, or optionally substituted $C_{1-9}$ heterocyclylene (e.g., each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene);
each $Q^5$ is independently absent, —CO—, —NH—, —O—, —S—, —SO$_2$—, —CH$_2$—, —C(O)O—, —OC(O)—, —C(O)NH—, —NH—C(O)—, —NH—CH(R$^a$)—C(O)—, or —C(O)—CH(R$^a$)—NH—; and each R$^a$ is independently H or an amino acid side chain; provided that at least one of Q$^3$, Q$^4$, and Q$^5$ is present.

84. The hybridized polynucleotide construct of item 83, or a salt thereof, or a stereoisomer thereof, wherein Q$^1$ is —O-Q$^L$-Q$^C$-, wherein Q$^L$ is optionally substituted C$_{2-12}$ heteroalkylene or optionally substituted C$_{1-12}$ alkylene, and Q$^C$ is (i) optionally substituted C$_{2-12}$ heteroalkylene comprising —C(O)—N(H)—, —N(H)—C(O)—, —S(O)$_2$—N(H)—, or —N(H)—S(O)$_2$—; (ii) optionally substituted C$_{1-12}$ heterocyclylene; (iii) optionally substituted C$_{1-12}$ thioheterocyclylene; (iv) cyclobut-3-ene-1,2-dione-3,4-diyl; or (v) pyrid-2-yl hydrazone.

85. The hybridized polynucleotide construct of item 83, or a salt thereof, or a stereoisomer thereof, wherein Q$^1$ comprises:

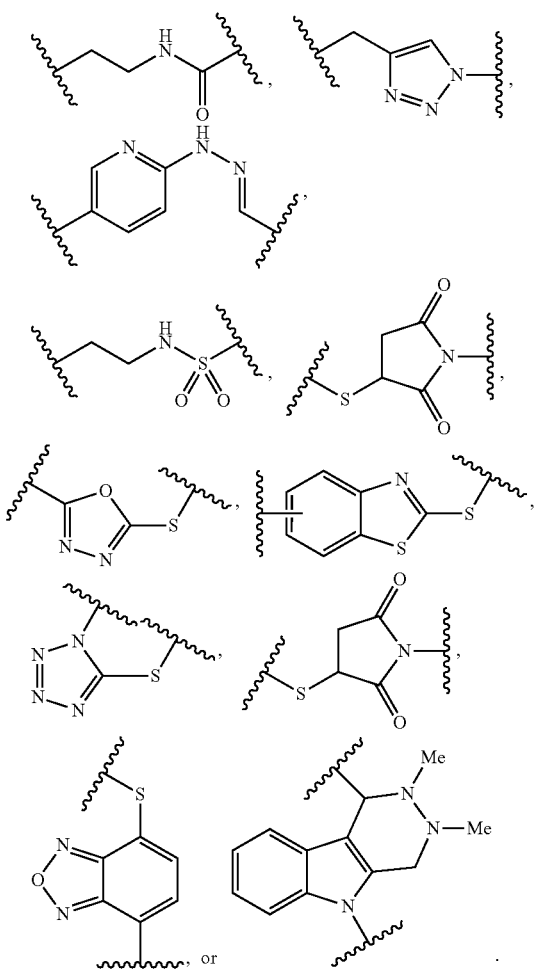

86. The hybridized polynucleotide construct of any one of items 83 to 85, or a salt thereof, or a stereoisomer thereof, wherein p is 1, and Q$^2$ is a linear group of formula -[Q$^3$-Q$^4$-Q$^5$]$_s$-.

87. The hybridized polynucleotide construct of any one of items 83 to 86, or a salt thereof, or a stereoisomer thereof, wherein p is an integer from 2 to 6, and Q$^2$ is a branched group -[Q$^3$-Q$^4$-Q$^5$]$_s$-Q$^7$(-[Q$^3$-Q$^4$-Q$^5$]$_s$-(Q$^7$)$_{p1}$)$_{p2}$, wherein Q$^7$ is optionally substituted C$_{1-6}$ alkane-triyl, optionally substituted C$_{1-6}$ alkane-tetrayl, optionally substituted C$_{2-6}$ heteroalkane-triyl, or optionally substituted C$_{2-6}$ heteroalkane-tetrayl;
wherein
p1 is 0 or 1;
p2 is 0, 1, 2, or 3;
wherein,
when p1 is 0, LinkA is a trivalent or tetravalent linker, and,
when p1 is 1, LinkA is a tetravalent, pentavalent, or hexavalent linker.

88. The hybridized polynucleotide construct of any one of items 81 to 87, or a salt thereof, or a stereoisomer thereof, wherein each -LinkA(-T)$_p$ is independently of formula (II).

89. The hybridized polynucleotide construct of any one of items 81 to 88, or a salt thereof, or a stereoisomer thereof, wherein at least one T is a targeting moiety.

90 The hybridized polynucleotide construct of any one of items 81 to 89, or a salt thereof, or a stereoisomer thereof, wherein at least one T is an asialoglycoprotein receptor ligand, mannose, folate, prostate specific membrane antigen (PSMA), or an antibody or an antigen-binding fragment thereof.

91. The hybridized polynucleotide construct of item 90, or a salt thereof, or a stereoisomer thereof, wherein at least one T is an asialoglycoprotein receptor ligand.

92. The hybridized polynucleotide construct of item 91, or a salt thereof, or a stereoisomer thereof, wherein at least one T is N-acetyl galactosamine.

93. The hybridized polynucleotide construct of item 92, or a salt thereof, or a stereoisomer thereof, wherein N-acetyl galactosamine comprises an anomeric carbon bonded to LinkA, wherein the anomeric carbon is part of a hemiaminal group.

94. The hybridized polynucleotide construct of item 93, or a salt thereof, or a stereoisomer thereof, wherein the anomeric carbon of N-acetyl galactosamine is bonded to an amide nitrogen atom.

95. The hybridized polynucleotide construct of any one of items 81 to 94, or a salt thereof, or a stereoisomer thereof, wherein at least one T is a cell penetrating peptide.

96. The hybridized polynucleotide construct of any one of items 81 to 94, or a salt thereof, or a stereoisomer thereof, wherein at least one T is an endosomal escape moiety.

97. The hybridized polynucleotide construct of any one of items 81 to 96, or a salt thereof, or a stereoisomer thereof, wherein the hybridized polynucleotide construct comprises from 1 to 6 groups of formula (I), wherein the groups of formula (I) are same or different.

98. The hybridized polynucleotide construct of any one of items 81 to 97, or a salt thereof, or a stereoisomer thereof, wherein the passenger strand comprises at least one non-bioreversible, internucleoside phosphotriester.

99. The hybridized polynucleotide construct of any one of items 81 to 98, or a salt thereof, or a stereoisomer thereof, wherein the guide strand comprises at least one non-bioreversible, internucleoside phosphotriester.

100. The hybridized polynucleotide construct of item 98 or 99, or a salt thereof, or a stereoisomer thereof, wherein the at least one non-bioreversible, internucleoside phosphotriester is a phosphate, phosphorothioate, or phosphorodithioate that is substituted with a substituent selected independently from the group consisting of optionally substituted C$_{2-16}$ alkyl; optionally substituted $C_{3-16}$ alkenyl; optionally substituted $C_{3-16}$ alkynyl; optionally substituted $C_{3-8}$ cycloalkyl; optionally substituted $C_{3-8}$ cycloalkenyl; optionally substituted ($C_{3-8}$ cycloalkyl)-$C_{1-4}$-alkyl; optionally substituted ($C_{3-8}$ cycloalkenyl)-$C_{1-4}$-alkyl; optionally substituted $C_{6-14}$ aryl; optionally substituted ($C_{6-14}$ aryl)-$C_{1-4}$-alkyl; optionally substituted $C_{1-9}$ heteroaryl having 1 to 4 heteroatoms selected from N, O, and S; optionally substituted ($C_{1-9}$ heteroaryl)-$C_{1-4}$-alkyl having 1 to 4 heteroatoms selected from N, O, and S; optionally substituted $C_{2-9}$ heterocyclyl having 1 to 4 heteroatoms selected from N, O, and S, wherein the heterocyclyl does not comprise an S—S bond; optionally substituted ($C_{2-9}$ heterocyclyl)-$C_{1-4}$-alkyl having 1 to 4 heteroatoms selected from N, O, and S, wherein the heterocyclyl does not comprise an S—S bond; and a group of the following structure:

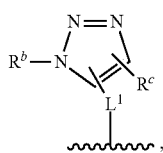

wherein
$L^1$ is $C_{1-6}$ alkylene;
$R^b$ is optionally substituted $C_{2-6}$ alkyl; optionally substituted $C_{6-14}$ aryl; optionally substituted ($C_{6-14}$ aryl)-$C_{1-4}$-alkyl; optionally substituted $C_{3-8}$ cycloalkyl; optionally substituted ($C_{3-8}$ cycloalkyl)-$C_{1-4}$-alkyl; optionally substituted $C_{1-9}$ heteroaryl having 1 to 4 heteroatoms selected from the group consisting of N, O, and S; optionally substituted ($C_{1-9}$ heteroaryl)-$C_{1-4}$-alkyl having 1 to 4 heteroatoms selected from the group consisting of N, O, and S; optionally substituted $C_{2-9}$ heterocyclyl having 1 to 4 heteroatoms selected from the group consisting of N, O, and S, wherein the heterocyclyl does not comprise an S—S bond; optionally substituted ($C_{2-9}$ heterocyclyl)-$C_{1-4}$-alkyl having 1 to 4 heteroatoms selected from N, O, and S, wherein the heterocyclyl does not comprise an S—S bond; and a poly(ethylene glycol) terminated with —OH, $C_{1-6}$ alkoxy, or —COOH; and
$R^c$ is H or $C_{1-6}$ alkyl.
101. The hybridized polynucleotide construct of item 98 or 99, or a salt thereof, or a stereoisomer thereof, wherein each of the non-bioreversible phosphotriesters is a phosphate, phosphorothioate, or phosphorodithioate substituted with a substituent that is $C_{2-16}$ alkyl,

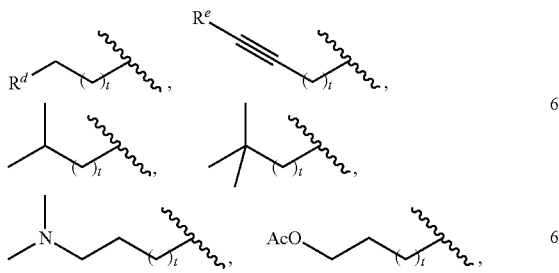

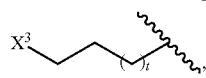

or a group formed by cycloaddition reaction of

with an azido-containing substrate,
wherein
t is an integer from 1 to 6;
$R^d$ is optionally substituted $C_6$ aryl; optionally substituted $C_{4-5}$ heteroaryl that is a six member ring comprising 1 or 2 nitrogen atoms; or optionally substituted $C_{4-5}$ heterocyclyl that is a six member ring comprising 1 or 2 nitrogen atoms;
$R^e$ is H or $C_{1-6}$ alkyl;
$X^3$ is a halogen, —COOR$^5$, or —CONR$^6{}_2$, wherein each of $R^5$ and $R^6$ is independently H, optionally substituted $C_{1-6}$ alkyl, optionally substituted $C_{6-14}$ aryl, optionally substituted $C_{1-9}$ heteroaryl, or optionally substituted $C_{2-9}$ heterocyclyl; and
the azido-containing substrate is

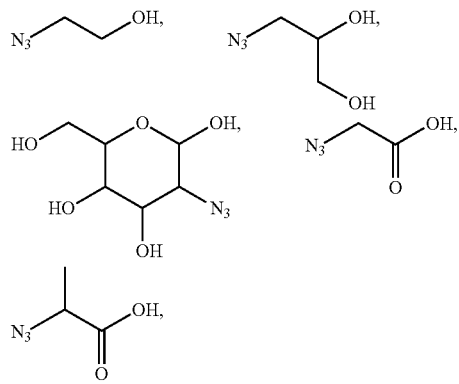

$N_3$-PEG-OH, $N_3$-PEG-COOH,

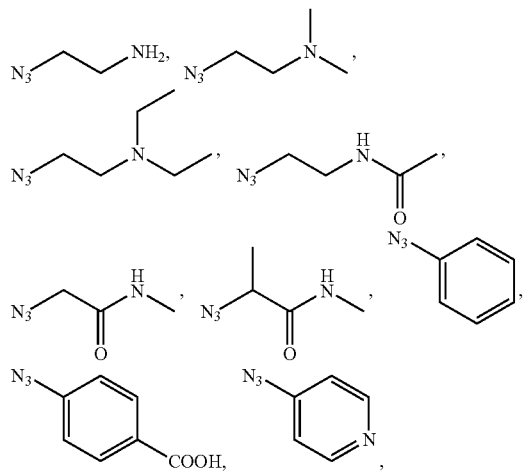

-continued

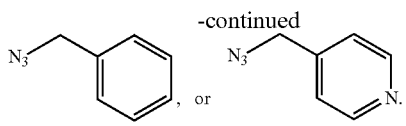

102. The hybridized polynucleotide construct of any one of items 99 to 101, or a salt thereof, or a stereoisomer thereof, wherein the guide strand comprises from 1 to 5 of the non-bioreversible, internucleoside phosphotriesters.
103. The hybridized polynucleotide construct of any one of items 99 to 102, or a salt thereof, or a stereoisomer thereof, wherein the at least one non-bioreversible, internucleoside phosphotriester connects two consecutive nucleosides that are two of six 5'- or six 3'-terminal nucleosides of the guide strand.
104. The hybridized polynucleotide construct of any one of items 99 to 103, or a salt thereof, or a stereoisomer thereof, wherein one of the non-bioreversible, internucleoside phosphotriesters connects the second nucleoside and the third nucleoside of the guide strand.
105. The hybridized polynucleotide construct of any one of items 99 to 104, or a salt thereof, or a stereoisomer thereof, wherein one of the non-bioreversible, internucleoside phosphotriesters connects the fifth nucleoside and the sixth nucleoside of the guide strand.
106. The hybridized polynucleotide construct of any one of items 99 to 105, or a salt thereof, or a stereoisomer thereof, wherein one of the non-bioreversible, internucleoside phosphotriesters connects the seventeenth nucleoside and the eighteenth nucleoside of the guide strand.
107. The hybridized polynucleotide construct of any one of items 99 to 106, or a salt thereof, or a stereoisomer thereof, wherein one of the non-bioreversible, internucleoside phosphotriesters connects the nineteenth nucleoside and the twentieth nucleoside of the guide strand.
108. The hybridized polynucleotide construct of any one of items 98 to 106, or a salt thereof, or a stereoisomer thereof, wherein one of the non-bioreversible, internucleoside phosphotriesters connects the twentieth nucleoside and the twenty-first nucleoside of the guide strand.
109. The hybridized polynucleotide construct of any one of items 97 to 108, or a salt thereof, or a stereoisomer thereof, wherein the passenger strand comprises from 1 to 5 of the non-bioreversible phosphotriesters.
110. The hybridized polynucleotide construct of any one of items 97 to 109, or a salt thereof, or a stereoisomer thereof, wherein the at least one non-bioreversible, internucleoside phosphotriester connects two consecutive nucleosides that are two of six 5'- or six 3'-terminal nucleosides of the passenger strand.
111. The hybridized polynucleotide construct of any one of items 81 to 110, or a salt thereof, or a stereoisomer thereof, wherein the passenger strand or the guide strand is interrupted by at least one internucleoside, abasic spacer.
112. The hybridized polynucleotide construct of item 111, or a salt thereof, or a stereoisomer thereof, wherein the guide strand is interrupted by one internucleoside, abasic spacer.
113. The hybridized polynucleotide construct of item 111 or 112, or a salt thereof, or a stereoisomer thereof, wherein the passenger strand is interrupted by one internucleoside, abasic spacer.
114. The hybridized polynucleotide construct of any one of items 79 to 113, or a salt thereof, or a stereoisomer thereof, wherein the guide strand or the passenger strand comprises one or more phosphonates.
115. The hybridized polynucleotide construct of any one of items 79 to 114, or a salt thereof, or a stereoisomer thereof, wherein the guide strand comprises 19 or more nucleosides.
116. The hybridized polynucleotide construct of any one of items 79 to 115, or a salt thereof, or a stereoisomer thereof, wherein the guide strand comprises fewer than 100 nucleosides.
117. The hybridized polynucleotide construct of item 116, or a salt thereof, or a stereoisomer thereof, wherein the guide strand comprises fewer than 50 nucleosides.
118. The hybridized polynucleotide construct of item 117, or a salt thereof, or a stereoisomer thereof, wherein the guide strand comprises fewer than 32 nucleosides.
119. The hybridized polynucleotide construct of any one of items 79 to 118, or a salt thereof, or a stereoisomer thereof, wherein the passenger strand comprises 19 or more nucleosides.
120. The hybridized polynucleotide construct of any one of items 79 to 119, or a salt thereof, or a stereoisomer thereof, wherein the passenger strand comprises fewer than 100 nucleosides.
121. The hybridized polynucleotide construct of item 120, or a salt thereof, or a stereoisomer thereof, wherein the passenger strand comprises fewer than 50 nucleosides.
122. The hybridized polynucleotide construct of item 121, or a salt thereof, or a stereoisomer thereof, wherein the passenger strand comprises fewer than 32 nucleosides.
123. The hybridized polynucleotide construct of any one of items 79 to 122, or a salt thereof, or a stereoisomer thereof, wherein the 3-end of the passenger strand is hybridized to the 5'-end of the guide strand to form a blunt.
124. The polynucleotide construct of any one of items 1 to 38, or the hybridized polynucleotide construct of any one of items 80 to 122, or a salt thereof, or a stereoisomer thereof, wherein $R^1$ and $R^2$ are attached to the same atom in MOIETY.
125. The polynucleotide construct or the hybridized polynucleotide construct of item 124, or a salt thereof, or a stereoisomer thereof, wherein MOIETY, $R^1$, and $R^2$ combine to form:

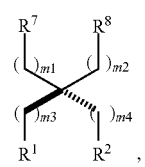

(Ia)

wherein
$R^7$ is a bond to an oxygen atom that is proximal to $R^4$,
$R^8$ is a bond to an oxygen atom that is proximal to the strand, and
each of m1, m2, m3, and m4 is independently an integer from 0 to 6,
provided that the quaternary carbon in formula (Ia) is bonded to O or 1 atoms other than carbon and hydrogen, and provided that the sum of m1, m2, m3 and m4 is less than 10.

126. A method of delivering a polynucleotide construct to a cell comprising contacting the cell with the polynucleotide construct of any one of items 1-78, 124, and 125, or a salt thereof, or a stereoisomer thereof, or with the hybridized polynucleotide construct of any one of items 79 to 123, or a salt thereof, or a stereoisomer thereof, wherein, after the contacting, the polynucleotide construct resides inside the cell.

127. A method of reducing the expression of a protein in a cell comprising contacting the cell with the polynucleotide construct of any one of items 1-78, 124, and 125, or a salt thereof, or a stereoisomer thereof, or with the hybridized polynucleotide construct of any one of items 79 to 123, or a salt thereof, or a stereoisomer thereof, wherein, after the contacting, expression of the protein in the cell is reduced.

128. A compound of formula (IV):

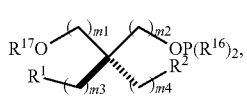

(IV)

wherein each of $R^1$ and $R^2$ is independently H, optionally substituted $C_{1-16}$ alkyl, optionally substituted $C_{2-16}$ heteroalkyl, or a conjugation moiety;

each $R^{16}$ is independently dialkylamino, 2-cyanoethyl, or a conjugation moiety, provided that at least one $R^{16}$ is dialkylamino;

$R^{17}$ is a hydroxyl protecting group; and each of m1, m2, m3, and m4 is independently an integer from 0 to 6, provided that the sum of m1 and m2 is not 0;

wherein, when both $R^1$ and $R^2$ are a conjugation moiety comprising optionally substituted $C_{2-16}$ alkynyl, $R^{16}$ is dialkylamino or a conjugation moiety.

129. The compound of item 128, wherein m1 is 0 or 1.

130. The compound of item 128 or 129, wherein m2 is 0 or 1.

131. The compound of any one of items 128 to 130, wherein $R^1$ is H or the conjugation moiety, wherein the conjugation moiety is $[-Q^3-Q^4-Q^5]_s-Q^{C1}$, wherein $Q^{C1}$ is optionally substituted $C_{1-6}$ alkyl comprising —$COOR^{21}$ or —CHO, optionally substituted $C_{2-12}$ alkynyl, optionally substituted N-protected amino, azido, N-maleimido, S-protected thiol,

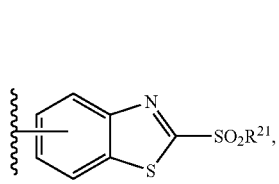

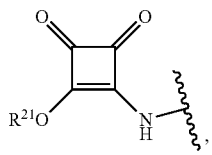

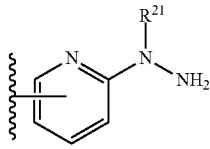

or N-protected version thereof,

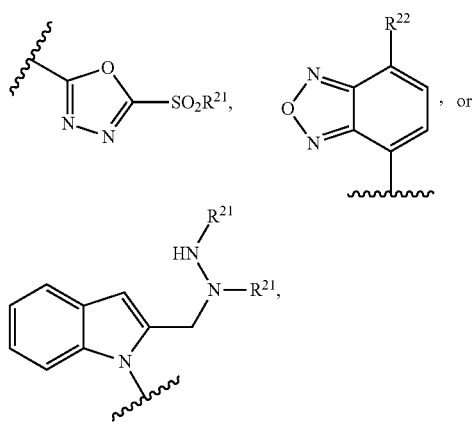

wherein each $R^{21}$ is independently H or optionally substituted $C_{1-6}$ alkyl, and $R^{22}$ is halogen;

each $Q^3$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—;

each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene;

each $Q^5$ is independently absent, —CO—, —NH—, —O—, —S—, —SO$_2$—, —CH$_2$—, —C(O)O—, —OC(O)—, —C(O)NH—, —NH—C(O)—, —NH—CH($R^a$)—C(O)—, or —C(O)—CH($R^a$)—NH—; and each s is independently an integer from 0 to 20.

132. The compound of item 131, wherein $Q^3$ in $R^1$ is —O—.

133. The compound of item 131 or 132, wherein $Q^4$ in $R^1$ is absent or optionally substituted $C_{2-12}$ heteroalkylene, and $Q^5$ in $R^1$ is absent.

134. The compound of any one of items 128 to 133, wherein $R^2$ is H or the conjugation moiety, wherein the conjugation moiety is $[-Q^3-Q^4-Q^5]_s-Q^{C1}$, wherein $Q^{C1}$ is optionally substituted $C_{1-6}$ alkyl comprising —$COOR^{21}$ or —CHO, optionally substituted $C_{2-12}$ alkynyl, optionally substituted N-protected amino, azido, N-maleimido, S-protected thiol,

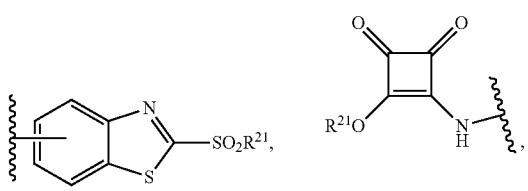

-continued

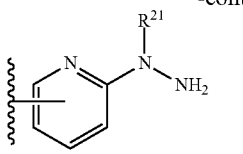

or N-protected version thereof,

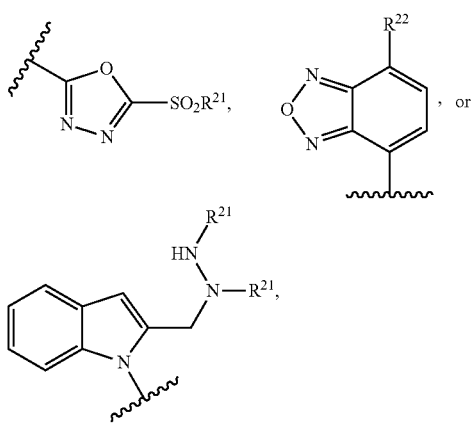

wherein each $R^{21}$ is independently H or optionally substituted $C_{1-6}$ alkyl, and $R^{22}$ is halogen;

each $Q^3$ is independently absent, —CO—, —NH—, —O—, —S—, —SO$_2$—, —OC(O)—, —COO—, —NHC(O)—, —C(O)NH—, —CH$_2$—, —CH$_2$NH—, —NHCH$_2$—, —CH$_2$O—, or —OCH$_2$—;

each $Q^4$ is independently absent, optionally substituted $C_{1-12}$ alkylene, optionally substituted $C_{2-12}$ alkenylene, optionally substituted $C_{2-12}$ alkynylene, optionally substituted $C_{2-12}$ heteroalkylene, or optionally substituted $C_{1-9}$ heterocyclylene;

each $Q^5$ is independently absent, —CO—, —NH—, —O—, —S—, —SO$_2$—, —CH$_2$—, —C(O)O—, —OC(O)—, —C(O)NH—, —NH—C(O)—, —NH—CH($R^a$)—C(O)—, or —C(O)—CH($R^a$)—NH—; and each s is independently an integer from 0 to 20.

135. The compound of item 134, wherein $Q^3$ in $R^2$ is —O—.

136. The compound of item 134 or 135, wherein $Q^4$ in $R^2$ is absent or optionally substituted $C_{2-12}$ heteroalkylene, and $Q^5$ in $R^2$ is absent.

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A polynucleotide construct or a salt thereof, comprising a linker conjugated to a polynucleotide and to a plurality of targeting moieties, wherein prior to conjugation of the targeting moieties, the linker has the structure X2,

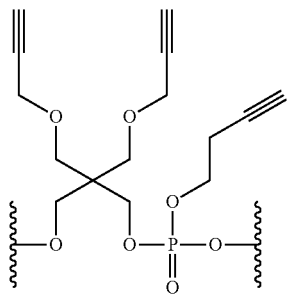

and wherein conjugation of the targeting moieties to the linker occurs through one or more of the alkyne moieties of X2, and wherein each of the targeting moieties comprises an N-acetyl galactosamine (GalNAc).

2. The polynucleotide construct of claim 1, wherein prior to conjugation of the targeting moieties to the linker X2, the polynucleotide construct comprises a structure of

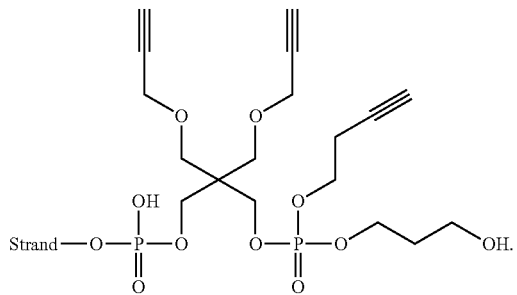

3. The polynucleotide construct of claim 1, wherein the targeting moieties are selected from NAG26, NAG37, NAG38, and NAG39.

4. The polynucleotide construct of claim 1, wherein prior to conjugation to the linker X2, each of the targeting moieties has the structure of (NAG26)

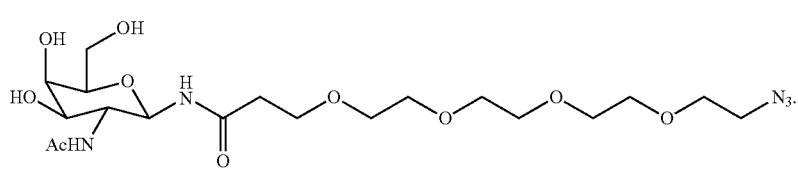

5. The polynucleotide construct of claim 1, wherein the polynucleotide comprises a passenger strand and a guide strand.

6. The polynucleotide construct of claim 5, wherein the X2 linker is bound to the passenger strand.

7. The polynucleotide construct of claim 6, wherein the X2 linker is bound to the 3'-terminus of the passenger strand.

8. The polynucleotide construct of claim 5, wherein the passenger strand is 15 to 32 nucleotides in length.

9. The polynucleotide construct of claim 5, wherein the guide strand is 15 to 32 nucleotides in length.

10. The polynucleotide construct of claim 1, wherein the X2 linker is conjugated with the targeting moieties by click reaction.

11. The polynucleotide construct of claim 1, wherein the X2 linker comprises a terminal phosphotriester.

12. The polynucleotide construct of claim 11, wherein the X2 linker is bound to a 3' $C_3$—OH group.

13. The polynucleotide construct of claim 1, wherein the polynucleotide construct comprises one X2 linker.

* * * * *

SEQUENCE LISTING

```
<160> NUMBER OF SEQ ID NOS: 88

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

Arg Arg Arg Arg Arg Arg Arg Arg
1               5

<210> SEQ ID NO 2
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 2
aaaaagauaa augucugcuu gcu                                                 23

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 3
aacaguguuc uugcucuaua a                                                   21
```

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: Description of Combined DNA/RNA Molecule:
      Synthetic oligonucleotide

<400> SEQUENCE: 4
aacaguguuc uugcucuaua attt                                          24

<210> SEQ ID NO 5
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 5
aagcaaaaca ggucuagaaa agu                                           23

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 6
aaguaaaugg uguuaaccag a                                             21

<210> SEQ ID NO 7
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 7
aaguaaaugg uguuaaccag aac                                           23

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 8 aauguguua accagaacca g                                              21

<210> SEQ ID NO 9
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 9
aaugguguua accagaacca ggg        23

<210> SEQ ID NO 10
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 10
acaaaagcaa aacaggucua gaa        23

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 11
acaccauuua cuucaagga        19

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 12
acaggcccuu gaaguaaaug g        21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 13
aggcccuuga aguaaauggu g        21

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 14
auuuacuuca agggccugu        19

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 15
caagcagaca uuuaucuuuu u                                             21

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 16
cauuuacuuc aagggccua                                                19

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 17
ccaaaacacc auuuacuuca a                                             21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 18
ccauaacacc auuuacuuca a                                             21

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 19
ccauuuacuu caagggccu                                                19

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 20
ccuuaacacc auuuacuuca a                                             21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 21
cguuaacacc auuuacuuca a                                             21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 22
cuagaccugu uuugcuuuug u                                              21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 23
cugguuaaca ccauuuacuu a                                              21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 24
cugguucugg uuaacaccau u                                              21

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 25
gguuaacacc auuuacuua                                                 19

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 26
gguuaacacc auuuacuuca a                                              21

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: Description of Combined DNA/RNA Molecule:
      Synthetic oligonucleotide

<400> SEQUENCE: 27
gguuaacacc auuuacuuca attt                    24

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 28
gguuaacacc auuuacuuca c                       21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 29
gguuaacacc auuuacuuca g                       21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 30
gguuaacacc auuuacuuca u                       21

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 31
gguucugguu aacaccauu                          19

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 32
gguucugguu aacaccauuu a                       21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 33
guuaacacca uuuacuucaa a                                      21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 34
guucugguua acaccauuua a                                      21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 35
uaaauggugu uaaccagaac c                                      21

<210> SEQ ID NO 36
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 36
uaaauggugu uaaccagaac cag                                    23

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 37
uaacaccauu uacuucaaa                                         19

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 38
uaacaccauu uacuucaagg a                                      21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 39
uaaguaaaug guguuaacca g                                      21

<210> SEQ ID NO 40
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 40
uaaguaaaug guguuaacca gaa                                          23

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 41
uaggcccuug aaguaaaugg u                                            21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 42
uccuugaagu aaauggguguu a                                           21

<210> SEQ ID NO 43
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 43
uccuugaagu aaaugguguu aac                                          23

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 44
ucugguuaac accauuuaa                                               19

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 45
ucugguuaac accauuuacu u                                            21

```
<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 46
ugguuaacac cauuuacuu                                                    19

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 47
uuaaauggug uuaaccagaa c                                                 21

<210> SEQ ID NO 48
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 48
uuaaauggug uuaaccagaa cca                                               23

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 49
uuaacaccau uuacuucaa                                                    19

<210> SEQ ID NO 50
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 50
uuauagagca agaacacugu uuu                                               23

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 51
uucugguuaa caccauuua                                                    19
```

```
<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 52
uugaaguaaa ugguguuaac c                                              21

<210> SEQ ID NO 53
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 53
uugaaguaaa ugguguuaac cag                                            23

<210> SEQ ID NO 54
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 54
uugaaguaaa ugguguuaac cuc                                            23

<210> SEQ ID NO 55
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 55
uugaaguaaa ugguguuaac guc                                            23

<210> SEQ ID NO 56
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 56
uugaaguaaa ugguguuaag guc                                            23

<210> SEQ ID NO 57
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 57
uugaaguaaa ugguguuaug guc                                            23

<210> SEQ ID NO 58
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 58
uugaaguaaa ugguguuuug guc                                              23

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 59
uuugaaguaa augguguuaa c                                                21

<210> SEQ ID NO 60
<211> LENGTH: 23
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 60
uuugaaguaa augguguuaa cca                                              23

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      construct

<400> SEQUENCE: 61
uuuucuagac cuguuuugcu u                                                21

<210> SEQ ID NO 62
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uugaaguaaa ugguguuaac cac                                              23

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
uuuugcuuuu guaacuugaa a                                                21

<210> SEQ ID NO 64
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uuucaaguua caaaagcaaa aca                                              23

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65 guuuguagc auuuuauua a                                                  21

<210> SEQ ID NO 66
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uuaauaaaaa ugcuacaaaa ccc                                              23

<210> SEQ ID NO 67
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uugaguaaau gguguuaacc ag                                               22

<210> SEQ ID NO 68
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uugaauaaau gguguuaacc ag                                               22

<210> SEQ ID NO 69
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uugaagaaau gguguuaacc ag                                               22

<210> SEQ ID NO 70
<211> LENGTH: 22
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 70
uuaugagcaa gaacacuguu uu                                               22

<210> SEQ ID NO 71
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uuauaggcaa gaacacuguu uu                                               22

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
uugcuuuugu aacuugaaga u                                                21

<210> SEQ ID NO 73
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aucucaaguu acaaaagcaa aa                                               22

<210> SEQ ID NO 74
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
aucuucaguu acaaaagcaa aa                                               22

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gcuuuuguaa cuugaagaua u                                                21

<210> SEQ ID NO 76
<211> LENGTH: 22
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 76
auauuucaag uuacaaaagc aa                                              22

<210> SEQ ID NO 77
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
auaucucaag uuacaaaagc aa                                              22

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
uaacuugaag auauuuauuc u                                               21

<210> SEQ ID NO 79
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
agaaaaauau cuucaaguua ca                                              22

<210> SEQ ID NO 80
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
agaauaauau cuucaaguua ca                                              22

<210> SEQ ID NO 81
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
uuaaaaaaau gcuacaaaac cc                                              22

<210> SEQ ID NO 82
<211> LENGTH: 22
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 82
uuaauaaaau gcuacaaaac cc                                                22

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uuguagcauu uuuauuaaua u                                                 21

<210> SEQ ID NO 84
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
auauaauaaa aaugcuacaa aa                                                22

<210> SEQ ID NO 85
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
auauuauaaa aaugcuacaa aa                                                22

<210> SEQ ID NO 86
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-OMe inosine nucleoside

<400> SEQUENCE: 86
uugnaguaaa ugguguuaac cag                                               23

<210> SEQ ID NO 87
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2'-OMe inosine nucleoside

<400> SEQUENCE: 87
uuganguaaa ugguguuaac cag                                              23

<210> SEQ ID NO 88
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-OMe inosine nucleoside

<400> SEQUENCE: 88
uugaanuaaa ugguguuaac cag                                              23
```